US010525117B2

(12) United States Patent
Bomchil et al.

(10) Patent No.: US 10,525,117 B2
(45) Date of Patent: Jan. 7, 2020

(54) *LEPTOSPIRA* IMMUNOPROTECTIVE PROTEINS AND METHODS OF IDENTIFICATION AND USE THEREOF

(71) Applicants: MERIAL, INC., Duluth, GA (US); CALIXAR, Lyons (FR); GENOSTAR, Montbonnot (FR); VETAGRO-SUP, Marcy l'Etoile (FR); INSTITUT PASTEUR, Paris (FR)

(72) Inventors: Natalia Ines Bomchil, Lyons (FR); Jean-Baptiste Claude, Oullins (FR); Lionel Pierre Christian Cupillard, Bourgoin Jallieu (FR); Célia Fontana, Lyons (FR); Anass Jawhari, Venissieux (FR); Elodie Mandon, Saint Genis Laval (FR); Angeli Kodjo, Fleurieux sur l'arbresles (FR); Mathieu Picardeau, Paris (FR); Azad Eshghi, Toronto (CA)

( * ) Notice: Subject to any disclaimer, the term of this patent is extended or adjusted under 35 U.S.C. 154(b) by 0 days.

(21) Appl. No.: 15/050,155

(22) Filed: Feb. 22, 2016

(65) Prior Publication Data

US 2017/0021004 A1  Jan. 26, 2017

Related U.S. Application Data

(60) Provisional application No. 62/118,790, filed on Feb. 20, 2015.

(51) Int. Cl.
| | | |
|---|---|---|
| *A61K 39/02* | (2006.01) | |
| *C12N 15/74* | (2006.01) | |
| *A61K 9/00* | (2006.01) | |
| *A61K 39/00* | (2006.01) | |

(52) U.S. Cl.
CPC ........ *A61K 39/0208* (2013.01); *A61K 9/0019* (2013.01); *C12N 15/74* (2013.01); *A61K 2039/54* (2013.01); *A61K 2039/545* (2013.01)

(58) Field of Classification Search
None
See application file for complete search history.

(56) References Cited

U.S. PATENT DOCUMENTS

2005/0271680 A1   12/2005   Chang et al.

FOREIGN PATENT DOCUMENTS

CN    101 874 898 A    11/2010
WO   WO 2009/042538 A2   4/2009

OTHER PUBLICATIONS

Ellis (Vaccines, W.B. Saunders Company, Chapter 29, 1988, pp. 568-574).*
Boslego et al (Vaccines and Immunotherapy, 1991, Chapter 17).*
Skolnick et al. (Trends in Biotechnology 18: 34-39, 2000).*
Nascimento et al. (Journal of Bacteriology vol. 186 No. 7, pp. 2164-2172).*
Chang Y F et al. "Immunogenicity of the recombinant leptospiral putative outer membrane proteins as vaccine candidates", Vaccine, Elsevier Ltd, GB, vol. 25, No. 48, Nov. 23, 2007, pp. 8190-8197, XP026865315.
Dong Haiyan et al. "Characterization of the omp L1 gene of pathogenic *Leptospira* species in China and cross-immunogenicity of the Omp L1 protein", BMC Microbiology, Biomed Central Ltd, GB. 8, vol. No. 1, 223, Dec. 17, 2008 (Dec. 17, 2008), p. 12PP, XP021048159.
Magudeswaran S K et al. "Evidence of cross reaction potential of recombinant leptospira Lip L41 protein", Indian Journal of Biotechnology, vol. 13, No. 1, Jan. 2014 (Jan. 2014), pp. 57-61, XP055286980.
R. U. M. Palaniappan et al. "Immunoprotection of Recombinant Leptospiral Immunoglobulin-Like Protein A against Leptospira interrogans Serovar Pomona Infection", Infection and Immunity, vol. 74, No. 3 , Feb. 22, 2006, pp. 1745-1750, XP055104410.
Maneewatch Santi et al. "Omp L1 DNA vaccine cross-protects against heterologous *Leptospira* spp. challenge", Asian Pacific Journal of Allergy and Immunology, Bangkok, TH, vol. 25, No. 1, Mar. 1, 2007, pp. 75-82, XP009110926.
C. Branger et al. "Identification of the Hemolysis-Associated Protein 1 as a Cross-Protective Immunogen of Leptospira interrogans by Adenovirus-Mediated Vaccination", Infection and Immunity, vol. 69, No. 11, Nov. 1, 2001, pp. 6831-6838, XP055104644.
Database UniProt [Online] Jul. 5, 2004, SubName: Full=Acriflavin resistance (EC0:0000313:EMBL:AAS71623.1); 11 , XP002759776.
Nascimento et al. "Comparative Genomics of two Leptospira interrogans serovars reveals novel insights into physiology and pathogenesis", Journal of Bacteriology, American Society for Microbiology, US, vol. 186, No. 7, Apr. 1, 2004, pp. 2164-2172, XP008127207.
Ling-Bing Zeng et al. "Comparative subproteome analysis of three representative Leptospira interrogans vaccine strains reveals cross-reactive antigens and novel virulence determinants", Journal of Proteomics, vol. 112, Jan. 1, 2015, pp. 27-37. XP055281796.
Yang Hong-Liang et al. "In silico and microarray-based genomic approaches to identifying potential vaccine candidates against Leptospira interrogans", BMC Genomics, Biomed Central Ltd. London, UK, vol. 7, No. 1, 293, Nov. 16, 2006, pp. 1-12, XP021022258.
Carolina Lessa-Aquino et al. "Identification of Seroreactive Proteins of Leptospira interrogans Serovar Copenhageni Using a High-Density Protein Microarray Approach", PLOS Neglected Tropical Diseases, vol. 7, No. 10, E2499, Oct. 17, 2013, pp. 1-13. XP055104272.

* cited by examiner

*Primary Examiner* — Robert A Zeman
(74) *Attorney, Agent, or Firm* — Judy Jarecki-Black; Richard A. Seeger

(57) ABSTRACT

The present invention provides compositions and methods for eliciting heterologous protective immunity in animals against *Leptospira* spp. The *Leptospira* spp. immunoprotective peptides disclosed herein elicit protective immunity against subsequent challenge or exposure to at least two *Leptospira* spp. serovars.

11 Claims, 9 Drawing Sheets
Specification includes a Sequence Listing.

SEQUENCE LISTING

```
<160> NUMBER OF SEQ ID NOS: 180

<210> SEQ ID NO 1
<211> LENGTH: 3249
<212> TYPE: DNA
<213> ORGANISM: Artificial Sequence
<220> FEATURE:
<223> OTHER INFORMATION: LIC13074

<400> SEQUENCE: 1
atgaacttag cttcgctttc gattcaaaga ccgattttcg tcacttgtac ggtcttactc     60
atcctggtcg cgggatacct ttctttgagc aaattggggg tagatttatt tcccaatgta    120
acgattccgg tcgtgaccgt aaccgtgcct tatccaggtg cggcgcctaa tgaaatcgaa    180
acactaattg caaaaccggt tgaagacgaa ctatctacga tttcgggagt gaaaagggtc    240
agagcggtct gtaacgaagg agtggggacc gttattgtag agtttactct ggaaactgat    300
gtaaagtatg cagaacaaca ggttcgagat aaagtatcta gtgttaaacc gaaattacca    360
aatgatgcaa aagaaccagt cattcgaaga atcgatccag cggaccaacc gatcgtaatc    420
attgcactaa gagctgaatt accagatgcg gaactttatg atattgctaa tgaagaagtg    480
aagcagattc ttctttctac caaagacgta ggaaacgtaa ccatctacgg aggacgtaaa    540
agagaaattc acgtagaact ggatcgaaac aaactcaaag aacatatgat tccagcttca    600
gttgtgtcta atcgacttgc ttcgggagga atgaacatcc ccgccggaaa agtaagtaaa    660
accgataagg aacttgtata tagaacgatc aatgaattcc aatctccaga ggaaatcaga    720
gacactccta tctctctttt tggaaatgaa gttcctatta aaattggaca attgggcgaa    780
gtcaaagata cagttgaaga cgaaacctct cgcgcttatc taaacggtcg aaaagccgtt    840
tttctcatgg tatataaaca gtccgggtcc aatacggttg cggttgcaca atctgtaaaa    900
aagaaagtct tagaaatcaa tcaagatctt tcgaaacgta acggttcacc tgagttgacg    960
tctacgaatg attcttctgt aacgatcgac aacaatatct atgatgtaaa agaaacgatt   1020
atcattggaa tcatacttac gatcatcgta gtgttattat tcttaggaag tgttcgttct   1080
```

```
actttgatta ctggacttgc acttccaaac tctttgttag gcgcgtttat tttaatggcg    1140
attgctggtt ttaccgtaaa cgtgatgact cttttggctc tcagccttgc ggttggactt    1200
cttatcgacg atgcgattgt agttcgagaa aatatttttca gacacagaga atgggaaaa    1260 actgcgagag aggcttctat cgaaggcacc aaagaagtaa cacttgcggt aattgctact    1320
acgatgacgg tgattgcggt ttttatgccg attgcattta tcagcggaat tgtgggacag    1380
ttcttaagag aatttggatt gactgtatgt tttgctcttc tcatttctct ttatgacgcg    1440
cttacgattg ctcctatgtt gtctgcatat tttggtggaa aggtaggaaa tcacgcacat    1500
aattcttccg aatcgattcc tgaaatcaca accaaagcag ttaaaggaaa aacaaaaggc    1560
gctactacta cgctggaaga gattgcttat tctaaaatcc gttctcagaa taaaacttcc    1620
agaggaattt tatccaccgt attttctcct attgtgttca ttttaggaaa gttagaagta    1680
ggactagatt ctatattaag tatttttaat gttttttcaat cttggttaga agaaaaatac    1740
gcttccgttt taaaattcac tttaaaaaga cctttttttta tactttctgg agcgatttta    1800
attttcgtag ttagtttggt tttgactaag tttattccaa aaacgtttct tcctgctcag    1860
gatgagggta aatttacagt gactttggat atgccacccg gaacgtcctt ggaaaaaatg    1920
tctcagattg ctcttcaagt agaccaaaag attcgttctt ataaggaaat caaaattgtt    1980
tccatgttta acacgaaccg tagtacgaat atgttcgtag aaatggttcc ttccagagat    2040
aggaagatga acacaactca gtttaaagcg tttcttcgta tgaactggc ggattttct    2100 tatgccaatc cgatcgtaaa ggacgtagac aatgtgggag gaggacaaag acctttact    2160 ctaacagtca gcggtcaaaa gagagaagtt gtagaagatt atgctaagaa gttgttcgaa    2220
cgtcttcaaa aatctccggc gcttttagac gtagatacga gttatcgaac gggagctcct    2280
gagtttagag tggttccgga tcgagaaaag gaagtacttt taggagttcc tggaacgatt    2340
ataggaactg aattgagaac tcttgtagaa ggaactacgc ctgcggttta tagagaaaat    2400
ggagttgagt atgatattcg agttcgactg aaggattctc aaagagattt aaaggaaaat    2460
ttttatagtt cttttgtacc taactttaac aacagattga ttccaattca aaacgtagca    2520
aaggcggaag aatccactgg tcttgcaacg atcaatcgtc tcaaccgaaa taaggccgtg    2580
gaaatttatg cagatgtaaa tccaaaaggt cctggaatgg gaggagctat ggaagaagtt    2640
acaaagatca gtcagattga aattcctctt ccttccggtg taaagatcgg ctattctgga    2700
caggcagaaa gttttaaaga gatgggagtt tctatggcga tcgccatggg acttgggatt    2760
ttatttatct acatggttct tgcttctctt tacgaaagtt ttatcactcc gattgcgatc    2820
atgctcgtat tacctcttgc gctttgtgga gcttttatcg ctcttttttat tacccaaaaa    2880 tccttggata tttttttctat gattgggctg attatgttga tcggtgtcgc taccaagaac    2940
tcaattcttc ttgtggactt tacgaatcaa ttgttgtcac aaggtaaaga aatgaaagaa    3000
gcgattatcg aagcgggaag agaaagattg agaccgattt tgatgacttc ttttgctctt    3060
atcgcgggaa tgttaccgat tgcaatcggg ttgaacgaag cttctcgtca agaacgagt    3120 atgggagttg cgatcattgg tggattgatt tcttctacga tacttacttt agtggtggtt    3180
cctgcagcat tttcttatat agaaaaactg aatcaaatgg taagaagaaa ttctccgaat    3240
cctgatgcg                                                            3249
```

<210> SEQ ID NO 2
<211> LENGTH: 1083
<212> TYPE: PRT
<213> ORGANISM: Artificial Sequence

<220> FEATURE:
<223> OTHER INFORMATION: LIC13074

<400> SEQUENCE: 2

```
Met Asn Leu Ala Ser Leu Ser Ile Gln Arg Pro Ile Phe Val Thr Cys
1               5                   10                  15

Thr Val Leu Leu Ile Leu Val Ala Gly Tyr Leu Ser Leu Ser Lys Leu
            20                  25                  30

Gly Val Asp Leu Phe Pro Asn Val Thr Ile Pro Val Thr Val Thr
        35                  40                  45

Val Pro Tyr Pro Gly Ala Ala Pro Asn Glu Ile Glu Thr Leu Ile Ala
    50                  55                  60

Lys Pro Val Glu Asp Glu Leu Ser Thr Ile Ser Gly Val Lys Arg Val
65                  70                  75                  80

Arg Ala Val Cys Asn Glu Gly Val Gly Thr Val Ile Val Glu Phe Thr
                85                  90                  95

Leu Glu Thr Asp Val Lys Tyr Ala Glu Gln Gln Val Arg Asp Lys Val
            100                 105                 110

Ser Ser Val Lys Pro Lys Leu Pro Asn Asp Ala Lys Glu Pro Val Ile
        115                 120                 125

Arg Arg Ile Asp Pro Ala Asp Gln Pro Ile Val Ile Ala Leu Arg
130                 135                 140

Ala Glu Leu Pro Asp Ala Glu Leu Tyr Asp Ile Ala Asn Glu Val
145                 150                 155                 160

Lys Gln Ile Leu Leu Ser Thr Lys Asp Val Gly Asn Val Thr Ile Tyr
                165                 170                 175

Gly Gly Arg Lys Arg Glu Ile His Val Glu Leu Asp Arg Asn Lys Leu
            180                 185                 190

Lys Glu His Met Ile Pro Ala Ser Val Val Ser Asn Arg Leu Ala Ser
        195                 200                 205

Gly Gly Met Asn Ile Pro Ala Gly Lys Val Ser Lys Thr Asp Lys Glu
210                 215                 220

Leu Val Tyr Arg Thr Ile Asn Glu Phe Gln Ser Pro Glu Glu Ile Arg
225                 230                 235                 240

Asp Thr Pro Ile Ser Leu Phe Gly Asn Glu Val Pro Ile Lys Ile Gly
                245                 250                 255

Gln Leu Gly Glu Val Lys Asp Thr Val Glu Asp Glu Thr Ser Arg Ala
            260                 265                 270

Tyr Leu Asn Gly Arg Lys Ala Val Phe Leu Met Val Tyr Lys Gln Ser
        275                 280                 285

Gly Ser Asn Thr Val Ala Val Ala Gln Ser Val Lys Lys Lys Val Leu
    290                 295                 300

Glu Ile Asn Gln Asp Leu Ser Lys Arg Asn Gly Ser Pro Glu Leu Thr
305                 310                 315                 320

Ser Thr Asn Asp Ser Ser Val Thr Ile Asp Asn Asn Ile Tyr Asp Val
                325                 330                 335

Lys Glu Thr Ile Ile Ile Gly Ile Ile Leu Thr Ile Val Val Leu
            340                 345                 350

Leu Phe Leu Gly Ser Val Arg Ser Thr Leu Ile Thr Gly Leu Ala Leu
        355                 360                 365

Pro Asn Ser Leu Leu Gly Ala Phe Ile Leu Met Ala Ile Ala Gly Phe
    370                 375                 380

Thr Val Asn Val Met Thr Leu Leu Ala Leu Ser Leu Ala Val Gly Leu
385                 390                 395                 400
```

```
Leu Ile Asp Asp Ala Ile Val Val Arg Glu Asn Ile Phe Arg His Arg
                405                 410                 415
Glu Met Gly Lys Thr Ala Arg Glu Ala Ser Ile Glu Gly Thr Lys Glu
            420                 425                 430
Val Thr Leu Ala Val Ile Ala Thr Thr Met Thr Val Ile Ala Val Phe
            435                 440                 445
Met Pro Ile Ala Phe Ile Ser Gly Ile Val Gly Gln Phe Leu Arg Glu
            450                 455                 460
Phe Gly Leu Thr Val Cys Phe Ala Leu Leu Ile Ser Leu Tyr Asp Ala
465                 470                 475                 480
Leu Thr Ile Ala Pro Met Leu Ser Ala Tyr Phe Gly Lys Val Gly
                485                 490                 495
Asn His Ala His Asn Ser Ser Glu Ser Ile Pro Glu Ile Thr Thr Lys
            500                 505                 510
Ala Val Lys Gly Lys Thr Lys Gly Ala Thr Thr Leu Glu Glu Ile
            515                 520                 525
Ala Tyr Ser Lys Ile Arg Ser Gln Asn Lys Thr Ser Arg Gly Ile Leu
            530                 535                 540
Ser Thr Val Phe Ser Pro Ile Val Phe Ile Leu Gly Lys Leu Glu Val
545                 550                 555                 560
Gly Leu Asp Ser Ile Leu Ser Ile Phe Asn Val Phe Gln Ser Trp Leu
                565                 570                 575
Glu Glu Lys Tyr Ala Ser Val Leu Lys Phe Thr Leu Lys Arg Pro Phe
            580                 585                 590
Phe Ile Leu Ser Gly Ala Ile Leu Ile Phe Val Val Ser Leu Val Leu
                595                 600                 605
Thr Lys Phe Ile Pro Lys Thr Phe Leu Pro Ala Gln Asp Glu Gly Lys
            610                 615                 620
Phe Thr Val Thr Leu Asp Met Pro Pro Gly Thr Ser Leu Glu Lys Met
625                 630                 635                 640
Ser Gln Ile Ala Leu Gln Val Asp Gln Lys Ile Arg Ser Tyr Lys Glu
                645                 650                 655
Ile Lys Ile Val Ser Met Phe Asn Thr Asn Arg Ser Thr Asn Met Phe
                660                 665                 670
Val Glu Met Val Pro Ser Arg Asp Arg Lys Met Asn Thr Thr Gln Phe
            675                 680                 685
Lys Ala Phe Leu Arg Asn Glu Leu Ala Glu Phe Ser Tyr Ala Asn Pro
690                 695                 700
Ile Val Lys Asp Val Asp Asn Val Gly Gly Gln Arg Pro Phe Thr
705                 710                 715                 720
Leu Thr Val Ser Gly Gln Lys Arg Glu Val Val Glu Asp Tyr Ala Lys
                725                 730                 735
Lys Leu Phe Glu Arg Leu Gln Lys Ser Pro Ala Leu Leu Asp Val Asp
            740                 745                 750
Thr Ser Tyr Arg Thr Gly Ala Pro Glu Phe Arg Val Pro Asp Arg
            755                 760                 765
Glu Lys Glu Val Leu Leu Gly Val Pro Gly Thr Ile Ile Gly Thr Glu
            770                 775                 780
Leu Arg Thr Leu Val Glu Gly Thr Thr Pro Ala Val Tyr Arg Glu Asn
785                 790                 795                 800
Gly Val Glu Tyr Asp Ile Arg Val Arg Leu Lys Asp Ser Gln Arg Asp
                805                 810                 815
```

```
Leu Lys Glu Asn Phe Tyr Ser Ser Phe Val Pro Asn Phe Asn Asn Arg
            820                 825                 830

Leu Ile Pro Ile Gln Asn Val Ala Lys Ala Glu Glu Ser Thr Gly Leu
        835                 840                 845

Ala Thr Ile Asn Arg Leu Asn Arg Asn Lys Ala Val Glu Ile Tyr Ala
    850                 855                 860

Asp Val Asn Pro Lys Gly Pro Gly Met Gly Gly Ala Met Glu Glu Val
865                 870                 875                 880

Thr Lys Ile Ser Gln Ile Glu Ile Pro Leu Pro Ser Gly Val Lys Ile
            885                 890                 895

Gly Tyr Ser Gly Gln Ala Glu Ser Phe Lys Glu Met Gly Val Ser Met
        900                 905                 910

Ala Ile Ala Met Gly Leu Gly Ile Leu Phe Ile Tyr Met Val Leu Ala
    915                 920                 925

Ser Leu Tyr Glu Ser Phe Ile Thr Pro Ile Ala Ile Met Leu Val Leu
930                 935                 940

Pro Leu Ala Leu Cys Gly Ala Phe Ile Ala Leu Phe Ile Thr Gln Lys
945                 950                 955                 960

Ser Leu Asp Ile Phe Ser Met Ile Gly Leu Ile Met Leu Ile Gly Val
            965                 970                 975

Ala Thr Lys Asn Ser Ile Leu Leu Val Asp Phe Thr Asn Gln Leu Leu
        980                 985                 990

Ser Gln Gly Lys Glu Met Lys Glu Ala Ile Ile Glu Ala Gly Arg Glu
            995                1000                1005

Arg Leu Arg Pro Ile Leu Met Thr Ser Phe Ala Leu Ile Ala Gly
        1010                1015                1020

Met Leu Pro Ile Ala Ile Gly Leu Asn Glu Ala Ser Arg Gln Arg
        1025                1030                1035

Thr Ser Met Gly Val Ala Ile Ile Gly Gly Leu Ile Ser Ser Thr
        1040                1045                1050

Ile Leu Thr Leu Val Val Val Pro Ala Ala Phe Ser Tyr Ile Glu
        1055                1060                1065

Lys Leu Asn Gln Met Val Arg Arg Asn Ser Pro Asn Pro Asp Ala
        1070                1075                1080

<210> SEQ ID NO 3
<211> LENGTH: 1098
<212> TYPE: DNA
<213> ORGANISM: Artificial Sequence
<220> FEATURE:
<223> OTHER INFORMATION: LIC13050

<400> SEQUENCE: 3
atgaagggtt ctactctcgt acgactcgca atcgctttat tcatgtttgt taacgtagtg    60 cttttttgccc aggaagatct ggatgaaagc tctactcctc aggcaaatac tcaaggacaa   120
tccgggagtt ccactcctgc aaaaacttcc caaaattctg gaactactca gggagaagaa   180
gttaaaaaag cggatcttta tgtgaactca aaagttctt ttgaaatttc cgcccaagac    240
gactccagca cggtcgatta tatcgaatat aaaatcggcg aaatggacta cgcaaaatat    300
acttctccaa tcacaattct aaaagaaggc gttaaccgac ttacttatag agccgtggat    360
aaagccggaa acaaagaacc tgctaaagcg ctcgtcgtcg ttgtggataa taccgctccg    420
actgtaaaaa ttgttccgag tgaaattctt tataatttgg acggctataa cttcggttcc    480
aaaaacgtaa cctatacaat ctctgcgatc gacgctcttt ccggtgtcaa agaaattaaa    540
```

```
tattccatca acggtggaga catgagatcc tatgataacc agcctattaa attagaaaag    600
gctggagtga atttgattaa atactccgct gtggataatt ctggaaactc ttcttccgag    660
gcaattcttg tagtaacctt ggatgacgta aaaccggaag ttgaaatcca agggaacact    720
cctctggtaa tcatcgatgg gaaaacatat tccagaaaag gaaactcatt tgcaatcaaa    780
gcggtcgacg gacaatccgg aattaaaaga attctaatta aattggataa aaattcagat    840
ttcgttcctt acgcagagcc tatcacgatc gatgctcaag gtgaacatac aatcgaagcc    900
aaagcgattg acaacgtagg aaacgaaagt gagaccaaaa aggtcagttt tgcagtagat    960
gtaaatccac ctacaacaca aattcgtaaa gtagaagtag aacaaacaa tggaagccaa    1020 tctacttccg aatcaaaacc tgctcccgct ccggcggctc ctgcagcgaa acctactact    1080
actcaaccta caaaaaaa                                                 1098
```

<210> SEQ ID NO 4
<211> LENGTH: 366
<212> TYPE: PRT
<213> ORGANISM: Artificial Sequence
<220> FEATURE:
<223> OTHER INFORMATION: LIC13050

<400> SEQUENCE: 4

```
Met Lys Gly Ser Thr Leu Val Arg Leu Ala Ile Ala Leu Phe Met Phe
1               5                   10                  15

Val Asn Val Val Leu Phe Ala Gln Glu Asp Leu Asp Glu Ser Ser Thr
            20                  25                  30

Pro Gln Ala Asn Thr Gln Gly Gln Ser Gly Ser Ser Thr Pro Ala Lys
        35                  40                  45

Thr Ser Gln Asn Ser Gly Thr Thr Gln Gly Glu Glu Val Lys Lys Ala
    50                  55                  60

Asp Leu Tyr Val Asn Ser Lys Ser Ser Phe Glu Ile Ser Ala Gln Asp
65                  70                  75                  80

Asp Ser Ser Thr Val Asp Tyr Ile Glu Tyr Lys Ile Gly Glu Met Asp
                85                  90                  95

Tyr Ala Lys Tyr Thr Ser Pro Ile Thr Ile Leu Lys Glu Gly Val Asn
            100                 105                 110

Arg Leu Thr Tyr Arg Ala Val Asp Lys Ala Gly Asn Lys Glu Pro Ala
        115                 120                 125

Lys Ala Leu Val Val Val Asp Asn Thr Ala Pro Thr Val Lys Ile
    130                 135                 140

Val Pro Ser Glu Ile Leu Tyr Asn Leu Asp Gly Tyr Asn Phe Gly Ser
145                 150                 155                 160

Lys Asn Val Thr Tyr Thr Ile Ser Ala Ile Asp Ala Leu Ser Gly Val
                165                 170                 175

Lys Glu Ile Lys Tyr Ser Ile Asn Gly Gly Asp Met Arg Ser Tyr Asp
            180                 185                 190

Asn Gln Pro Ile Lys Leu Glu Lys Ala Gly Val Asn Leu Ile Lys Tyr
        195                 200                 205

Ser Ala Val Asp Asn Ser Gly Asn Ser Ser Glu Ala Ile Leu Val
    210                 215                 220

Val Thr Leu Asp Asp Val Lys Pro Glu Val Glu Ile Gln Gly Asn Thr
225                 230                 235                 240

Pro Leu Val Ile Ile Asp Gly Lys Thr Tyr Ser Arg Lys Gly Asn Ser
                245                 250                 255

Phe Ala Ile Lys Ala Val Asp Gly Gln Ser Gly Ile Lys Arg Ile Leu
```

```
                260                 265                 270
Ile Lys Leu Asp Lys Asn Ser Asp Phe Val Pro Tyr Ala Glu Pro Ile
            275                 280                 285

Thr Ile Asp Ala Gln Gly Glu His Thr Ile Glu Ala Lys Ala Ile Asp
        290                 295                 300

Asn Val Gly Asn Glu Ser Glu Thr Lys Lys Val Ser Phe Ala Val Asp
305                 310                 315                 320

Val Asn Pro Pro Thr Thr Gln Ile Arg Lys Val Glu Val Gly Thr Asn
                325                 330                 335

Asn Gly Ser Gln Ser Thr Ser Glu Ser Lys Pro Ala Pro Ala Pro Ala
            340                 345                 350

Ala Pro Ala Ala Lys Pro Thr Thr Thr Gln Pro Thr Lys Lys
        355                 360                 365

<210> SEQ ID NO 5
<211> LENGTH: 1995
<212> TYPE: DNA
<213> ORGANISM: Artificial Sequence
<220> FEATURE:
<223> OTHER INFORMATION: LIC13314

<400> SEQUENCE: 5
atggagagga tgaaaaccat attgttaaga attttccctt gggtttcact cgcttcttta     60
tttctctatt ttccggttag agatagcata caattaccca ccaatcgttg ctttggttg    120
ggttttgtat tggttatttt aatattagaa ccagcttata gatggtttca gaaaaaaaac    180
attcaagaag aatggaattc ttatatagct gcgggactgg gacttgtggc ctttggaatt    240
tatcaccta gagtgttttt agaagagtat gcgctgaagt ctaattcgat cggatccgga    300
aacgaaagac tcagagaaat tcttttagta cttttgatat tttctctgat agggtttta    360
attctaacct tgttaaagga gttagggaaa gattccgcag gtgctcagag tgttttaaaa    420
acttcaaaac aagcgttgat cagatatttt attctgaatt tggcgatcgt ttttgtagtt    480
cttgtaattg taaattacat ttccgtaatg cgaaatcata acttcgatct gagttctaaa    540
ggacagtatt cttttagtcc ggctgcgatt aaaattctaa agaacgtcaa caaagaagtt    600
gatgtagtcg cttttaccc aagacctttg gaaaattctc cttcgagcga aaagcaaat    660
tcttttttctt taagaagaat ccggcccgat ttagaaattt atttggatca actgaagtct    720
ttgagtcctc agtttaaggt tcgttttatc aatgcagacg tagagctgga cgagcttgct    780
gagtttgatc aggtttctaa tggagtcatt ttactaagaa ccaaaaaacc tttagcagag    840
gtgaccggaa acaatacgc ggaacaaaga ctttccatcc gagagaaaaa tgatctagaa    900
gatttagaac gtaagatcgt gcaggcggta gtaaacataa cgaccgaaga aaaaaatatt    960
tattttactc aatcgaacgg agaaagattt tcgcctatct ttcaaaatct tccaaatgaa   1020
aaagttggaa tttatccaa ttctttgagt tttttaaact ttaaagtaaa gggacttggg   1080
attgcagaag gttggccgac tcggattccg gaggacgcgg acgttttgat gattgccgga   1140
cctacggttg cttttcgaa agaagcccag agttctctta tcgattttgt agaaaagaaa   1200
aagggaaaaaa ttttatcac gatcgatcca aaggaactg aaaattttgg atggctttta   1260
gaaaaatctg gatatgagtt tgtaaaaggt ccaatttctc aagtacaagg acaagcgggc   1320
atggtgcttg caaagtcttt taaaaacat ccgattgaag aagctttaac tagaaaagac   1380
acgggaacca tgtttccctt tgctggttat tttgttccac agacaaatca agggccgggc   1440
ggaaaaaatc tagaggcata tcctttgatg gaatctggag gggacgctat attagataaa   1500
```

```
aataataatg gaaaattgga tgcaggagag gaaagaagaa acgtaatttt aggaatggtt    1560
ttaaaaacag ttttaaaggt tcaaaaagaa tcggccgcag cgaatccaaa aacggacgaa    1620
tctaaacagg gtttgcaaaa agatctgaat tctacagggt tgaattcaga tcaaaaagat    1680
atttctcaaa atacgaatgt agattcaaaa gaagaaggtc gagtagtaat tttttcggga    1740
acttcttgga ttacagatca gttcatttct tacggagtga attacgaact tgcaacttcc    1800
tcaattactt ggatgtatca agacctttcc ttgtcttcca ttcaaccgaa aaagaggaa     1860 gtaaatacgg tttctttgac tgacgttcaa aaacgagtcg tttggatttt aggaatgttt    1920 attttttccag gattgatcgc gtttgtttct gcggcgatgc ttattcaaaa gcgtagaaaa    1980
gaaggacaag aatct                                                     1995
```

<210> SEQ ID NO 6
<211> LENGTH: 665
<212> TYPE: PRT
<213> ORGANISM: Artificial Sequence
<220> FEATURE:
<223> OTHER INFORMATION: LIC13314

<400> SEQUENCE: 6

```
Met Glu Arg Met Lys Thr Ile Leu Leu Arg Ile Phe Pro Trp Val Ser
1               5                   10                  15

Leu Ala Ser Leu Phe Leu Tyr Phe Pro Val Arg Asp Ser Ile Gln Leu
            20                  25                  30

Pro Thr Asn Arg Trp Leu Trp Leu Gly Phe Val Leu Val Ile Leu Ile
        35                  40                  45

Leu Glu Pro Ala Tyr Arg Trp Phe Gln Lys Lys Asn Ile Gln Glu Glu
    50                  55                  60

Trp Asn Ser Tyr Ile Ala Ala Gly Leu Gly Leu Val Ala Phe Gly Ile
65                  70                  75                  80

Tyr His Leu Arg Val Phe Leu Glu Glu Tyr Ala Leu Lys Ser Asn Ser
                85                  90                  95

Ile Gly Ser Gly Asn Glu Arg Leu Arg Glu Ile Leu Leu Val Leu Leu
            100                 105                 110

Ile Phe Ser Leu Ile Gly Phe Leu Ile Leu Thr Leu Leu Lys Glu Leu
        115                 120                 125

Gly Lys Asp Ser Ala Gly Ala Gln Ser Val Leu Lys Thr Ser Lys Gln
    130                 135                 140

Ala Leu Ile Arg Tyr Phe Ile Leu Asn Leu Ala Ile Val Phe Val Val
145                 150                 155                 160

Leu Val Ile Val Asn Tyr Ile Ser Val Met Arg Asn His Asn Phe Asp
                165                 170                 175

Leu Ser Ser Lys Gly Gln Tyr Ser Phe Ser Pro Ala Ala Ile Lys Ile
            180                 185                 190

Leu Lys Asn Val Asn Lys Glu Val Asp Val Val Ala Phe Tyr Pro Arg
        195                 200                 205

Pro Leu Glu Asn Ser Pro Ser Ser Glu Lys Ala Asn Ser Phe Ser Leu
    210                 215                 220

Arg Arg Ile Arg Pro Asp Leu Glu Ile Tyr Leu Asp Gln Leu Lys Ser
225                 230                 235                 240

Leu Ser Pro Gln Phe Lys Val Arg Phe Ile Asn Ala Asp Val Glu Leu
                245                 250                 255

Asp Glu Leu Ala Glu Phe Asp Gln Val Ser Asn Gly Val Ile Leu Leu
            260                 265                 270
```

```
Arg Thr Lys Lys Pro Leu Ala Glu Val Thr Gly Lys Gln Tyr Ala Glu
            275                 280                 285

Gln Arg Leu Ser Ile Arg Glu Lys Asn Asp Leu Glu Asp Leu Glu Arg
        290                 295                 300

Lys Ile Val Gln Ala Val Val Asn Ile Thr Thr Glu Glu Lys Asn Ile
305                 310                 315                 320

Tyr Phe Thr Gln Ser Asn Gly Glu Arg Phe Ser Pro Ile Phe Gln Asn
                325                 330                 335

Leu Pro Asn Glu Lys Val Gly Ile Leu Ser Asn Ser Leu Ser Phe Leu
            340                 345                 350

Asn Phe Lys Val Lys Gly Leu Gly Ile Ala Glu Gly Trp Pro Thr Arg
        355                 360                 365

Ile Pro Glu Asp Ala Asp Val Leu Met Ile Ala Gly Pro Thr Val Ala
370                 375                 380

Phe Ser Lys Glu Ala Gln Ser Ser Leu Ile Asp Phe Val Glu Lys Lys
385                 390                 395                 400

Lys Gly Lys Ile Phe Ile Thr Ile Asp Pro Lys Gly Thr Glu Asn Phe
                405                 410                 415

Gly Trp Leu Leu Glu Lys Ser Gly Tyr Glu Phe Val Lys Gly Pro Ile
            420                 425                 430

Ser Gln Val Gln Gly Gln Ala Gly Met Val Leu Ala Lys Ser Phe Lys
        435                 440                 445

Lys His Pro Ile Glu Glu Ala Leu Thr Arg Lys Asp Thr Gly Thr Met
    450                 455                 460

Phe Pro Phe Ala Gly Tyr Phe Val Pro Gln Thr Asn Gln Gly Pro Gly
465                 470                 475                 480

Gly Lys Asn Leu Glu Ala Tyr Pro Leu Met Glu Ser Gly Gly Asp Ala
                485                 490                 495

Ile Leu Asp Lys Asn Asn Gly Lys Leu Asp Ala Gly Glu Glu Arg
            500                 505                 510

Arg Asn Val Ile Leu Gly Met Val Leu Lys Thr Val Leu Lys Val Gln
        515                 520                 525

Lys Glu Ser Ala Ala Ala Asn Pro Lys Thr Asp Glu Ser Lys Gln Gly
    530                 535                 540

Leu Gln Lys Asp Leu Asn Ser Thr Gly Leu Asn Ser Asp Gln Lys Asp
545                 550                 555                 560

Ile Ser Gln Asn Thr Asn Val Asp Ser Lys Glu Glu Gly Arg Val Val
                565                 570                 575

Ile Phe Ser Gly Thr Ser Trp Ile Thr Asp Gln Phe Ile Ser Tyr Gly
            580                 585                 590

Val Asn Tyr Glu Leu Ala Thr Ser Ser Ile Thr Trp Met Tyr Gln Asp
        595                 600                 605

Leu Ser Leu Ser Ser Ile Gln Pro Lys Lys Glu Glu Val Asn Thr Val
    610                 615                 620

Ser Leu Thr Asp Val Gln Lys Arg Val Val Trp Ile Leu Gly Met Phe
625                 630                 635                 640

Ile Phe Pro Gly Leu Ile Ala Phe Val Ser Ala Ala Met Leu Ile Gln
                645                 650                 655

Lys Arg Arg Lys Glu Gly Gln Glu Ser
            660                 665

<210> SEQ ID NO 7
<211> LENGTH: 1821
```

<212> TYPE: DNA
<213> ORGANISM: Artificial Sequence
<220> FEATURE:
<223> OTHER INFORMATION: LIC10117

<400> SEQUENCE: 7

```
atgtcaaaat tttctatttt caaaaaaatt ctctttggaa ttttaatctt actttcttta     60
gcatttactc tgattttaca tacgatttt tttaaaccta ttacacttgg attattttat    120
gaaaaatt  tctgggaatc aattttagaa gatccagaat atctaacttc tcttggtatt    180
ttgaatcgct ttagaattgg aggttatcaa aaaaaactta cggatatatc gattgaaaaa    240
caagaacaag acttaaaaaa agcaaaaaag gatctagaga ttcttttatc ttacggaaaa    300
gaaaatttat caggacaaga attacttttct tttgaaattc tagaatggtc tcttcgatta    360
aaaatttctg gtgaaagatt tttatttcac gattatcctg caaatcaact atttggagtt    420
caaagtcagc tccctacttt tttagctaca caacatcctg tcacatcttc tcaagatgta    480
gaagattaca ttgcaagatt ggaagctatt cctaaaaaaa tagatcaact catagaagga    540
attttgttta gggataaaaa cggtattcta ccgccagatt ttattttgga tcgattgatt    600
tcggaagtca aagggtttgt agcggttccg gcaaagaaaa atcttcttta tacgacattc    660
gaaagaaaaa ttaaaaaaat cgattcggtt ccgtggatt ttcaaaatcg ttctttagaa    720
cgagtgaaac aatcgattga atcaaaagta tatcctgcat attcaaaatt actaattctt    780
tttttaaaac agaaagaaca cgcggattca agggcagggg tttggaaact tccagatgga    840
gatctttatt atattcatga attaaaaaaa catactacga ccgaattgac tccagaagaa    900
attcataata taggattatc cgaagtttct agaattcaaa cgaaatgaa  ataatttttg    960
aaaaaggtcg gaaagaatat gcctattccg attgctatgt cggaacttag aaaagatcct   1020
aagttcttat ttccagacac cgaagaaggc aaacttcatg ctttagaaga atataagaaa   1080
attctaaaag attctgaaga aaaaactaaa tccttattt  ttagaatgcc gaaaagtaag   1140
gttgaagtag aaagaattcc agtctttaaa gaaaagactg caccgggagc gtattacgac   1200
gaacctgcgt tagacggttc tcgacctggt atttttatg cgaatcttcg agatacaaaa   1260
gaaattccta aatttggcat gaaaactttg acgtatcacg aaacaattcc tgggcatcac   1320
ttacagattg caatcatgca agaattagaa aaacttcctc gttttagaaa cacggctaca   1380
tttacggctt atgtagaagg ttgggcctta tatgcgaaac gtcttgcaaa ggactatgat   1440
ttttttcaag atccatactc ggatttagga aggcttcaag cggaattgtt ccgtgcggtt   1500
cggctcgttg tcgatacagg gttgcactat aaaaggtgga atagaaaca agcgatctct   1560
tatatgatac aaaatactgg aatggctccg aaagacgtga ctgcggaaat agaaagatat   1620
gtagtttatc ctggccaggc ttgttcttat aaactcggga tgttgaaaat tttagaactc   1680
agagaaaaag taaaggctcg taaaaaggaa acttttgata ttcgagagtt tcattcagtg   1740
gttttgaata atggttcttt gccgctgaac atcttagaaa aacttataca agatgaattg   1800
ttaaacgacc aggaaaaaaa a                                               1821
```

<210> SEQ ID NO 8
<211> LENGTH: 607
<212> TYPE: PRT
<213> ORGANISM: Artificial Sequence
<220> FEATURE:
<223> OTHER INFORMATION: LIC10117

<400> SEQUENCE: 8

```
Met Ser Lys Phe Ser Ile Phe Lys Lys Ile Leu Phe Gly Ile Leu Ile
1               5                   10                  15

Leu Leu Ser Leu Ala Phe Thr Leu Ile Leu His Thr Ile Phe Phe Lys
            20                  25                  30

Pro Ile Thr Leu Gly Leu Phe Tyr Glu Lys Ile Phe Trp Glu Ser Ile
                35                  40                  45

Leu Glu Asp Pro Glu Tyr Leu Thr Ser Leu Gly Ile Leu Asn Arg Phe
        50                  55                  60

Arg Ile Gly Gly Tyr Gln Lys Lys Leu Thr Asp Ile Ser Ile Glu Lys
65                  70                  75                  80

Gln Glu Gln Asp Leu Lys Lys Ala Lys Lys Asp Leu Glu Ile Leu Leu
                85                  90                  95

Ser Tyr Gly Lys Glu Asn Leu Ser Gly Gln Glu Leu Leu Ser Phe Glu
                100                 105                 110

Ile Leu Glu Trp Ser Leu Arg Leu Lys Ile Ser Gly Glu Arg Phe Leu
                115                 120                 125

Phe His Asp Tyr Pro Ala Asn Gln Leu Phe Gly Val Gln Ser Gln Leu
            130                 135                 140

Pro Thr Phe Leu Ala Thr Gln His Pro Val Thr Ser Ser Gln Asp Val
145                 150                 155                 160

Glu Asp Tyr Ile Ala Arg Leu Glu Ala Ile Pro Lys Lys Ile Asp Gln
                165                 170                 175

Leu Ile Glu Gly Ile Leu Phe Arg Asp Lys Asn Gly Ile Leu Pro Pro
            180                 185                 190

Asp Phe Ile Leu Asp Arg Leu Ile Ser Glu Val Lys Gly Phe Val Ala
        195                 200                 205

Val Pro Ala Lys Lys Asn Leu Leu Tyr Thr Thr Phe Glu Lys Lys Ile
210                 215                 220

Lys Lys Ile Asp Ser Val Ser Val Asp Phe Gln Asn Arg Ser Leu Glu
225                 230                 235                 240

Arg Val Lys Gln Ser Ile Glu Ser Lys Val Tyr Pro Ala Tyr Ser Lys
                245                 250                 255

Leu Leu Ile Leu Phe Leu Lys Gln Lys Glu His Ala Asp Ser Arg Ala
            260                 265                 270

Gly Val Trp Lys Leu Pro Asp Gly Asp Leu Tyr Tyr Ile His Glu Leu
            275                 280                 285

Lys Lys His Thr Thr Thr Glu Leu Thr Pro Glu Glu Ile His Asn Ile
            290                 295                 300

Gly Leu Ser Glu Val Ser Arg Ile Gln Asn Glu Met Lys Ile Ile Leu
305                 310                 315                 320

Lys Lys Val Gly Lys Asn Met Pro Ile Pro Ile Ala Met Ser Glu Leu
                325                 330                 335

Arg Lys Asp Pro Lys Phe Leu Phe Pro Asp Thr Glu Glu Gly Lys Leu
            340                 345                 350

His Ala Leu Glu Glu Tyr Lys Lys Ile Leu Lys Asp Ser Glu Glu Lys
            355                 360                 365

Thr Lys Ser Leu Phe Phe Arg Met Pro Lys Ser Lys Val Glu Val Glu
            370                 375                 380

Arg Ile Pro Val Phe Lys Glu Lys Thr Ala Pro Gly Ala Tyr Tyr Asp
385                 390                 395                 400

Glu Pro Ala Leu Asp Gly Ser Arg Pro Gly Ile Phe Tyr Ala Asn Leu
                405                 410                 415

Arg Asp Thr Lys Glu Ile Pro Lys Phe Gly Met Lys Thr Leu Thr Tyr
```

```
                    420            425            430
His Glu Thr Ile Pro Gly His His Leu Gln Ile Ala Ile Met Gln Glu
            435                440                445

Leu Glu Lys Leu Pro Arg Phe Arg Asn Thr Ala Thr Phe Thr Ala Tyr
        450                455                460

Val Glu Gly Trp Ala Leu Tyr Ala Glu Arg Leu Ala Lys Asp Tyr Asp
465                470                475                480

Phe Phe Gln Asp Pro Tyr Ser Asp Leu Gly Arg Leu Gln Ala Glu Leu
                485                490                495

Phe Arg Ala Val Arg Leu Val Val Asp Thr Gly Leu His Tyr Lys Arg
                500                505                510

Trp Asn Arg Glu Gln Ala Ile Ser Tyr Met Ile Gln Asn Thr Gly Met
            515                520                525

Ala Pro Lys Asp Val Thr Ala Glu Ile Glu Arg Tyr Val Val Tyr Pro
        530                535                540

Gly Gln Ala Cys Ser Tyr Lys Leu Gly Met Leu Lys Ile Leu Glu Leu
545                550                555                560

Arg Glu Lys Val Lys Ala Arg Lys Glu Thr Phe Asp Ile Arg Glu
                565                570                575

Phe His Ser Val Val Leu Asn Asn Gly Ser Leu Pro Leu Asn Ile Leu
                580                585                590

Glu Lys Leu Ile Gln Asp Glu Leu Leu Asn Asp Gln Glu Lys Lys
        595                600                605

<210> SEQ ID NO 9
<211> LENGTH: 477
<212> TYPE: DNA
<213> ORGANISM: Artificial Sequence
<220> FEATURE:
<223> OTHER INFORMATION: LIC10879

<400> SEQUENCE: 9
atgaaaagaa atattacact cgttgttcta tcaattggaa tcgctcttct tttaggagca      60
tgttccaaat ggcgcaggt tacaaatcat aaaaattgtg atccttcctt actcaatgct      120
tctttggaac ctacggttcc tatttttgcg gatgccgatg cgacttctgt agtaaaagaa      180
agaatagcgc ccggttctat agtaaggggtt tatgattata gaaatcacca agcaaatcca      240 aaacctttg tacgtgtaaa aactgaaaaa gtagaaggat ggatgaatcc tcgttgttta      300
gtagtaggac aggatccgga aaagtccgtt tttacttggg ttatcgtaa ggactatatt      360 cacttttaca gtccggatga ccatgaacac tatcctaacg gatacgagtt taaggattat      420
gcatctcttc caaaggataa ggttccgttg gcggagcttg cgcctgagtt aaaaaag      477

<210> SEQ ID NO 10
<211> LENGTH: 159
<212> TYPE: PRT
<213> ORGANISM: Artificial Sequence
<220> FEATURE:
<223> OTHER INFORMATION: LIC10879

<400> SEQUENCE: 10

Met Lys Arg Asn Ile Thr Leu Val Val Leu Ser Ile Gly Ile Ala Leu
1               5                   10                  15

Leu Leu Gly Ala Cys Ser Lys Leu Ala Gln Val Thr Asn His Lys Asn
            20                  25                  30

Cys Asp Pro Ser Leu Leu Asn Ala Ser Leu Glu Pro Thr Val Pro Ile
        35                  40                  45
```

```
Phe Ala Asp Ala Asp Ala Thr Ser Val Val Lys Glu Arg Ile Ala Pro
            50                  55                  60

Gly Ser Ile Val Arg Val Tyr Asp Tyr Arg Asn His Gln Ala Asn Pro
 65                  70                  75                  80

Lys Pro Phe Val Arg Val Lys Thr Glu Lys Val Glu Gly Trp Met Asn
                    85                  90                  95

Pro Arg Cys Leu Val Val Gly Gln Asp Pro Glu Lys Ser Val Phe Thr
                100                 105                 110

Trp Gly Tyr Arg Lys Asp Tyr Ile His Phe Tyr Ser Pro Asp Asp His
                115                 120                 125

Glu His Tyr Pro Asn Gly Tyr Glu Phe Lys Asp Tyr Ala Ser Leu Pro
            130                 135                 140

Lys Asp Lys Val Pro Leu Ala Glu Leu Ala Pro Glu Leu Lys Lys
145                 150                 155
```

<210> SEQ ID NO 11
<211> LENGTH: 1671
<212> TYPE: DNA
<213> ORGANISM: Artificial Sequence
<220> FEATURE:
<223> OTHER INFORMATION: LIC10314

<400> SEQUENCE: 11

```
atgttcagaa tctggatcgt attttatgt ttcggttttt ctttatcgtt attttctcag    60
gaaagttcta aactcggaga aaagaaatt cgatcttctc aaagagttcg gtttattaat   120
cgatcttctg cgcgagcagg agaagaggtt agaggaacca atgaaaaggt aggttccgga   180
cttgcagaat ctctcaaaaa agagccagat aaaactcata caccaaggtgg aatcagcgta   240
accagaattg cacctgaaga aaaaaaattt ggagcagatg tgatctcggt tttagaagat   300
tccgattttg gtcatatcaa ttctatccag agaattctaa ccggttttgt aaaactcaac   360
ttcggctatg acgataaaaa ttcggatata cttgccacct atattttgta ttacaacgcc   420
attcatagaa aagataaatc ttatatctcc aaaagtatt ccaattctgt aattaagttt   480
gtaactcctc agtccatagg aatttctaaa cgttattcgg aatggcccgg aaaaactcag   540
attttgattc cacttgtaga gacgttttta ggtaaggatg ttcatacgga tgaattggaa   600
gacgaagtta ataagaatt ggataagaaa aagacggac aatccgaaaa agataagttt   660
ggagatcttc aaaacgaaaa aacaaaaaa gaattagaag aactaaaacg tagaaaagaa   720
gagaatcaaa acaaacagaa agaaatttcc gataaagaaa caaaaacgga taagaacctt   780
caagaactca ataagagatcc agtaaaaaat aaagttcaaa tcgtagaaaa gaaaaagaa   840
aagaacaaa ttcaaaaaga aaagaagcc gttaaaaagg aagaacagaa gttaaaggaa   900
aagaaaaagg aagtcgtaaa gaaagacgaa gaaagaaaaa acaataatag ctcttcaagt   960
tcttcgagct catccagttc ttctaaatcc gattctaaaa gcgattcgag tagtagtaaa  1020
tccggaagcg ataagtctgc gtccgatgac aaaaaatcag aagcggaatt gaaaaagaa  1080
ctcgcagata ctaaaaaaga attggaaaca aaaaagaag aggagaagaa aaagaagaa  1140
ttcgataaga acgtcgtcgg aggaaaaatt ctttctctaa aaactctaaa gtatttagat  1200
aaaggacatt ataacaacga attacaggtg ttagatccca caaaagacga tacgattatc  1260
agaggagatt ttaacaaaat ttgtggtaga acgtttgaga tcgtagacgg aaaggcactt  1320
gtaattggct tcgaagacgg tcactcttct aaccataaac tgattttaat cgaccaagaa  1380
actttaaagc cagtcttatt cgcagaagac aatatatttt ggagatctcc tatgatcatc  1440
```

```
aaaggagacg agatctacgc gtttgaagaa gtagaagaga atattatct ttctcgtttc    1500 ggtaaggatc tcaaaaaaca agccaagtct tctgaggaaa ttagcccaaa ttcaaacgtc    1560
actttctatg gagaaaaaat ttatgttacc ggcaaggaag aaagttcggg taatattcaa    1620
atcaccgttt ttaataaagc cgatctaaaa ctgattaaaa aaattaaacc t             1671

<210> SEQ ID NO 12
<211> LENGTH: 557
<212> TYPE: PRT
<213> ORGANISM: Artificial Sequence
<220> FEATURE:
<223> OTHER INFORMATION: LIC10314

<400> SEQUENCE: 12

Met Phe Arg Ile Trp Ile Val Phe Leu Cys Phe Gly Phe Ser Leu Ser
1               5                   10                  15

Leu Phe Ser Gln Glu Ser Ser Lys Leu Gly Glu Lys Glu Ile Arg Ser
            20                  25                  30

Ser Gln Arg Val Arg Phe Ile Asn Arg Ser Ser Ala Arg Ala Gly Glu
        35                  40                  45

Glu Val Arg Gly Thr Asn Glu Lys Val Gly Ser Gly Leu Ala Glu Ser
    50                  55                  60

Leu Lys Lys Glu Pro Asp Lys Thr His Thr Gln Gly Gly Ile Ser Val
65                  70                  75                  80

Thr Arg Ile Ala Pro Glu Glu Lys Lys Phe Gly Ala Asp Val Ile Ser
                85                  90                  95

Val Leu Glu Asp Ser Asp Phe Gly His Ile Asn Ser Ile Gln Arg Ile
            100                 105                 110

Leu Thr Gly Phe Val Lys Leu Asn Phe Gly Tyr Asp Asp Lys Asn Ser
        115                 120                 125

Asp Ile Leu Ala Thr Tyr Ile Leu Tyr Tyr Asn Ala Ile His Arg Lys
    130                 135                 140

Asp Lys Ser Tyr Ile Ser Lys Lys Tyr Ser Asn Ser Val Ile Lys Phe
145                 150                 155                 160

Val Thr Pro Gln Ser Ile Gly Ile Ser Lys Arg Tyr Ser Glu Trp Pro
                165                 170                 175

Gly Lys Thr Gln Ile Leu Ile Pro Leu Val Glu Asp Val Leu Gly Lys
            180                 185                 190

Asp Val His Thr Asp Glu Leu Glu Asp Glu Val Asn Lys Glu Leu Asp
        195                 200                 205

Lys Lys Lys Asp Gly Gln Ser Glu Lys Asp Lys Phe Gly Asp Leu Gln
    210                 215                 220

Asn Glu Lys Asn Lys Lys Glu Leu Glu Glu Leu Lys Arg Arg Lys Glu
225                 230                 235                 240

Glu Asn Gln Asn Lys Gln Lys Glu Ile Ser Asp Lys Glu Thr Lys Thr
                245                 250                 255

Asp Lys Glu Leu Gln Glu Leu Asn Lys Asp Pro Val Lys Asn Lys Val
            260                 265                 270

Gln Ile Val Glu Lys Lys Glu Lys Glu Gln Ile Gln Lys Glu Lys
        275                 280                 285

Glu Ala Val Lys Lys Glu Glu Gln Leu Lys Glu Lys Glu Lys Glu
    290                 295                 300

Val Val Lys Lys Asp Glu Glu Arg Lys Asn Asn Asn Ser Ser Ser Ser
305                 310                 315                 320
```

| | | | | | | | | | | | |
|---|---|---|---|---|---|---|---|---|---|---|---|
|Ser|Ser|Ser|Ser|Ser|Ser|Ser|Lys|Ser|Asp|Lys|Ser|Asp|Ser|
| | | |325| | | |330| | |335| |
|Ser|Ser|Ser|Lys|Ser|Gly|Ser|Asp|Lys|Ser|Ala|Ser|Asp|Lys|Lys|
| | |340| | | |345| | | |350| |
|Ser|Glu|Ala|Glu|Leu|Lys|Lys|Glu|Leu|Ala|Asp|Thr|Lys|Lys|Glu|Leu|
| | |355| | | |360| | | |365| |
|Glu|Thr|Lys|Lys|Glu|Glu|Lys|Lys|Glu|Glu|Phe|Asp|Lys|Asn|
| |370| | | |375| | | |380| |
|Val|Val|Gly|Gly|Lys|Ile|Leu|Phe|Leu|Lys|Thr|Leu|Lys|Tyr|Leu|Asp|
|385| | |390| | | |395| | | |400|
|Lys|Gly|His|Tyr|Asn|Asn|Glu|Leu|Gln|Val|Leu|Asp|Pro|Thr|Lys|Asp|
| | |405| | | |410| | | |415| |
|Asp|Thr|Ile|Ile|Arg|Gly|Asp|Phe|Asn|Lys|Ile|Cys|Gly|Arg|Thr|Phe|
| | |420| | | |425| | | |430| |
|Glu|Ile|Val|Asp|Gly|Lys|Ala|Leu|Val|Ile|Gly|Phe|Glu|Asp|Gly|His|
| | |435| | | |440| | | |445| |
|Ser|Ser|Asn|His|Lys|Leu|Ile|Leu|Ile|Asp|Gln|Glu|Thr|Leu|Lys|Pro|
| | |450| | | |455| | | |460| |
|Val|Leu|Phe|Ala|Glu|Asp|Asn|Ile|Phe|Trp|Arg|Ser|Pro|Met|Ile|Ile|
|465| | |470| | | |475| | | |480|
|Lys|Gly|Asp|Glu|Ile|Tyr|Ala|Phe|Glu|Glu|Val|Glu|Glu|Lys|Tyr|Tyr|
| | |485| | | |490| | | |495| |
|Leu|Ser|Arg|Phe|Gly|Lys|Asp|Leu|Lys|Lys|Gln|Ala|Lys|Ser|Ser|Glu|
| | |500| | | |505| | | |510| |
|Glu|Ile|Ser|Pro|Asn|Ser|Asn|Val|Thr|Phe|Tyr|Gly|Glu|Lys|Ile|Tyr|
| | |515| | | |520| | | |525| |
|Val|Thr|Gly|Lys|Glu|Glu|Ser|Ser|Gly|Asn|Ile|Gln|Ile|Thr|Val|Phe|
| |530| | | |535| | | |540| |
|Asn|Lys|Ala|Asp|Leu|Lys|Leu|Ile|Lys|Lys|Ile|Lys|Pro|
|545| | |550| | | |555| |

```
<210> SEQ ID NO 13
<211> LENGTH: 1533
<212> TYPE: DNA
<213> ORGANISM: Artificial Sequence
<220> FEATURE:
<223> OTHER INFORMATION: LIC10326

<400> SEQUENCE: 13
atgatactcg tttcctttcc gggagctcag gaccacacat tcaatcaaaa tcaggtagaa      60
aactatagta tcgcaaattc cattcatgca gaaattttaa aaaaggatga gaattcagtc     120
aggatctttt gggacgctcc aaaagaaacc ggagaaatta tagtcgcccg ttcctcttct     180
atgatcgaca cccctgaaaa atgtatggtt gcagattcct tgggaaaata tccaagcggg     240
attgccggag ggtaactca aatctttgac tacaacctca accaggaac ttattattac      300 gcggtcattt tggctcatag agttaaaaat ggtacagtca aactaattcc agggagaaac     360
ttcactacaa ttccggtcgt catcgaacac gcgttaactc aacgaaaaa caaaatcccg     420 gaaatcccag acgacgcaag ggttatcgat ctaacagtta aaagggaagg taaatacctt     480
cgattgaatt ggacccccta cgaaaaggca atcccaaacg cgactgttta tactgtttat     540
cgttctgcag aacctatgtc ttctttatcc ttgatgagaa aagcagaaaa actcaccgaa     600
ctcagtcacc ccgaatccac tttttggat caagatttga ataaatctca gacgatttac     660
tatggggtaa gcgttcgctc cggagccaaa gaagttttac ctctgatcaa cggacaatct     720
```

```
tttatccgat acttttacat tggaaacccc aacaaggtg gctctgaaaa tattacaaat    780
ccagaatatt cagaagatga aatgcgcata aaagatctta ccgccgaagt ggacgatcta    840
aatgtaaaac tctcttggaa ggcccctgaa aaggcagacg caaatacggt ttatacaatc    900
tatcaagcgt taaaaccttt aagcggtgga accgctacat ttttaggcgg aaatgtgcga    960
aagttaggag aagtcaatca tccagatacc gaagcccaga tcaaaatgaa atccttggat   1020
gcgaaagttt attttggagt cactgtaaaa cataaggaca agaagggtt caaccttgta   1080
gaaaatgaat ctttttatagc aatctctcca acaagaaac ccgaaaactc agaagaaaat   1140
agtgcagaag agacacctca ggaaaatcag gaagaaacat ctgcttcaga tccagaaaaa   1200
gaacaagaaa aagtgaaga agtttctaaa gatacaaac aagaagaaga attttccggg    1260
aataacgatg aactagataa aattctaaga gaaacctact ggaaaaaaga atactcccgc   1320
acgattcgag atctgaaacc gtatgcaaaa aacggaaatt cagtgtacat gaaaggaaaa   1380
gcaaaatttt tcactggact ctcttactat aaaaaaggga attacaaaga agcacttaag   1440
tatttcatca ataaagatag taaatttac aatacgaac gctctgagtt ttggtcgaag   1500
cgctgtctgt ctcggatctc cggaggaaat cca                                1533
```

<210> SEQ ID NO 14
<211> LENGTH: 524
<212> TYPE: PRT
<213> ORGANISM: Artificial Sequence
<220> FEATURE:
<223> OTHER INFORMATION: LIC10326

<400> SEQUENCE: 14

```
Met Lys Ile Ser Thr Arg Ile Leu Leu Phe Ser Leu Met Ile Leu
 1               5                  10                  15

Val Ser Phe Pro Gly Ala Gln Asp His Thr Phe Asn Gln Asn Gln Val
            20                  25                  30

Glu Asn Tyr Ser Ile Ala Asn Ser Ile His Ala Glu Ile Leu Lys Lys
        35                  40                  45

Asp Glu Asn Ser Val Arg Ile Phe Trp Asp Ala Pro Lys Glu Thr Gly
    50                  55                  60

Glu Ile Ile Val Ala Arg Ser Ser Met Ile Asp Thr Pro Glu Lys
65                  70                  75                  80

Cys Met Val Ala Asp Ser Leu Gly Lys Tyr Pro Ser Gly Ile Ala Gly
                85                  90                  95

Gly Val Thr Gln Ile Phe Asp Tyr Asn Leu Lys Pro Gly Thr Tyr Tyr
            100                 105                 110

Tyr Ala Val Ile Leu Ala His Arg Val Lys Asn Gly Thr Val Lys Leu
        115                 120                 125

Ile Pro Gly Arg Asn Phe Thr Thr Ile Pro Val Val Ile Glu His Ala
    130                 135                 140

Leu Thr Pro Thr Glu Asn Lys Ile Pro Glu Ile Pro Asp Asp Ala Arg
145                 150                 155                 160

Val Ile Asp Leu Thr Val Lys Arg Glu Gly Lys Tyr Leu Arg Leu Asn
                165                 170                 175

Trp Thr Pro Tyr Glu Lys Ala Ile Pro Asn Ala Thr Val Tyr Thr Val
            180                 185                 190

Tyr Arg Ser Ala Glu Pro Met Ser Ser Leu Ser Leu Met Arg Lys Ala
        195                 200                 205

Glu Lys Leu Thr Glu Leu Ser His Pro Glu Ser Thr Phe Leu Asp Gln
    210                 215                 220
```

Asp Leu Asn Lys Ser Gln Thr Ile Tyr Tyr Gly Val Ser Val Arg Ser
225                 230                 235                 240

Gly Ala Lys Glu Val Leu Pro Leu Ile Asn Gly Gln Ser Phe Ile Arg
            245                 250                 255

Tyr Phe Tyr Ile Gly Asn Pro Asn Lys Gly Gly Ser Glu Asn Ile Thr
        260                 265                 270

Asn Pro Glu Tyr Ser Glu Asp Glu Met Arg Ile Lys Asp Leu Thr Ala
    275                 280                 285

Glu Val Asp Asp Leu Asn Val Lys Leu Ser Trp Lys Ala Pro Glu Lys
290                 295                 300

Ala Asp Ala Asn Thr Val Tyr Thr Ile Tyr Gln Ala Leu Lys Pro Leu
305                 310                 315                 320

Ser Gly Gly Thr Ala Thr Phe Leu Gly Gly Asn Val Arg Lys Leu Gly
            325                 330                 335

Glu Val Asn His Pro Asp Thr Glu Ala Gln Ile Lys Met Lys Ser Leu
        340                 345                 350

Asp Ala Lys Val Tyr Phe Gly Val Thr Val Lys His Lys Asp Lys Glu
    355                 360                 365

Gly Phe Asn Leu Val Glu Asn Glu Ser Phe Ile Ala Ile Ser Pro Asn
370                 375                 380

Lys Lys Pro Glu Asn Ser Glu Glu Asn Ser Ala Glu Glu Thr Pro Gln
385                 390                 395                 400

Glu Asn Gln Glu Glu Thr Ser Ala Ser Asp Pro Glu Lys Glu Gln Glu
            405                 410                 415

Lys Ser Glu Glu Val Ser Lys Asp Thr Lys Gln Glu Glu Phe Ser
        420                 425                 430

Gly Asn Asn Asp Glu Leu Asp Lys Ile Leu Arg Glu Thr Tyr Trp Lys
    435                 440                 445

Lys Glu Tyr Ser Arg Thr Ile Arg Asp Leu Lys Pro Tyr Ala Lys Asn
450                 455                 460

Gly Asn Ser Val Tyr Met Lys Gly Lys Ala Lys Phe Phe Thr Gly Leu
465                 470                 475                 480

Ser Tyr Tyr Lys Lys Gly Asn Tyr Lys Glu Ala Leu Lys Tyr Phe Ile
            485                 490                 495

Asn Lys Asp Ser Lys Phe Tyr Asn Thr Glu Arg Ser Glu Phe Trp Ser
        500                 505                 510

Lys Arg Cys Leu Ser Arg Ile Ser Gly Gly Asn Pro
    515                 520

<210> SEQ ID NO 15
<211> LENGTH: 1491
<212> TYPE: DNA
<213> ORGANISM: Artificial Sequence
<220> FEATURE:
<223> OTHER INFORMATION: LIC10927

<400> SEQUENCE: 15
ttgaagaatc aaaagtggaa aaaggaaaag gggcttaaaa aaatgaaacg atggattcta    60
tatataacaa cgatttgtct atttcttacc tttataaatt gtaaaaaaga cgacgatgat   120
caagataaaa ctctcttagc gttaatctta gccgatcttt tatacaatcc ttacgaaaag   180
attactcctt ctcctggaac gattactatt tccggagcca attattcaaa cagagcttat   240
aaccctgctt gttccggttc tactgaaaat aaaacgtttt cattctatag aaaaaaagta   300
aaaacatcca atagcaaatt gctcatcaat tttatgggag gtggagcttg ttggagtgga   360

-continued

```
tataactgct tcggaaataa tacaactact tattttaacc agctcgaaaa ggttccggat      420
ttgttcgtaa aatttgtttt tcaaggtgta atgaacacaa acaacgcttc caatccattc      480
aaagactatg atgtagtttt tattccctat tgcactggag atctacactt cggttctaaa      540
gacatgactt atatcgatcc aaccacagga tcttcagtag tagtaaaaca taagggttat      600
gacaatgtgc tctcggtatt aaagtatatt cagaccgagt atcctcaagt tcaaaatgta      660
ttcgtaactg dacaaagcgc aggaggttat ggaactctac tcaattatcc tatcgtacgt      720
gaaactattt caggactgaa ttcatccgca aaaatgaaca tgctgattga tgcgtctaac      780
ggaattgttc caaacggttt tttctccaat ctaagcactc agtggggagc cgattcaaat      840
ttgcctactt gggtagctgg aatcgcggct aactatctca ctgtaggaaa cccttctatt      900
caagattttt ttacaaaggt atccacacac tacaatggat cgggagataa aacgggtcaa      960
tacactgcta cttttgacgg aaaccaaaga ttttttttaca aagtgatgca tatcatcaac     1020
tcggctccac cttattcaga tgaaaaaacg acagacccct tacgattcctc taaaacctat     1080 tccttcttat ttggagacag tgatggtagt tccattccag acggaacgac agcgtccaca     1140
gatggatcca gttgcggttg gacacaacag gcggttactt ccatgaatgg gatttcggcc     1200
ggaactacaa attattcgta ttacatcgct ccgggtgacg tacacacaat tactacgtca     1260
gaagatatgt ataaactgga ttcgggagga accaacttcg ttacttggct tacaaccctt     1320
tctacaggca caaaccagg aaaatgcgaag tgtacaaaca acggaggaaa ctgtgccaac     1380 tctaattta caaaaagtaa aatcaatctt actttgaatg cggctacttc agatcaatct     1440
tatgtaaata atacagatct agcaactact tgtagaccta ttgtaggcct t              1491
```

<210> SEQ ID NO 16
<211> LENGTH: 497
<212> TYPE: PRT
<213> ORGANISM: Artificial Sequence
<220> FEATURE:
<223> OTHER INFORMATION: LIC10927

<400> SEQUENCE: 16

```
Met Lys Asn Gln Lys Trp Lys Lys Glu Lys Gly Leu Lys Lys Met Lys
1               5                   10                  15

Arg Trp Ile Leu Tyr Ile Thr Thr Ile Cys Leu Phe Leu Thr Phe Ile
            20                  25                  30

Asn Cys Lys Lys Asp Asp Asp Gln Asp Lys Thr Leu Leu Ala Leu
        35                  40                  45

Ile Leu Ala Asp Leu Leu Tyr Asn Pro Tyr Glu Lys Ile Thr Pro Ser
    50                  55                  60

Pro Gly Thr Ile Thr Ile Ser Gly Ala Asn Tyr Ser Asn Arg Ala Tyr
65                  70                  75                  80

Asn Pro Ala Cys Ser Gly Ser Thr Glu Asn Lys Thr Phe Ser Phe Tyr
                85                  90                  95

Arg Lys Lys Val Lys Thr Ser Asn Ser Lys Leu Leu Ile Asn Phe Met
            100                 105                 110

Gly Gly Gly Ala Cys Trp Ser Gly Tyr Asn Cys Phe Gly Asn Asn Thr
        115                 120                 125

Thr Thr Tyr Phe Asn Gln Leu Glu Lys Val Pro Asp Leu Phe Val Lys
    130                 135                 140

Phe Val Phe Gln Gly Val Met Asn Thr Asn Asn Ala Ser Asn Pro Phe
145                 150                 155                 160
```

```
Lys Asp Tyr Asp Val Val Phe Ile Pro Tyr Cys Thr Gly Asp Leu His
                165                 170                 175
Phe Gly Ser Lys Asp Met Thr Tyr Ile Asp Pro Thr Thr Gly Ser Ser
            180                 185                 190
Val Val Val Lys His Lys Gly Tyr Asp Asn Val Leu Ser Val Leu Lys
        195                 200                 205
Tyr Ile Gln Thr Glu Tyr Pro Gln Val Gln Asn Val Phe Val Thr Gly
    210                 215                 220
Gln Ser Ala Gly Gly Tyr Gly Thr Leu Leu Asn Tyr Pro Ile Val Arg
225                 230                 235                 240
Glu Thr Ile Ser Gly Leu Asn Ser Ser Ala Lys Met Asn Met Leu Ile
                245                 250                 255
Asp Ala Ser Asn Gly Ile Val Pro Asn Gly Phe Phe Ser Asn Leu Ser
            260                 265                 270
Thr Gln Trp Gly Ala Asp Ser Asn Leu Pro Thr Trp Val Ala Gly Ile
        275                 280                 285
Ala Ala Asn Tyr Leu Thr Val Gly Asn Pro Ser Ile Gln Asp Phe Phe
    290                 295                 300
Thr Lys Val Ser Thr His Tyr Asn Gly Ser Gly Asp Lys Thr Gly Gln
305                 310                 315                 320
Tyr Thr Ala Thr Phe Asp Gly Asn Gln Arg Phe Phe Tyr Lys Val Met
                325                 330                 335
His Ile Ile Asn Ser Ala Pro Pro Tyr Ser Asp Glu Lys Thr Thr Asp
            340                 345                 350
Pro Tyr Asp Ser Ser Lys Thr Tyr Ser Phe Leu Phe Gly Asp Ser Asp
        355                 360                 365
Gly Ser Ser Ile Pro Asp Gly Thr Thr Ala Ser Thr Asp Gly Ser Ser
    370                 375                 380
Cys Gly Trp Thr Gln Gln Ala Val Thr Ser Met Asn Gly Ile Ser Ala
385                 390                 395                 400
Gly Thr Thr Asn Tyr Ser Tyr Tyr Ile Ala Pro Gly Asp Val His Thr
                405                 410                 415
Ile Thr Thr Ser Glu Asp Met Tyr Lys Leu Asp Ser Gly Gly Thr Asn
            420                 425                 430
Phe Val Thr Trp Leu Thr Thr Leu Ser Thr Gly Thr Lys Pro Gly Asn
        435                 440                 445
Ala Lys Cys Thr Asn Asn Gly Asn Cys Ala Asn Ser Asn Phe Thr
    450                 455                 460
Lys Ser Lys Ile Asn Leu Thr Leu Asn Ala Ala Thr Ser Asp Gln Ser
465                 470                 475                 480
Tyr Val Asn Asn Thr Asp Leu Ala Thr Thr Cys Arg Pro Ile Val Gly
                485                 490                 495
Leu

<210> SEQ ID NO 17
<211> LENGTH: 996
<212> TYPE: DNA
<213> ORGANISM: Artificial Sequence
<220> FEATURE:
<223> OTHER INFORMATION: LIC10968

<400> SEQUENCE: 17
atgagccagg cttggattga aaacacgatc ctggactgta ttcttaaaga atgttatctt      60
tgttctctca aaattacaaa caaacctgtt gttagtttgt ttgccggtac tggtgtagca     120
```

```
gcaagcgtag atggtaccac ttccacagcc tctttcaaaa ctcctttcgg tttagaagta     180
gatacttccg gaaatatcta tgtgagcgat caaataaaca acctgattcg taaaattgat     240
ccctccggaa atgtaaaaac tctttctaca aacttacctt tacaagatcc ttccggcatc     300
aagttcgatc cgcttactgg agacaaatac gtttcctgca aagacagtaa tcaaatttat     360
aagatagatt ctacggaaca attttcctta tttgccggaa gttcttccga cttgagtggt     420
cttcaaaacg gggatagact caattccttg tttgacagtc cttttttta tggacatcgat    480 ccagaaagaa acttatacgt gggagagtta agcaatcata cgattcgaaa atcaatctc     540 aactcaggta cggtgagtac tctttccgga ggaatttctg ttatttaga cggagattta    600 gcttcagctc gttttaaatc tccattagga attgcttata atcgtaaaat gaatagttta    660
ttggctgcag atattcagga tcatagaatt cgaaaaatag atctcaaaaa ttctaccgta    720
tccactcttt tgggaaacgg aatcggagca gacgtagatg gaaatggaac aaacgcttcg    780
ttttttggtc ccgctttcat ttctatagat aacagcggtt atatgtttgt atcggacgct    840
aattctaaca gaatccgcat gtggatcct ttacttaacg tttctacaat tgatcatacg     900
tttatggaga tagggacagt taaagttgat tgtttgaacc aaagattgtt agtcgccgat    960
tctcgtgcaa atcagatttt ccaagttaaa tttgaa                               996
```

<210> SEQ ID NO 18
<211> LENGTH: 358
<212> TYPE: PRT
<213> ORGANISM: Artificial Sequence
<220> FEATURE:
<223> OTHER INFORMATION: LIC10968

<400> SEQUENCE: 18

```
Met Phe Tyr Arg Ile Leu Ile Phe Val Leu Val Leu Ser Cys Ser
1               5                   10                  15

Pro Ala Ser Ile Tyr Asn Pro Ser Ile Phe Met Ser Gln Ala Trp Ile
            20                  25                  30

Glu Asn Thr Ile Leu Asp Cys Ile Leu Lys Glu Cys Tyr Leu Cys Ser
        35                  40                  45

Leu Lys Ile Thr Asn Lys Pro Val Val Ser Leu Phe Ala Gly Thr Gly
    50                  55                  60

Val Ala Ala Ser Val Asp Gly Thr Thr Ser Thr Ala Ser Phe Lys Thr
65                  70                  75                  80

Pro Phe Gly Leu Glu Val Asp Thr Ser Gly Asn Ile Tyr Val Ser Asp
                85                  90                  95

Gln Ile Asn Asn Leu Ile Arg Lys Ile Asp Pro Ser Gly Asn Val Lys
            100                 105                 110

Thr Leu Ser Thr Asn Leu Pro Leu Gln Asp Pro Ser Gly Ile Lys Phe
        115                 120                 125

Asp Pro Leu Thr Gly Asp Lys Tyr Val Ser Cys Lys Asp Ser Asn Gln
    130                 135                 140

Ile Tyr Lys Ile Asp Ser Thr Glu Gln Phe Ser Leu Phe Ala Gly Ser
145                 150                 155                 160

Ser Ser Asp Leu Ser Gly Leu Gln Asn Gly Asp Arg Leu Asn Ser Leu
                165                 170                 175

Phe Asp Ser Pro Phe Phe Met Asp Ile Asp Pro Glu Arg Asn Leu Tyr
            180                 185                 190

Val Gly Glu Leu Ser Asn His Thr Ile Arg Lys Ile Asn Leu Asn Ser
        195                 200                 205
```

Gly Thr Val Ser Thr Leu Ser Gly Gly Ile Ser Gly Tyr Leu Asp Gly
    210                 215                 220

Asp Leu Ala Ser Ala Arg Phe Lys Ser Pro Leu Gly Ile Ala Tyr Asn
225                 230                 235                 240

Arg Lys Met Asn Ser Leu Leu Ala Ala Asp Ile Gln Asp His Arg Ile
                245                 250                 255

Arg Lys Ile Asp Leu Lys Asn Ser Thr Val Ser Thr Leu Leu Gly Asn
            260                 265                 270

Gly Ile Gly Ala Asp Val Asp Gly Asn Gly Thr Asn Ala Ser Phe Phe
        275                 280                 285

Gly Pro Ala Phe Ile Ser Ile Asp Asn Ser Gly Tyr Met Phe Val Ser
    290                 295                 300

Asp Ala Asn Ser Asn Arg Ile Arg Ile Val Asp Pro Leu Leu Asn Val
305                 310                 315                 320

Ser Thr Ile Asp His Thr Phe Met Glu Ile Gly Thr Val Lys Val Asp
                325                 330                 335

Cys Leu Asn Gln Arg Leu Leu Val Ala Asp Ser Arg Ala Asn Gln Ile
            340                 345                 350

Phe Gln Val Lys Phe Glu
        355

<210> SEQ ID NO 19
<211> LENGTH: 1665
<212> TYPE: DNA
<213> ORGANISM: Artificial Sequence
<220> FEATURE:
<223> OTHER INFORMATION: LIC11003

<400> SEQUENCE: 19
atgaaatcga ctcaaagaaa aatactttct tcttttataa tcttactcgc aggattttt       60 atttcctgtg gagctgaact tcctattgag gaattaagtg atgcaaaaaa ctcgatcaca     120
agagctaagt ctgcaggtgc tgaaaaatat gctccttcag aattagaaga agcccgtaaa     180
aacttactca cagctcatca aaaagcttcg gaagaaaatc ttacagagac taaaaaatcc     240
gcgttgtatg caagagcaaa ggctttagac gcttccgaga atccttccc ttcttctgtt     300 gatgatgcac gtaaagaatc cagctcttca atcgaatctg cagaagaagc ctatgcttct     360
cagcttgctt ctgaacctta taatacttct gtacaacttc gcaaagaggg tgattctcta     420
cgcgaaactg ctgaccgcac tttagaatcg tatccgaaag aatccggaga tgacgcaaaa     480
ctgaggatga gattagcagc attcgatcag tatgaggctc tcgtcaaaa atatgcggat      540 tctaaaaagg ccgcagacga atccaaggta ttagctcttt ctcagaaaca caactaatc     600 gattcttttg cagacataga taaaaatcta aatgatgcag ataagtatgc agaaggaaaa     660
gatccggaag tttccgaaac tagaaatcgt ctcgattcct ctaaatccaa aatagaagaa     720
gggaagatca agaaggata ttccgaaata gatgatattc gtaaaaaatc cggcgaactt     780
gttgctaaga atattaagat ttacgcagaa aaacagaagg aacttgcaaa acaaagcgta     840
gcatctgcga ctacaaggtt agcttccttc gatcgaaata aaatcaattc ctctagagat     900
tttcaagttt cttaccaaag agcagaagaa aaccttaaag cagctgaaga tcgagagta      960 gctgcagaag atctatattc ttcggaaaaa tacgaagatt ctatttcgcg ttctgaagaa    1020
gcaattcgcc tttccagaat cttagtagac caagccactg agttggccga agaatagaa    1080 agaaaagcaa cgactgataa gatcgctggt cgtgatacaa aaaccgaagg gaataaaaat    1140
actaaaaacc aatccacaac cgaaggcaaa aattcttcat ctaaaattgg agaagatggt    1200

-continued

```
ttaccggaag gttggaaacg ttatgtggtt cggaaaaaag ttcctgcaga ttgtctttgg    1260
agaatcgcaa aagataaaag acattatgga acttctaaac tttggagaag aatctacgaa    1320
gcaaaccgaa acaaaatcaa aaacccaaac ttgatttatc cgaaacaagt attattaatt    1380
cctcctagaa aaggcccgac tcgattggac aaagtagaat ctgcgccgtc cagaaagaaa    1440
aaaccggcca cagaagaagt agaggctatt gaagaaaacc gaaagcccac tacacattct    1500
tctgaagatt ccgaagctgg agaatcgaat aacaagaaaa aggcggaagc aactcctcca    1560
tctaccgata cttcggaaga agaaggaggt ggagaatctt cagaaaatga ggaatcttca    1620
cccgaagaag aaaatggaga ggaagaaaat ccggaaaatc ttcaa                    1665
```

<210> SEQ ID NO 20
<211> LENGTH: 555
<212> TYPE: PRT
<213> ORGANISM: Artificial Sequence
<220> FEATURE:
<223> OTHER INFORMATION: LIC11003

<400> SEQUENCE: 20

```
Met Lys Ser Thr Gln Arg Lys Ile Leu Ser Ser Phe Ile Ile Leu Leu
1               5                   10                  15

Ala Gly Phe Phe Ile Ser Cys Gly Ala Glu Leu Pro Ile Glu Glu Leu
            20                  25                  30

Ser Asp Ala Lys Asn Ser Ile Thr Arg Ala Lys Ser Ala Gly Ala Glu
        35                  40                  45

Lys Tyr Ala Pro Ser Glu Leu Glu Glu Ala Arg Lys Asn Leu Leu Thr
    50                  55                  60

Ala His Gln Lys Ala Ser Glu Glu Asn Leu Thr Glu Thr Lys Lys Ser
65                  70                  75                  80

Ala Leu Tyr Ala Arg Ala Lys Ala Leu Asp Ala Ser Glu Lys Ser Phe
                85                  90                  95

Pro Ser Ser Val Asp Asp Ala Arg Lys Glu Ser Ser Ser Ile Glu
            100                 105                 110

Ser Ala Glu Glu Ala Tyr Ala Ser Gln Leu Ala Ser Glu Pro Tyr Asn
        115                 120                 125

Thr Ser Val Gln Leu Arg Lys Glu Gly Asp Ser Leu Arg Glu Thr Ala
    130                 135                 140

Asp Arg Thr Leu Glu Ser Tyr Pro Lys Glu Ser Gly Asp Asp Ala Lys
145                 150                 155                 160

Leu Arg Met Arg Leu Ala Ala Phe Asp Gln Tyr Glu Ala Ser Arg Gln
                165                 170                 175

Lys Tyr Ala Asp Ser Lys Lys Ala Ala Asp Glu Ser Lys Val Leu Ala
            180                 185                 190

Leu Ser Gln Lys Gln Gln Leu Ile Asp Ser Phe Ala Asp Ile Asp Lys
        195                 200                 205

Asn Leu Asn Asp Ala Asp Lys Tyr Ala Glu Gly Lys Asp Pro Glu Val
    210                 215                 220

Ser Glu Thr Arg Asn Arg Leu Asp Ser Ser Lys Ser Lys Ile Glu Glu
225                 230                 235                 240

Gly Lys Ile Lys Glu Gly Tyr Ser Glu Ile Asp Ile Arg Lys Lys
                245                 250                 255

Ser Gly Glu Leu Val Ala Lys Asn Ile Lys Ile Tyr Ala Glu Lys Gln
            260                 265                 270

Lys Glu Leu Ala Lys Gln Ser Val Ala Ser Ala Thr Thr Arg Leu Ala
```

Ser Phe Asp Arg Asn Lys Ile Asn Ser Ser Arg Asp Phe Gln Val Ser
            275                 280                 285
Tyr Gln Arg Ala Glu Glu Asn Leu Lys Ala Ala Glu Glu Ser Arg Val
290                 295                 300
Ala Ala Glu Asp Leu Tyr Ser Ser Lys Tyr Glu Asp Ser Ile Ser
305                 310                 315                 320
Arg Ser Glu Glu Ala Ile Arg Leu Ser Arg Ile Leu Val Asp Gln Ala
    325                 330                 335
Thr Glu Leu Ala Glu Arg Ile Glu Arg Lys Ala Thr Thr Asp Lys Ile
340                 345                 350
Ala Gly Arg Asp Thr Lys Thr Glu Gly Asn Lys Asn Thr Lys Asn Gln
    355                 360                 365
Ser Thr Thr Glu Gly Lys Asn Ser Ser Lys Ile Gly Glu Asp Gly
370                 375                 380
Leu Pro Glu Gly Trp Lys Arg Tyr Val Val Arg Lys Lys Val Pro Ala
385                 390                 395                 400
Asp Cys Leu Trp Arg Ile Ala Lys Asp Lys Arg His Tyr Gly Thr Ser
    405                 410                 415
Lys Leu Trp Arg Arg Ile Tyr Glu Ala Asn Arg Asn Lys Ile Lys Asn
420                 425                 430
Pro Asn Leu Ile Tyr Pro Lys Gln Val Leu Leu Ile Pro Pro Arg Lys
    435                 440                 445
Gly Pro Thr Arg Leu Asp Lys Val Glu Ser Ala Pro Ser Arg Lys Lys
450                 455                 460
Lys Pro Ala Thr Glu Glu Val Glu Ala Ile Glu Glu Asn Arg Lys Pro
465                 470                 475                 480
Thr Thr His Ser Ser Glu Asp Ser Glu Ala Gly Glu Ser Asn Asn Lys
    485                 490                 495
Lys Lys Ala Glu Ala Thr Pro Pro Ser Thr Asp Thr Ser Glu Glu Glu
500                 505                 510
Gly Gly Gly Glu Ser Ser Glu Asn Glu Glu Ser Ser Pro Glu Glu Glu
    515                 520                 525
Asn Gly Glu Glu Glu Asn Pro Glu Asn Leu Gln
530                 535                 540
545                 550                 555

<210> SEQ ID NO 21
<211> LENGTH: 1431
<212> TYPE: DNA
<213> ORGANISM: Artificial Sequence
<220> FEATURE:
<223> OTHER INFORMATION: LIC12576

<400> SEQUENCE: 21
ttgagaaaga gttttttttgt agtcctcggt attatcttca cttccatatt actcggtttt      60
tttgtttgga aaattctcac tcgtaaaacc gattccgttt atagaaattt ttctaaatcg     120
aattgggaag acgtaatttt agaagttcta agtaaaaaag atccggacct agaagattat     180
tcttatgctt ctatgtctct tgcggaattt aacttccatc ttttaaccgt tccttccgaa     240
aaaagagaaa aagtagcttc caggtttgca gaaaaatcag gactaaaatt ttttaaaaga     300
gaagtaggag gaagaacgat ctttactttc gaagacagat ttttttctttt tttacccgaa     360 ggttcgtttc tcaaaacgag agcactttgt aaaaaaactat ttctaggtgc ggaatacgaa     420
actgtagacg ttcttccag atatttagtg aaactaattt catctaaccc acttccactt     480

```
tacaacgaat acaatcaggc cttgctcaaa tctctttccg ttggttctgc aaaagaattg      540
gatgaaaatg gcagatctaa actttctaaa ttactagaat acttttctgg aaaagaagac      600
tctccgttta acggtagcaa ggcggtaatc gaagggaaaa atctaaacgt tagaaccggc      660
cccggaaccg aaaacccgat ttcgtttcag ttcaaaggtg gagaaatcgt ttttatactc      720
gatagagact cacgaaccga aaccatagcc ggtaaaagag gaagttggaa ccaaattgta      780
gatctgagaa acggaaatgt gggttggatc ttttccggtt ttttaaaaaa cattccttcg      840
gatctttcta tctctcaaac aatggaagaa tattttcgtg ctttagaccg ctctccggtt      900
tgggattttg aatcttggaa agaagcctcc cctccaaacg gatttcaggg cgagtatcac      960
cccaccgaaa aaatcgcgtt agatggagac tccggaatgg ttctacattc ttccaaaagt     1020
aaatatgatc taatttgccg gtccgtagac gaacctttcc gagatttgga attttacgtt     1080
tcttttttag aaggaaacga aacgattccc gtctttacat tgttagctgg ttctcctgga     1140
gatttacgta aaactttcga aatagaaatg gacaaagaaa gtatttctat caaccgaaac     1200
cgatatatta ccggagacaa ttttttccaaa agaaagattttc gcctaaatat tcaaaacggc     1260
tcttccggtt ccaagccggt tttaatcgtt tccgaaaaaa tggccctttc cggtatcgat     1320
tccttgaata caatagaccc tacttccgga atacgatgga gactttgcct tcctatgtcg     1380
agggaaagtg gagattctag tttgagcgtt tttcaattta aatttattcc a              1431

<210> SEQ ID NO 22
<211> LENGTH: 477
<212> TYPE: PRT
<213> ORGANISM: Artificial Sequence
<220> FEATURE:
<223> OTHER INFORMATION: LIC12576

<400> SEQUENCE: 22

Met Arg Lys Ser Phe Val Val Leu Gly Ile Ile Phe Thr Ser Ile
1               5                   10                  15

Leu Leu Gly Phe Phe Val Trp Lys Ile Leu Thr Arg Lys Thr Asp Ser
            20                  25                  30

Val Tyr Arg Asn Phe Ser Lys Ser Asn Trp Glu Asp Val Ile Leu Glu
        35                  40                  45

Val Leu Ser Lys Lys Asp Pro Asp Leu Glu Asp Tyr Ser Tyr Ala Ser
    50                  55                  60

Met Ser Leu Ala Glu Phe Asn Phe His Leu Leu Thr Val Pro Ser Glu
65                  70                  75                  80

Lys Arg Glu Lys Val Ala Ser Arg Phe Ala Glu Lys Ser Gly Leu Lys
                85                  90                  95

Phe Phe Lys Arg Glu Val Gly Gly Arg Thr Ile Phe Thr Phe Glu Asp
            100                 105                 110

Arg Phe Phe Ser Phe Leu Pro Glu Gly Ser Phe Leu Lys Thr Arg Ala
        115                 120                 125

Leu Cys Lys Lys Leu Phe Leu Gly Ala Glu Tyr Glu Thr Val Asp Val
    130                 135                 140

Leu Ser Arg Tyr Leu Val Lys Leu Ile Ser Ser Asn Pro Leu Pro Leu
145                 150                 155                 160

Tyr Asn Glu Tyr Asn Gln Ala Leu Leu Lys Ser Leu Ser Val Gly Ser
                165                 170                 175

Ala Lys Glu Leu Asp Glu Asn Gly Arg Ser Lys Leu Ser Lys Leu Leu
            180                 185                 190

Glu Tyr Phe Ser Gly Lys Glu Asp Ser Pro Phe Asn Gly Ser Lys Ala
```

```
              195                 200                 205
    Val Ile Glu Gly Lys Asn Leu Asn Val Arg Thr Gly Pro Thr Glu
        210                 215                 220

Asn Pro Ile Ser Phe Gln Phe Lys Gly Gly Glu Ile Val Phe Ile Leu
    225                 230                 235                 240

Asp Arg Asp Ser Arg Thr Glu Thr Ile Ala Gly Lys Arg Gly Ser Trp
                        245                 250                 255

Asn Gln Ile Val Asp Leu Arg Asn Gly Asn Val Gly Trp Ile Phe Ser
                260                 265                 270

Gly Phe Leu Lys Asn Ile Pro Ser Asp Leu Ser Ile Ser Gln Thr Met
            275                 280                 285

Glu Glu Tyr Phe Arg Ala Leu Asp Arg Ser Pro Val Trp Asp Phe Glu
        290                 295                 300

Ser Trp Lys Glu Ala Ser Pro Pro Asn Gly Phe Gln Gly Glu Tyr His
    305                 310                 315                 320

Pro Thr Glu Lys Ile Ala Leu Asp Gly Asp Ser Gly Met Val Leu His
                        325                 330                 335

Ser Ser Lys Ser Lys Tyr Asp Leu Ile Cys Arg Ser Val Asp Glu Pro
                340                 345                 350

Phe Arg Asp Leu Glu Phe Tyr Val Ser Phe Leu Glu Gly Asn Glu Thr
            355                 360                 365

Ile Pro Val Phe Thr Leu Leu Ala Gly Ser Pro Gly Asp Leu Arg Lys
        370                 375                 380

Thr Phe Glu Ile Glu Met Asp Lys Glu Ser Ile Ser Ile Asn Arg Asn
    385                 390                 395                 400

Arg Tyr Ile Thr Gly Asp Asn Phe Ser Lys Arg Arg Phe Arg Leu Asn
                        405                 410                 415

Ile Gln Asn Gly Ser Ser Gly Phe Gln Ala Gly Leu Ile Val Ser Glu
                420                 425                 430

Lys Met Ala Leu Ser Gly Ile Asp Ser Leu Asn Thr Ile Asp Pro Thr
            435                 440                 445

Ser Gly Ile Arg Trp Arg Leu Cys Leu Pro Met Ser Arg Glu Ser Gly
        450                 455                 460

Asp Ser Ser Leu Ser Val Phe Gln Phe Lys Phe Ile Pro
    465                 470                 475

<210> SEQ ID NO 23
<211> LENGTH: 1440
<212> TYPE: DNA
<213> ORGANISM: Artificial Sequence
<220> FEATURE:
<223> OTHER INFORMATION: LIC13434

<400> SEQUENCE: 23
atgttaaaaa aatcctcggc tttaatttta gttttttgtt ttcttgcatg gggttgttct      60
ttcaataaag gcaaagacga taattctaaa aacttagaac ttcttttagg attgtattta     120
ctcaacgaag caaattacta ttgcgcccca gaagaaaacg ttcgaacaag cggaagcgca     180
ccaaatttta gcatatctac ttctaatctc agtcaagtcc ttttaacaga aaacggagta     240
tacgcggatg gtggaacggc atatctagta ggtacggtag agtttcccgg aattggtaga     300
aacaatccgt taggaatcgt ttatgccgaa caaaatcatc aatttgcatc caactcaaat     360
cgttttatat atccttttatg gataaataag tctggagatc taattcaaga cgatcaaaag     420
agcgaatcac ccggatacag atctaccaca accgcttttc ccataggctc aactcctggc     480
```

```
tactatgcac ctagtgccga ttataataac tttaacagta atctattagg aacaactttt      540
gttgttccag ctaatttaag tacaccagtt ataactaaaa aagttacgaa caacacacct      600
caaacttgcg aagagtataa atttcgcact gaacaaaacg gtttattagg aagttcctct      660
tcaggtttaa gtaaagtttg gcaatccaga aaaaaactga atatcaactt aatctttatt      720
ccagggcag tagccactcc taccgttgca ggtatggcca cgatgattca acattaaaa      780
gatatttatg ctcaaaacac agtaaaaatc gacgtgaccg tgacggcttc catagcagca      840
gcaggtgcgc cttatttaac aattcaaaat atcacggacg actatggaga cgttgctaat      900
tcattaggaa atctttataa aacaaatccc aataacgcac aagattcaaa ttctttgaat      960
atatacatta caagagatta tacggtttca aacgatgcgc ccgctggaat tttagggatt     1020
tcctccggca tacctggaat tccagttaca ggtacaccta gatctggtat gatcgtatt     1080
atagaaaatc atagaactgc ttccggatgt ggagtacaag acaagatttt gatctgtgca     1140
tcagatcaag ttttctcgc aaaaacaatc gctcatgaag gcggccatta tttgggtctt     1200
tatcatctag tcgaaaaga cgtaatcaaa ggacgttatt ccttagaccc tttaccagaa     1260
actccggaat gtaaagatca aaatggaaat aatatcgtag gtttaacgga atgtttagga     1320
gaaggatttt acaacagcgg aggattaaat ctaatgtttt gggcgggaaa tcctaaaatc     1380
gatcaaactc aattgacagg ggaacaaggt tgggtgctcc gttctcaccc tcttgtatat     1440
```

<210> SEQ ID NO 24
<211> LENGTH: 480
<212> TYPE: PRT
<213> ORGANISM: Artificial Sequence
<220> FEATURE:
<223> OTHER INFORMATION: LIC13434

<400> SEQUENCE: 24

```
Met Leu Lys Lys Ser Ser Ala Leu Ile Leu Val Phe Cys Phe Leu Ala
1               5                   10                  15

Trp Gly Cys Ser Phe Asn Lys Gly Lys Asp Asp Asn Ser Lys Asn Leu
            20                  25                  30

Glu Leu Leu Leu Gly Leu Tyr Leu Leu Asn Glu Ala Asn Tyr Tyr Cys
        35                  40                  45

Ala Pro Glu Glu Asn Val Arg Thr Ser Gly Ser Ala Pro Asn Phe Ser
    50                  55                  60

Ile Ser Thr Ser Asn Leu Ser Gln Val Leu Leu Thr Glu Asn Gly Val
65                  70                  75                  80

Tyr Ala Asp Gly Gly Thr Ala Tyr Leu Val Gly Thr Val Glu Phe Pro
                85                  90                  95

Gly Ile Gly Arg Asn Asn Pro Leu Gly Ile Val Tyr Ala Glu Gln Asn
            100                 105                 110

His Gln Phe Ala Ser Asn Ser Asn Arg Phe Ile Tyr Pro Leu Trp Ile
        115                 120                 125

Asn Lys Ser Gly Asp Leu Ile Gln Asp Gln Lys Ser Glu Ser Pro
    130                 135                 140

Gly Tyr Arg Ser Thr Thr Thr Ala Phe Pro Ile Gly Ser Thr Pro Gly
145                 150                 155                 160

Tyr Tyr Ala Pro Ser Ala Asp Tyr Asn Asn Phe Asn Ser Asn Leu Leu
                165                 170                 175

Gly Thr Thr Phe Val Val Pro Ala Asn Leu Ser Thr Pro Val Ile Thr
            180                 185                 190

Lys Lys Val Thr Asn Asn Thr Pro Gln Thr Cys Glu Glu Tyr Lys Phe
```

```
                    195                 200                 205
Arg Thr Glu Gln Asn Gly Leu Leu Gly Ser Ser Ser Gly Leu Ser
    210                 215                 220
Lys Val Trp Gln Ser Arg Lys Lys Leu Asn Ile Asn Leu Ile Phe Ile
225                 230                 235                 240
Pro Gly Ala Val Ala Thr Pro Thr Val Ala Gly Met Ala Thr Met Ile
                    245                 250                 255
Gln Thr Leu Lys Asp Ile Tyr Ala Gln Asn Thr Val Lys Ile Asp Val
                260                 265                 270
Thr Val Thr Ala Ser Ile Ala Ala Ala Gly Ala Pro Tyr Leu Thr Ile
            275                 280                 285
Gln Asn Ile Thr Asp Asp Tyr Gly Asp Val Ala Asn Ser Leu Gly Asn
    290                 295                 300
Leu Tyr Lys Thr Asn Pro Asn Asn Ala Gln Asp Ser Asn Ser Leu Asn
305                 310                 315                 320
Ile Tyr Ile Thr Arg Asp Tyr Thr Val Ser Asn Asp Ala Pro Ala Gly
                325                 330                 335
Ile Leu Gly Ile Ser Ser Gly Ile Pro Gly Ile Pro Val Thr Gly Thr
            340                 345                 350
Pro Arg Ser Gly Met Ile Val Phe Ile Glu Asn His Arg Thr Ala Ser
    355                 360                 365
Gly Cys Gly Val Gln Gly Gln Asp Leu Ile Cys Ala Ser Asp Gln Val
370                 375                 380
Phe Leu Ala Lys Thr Ile Ala His Glu Gly Gly His Tyr Leu Gly Leu
385                 390                 395                 400
Tyr His Leu Val Glu Lys Asp Val Ile Lys Gly Arg Tyr Ser Leu Asp
                405                 410                 415
Pro Leu Pro Glu Thr Pro Glu Cys Lys Asp Gln Asn Gly Asn Asn Ile
            420                 425                 430
Val Gly Leu Thr Glu Cys Leu Gly Gly Phe Tyr Asn Ser Gly Gly
    435                 440                 445
Leu Asn Leu Met Phe Trp Ala Gly Asn Pro Lys Ile Asp Gln Thr Gln
450                 455                 460
Leu Thr Gly Glu Gln Gly Trp Val Leu Arg Ser His Pro Leu Val Tyr
465                 470                 475                 480
```

<210> SEQ ID NO 25
<211> LENGTH: 543
<212> TYPE: DNA
<213> ORGANISM: Artificial Sequence
<220> FEATURE:
<223> OTHER INFORMATION: LIC13071

<400> SEQUENCE: 25

```
atgaaaatca atggtttat  atttgttttt  ttgtttagcg  ttagctggct  tcaagcggaa      60
ccgtttcagt taaaaagtcc tgaattgaca tcggttaaat taattgccaa cgaacaagtg     120
tttaatggct ttggatgttc tggagggaat atttctcctt ctctatcttg  acgggtctt     180
ccgaaagata ctaaaagtat tgcgttaact gtgtatgatc ctgatgctcc gactggaagc     240
gggtggtggc actgggtggt ttttaatctt ccatctacga ttacttcaat tccagctaat     300
gctggcaact tggaaaaaaa ccttcttcct aaagaagcga ttcaaagtag aaccgatttt     360
ggaacgtctg gttacggcgg gccttgtcct ccaaaaggtc ataagccgca tcgttattat     420
tttacggtgt acgcccttaa agataaaatc ccggcggatc aaaattcttc tggagctttg     480
```
atcggatttt tatcaatca acttaaaatc ggcgaagcac agattttagc aaaatacggc    540
aga    543

<210> SEQ ID NO 26
<211> LENGTH: 181
<212> TYPE: PRT
<213> ORGANISM: Artificial Sequence
<220> FEATURE:
<223> OTHER INFORMATION: LIC13071

<400> SEQUENCE: 26

Met Lys Ile Lys Trp Phe Ile Phe Val Phe Leu Phe Ser Val Ser Trp
1               5                   10                  15

Leu Gln Ala Glu Pro Phe Gln Leu Lys Ser Pro Glu Leu Thr Ser Val
            20                  25                  30

Lys Leu Ile Ala Asn Glu Gln Val Phe Asn Gly Phe Gly Cys Ser Gly
        35                  40                  45

Gly Asn Ile Ser Pro Ser Leu Ser Trp Thr Gly Leu Pro Lys Asp Thr
    50                  55                  60

Lys Ser Ile Ala Leu Thr Val Tyr Asp Pro Asp Ala Pro Thr Gly Ser
65                  70                  75                  80

Gly Trp Trp His Trp Val Val Phe Asn Leu Pro Ser Thr Ile Thr Ser
                85                  90                  95

Ile Pro Ala Asn Ala Gly Asn Leu Glu Lys Asn Leu Leu Pro Lys Glu
            100                 105                 110

Ala Ile Gln Ser Arg Thr Asp Phe Gly Thr Ser Gly Tyr Gly Gly Pro
        115                 120                 125

Cys Pro Pro Lys Gly His Lys Pro His Arg Tyr Tyr Phe Thr Val Tyr
    130                 135                 140

Ala Leu Lys Asp Lys Ile Pro Ala Asp Gln Asn Ser Ser Gly Ala Leu
145                 150                 155                 160

Ile Gly Phe Tyr Ile Asn Gln Leu Lys Ile Gly Glu Ala Gln Ile Leu
                165                 170                 175

Ala Lys Tyr Gly Arg
            180

<210> SEQ ID NO 27
<211> LENGTH: 1104
<212> TYPE: DNA
<213> ORGANISM: Artificial Sequence
<220> FEATURE:
<223> OTHER INFORMATION: LIC11224

<400> SEQUENCE: 27
atggcgtttg aaagtccgga cggaatgtcc tcaactgaga gtgtaggttt tttatcccag    60
atgggaaatt cttttaaaag tattcttacg ggaattgtat tattgcccgt atcttttatc    120
attatttaca atgtagaaac ttgtgagcaa gcaagtgctg ctctaaaaaa tgcaatgccc    180
gtcggacaag caaaagaagg ccaaccttcc tatgtgactg gaactttaaa agcgagtcct    240
cttggcggtg aattttaag aagtggttct ttcatttctt attccataag ttcggaagta    300
tatgcttggg acgaacaagt aaaaacggaa ggttctggaa gtaataaaaa agaagtcaga    360
aattgtatat aaaatggac ttcttctccg gagaatcctt ctggttttaa actttctgga    420
tgtcgtacaa aacgctatta tagaaaatcc gttcaagacc agtctgattc tgcatcgggt    480
gctctagttc atgcagatgg taaaaattat tcggttcaat agaagatgt agattttact    540 tctcaagttc cttccagaga tgcaaatgaa acgaaattc ttgccgggcg ttttgtttac    600

-continued

```
ggtgatggat atttatatag ttctaaatct tgtgtggagt ctgaaaaaga aggttgtgaa    660
aggattaaga tctctgttat tccgattccg aaggagata tgacttttgt aggagacgta    720
aaaggaaata gagtaggtca gtttgtttct tcggagggaa ataaattttt gaatgcgagt    780
gttggtaatt ttgcggaaac gatggcggat attaagtcgg atgataacac gatgaaatgg    840
gttgggagat tgattggatt tatagcaatg ttttctagtt ttactctgat ggcgggacct    900
ttgacttctc ttttaagttt tattccattt gtaggagatt tgggaggagg tttgatcaaa    960
gtggttttag gaatcgttgc ttttataatc actgcgatta caattctact cattaaattt   1020
tggtatatct ggttggttat acttttaggt ggaatcggct acggtatttta taagaaaaaa   1080 tattcggtcc aaaaagttgg aggt                                          1104
```

<210> SEQ ID NO 28
<211> LENGTH: 368
<212> TYPE: PRT
<213> ORGANISM: Artificial Sequence
<220> FEATURE:
<223> OTHER INFORMATION: LIC11224

<400> SEQUENCE: 28

```
Met Ala Phe Glu Ser Pro Asp Gly Met Ser Thr Glu Ser Val Gly
 1               5                  10                  15

Phe Leu Ser Gln Met Gly Asn Ser Phe Lys Ser Ile Leu Thr Gly Ile
                20                  25                  30

Val Leu Leu Pro Val Ser Phe Ile Ile Ile Tyr Asn Val Glu Thr Cys
            35                  40                  45

Glu Gln Ala Ser Ala Ala Leu Lys Asn Ala Met Pro Val Gly Gln Ala
        50                  55                  60

Lys Glu Gly Gln Pro Ser Tyr Val Thr Gly Thr Leu Lys Ala Ser Pro
 65                  70                  75                  80

Leu Gly Gly Glu Phe Leu Arg Ser Gly Ser Phe Ile Ser Tyr Ser Ile
                 85                  90                  95

Ser Ser Glu Val Tyr Ala Trp Asp Glu Gln Val Lys Thr Glu Gly Ser
            100                 105                 110

Gly Ser Asn Lys Lys Glu Val Arg Asn Cys Ile Leu Lys Trp Thr Ser
        115                 120                 125

Ser Pro Glu Asn Pro Ser Gly Phe Lys Leu Ser Gly Cys Arg Thr Lys
    130                 135                 140

Arg Tyr Tyr Arg Lys Ser Val Gln Asp Gln Ser Asp Ser Ala Ser Gly
145                 150                 155                 160

Ala Leu Val His Ala Asp Gly Lys Asn Tyr Ser Val Gln Leu Glu Asp
                165                 170                 175

Val Asp Phe Thr Ser Gln Val Pro Ser Arg Asp Ala Asn Glu Asn Glu
            180                 185                 190

Ile Leu Ala Gly Arg Phe Val Tyr Gly Asp Gly Tyr Leu Tyr Ser Ser
        195                 200                 205

Lys Ser Cys Val Glu Ser Glu Lys Glu Gly Cys Glu Arg Ile Lys Ile
    210                 215                 220

Ser Val Ile Pro Ile Pro Glu Gly Asp Met Thr Phe Val Gly Asp Val
225                 230                 235                 240

Lys Gly Asn Arg Val Gly Gln Phe Val Ser Ser Glu Gly Asn Lys Phe
                245                 250                 255

Leu Asn Ala Ser Val Gly Asn Phe Ala Glu Thr Met Ala Asp Ile Lys
            260                 265                 270
```

```
Ser Asp Asp Asn Thr Met Lys Trp Val Gly Arg Leu Ile Gly Phe Ile
        275                 280                 285

Ala Met Phe Ser Ser Phe Thr Leu Met Ala Gly Pro Leu Thr Ser Leu
    290                 295                 300

Leu Ser Phe Ile Pro Phe Val Gly Asp Leu Gly Gly Gly Leu Ile Lys
305                 310                 315                 320

Val Val Leu Gly Ile Val Ala Phe Ile Ile Thr Ala Ile Thr Ile Leu
                325                 330                 335

Leu Ile Lys Phe Trp Tyr Ile Trp Leu Val Ile Leu Leu Gly Gly Ile
            340                 345                 350

Gly Tyr Gly Ile Tyr Lys Lys Tyr Ser Val Gln Lys Val Gly Gly
        355                 360                 365

<210> SEQ ID NO 29
<211> LENGTH: 702
<212> TYPE: DNA
<213> ORGANISM: Artificial Sequence
<220> FEATURE:
<223> OTHER INFORMATION: LIC10027

<400> SEQUENCE: 29
atggacggaa tcgctctttt tacaagtcaa ggcttgtatt ttattttaa atggatccat      60
tttcttgcag gtgttgcatg gatcgggtta ctttggtaca ttaactttgt acaaggttct    120
ttctttgcag aaaccgacgc agatacaaag aaaaaagcca ctcaacaatt ggttccaaga    180
gttctttggt ggtttcgttg gggtgcgatg ttcactttcc ttagcggctg gtgtatgatc    240
attcatcaaa ttataaacgg agctactctt tccagtggcc aatggcttgc gataattctc    300
ggcggggat tgctcggttc tttgatgtgg tttaacgttt ggtttgtgat ttggcctgcg    360
caaaaagtag tgattgcatc tgcaaaggga gaaactacgg aaaatccggc tcctcgtgct    420
gcaagaggtc ttttagcttc taggacaaat actttacttt ctatccctat gttattttg    480
atgggagctg caagaaatct ttctatttct tttgatgtaa ctagcgcgga agctcatacg    540
tttttgggag tgattttagg aattcttgca atcgtagaaa tcaacgcgtt aaccgcaaca    600
ccggaaagcg ctagttttaa accgatcaaa accgttaagg gtgtaattac ttccggattt    660
attctttgtt taattatcta cgttttactt gaggctcttc tt                       702

<210> SEQ ID NO 30
<211> LENGTH: 234
<212> TYPE: PRT
<213> ORGANISM: Artificial Sequence
<220> FEATURE:
<223> OTHER INFORMATION: LIC10027

<400> SEQUENCE: 30

Met Asp Gly Ile Ala Leu Phe Thr Ser Gln Gly Leu Tyr Phe Ile Phe
1               5                   10                  15

Lys Trp Ile His Phe Leu Ala Gly Val Ala Trp Ile Gly Leu Leu Trp
            20                  25                  30

Tyr Ile Asn Phe Val Gln Gly Ser Phe Phe Ala Glu Thr Asp Ala Asp
        35                  40                  45

Thr Lys Lys Lys Ala Thr Gln Gln Leu Val Pro Arg Val Leu Trp Trp
    50                  55                  60

Phe Arg Trp Gly Ala Met Phe Thr Phe Leu Ser Gly Trp Cys Met Ile
65                  70                  75                  80

Ile His Gln Ile Ile Asn Gly Ala Thr Leu Ser Ser Gly Gln Trp Leu
```

```
                    85                  90                  95
Ala Ile Ile Leu Gly Gly Gly Leu Leu Gly Ser Leu Met Trp Phe Asn
            100                 105                 110

Val Trp Phe Val Ile Trp Pro Ala Gln Lys Val Val Ile Ala Ser Ala
        115                 120                 125

Lys Gly Glu Thr Thr Glu Asn Pro Ala Pro Arg Ala Ala Arg Gly Leu
    130                 135                 140

Leu Ala Ser Arg Thr Asn Thr Leu Leu Ser Ile Pro Met Leu Phe Leu
145                 150                 155                 160

Met Gly Ala Ala Arg Asn Leu Ser Ile Ser Phe Asp Val Thr Ser Ala
                165                 170                 175

Glu Ala His Thr Phe Leu Gly Val Ile Leu Gly Ile Leu Ala Ile Val
            180                 185                 190

Glu Ile Asn Ala Leu Thr Ala Thr Pro Glu Ser Ala Ser Phe Lys Pro
        195                 200                 205

Ile Lys Thr Val Lys Gly Val Ile Thr Ser Gly Phe Ile Leu Cys Leu
    210                 215                 220

Ile Ile Tyr Val Leu Leu Glu Ala Leu Leu
225                 230

<210> SEQ ID NO 31
<211> LENGTH: 426
<212> TYPE: DNA
<213> ORGANISM: Artificial Sequence
<220> FEATURE:
<223> OTHER INFORMATION: LIC10474

<400> SEQUENCE: 31
atggtatcag gaattacact catcgtgctc agcattctcg ctgtgccttc cctgcttttg      60
gcaaaaaaac cagatgcaaa agagttactt gcaaagattt caccttatca aggttggatc    120
ggtctggttt tctgcttttg gggaatttat ggaatcgtat ttcaaggact tctcggtctt    180
ggatggcttc ctacttggcc aatttactgg gtaactgctc ttttgggaaa catcgttcaa    240
gcagttctcg gattcattct cggtttcgga acaatctcta cttatgttct ttctaagaac    300
gaagaagcta agaaaaaagg tgctgaactc ttagcaaaat tggctcccat ccaaggtaaa    360
ttgggaattt ttggaattgc agtgggaatt tggacaatcg ttgcgtcctt ccttttctac    420
ggagta                                                                426

<210> SEQ ID NO 32
<211> LENGTH: 142
<212> TYPE: PRT
<213> ORGANISM: Artificial Sequence
<220> FEATURE:
<223> OTHER INFORMATION: LIC10474

<400> SEQUENCE: 32

Met Val Ser Gly Ile Thr Leu Ile Val Leu Ser Ile Leu Ala Val Pro
1               5                   10                  15

Ser Leu Leu Leu Ala Lys Lys Pro Asp Ala Lys Glu Leu Leu Ala Lys
            20                  25                  30

Ile Ser Pro Tyr Gln Gly Trp Ile Gly Leu Val Phe Cys Phe Trp Gly
        35                  40                  45

Ile Tyr Gly Ile Val Phe Gln Gly Leu Leu Gly Leu Gly Trp Leu Pro
    50                  55                  60

Thr Trp Pro Ile Tyr Trp Val Thr Ala Leu Leu Gly Asn Ile Val Gln
65                  70                  75                  80
```

```
Ala Val Leu Gly Phe Ile Leu Gly Phe Gly Thr Ile Ser Thr Tyr Val
                 85                  90                  95

Leu Ser Lys Asn Glu Glu Ala Lys Lys Gly Ala Glu Leu Leu Ala
            100                 105                 110

Lys Leu Ala Pro Ile Gln Gly Lys Leu Gly Ile Phe Gly Ile Ala Val
        115                 120                 125

Gly Ile Trp Thr Ile Val Ala Ser Phe Leu Phe Tyr Gly Val
    130                 135                 140

<210> SEQ ID NO 33
<211> LENGTH: 471
<212> TYPE: DNA
<213> ORGANISM: Artificial Sequence
<220> FEATURE:
<223> OTHER INFORMATION: LIC10411

<400> SEQUENCE: 33
atgaaatttc gttctattgt cattcttatg ttcgccgttt tttttacatc tggcgcgcta     60
ttcgcagaaa atctactga ggaacatatt aaatcgcttt cttccggttc cgattccgaa    120
aaatacgaat ctgcagttgc tcttggaaag acaaagaaa atccgcaat tccggaacta    180 atccaacttt taaatcgtaa caacgaacct aaaatcgcaa cggctgcagc gatctctttg    240
ggaaaaatag cggaacctgg tgattctaca atcgctttaa aaacaaaat tatttcctcc    300 gaaaacggag atatagttta tgcttctttg gcttctcttt taaacattac acaaaaaat    360 gaaaagttag aagattctac aaaagaagcc tttgaatacg cagataaaaa tcgtagaagt    420
gatgaatttg tagcggatct tttagaccta atcaaaaaga aactcaaact c             471

<210> SEQ ID NO 34
<211> LENGTH: 157
<212> TYPE: PRT
<213> ORGANISM: Artificial Sequence
<220> FEATURE:
<223> OTHER INFORMATION: LIC10411

<400> SEQUENCE: 34

Met Lys Phe Arg Ser Ile Val Ile Leu Met Phe Ala Val Phe Phe Thr
1               5                   10                  15

Ser Gly Ala Leu Phe Ala Glu Lys Ser Thr Glu Glu His Ile Lys Ser
            20                  25                  30

Leu Ser Ser Gly Ser Asp Ser Glu Lys Tyr Glu Ser Ala Val Ala Leu
        35                  40                  45

Gly Lys Asn Lys Glu Lys Ser Ala Ile Pro Glu Leu Ile Gln Leu Leu
    50                  55                  60

Asn Arg Asn Asn Glu Pro Lys Ile Ala Thr Ala Ala Ala Ile Ser Leu
65                  70                  75                  80

Gly Lys Ile Ala Glu Pro Gly Asp Ser Thr Ile Ala Leu Lys Asn Lys
                85                  90                  95

Ile Ile Ser Ser Glu Asn Gly Asp Ile Val Tyr Ala Ser Leu Ala Ser
            100                 105                 110

Leu Leu Asn Ile Thr Thr Lys Asn Glu Lys Leu Glu Asp Ser Thr Lys
        115                 120                 125

Glu Ala Phe Glu Tyr Ala Asp Lys Asn Arg Arg Ser Asp Glu Phe Val
    130                 135                 140

Ala Asp Leu Leu Asp Leu Ile Lys Lys Lys Leu Lys Leu
145                 150                 155
```

<210> SEQ ID NO 35
<211> LENGTH: 1320
<212> TYPE: DNA
<213> ORGANISM: Artificial Sequence
<220> FEATURE:
<223> OTHER INFORMATION: LIC20035

<400> SEQUENCE: 35

```
atgatgaaac gattttgttt ggctattgtt acggttgcga tttcttattg taactccact      60
cctaatgtgg agaataaagg taaagattta gaagttcaaa ttcttcctcc aaatatccgt     120
gtggaaaagt ataagaaac tttcaacatg aaagcagaag gtccggttgt taccgattgt     180
agtggtaaac cttgttctac tgaacagtta gatggtttaa aatcggatca aatcaaaaag     240
ttcaaaaaga acggagcttg gaaagaatat caggaaaaag aagattctgc tacgaaaaag     300
aaagtttctg ttctaattcg aaccggtgaa tataaggatg ataaagggga aggttcttgg     360
aagactcttt acgaaaccgg tgaggttctg cgtgacactc cttacgtagg tggtgtaaaa     420
gaaggagaag aaaagaaatt caaaagagat ggtgttcaaa cagagagtat tacttataaa     480
gccgataaaa agaacgggcc ttattggaaa aaaaacaacg aaggtttgat ggacgaagaa     540
ggttcctata agaagatca aaaagatggt ctttggactg aatactacgc ggaccccggt     600
caaaatggtg ctaagaaaaa agtgtccaac tattctaacg gtttaaaaca aggtcaggaa     660
acttcttttc ataaggacgg gagtacggtt caaagcgaag gttcttacaa ggatgatctg     720
aaaaccggta tctggaaaac ctattatgat aacggttcga ttcagatgga aggtggttac     780
aaacctaagt tagaacctgg aaccgaaaaa gaaaagatc caaaagaaaa aaaggcccctt     840
cgttccggtt actggaaaga atattataaa aatggaaata tatttgcaga aggtcaaaga     900
gagcatactc gaaaaggaat ttggaaattt aattggagta atggaaatcc cgcctacaaa     960
ggtgagatga tgaacgagtt tatgatgtcc tctgcggaag cttataacaa agaaggacag    1020
ttgatcggaa aaggaaaact tcagttttcc atcatgaaca tagacgaggc tacaaacgaa    1080
ctcaaagcga gttataaacc agacatccca tttacatatt ataaggacgg taaaaaacaa    1140
tttgaaattg taagcgattc taaagcgatc gaatacgacg aaaatggttc taaaaccgga    1200
gagggcccca tcatggtcgg tacaaataag aaaaacggct gctggacggt tggttctgga    1260
aaagtgtatt acataaacgg aaacgaaaac aaaagaatgg gagaaatgca aggttgtaaa    1320
```

<210> SEQ ID NO 36
<211> LENGTH: 440
<212> TYPE: PRT
<213> ORGANISM: Artificial Sequence
<220> FEATURE:
<223> OTHER INFORMATION: LIC20035

<400> SEQUENCE: 36

```
Met Met Lys Arg Phe Cys Leu Ala Ile Val Thr Val Ala Ile Ser Tyr
1               5                   10                  15

Cys Asn Ser Thr Pro Asn Val Glu Asn Lys Gly Lys Asp Leu Glu Val
            20                  25                  30

Gln Ile Leu Pro Pro Asn Ile Arg Val Glu Lys Tyr Lys Glu Thr Phe
        35                  40                  45

Asn Met Lys Ala Glu Gly Pro Val Val Thr Asp Cys Ser Gly Lys Pro
    50                  55                  60

Cys Ser Thr Glu Gln Leu Asp Gly Leu Lys Ser Asp Gln Ile Lys Lys
65                  70                  75                  80
```

-continued

```
Phe Lys Lys Asn Gly Ala Trp Lys Glu Tyr Gln Glu Lys Glu Asp Ser
                 85                  90                  95
Ala Thr Lys Lys Val Ser Val Leu Ile Arg Thr Gly Glu Tyr Lys
            100                 105                 110
Asp Asp Lys Arg Glu Gly Ser Trp Lys Thr Leu Tyr Glu Thr Gly Glu
            115                 120                 125
Val Leu Arg Asp Thr Pro Tyr Val Gly Val Lys Glu Gly Glu Glu
        130                 135                 140
Lys Lys Phe Lys Arg Asp Gly Val Gln Thr Glu Ser Ile Thr Tyr Lys
145                 150                 155                 160
Ala Asp Lys Lys Asn Gly Pro Tyr Trp Lys Lys Asn Glu Gly Leu
            165                 170                 175
Met Asp Glu Glu Gly Ser Tyr Lys Glu Asp Gln Lys Asp Gly Leu Trp
            180                 185                 190
Thr Glu Tyr Tyr Ala Asp Pro Gly Gln Asn Gly Ala Lys Lys Lys Val
        195                 200                 205
Ser Asn Tyr Ser Asn Gly Leu Lys Gln Gly Gln Glu Thr Ser Phe His
        210                 215                 220
Lys Asp Gly Ser Thr Val Gln Ser Glu Gly Ser Tyr Lys Asp Asp Leu
225                 230                 235                 240
Lys Thr Gly Ile Trp Lys Thr Tyr Tyr Asp Asn Gly Ser Ile Gln Met
            245                 250                 255
Glu Gly Gly Tyr Lys Pro Lys Leu Glu Pro Gly Thr Glu Lys Glu Lys
            260                 265                 270
Asp Pro Lys Glu Lys Lys Ala Leu Arg Ser Gly Tyr Trp Lys Glu Tyr
        275                 280                 285
Tyr Lys Asn Gly Asn Ile Phe Ala Glu Gly Gln Arg Glu His Thr Arg
290                 295                 300
Lys Gly Ile Trp Lys Phe Asn Trp Ser Asn Gly Asn Pro Ala Tyr Lys
305                 310                 315                 320
Gly Glu Met Met Asn Glu Phe Met Met Ser Ser Ala Glu Ala Tyr Asn
            325                 330                 335
Lys Glu Gly Gln Leu Ile Gly Lys Gly Lys Leu Gln Phe Ser Ile Met
            340                 345                 350
Asn Ile Asp Glu Ala Thr Asn Glu Leu Lys Ala Ser Tyr Lys Pro Asp
        355                 360                 365
Ile Pro Phe Thr Tyr Tyr Lys Asp Gly Lys Lys Gln Phe Glu Ile Val
        370                 375                 380
Ser Asp Ser Lys Ala Ile Glu Tyr Asp Glu Asn Gly Ser Lys Thr Gly
385                 390                 395                 400
Glu Gly Pro Ile Met Val Gly Thr Asn Lys Lys Asn Gly Cys Trp Thr
            405                 410                 415
Val Gly Ser Gly Lys Val Tyr Tyr Ile Asn Gly Asn Glu Asn Lys Arg
            420                 425                 430
Met Gly Glu Met Gln Gly Cys Lys
            435                 440

<210> SEQ ID NO 37
<211> LENGTH: 2397
<212> TYPE: DNA
<213> ORGANISM: Artificial Sequence
<220> FEATURE:
<223> OTHER INFORMATION: LIC20197

<400> SEQUENCE: 37
```

```
atgagaattt taaaatattc tatttaatt attatttat tactaaactt ccaaacttct    60 attttgcac aaccttcctt tcgttcttta ggaatgaaac aggaatcctc cgaacttcta   120
tcttctttaa aagaaacaaa tccttatggg atttctcaca gaggacttga ttccaaagtg   180
gatctttctc cttctatgcc tcccgtagga aaccaaggag aacaaggtag ttgtgttgct   240
tggtctactg cctacgcgac taaaagtttt caggaatata tagaaagaaa aagttctaag   300
gattggtctc tcagaaccgc ccaaggagct cctaattaca gtaaaatttt ttctcccgca   360
tttatataca accagatcaa cggtggaaga gacaacggat ctttaatttc agacgcaatg   420
agagttatgg tggaaatggg agcagctccc tgggaaacta tgccttacaa tcccgcagat   480
tatagaaccc gtccttctca agctgcaatt gaagctgctt ctaaatacaa agcgaaagaa   540
ttcttaagag taaaaactac cgatatgaac gaagtcaaag ctcaactttc ggaaggcaaa   600
cctgtcgttg ccggggtttt ggtttatgag aatttttta atctcaaagg agatcaaatt   660 tataagaag gtttaggcaa aacctacgga ggacacgcga tcgccttagt aggttatgac   720
gattctaaaa acgcagtcaa atttattaat tcttggggaa ccgattgggg agaccaaggc   780
tacggatata ttgactatcg ttggtttact aaaatctgcc aaggcgcttt tgtaatgatc   840
gatcaagtag aaaccgtcat agatcaagga aagccggatt ccaatacacc cgaacctact   900
tcagttgcaa acgattctaa tcctatagca ccctcttcta tcaccgcttc tcaaggaagt   960
tttatagata aggttttgat caattgggaa gttgttccag gtgcggtcgg ttatgaaatt  1020
catagaaaag gccccggaga ttccaacttt ggaaaaatag gattgtctgg taccaatagt  1080
tttaacgacg atggggttca acccaacctt gcttacaaat ataagattct aaccttgacg  1140
gattcttccg cttccgattt gtcccaagga gaagtgatcg gatttgcaaa aacagaggaa  1200
ttaaaacctc ctcctaaagt tttaggagtc aaagcaactc aaggacaata cgataacaaa  1260
gtcgaactcg tttgggaacc tggggacgct tcttccgaat atcaaatttt taaatggaat  1320
aaaactcaga aaagatacag tccgattgga acttctaaaa tcaatagtta cgtagataca  1380
tccgcagcaa aaaagggat tgtagaaatt tacgttgttt ccgcaaaact aggaggcaaa  1440
acaggagaac cttcggatgc agcgagcggt tttactttc aacctaaaac tcctcctgca  1500
aaaccgttag ggttaatcgc cagtcgaggt gcgtaccaaa acaaagtaga actaaaatgg  1560
cagaaagttt ctggagcttc taaatatcta atatttcgat atattaagtc cggttggatc  1620
ggaggtggcg cttgggaaaa aatttccgag actggtaagg aagaatttat cgatgaaaat  1680
cttcccgcac gttacgcgta ttattctgtg actgcggtca atacgaagg taaaaatgga  1740 cctttttcta gttttgctta cggttatacg gatccaaata aacaagagg tgttaaactc  1800 tcttccccag aaaacgtcaa aggtgttta gacgttaaag aagccaaaat cagtataact  1860
tgggacccgg ttaagaagc atcagaatat tatgttttc gtaagaagag aggggaatca  1920
aaatggactt ttctaggctc tgcgggaaat aaaaacactt acgtggccga agtgcctgaa  1980
aaagaaacct tatttcttta ttctgtaact tctaaaaccg atttaggagg ggaaagtgga  2040
aattcacttc cagtctccgc tgtaatttcc acggcagttg tagctcctaa aaaaagaacc  2100
tttggtggag attccagtct tgaaaaattc aagggtcctt ggaccgcaat ggcatgggat  2160
ggtaacaacg gagttagcca agtacttta gaaatcgaaa gtcaggataa cgtcaattat  2220
acggtcaaat ttaataagaa aaagatcttt gaaggtaaat atgtagaaga atctccgatc  2280
atagacaagg acgaaaatt caagatagag atcgaaaaaa cgggtgacgc actttcagtt  2340
acgatgaaag atccgtcgat cgtaaatcaa aaatctaatt tatcttttct taaagaa    2397
```

<210> SEQ ID NO 38
<211> LENGTH: 799
<212> TYPE: PRT
<213> ORGANISM: Artificial Sequence
<220> FEATURE:
<223> OTHER INFORMATION: LIC20197

<400> SEQUENCE: 38

```
Met Arg Ile Leu Lys Tyr Ser Ile Leu Ile Ile Leu Leu Asn
1               5                   10                  15

Phe Gln Thr Ser Ile Phe Ala Gln Pro Ser Phe Arg Ser Leu Gly Met
                20                  25                  30

Lys Gln Glu Ser Ser Glu Leu Leu Ser Ser Leu Lys Glu Thr Asn Pro
            35                  40                  45

Tyr Gly Ile Ser His Arg Gly Leu Asp Ser Lys Val Asp Leu Ser Pro
50                  55                  60

Ser Met Pro Pro Val Gly Asn Gln Gly Glu Gln Gly Ser Cys Val Ala
65                  70                  75                  80

Trp Ser Thr Ala Tyr Ala Thr Lys Ser Phe Gln Glu Tyr Ile Glu Arg
                85                  90                  95

Lys Ser Ser Lys Asp Trp Ser Leu Arg Thr Ala Gln Gly Ala Pro Asn
            100                 105                 110

Tyr Ser Lys Ile Phe Ser Pro Ala Phe Ile Tyr Asn Gln Ile Asn Gly
        115                 120                 125

Gly Arg Asp Asn Gly Ser Leu Ile Ser Asp Ala Met Arg Val Met Val
    130                 135                 140

Glu Met Gly Ala Ala Pro Trp Glu Thr Met Pro Tyr Asn Pro Ala Asp
145                 150                 155                 160

Tyr Arg Thr Arg Pro Ser Gln Ala Ala Ile Glu Ala Ala Ser Lys Tyr
                165                 170                 175

Lys Ala Lys Glu Phe Leu Arg Val Lys Thr Thr Asp Met Asn Glu Val
            180                 185                 190

Lys Ala Gln Leu Ser Glu Gly Lys Pro Val Val Ala Gly Val Leu Val
        195                 200                 205

Tyr Glu Asn Phe Phe Asn Leu Lys Gly Asp Gln Ile Tyr Lys Glu Gly
    210                 215                 220

Leu Gly Lys Thr Tyr Gly Gly His Ala Ile Ala Leu Val Gly Tyr Asp
225                 230                 235                 240

Asp Ser Lys Asn Ala Val Lys Phe Ile Asn Ser Trp Gly Thr Asp Trp
                245                 250                 255

Gly Asp Gln Gly Tyr Gly Tyr Ile Asp Tyr Arg Trp Phe Thr Lys Ile
            260                 265                 270

Cys Gln Gly Ala Phe Val Met Ile Asp Gln Val Glu Thr Val Ile Asp
        275                 280                 285

Gln Gly Lys Pro Asp Ser Asn Thr Pro Glu Pro Thr Ser Val Ala Asn
    290                 295                 300

Asp Ser Asn Pro Ile Ala Pro Ser Ser Ile Thr Ala Ser Gln Gly Ser
305                 310                 315                 320

Phe Ile Asp Lys Val Leu Ile Asn Trp Glu Val Val Pro Gly Ala Val
                325                 330                 335

Gly Tyr Glu Ile His Arg Lys Gly Pro Gly Asp Ser Asn Phe Gly Lys
            340                 345                 350

Ile Gly Leu Ser Gly Thr Asn Ser Phe Asn Asp Asp Gly Val Gln Pro
        355                 360                 365
```

```
Asn Leu Ala Tyr Lys Tyr Lys Ile Leu Thr Leu Thr Asp Ser Ser Ala
    370                 375                 380

Ser Asp Leu Ser Gln Gly Glu Val Ile Gly Phe Ala Lys Thr Glu Glu
385                 390                 395                 400

Leu Lys Pro Pro Lys Val Leu Gly Val Lys Ala Thr Gln Gly Gln
            405                 410                 415

Tyr Asp Asn Lys Val Glu Leu Val Trp Glu Pro Gly Asp Ala Ser Ser
            420                 425                 430

Glu Tyr Gln Ile Phe Lys Trp Asn Lys Thr Gln Lys Arg Tyr Ser Pro
        435                 440                 445

Ile Gly Thr Ser Lys Ile Asn Ser Tyr Val Asp Thr Ser Ala Ala Lys
    450                 455                 460

Lys Gly Ile Val Glu Ile Tyr Val Val Ser Ala Lys Leu Gly Gly Lys
465                 470                 475                 480

Thr Gly Glu Pro Ser Asp Ala Ala Ser Gly Phe Thr Phe Gln Pro Lys
            485                 490                 495

Thr Pro Pro Ala Lys Pro Leu Gly Leu Ile Ala Ser Arg Gly Ala Tyr
            500                 505                 510

Gln Asn Lys Val Glu Leu Lys Trp Gln Lys Val Ser Gly Ala Ser Lys
        515                 520                 525

Tyr Leu Ile Phe Arg Tyr Ile Lys Ser Gly Trp Ile Gly Gly Ala
    530                 535                 540

Trp Glu Lys Ile Ser Glu Thr Gly Lys Glu Glu Phe Ile Asp Glu Asn
545                 550                 555                 560

Leu Pro Ala Arg Tyr Ala Tyr Tyr Ser Val Thr Ala Val Asn Thr Glu
            565                 570                 575

Gly Lys Asn Gly Pro Phe Ser Ser Phe Ala Tyr Gly Tyr Thr Asp Pro
            580                 585                 590

Asn Lys Gln Arg Gly Val Lys Leu Ser Pro Glu Asn Val Lys Gly
        595                 600                 605

Val Leu Asp Val Lys Glu Ala Lys Ile Ser Ile Thr Trp Asp Pro Val
    610                 615                 620

Lys Glu Ala Ser Glu Tyr Tyr Val Phe Arg Lys Lys Arg Gly Glu Ser
625                 630                 635                 640

Lys Trp Thr Phe Leu Gly Ser Ala Gly Asn Lys Asn Thr Tyr Val Ala
            645                 650                 655

Glu Val Pro Glu Lys Glu Thr Leu Phe Leu Tyr Ser Val Thr Ser Lys
            660                 665                 670

Thr Asp Leu Gly Gly Glu Ser Gly Asn Ser Leu Pro Val Ser Ala Val
        675                 680                 685

Ile Ser Thr Ala Val Val Ala Pro Lys Lys Arg Thr Phe Gly Gly Asp
    690                 695                 700

Ser Ser Leu Glu Lys Phe Lys Gly Pro Trp Thr Ala Met Ala Trp Asp
705                 710                 715                 720

Gly Asn Asn Gly Val Ser Gln Val Leu Leu Glu Ile Glu Ser Gln Asp
            725                 730                 735

Asn Val Asn Tyr Thr Val Lys Phe Asn Lys Lys Ile Phe Glu Gly
            740                 745                 750

Lys Tyr Val Glu Glu Ser Pro Ile Ile Asp Lys Asp Gly Lys Phe Lys
        755                 760                 765

Ile Glu Ile Glu Lys Thr Gly Asp Ala Leu Ser Val Thr Met Lys Asp
    770                 775                 780
```

Pro Ser Ile Val Asn Gln Lys Ser Asn Leu Ser Phe Leu Lys Glu
785                 790                 795

<210> SEQ ID NO 39
<211> LENGTH: 1197
<212> TYPE: DNA
<213> ORGANISM: Artificial Sequence
<220> FEATURE:
<223> OTHER INFORMATION: LIC11088

<400> SEQUENCE: 39

| | | | | | |
|---|---|---|---|---|---|
| atgaggtttt | tagtatattc | tatttctttg | ttattttaa | ttcgttgcgg | atctggaatt | 60 |
| cttcccttct | ctcccttaa | caaaaaagaa | tccaatttaa | acgaactttt | actactttt | 120 |
| ttgattccac | aaaactctta | cgtttggaac | ttacctcctg | gttttcccac | tccggttgtt | 180 |
| cccgcttcca | atcctatgac | tcaagagaaa | gtagatttag | gaagattttt | attttatgat | 240 |
| cgcaaacttt | cgggcaacca | gactcagtct | tgtgcctctt | gtcataaaca | atccctcgct | 300 |
| tttacggatg | gtctgaccaa | aggaattggt | tctacgggag | aagtacatcc | cagaaacgct | 360 |
| caaggaatta | tcaacgttgc | atataacgtg | cgtcagactt | gggtcaatcc | gactctaaaa | 420 |
| gatttagaag | atcaaatgct | cgttcccatg | ttcggagaac | acccagtaga | acttggtcta | 480 |
| gccaaccacg | aaaacgaatt | actcgatcgt | ttgagatcag | aaaatcgtta | tcaatctatg | 540 |
| tttcaaaagg | cgtttccact | cggagatcct | tttacggttt | ccaatgtaat | caaggcaatc | 600 |
| gcctgttttg | aaagaaccct | catctccgga | cgttctccct | acgataaata | tttgtatgac | 660 |
| ggaaatattt | ccgcgcttgg | caattccgcc | caaagagctt | ctattctcag | aggagcccaa | 720 |
| attttctttt | cagaaaaagg | agaatgtttt | cattgccacg | gaggttttaa | ctttacggaa | 780 |
| acgagtattc | actccggaag | cgtcaattca | gaattacat | ttcataataa | cggtttatac | 840 |
| aatataggtg | ggactgggga | ttatccagta | gacaatcctg | gattgtttga | atttacagga | 900 |
| ttagcttctg | ataaaggtaa | attcagagct | ccttctatta | gaaatattga | attaactgct | 960 |
| ccttatatgc | acgacggttc | gatcgattct | ttggagaacg | tcgtagaaca | ttacaacgcg | 1020 |
| ggaggcagaa | acatactcaa | cggtctttat | gcgggagacg | gaagagccaa | tccaaataaa | 1080 |
| aacgcatttg | tttttccaat | tggtctgacc | gcaggcgaaa | aaacggacct | agttaatttt | 1140 |
| ctaaaaagtt | taacggatac | ggagttcgta | aatgatccga | acacagtaa | tcctttc | 1197 |

<210> SEQ ID NO 40
<211> LENGTH: 399
<212> TYPE: PRT
<213> ORGANISM: Artificial Sequence
<220> FEATURE:
<223> OTHER INFORMATION: LIC11088

<400> SEQUENCE: 40

Met Arg Phe Leu Val Tyr Ser Ile Ser Leu Leu Phe Leu Ile Arg Cys
1               5                   10                  15

Gly Ser Gly Ile Leu Pro Phe Pro Phe Asn Lys Lys Glu Ser Asn
            20                  25                  30

Leu Asn Glu Leu Leu Leu Leu Phe Leu Ile Pro Gln Asn Ser Tyr Val
        35                  40                  45

Trp Asn Leu Pro Pro Gly Phe Pro Thr Pro Val Val Pro Ala Ser Asn
    50                  55                  60

Pro Met Thr Gln Glu Lys Val Asp Leu Gly Arg Phe Leu Phe Tyr Asp
65                  70                  75                  80

Arg Lys Leu Ser Gly Asn Gln Thr Gln Ser Cys Ala Ser Cys His Lys 85                  90                  95
Gln Ser Leu Ala Phe Thr Asp Gly Leu Thr Lys Gly Ile Gly Ser Thr
                100                 105                 110

Gly Glu Val His Pro Arg Asn Ala Gln Gly Ile Ile Asn Val Ala Tyr
                115                 120                 125

Asn Val Arg Gln Thr Trp Val Asn Pro Thr Leu Lys Asp Leu Glu Asp
    130                 135                 140

Gln Met Leu Val Pro Met Phe Gly Glu His Pro Val Glu Leu Gly Leu
145                 150                 155                 160

Ala Asn His Glu Asn Glu Leu Leu Asp Arg Leu Arg Ser Glu Asn Arg
                165                 170                 175

Tyr Gln Ser Met Phe Gln Lys Ala Phe Pro Leu Gly Asp Pro Phe Thr
                180                 185                 190

Val Ser Asn Val Ile Lys Ala Ile Ala Cys Phe Glu Arg Thr Leu Ile
                195                 200                 205

Ser Gly Arg Ser Pro Tyr Asp Lys Tyr Leu Tyr Asp Gly Asn Ile Ser
                210                 215                 220

Ala Leu Gly Asn Ser Ala Gln Arg Ala Ser Ile Leu Arg Gly Ala Gln
225                 230                 235                 240

Ile Phe Phe Ser Glu Lys Gly Glu Cys Phe His Cys His Gly Gly Phe
                245                 250                 255

Asn Phe Thr Glu Thr Ser Ile His Ser Gly Ser Val Asn Ser Glu Ile
                260                 265                 270

Thr Phe His Asn Asn Gly Leu Tyr Asn Ile Gly Gly Thr Gly Asp Tyr
                275                 280                 285

Pro Val Asp Asn Pro Gly Leu Phe Glu Phe Thr Gly Leu Ala Ser Asp
                290                 295                 300

Lys Gly Lys Phe Arg Ala Pro Ser Ile Arg Asn Ile Glu Leu Thr Ala
305                 310                 315                 320

Pro Tyr Met His Asp Gly Ser Ile Asp Ser Leu Glu Asn Val Val Glu
                325                 330                 335

His Tyr Asn Ala Gly Gly Arg Asn Ile Leu Asn Gly Leu Tyr Ala Gly
                340                 345                 350

Asp Gly Arg Ala Asn Pro Asn Lys Asn Ala Phe Val Phe Pro Ile Gly
                355                 360                 365

Leu Thr Ala Gly Glu Lys Thr Asp Leu Val Asn Phe Leu Lys Ser Leu
            370                 375                 380

Thr Asp Thr Glu Phe Val Asn Asp Pro Lys His Ser Asn Pro Phe
385                 390                 395

<210> SEQ ID NO 41
<211> LENGTH: 945
<212> TYPE: DNA
<213> ORGANISM: Artificial Sequence
<220> FEATURE:
<223> OTHER INFORMATION: LIC11089

<400> SEQUENCE: 41
atgactaaaa aagttttagt cttaggttct atcgttttat tttgttttc tttgattcat      60 tgttctccaa ataaaataa taatgattcc aaattgttat cattagctgc ttgatcgca      120 ctcggaaatc aaggaattca gttttccgct tacgccggtt ctcaaaaatt agaatgtggt    180 caaacccctca gaggtcattc tagatcttta gaaacgatct ccttcattcc caatgcacac   240
attgcagaga gcactacgtt tcaattacac gactttcgtc ttttttgtaca cggagttact   300

```
ttgatccaaa actctggaga agaaactcct ctcactctca atcaagacgg taagtttcaa    360
tccggagaaa tcgctctttt agattttgaa aataaaacag gaaagtgtaa tggtactacg    420
gatacaaata acgtcgtttc tgcgttaatt ccttcgggta cgtatcaagg tattaagttt    480
atcgtcggga tacctgaaaa caaaaatcac ttagatgcag acaatcaatc tcccccactc    540
gataactctg gaatgttctg gagttggaca agcggttata agttttaaa gctggatttt      600
gaaaccgccg aaaccttagg cgtagaaact tcggtccaca taggttctgc caattgtgta    660
ggctctggaa gttcgagtac ttgcgcgaga gtcaatcgta ttccggtcac cctaattccg    720
gaaggtggtt ttaatccttc cactcaagaa attaaaatca acattcaagc tcttttacaa    780
ggaattgatc ttaccgccaa cccaaacgca gcgatgtgta tgtcaggact tgtaggcgca    840
acaagcaccg gttgtcctac catctttgca aacataggtt tggatctaaa tgcaggcacc    900
ccgattactc cggccaaaac cgttttttcg atcaaggcta aaaat                    945
```

<210> SEQ ID NO 42
<211> LENGTH: 315
<212> TYPE: PRT
<213> ORGANISM: Artificial Sequence
<220> FEATURE:
<223> OTHER INFORMATION: LIC11089

<400> SEQUENCE: 42

```
Met Thr Lys Lys Val Leu Val Leu Gly Ser Ile Val Leu Phe Cys Phe
 1               5                  10                  15

Ser Leu Ile His Cys Ser Pro Asn Lys Asn Asn Asp Ser Lys Leu
            20                  25                  30

Leu Ser Leu Ala Ala Leu Ile Ala Leu Gly Asn Gln Gly Ile Gln Phe
        35                  40                  45

Ser Ala Tyr Ala Gly Ser Gln Lys Leu Glu Cys Gly Gln Thr Leu Arg
    50                  55                  60

Gly His Ser Arg Ser Leu Glu Thr Ile Ser Phe Ile Pro Asn Ala His
65                  70                  75                  80

Ile Ala Glu Ser Thr Thr Phe Gln Leu His Asp Phe Arg Leu Phe Val
                85                  90                  95

His Gly Val Thr Leu Ile Gln Asn Ser Gly Glu Thr Pro Leu Thr
            100                 105                 110

Leu Asn Gln Asp Gly Lys Phe Gln Ser Gly Glu Ile Ala Leu Leu Asp
        115                 120                 125

Phe Glu Asn Lys Thr Gly Lys Cys Asn Gly Thr Thr Asp Thr Asn Asn
    130                 135                 140

Val Val Ser Ala Leu Ile Pro Ser Gly Thr Tyr Gln Gly Ile Lys Phe
145                 150                 155                 160

Ile Val Gly Ile Pro Glu Asn Lys Asn His Leu Asp Ala Asp Asn Gln
                165                 170                 175

Ser Pro Pro Leu Asp Asn Ser Gly Met Phe Trp Ser Trp Thr Ser Gly
            180                 185                 190

Tyr Lys Phe Leu Lys Leu Asp Phe Glu Thr Ala Glu Thr Leu Gly Val
        195                 200                 205

Glu Thr Ser Val His Ile Gly Ser Ala Asn Cys Val Gly Ser Gly Ser
    210                 215                 220

Ser Ser Thr Cys Ala Arg Val Asn Arg Ile Pro Val Thr Leu Ile Pro
225                 230                 235                 240

Glu Gly Gly Phe Asn Pro Ser Thr Gln Glu Ile Lys Ile Asn Ile Gln
                245                 250                 255
```

```
Ala Leu Leu Gln Gly Ile Asp Leu Thr Ala Asn Pro Asn Ala Ala Met
            260                 265                 270

Cys Met Ser Gly Leu Val Gly Ala Thr Ser Thr Gly Cys Pro Thr Ile
        275                 280                 285

Phe Ala Asn Ile Gly Leu Asp Leu Asn Ala Gly Thr Pro Ile Thr Pro
    290                 295                 300

Ala Lys Thr Val Phe Ser Ile Lys Ala Lys Asn
305                 310                 315

<210> SEQ ID NO 43
<211> LENGTH: 924
<212> TYPE: DNA
<213> ORGANISM: Artificial Sequence
<220> FEATURE:
<223> OTHER INFORMATION: LIC11687

<400> SEQUENCE: 43
ttgcttgtat ttcaacaaat tcaatttaag aaaaggagtt ttatgaaaaa ggttttttt       60 cagataaagt ttttaactt tgtgattatt tttttattat gtaattataa tgtttatgct     120
tggggatggg aagggcatcg tacaattgga attattgcgc aacaattatt gataaattct     180 aaaaagttg atccaataaa tgatatttta ggagatctaa ctttagaaca aatttctact     240
tgtccggatg agtaaaaagc atttcagtct caaagaagag agatgagtcc agtttgtagt     300
caagtgttta gcagtccagc acctccgaca aatacaggtc cttggcattt tatagatatt     360
cccatttcat tgacgaatcc tacccatgac gatatagaaa aaatttgtaa atctacctgt     420
gtagtagctg aaattaataa atggagtagt gtgttagcgg atacaactca gacaaaagca     480
aaacgattac aagctctttc ttttgttgta cattttattg gggatttaca tcaaccttta     540
catactgcgg aaagaaacaa tgatcttggg ggaaatcggg tgagtgtgca aattggaaaa     600
cgtaagacta atttgcatag tatgtgggat atcaatttag taattatat cagtacaaac     660 ccagtcacgg tgactattat tttaaaatcg gacatagctt ttgcacaaag tgaaactcaa     720
atgaatcctg aggtttggac gttttcaaagt tttcatttg ctcgcaatgt cgcttatgat     780
ggaattccaa gtggtcgttc aattacaaga atttcagatt catatattca aaatgcgttg     840
ccagttgtaa aacatcagct tgcaaatgca ggcgttagat tagctaggca tttggagaaa     900 ttatttcta agcctggttc tgaa                                             924

<210> SEQ ID NO 44
<211> LENGTH: 308
<212> TYPE: PRT
<213> ORGANISM: Artificial Sequence
<220> FEATURE:
<223> OTHER INFORMATION: LIC11687

<400> SEQUENCE: 44

Met Leu Val Phe Gln Gln Ile Gln Phe Lys Lys Arg Ser Phe Met Lys
1               5                   10                  15

Lys Val Phe Phe Gln Ile Lys Phe Leu Thr Phe Val Ile Ile Phe Leu
            20                  25                  30

Leu Cys Asn Tyr Asn Val Tyr Ala Trp Gly Trp Glu Gly His Arg Thr
        35                  40                  45

Ile Gly Ile Ile Ala Gln Gln Leu Leu Ile Asn Ser Lys Lys Phe Asp
    50                  55                  60

Pro Ile Asn Asp Ile Leu Gly Asp Leu Thr Leu Glu Gln Ile Ser Thr
65                  70                  75                  80
```

Cys Pro Asp Glu Leu Lys Ala Phe Gln Ser Gln Arg Arg Glu Met Ser
                85                  90                  95

Pro Val Cys Ser Gln Val Phe Ser Ser Pro Ala Pro Thr Asn Thr
            100                 105                 110

Gly Pro Trp His Phe Ile Asp Ile Pro Ile Ser Leu Thr Asn Pro Thr
            115                 120                 125

His Asp Asp Ile Glu Lys Ile Cys Lys Ser Thr Cys Val Val Ala Glu
130                 135                 140

Ile Asn Lys Trp Ser Ser Val Leu Ala Asp Thr Thr Gln Thr Lys Ala
145                 150                 155                 160

Lys Arg Leu Gln Ala Leu Ser Phe Val His Phe Ile Gly Asp Leu
                165                 170                 175

His Gln Pro Leu His Thr Ala Glu Arg Asn Asn Asp Leu Gly Gly Asn
            180                 185                 190

Arg Val Ser Val Gln Ile Gly Lys Arg Lys Thr Asn Leu His Ser Met
            195                 200                 205

Trp Asp Ile Asn Leu Val Asn Tyr Ile Ser Thr Asn Pro Val Thr Val
210                 215                 220

Thr Ile Ile Leu Lys Ser Asp Ile Ala Phe Ala Gln Ser Glu Thr Gln
225                 230                 235                 240

Met Asn Pro Glu Val Trp Thr Phe Gln Ser Phe His Phe Ala Arg Asn
                245                 250                 255

Val Ala Tyr Asp Gly Ile Pro Ser Gly Arg Ser Ile Thr Arg Ile Ser
            260                 265                 270

Asp Ser Tyr Ile Gln Asn Ala Leu Pro Val Val Lys His Gln Leu Ala
            275                 280                 285

Asn Ala Gly Val Arg Leu Ala Arg His Leu Glu Lys Leu Phe Ser Lys
290                 295                 300

Pro Gly Ser Glu
305

<210> SEQ ID NO 45
<211> LENGTH: 648
<212> TYPE: DNA
<213> ORGANISM: Artificial Sequence
<220> FEATURE:
<223> OTHER INFORMATION: LIC11711

<400> SEQUENCE: 45
atgtcggcta taaatcaaa atccattttt aaaaatgcct tattttttt aggaataagc       60 ggattgttat ttttgttact tcttgtttt actacaaaaa gtacagataa cgaatcgata      120
aaatacgaat cggttcctaa tccagcagga gaaaacgaag ttgtattaaa cgaagaaggc    180
caagaaacaa ctttaaatac gggagatccc gcttcttttt taaaaccttc caaagaccct    240
ttagaatatt ttagagttca tatttcgagc gacggttatc agctacgtca attgagaggt    300
tctaaattta tcaaaagaaa agtagataaa ggggagacg ttttgatcag cgaagaattg     360
gctcgttata caaaatcaa ttttatagac gatggaatca tcatcgtagt attgaacgga     420
aatacgggag catttgaaac gattcgtttt aataccaggg tccccagaat taatgatctc    480
gctaaaatcg ttcaaaacga cgtaacacgt tggtctatgg aacattccga agaaaaaccg    540
gttgtgacca aatttcagat ccactattct ttagaattaa aaaataaaac cggcagcact    600
cgagacgcgg tcaagaagaa attaaaaaaa gaagtgattc gcagaaaa                 648

<210> SEQ ID NO 46
<211> LENGTH: 216
<212> TYPE: PRT
<213> ORGANISM: Artificial Sequence
<220> FEATURE:
<223> OTHER INFORMATION: LIC11711

<400> SEQUENCE: 46

```
Met Ser Ala Ile Lys Ser Lys Ser Ile Phe Lys Asn Ala Leu Phe Phe
1               5                   10                  15

Leu Gly Ile Ser Gly Leu Leu Phe Leu Leu Ser Cys Phe Thr Thr
            20                  25                  30

Lys Ser Thr Asp Asn Glu Ser Ile Lys Tyr Glu Ser Val Pro Asn Pro
        35                  40                  45

Ala Gly Glu Asn Glu Val Val Leu Asn Glu Glu Gly Gln Glu Thr Thr
    50                  55                  60

Leu Asn Thr Gly Asp Pro Ala Ser Phe Leu Lys Pro Ser Lys Asp Pro
65                  70                  75                  80

Leu Glu Tyr Phe Arg Val His Ile Ser Ser Asp Gly Tyr Gln Leu Arg
                85                  90                  95

Gln Leu Arg Gly Ser Lys Phe Ile Lys Arg Lys Val Asp Lys Gly Gly
            100                 105                 110

Asp Val Leu Ile Ser Glu Glu Leu Ala Arg Tyr Asn Lys Ile Asn Phe
        115                 120                 125

Ile Asp Asp Gly Ile Ile Ile Val Val Leu Asn Gly Asn Thr Gly Ala
    130                 135                 140

Phe Glu Thr Ile Arg Phe Asn Thr Arg Val Pro Arg Ile Asn Asp Leu
145                 150                 155                 160

Ala Lys Ile Val Gln Asn Asp Val Thr Arg Trp Ser Met Glu His Ser
                165                 170                 175

Glu Glu Lys Pro Val Val Thr Lys Phe Gln Ile His Tyr Ser Leu Glu
            180                 185                 190

Leu Lys Asn Lys Thr Gly Ser Thr Arg Asp Ala Val Lys Glu Glu Leu
        195                 200                 205

Lys Lys Glu Val Ile Arg Arg Lys
    210                 215
```

<210> SEQ ID NO 47
<211> LENGTH: 1212
<212> TYPE: DNA
<213> ORGANISM: Artificial Sequence
<220> FEATURE:
<223> OTHER INFORMATION: LIC10115

<400> SEQUENCE: 47

```
atgaatcaat ttctaaaaaa taaaatatca attatactct ccgtgttggg gctgattttt      60
tcttttttac tcatccaaaa atattacggt gatcctagtt cggtgggaga aaccatttgt     120
aatgcactga gtgaatctgg ttcttgtgat aaggtttctg aaagcgctta ttctgcaatt     180
cgaaacgttc ctggtttagg agatcttccg atcgctttgt tcggttttct gttttatggt     240
tttgtaggtt ttcttttttgt tttttcagaa attaaaaaag aatccgcaga agcaaatctt     300
agattagcgt tttatgtttt agttcttgga cttgttgccg acttaggatt attttttactc     360 tctgttggag taattaaagc gttatgcggt ctttgtgctg caacgtatgt agtaacgatt     420
gcacttctta tcgtgaattt tcccacattt aaatctcttt cggataaatc gattggaacc     480
gttttaaatt cttaaacgg aaatgttttc aattttatta tcgttatact ttccttttt      540
```

```
gttctaggac tttacggggg aaaaatttct acgggtggag caagacttgt atccggggct    600
gccaatgggg aaaagtctat ttcggaacaa ttgaaagaat ttggaacaac tccaacggtt    660
tccattgatt taaaagatgt acctgttgta ggcgatccaa atgcaccgat tacgattgta    720
aaatatgcag attttaattg tggtcattgt atgcatacaa gtaagattct aaaatctttc    780
ttaagcgagt ataacggaat tattaaagtc gcttataaaa attttccttt ggatggaaat    840
tgtaatcgtc ttgtcggaag aaaatctccc gaagcgagct cttgtgtggc tgcaagtgcg    900
gcgctttgtg ctaatgagca gaaaaagttt tacccggttt atactggtct ttatgatgat    960
aatgaggcag gggtgatgca cactgcagta accgttactc gtcttgctga aaagaacggt   1020
ctgaacatga accagtttag atcttgtatg agttctacaa aaattagaga tcagatcaat   1080
cgtgaagtgg atgaggccga aaaactgaaa atcaattcga ctcctacctt gttcattaac   1140
agcaaacctc ttccaaaaag tggaactcct aacgttgatt tcttacacca attgattcgg   1200
cagcttatca at                                                       1212
```

<210> SEQ ID NO 48
<211> LENGTH: 404
<212> TYPE: PRT
<213> ORGANISM: Artificial Sequence
<220> FEATURE:
<223> OTHER INFORMATION: LIC10115

<400> SEQUENCE: 48

```
Met Asn Gln Phe Ser Lys Asn Lys Ile Ser Ile Ile Leu Ser Val Leu
1               5                   10                  15

Gly Leu Ile Phe Ser Phe Leu Leu Ile Gln Lys Tyr Tyr Gly Asp Pro
            20                  25                  30

Ser Ser Val Gly Glu Thr Ile Cys Asn Ala Leu Ser Glu Ser Gly Ser
        35                  40                  45

Cys Asp Lys Val Ser Glu Ser Ala Tyr Ser Ala Ile Arg Asn Val Pro
    50                  55                  60

Gly Leu Gly Asp Leu Pro Ile Ala Leu Phe Gly Phe Leu Phe Tyr Gly
65                  70                  75                  80

Phe Val Gly Phe Leu Phe Val Phe Ser Glu Ile Lys Lys Glu Ser Ala
                85                  90                  95

Glu Ala Asn Leu Arg Leu Ala Phe Tyr Val Leu Val Leu Gly Leu Val
            100                 105                 110

Ala Asp Leu Gly Leu Phe Leu Leu Ser Val Gly Val Ile Lys Ala Leu
        115                 120                 125

Cys Gly Leu Cys Ala Ala Thr Tyr Val Val Thr Ile Ala Leu Leu Ile
    130                 135                 140

Val Asn Phe Pro Thr Phe Lys Ser Leu Ser Asp Lys Ser Ile Gly Thr
145                 150                 155                 160

Val Leu Asn Ser Leu Asn Gly Asn Val Phe Asn Phe Ile Ile Val Ile
                165                 170                 175

Leu Ser Phe Phe Val Leu Gly Leu Tyr Gly Gly Lys Ile Ser Thr Gly
            180                 185                 190

Gly Ala Arg Leu Val Ser Gly Ala Ala Asn Gly Glu Lys Ser Ile Ser
        195                 200                 205

Glu Gln Leu Lys Glu Phe Gly Thr Thr Pro Thr Val Ser Ile Asp Leu
    210                 215                 220

Lys Asp Val Pro Val Val Gly Asp Pro Asn Ala Pro Ile Thr Ile Val
225                 230                 235                 240
```

```
Lys Tyr Ala Asp Phe Asn Cys Gly His Cys Met His Thr Ser Lys Ile
                245                 250                 255

Leu Lys Ser Phe Leu Ser Glu Tyr Asn Gly Ile Ile Lys Val Ala Tyr
            260                 265                 270

Lys Asn Phe Pro Leu Asp Gly Asn Cys Asn Arg Leu Val Gly Arg Lys
        275                 280                 285

Ser Pro Glu Ala Ser Ser Cys Val Ala Ala Ser Ala Ala Leu Cys Ala
    290                 295                 300

Asn Glu Gln Lys Lys Phe Tyr Pro Val Tyr Thr Gly Leu Tyr Asp Asp
305                 310                 315                 320

Asn Glu Ala Gly Val Met His Thr Ala Val Thr Val Thr Arg Leu Ala
                325                 330                 335

Glu Lys Asn Gly Leu Asn Met Asn Gln Phe Arg Ser Cys Met Ser Ser
            340                 345                 350

Thr Lys Ile Arg Asp Gln Ile Asn Arg Glu Val Asp Glu Ala Glu Lys
        355                 360                 365

Leu Lys Ile Asn Ser Thr Pro Thr Leu Phe Ile Asn Ser Lys Pro Leu
    370                 375                 380

Pro Lys Ser Gly Thr Pro Asn Val Asp Phe Leu His Gln Leu Ile Arg
385                 390                 395                 400

Gln Leu Ile Asn

<210> SEQ ID NO 49
<211> LENGTH: 1986
<212> TYPE: DNA
<213> ORGANISM: Artificial Sequence
<220> FEATURE:
<223> OTHER INFORMATION: LIC12433

<400> SEQUENCE: 49
atgtttcaac gttaccatc ccactttaaa cttatcttag gttatgttct ctacttcgct      60
cttatacttc tagtttataa gatctcgttt cttttggtct attcttatag acttcaagga    120
gttcctttcc aagagttggc atacgcgttt ttattaggtt ttcgttttga tctagtagta    180
atcggaatga cactcggatt atttgcattt ctctccgtct taccttattt taatcaattc    240
aagttgtatc gttttttctg gggctatact cctttgcttt taggaatttg gatgatagca    300
catctaatcg cagacatcat ctattttgaa aacgcaaata acatataggt tatgaagga    360 tttgtatttc tcggaaaaga tctaggtgtg attcttaaat ccgcattaga acaaaacacg    420
atcacttttt taataggagt tatattttta ctcatctttc ttccgttatc tacttggtta    480
tttcttaaat acaatccata tcgttatcaa aaagaatctt ggaaatccac aaccattcaa    540
attgtactcg tatcgatcat aacgatcatt gcaattcgag gaggaatcca agaatcacct    600
ataagagcga ctaacgctat tgtttccgga acaattttg ttaacaacat tgcattaaac    660
ggcgttttta cttccatcat ggatttaaaa agccaatcca ttcctaaatt cctcaagtta    720
gaaacgcaag aagcaatcac aattgtacga aaagaaaccg cctacgcagg cgcagaattt    780
atcagcgata aatatccaat tttacgagtt caaaagaaa ccaatccagg gacaccacct    840
aacgtagtat taattatgtt ggaaaactgg accggaaaat ttatcagccc catttcgaac    900
ggacttgtag aagggaagga aatcactccg tatttcaacc aacttttaaa aagggaaga    960 ttctataatc gttttatcgc ttcaggaggg agaacgacta atggaatgat gtcgatactt   1020
actggaattc cagatcgtcc agggctaacc gttgtaagaa cacatcaggt tctaggaaat   1080
ttttccggaa tcggaaacat attcaaaaga atgggttatg atacgtattt tgtgacggga   1140
```

-continued

```
ggtgatttga gttttgataa taaaagcact ctaatgcctc attggggttt cgatacagta   1200
ctcggagaaa aggaaattac aaaattagga agatttaaac taggagcttg gggatacgac   1260
gatgcagacg tattacaatt attgcatgaa cgaatttcca cctctaaaaa accaatttta   1320
ggtttggctc taacactaac cactcactat ccttacagaa ctccttcgga aaaatttagg   1380 attttttgatc cttctacaag agactacgat ttcttaaacg tttacaacta cgcagattgg   1440
gccgttcaca actttatcac tcaggcagaa aaatccggat atttcaaaaa tacaattttc   1500 gttttttgtgg cagaccatac gcatcacaga tatttagatt actacgaaga tagaaatgtg   1560
ccttttctaa tatatgctcc tggaaaagta gaaccagcgt tagacgaaac tatagcttcc   1620
caattagata ttatcccgac aattttaggg cttgtaggaa aaaagcccta ttttctgca    1680 atgggcagaa acctattggc tccagaaaga actaaaaccg cctactttgc atacggaaat   1740
ctatttgggt ggatagaaaa agaactttt tacttaagat tttttgacgg aaaagaagat    1800
ctttcttaca acatcaatcc accacgcgaa aaaataatt tttgtagtaa ggatcctttc    1860
gtatgtgaag aaatgagtaa aaaagcaaaa gcttatttaa acctaagcta cgatttatta   1920
aatcgaaata tagttttcc ttcggacgcg gaattacaaa aataatgtc accgaatacg     1980 actcca                                                              1986
```

<210> SEQ ID NO 50
<211> LENGTH: 662
<212> TYPE: PRT
<213> ORGANISM: Artificial Sequence
<220> FEATURE:
<223> OTHER INFORMATION: LIC12433

<400> SEQUENCE: 50

```
Met Phe Gln Arg Leu Pro Ser His Phe Lys Leu Ile Leu Gly Tyr Val
1               5                   10                  15

Leu Tyr Phe Ala Leu Ile Leu Leu Val Tyr Lys Ile Ser Phe Leu Leu
            20                  25                  30

Val Tyr Ser Tyr Arg Leu Gln Gly Val Pro Phe Gln Glu Leu Ala Tyr
        35                  40                  45

Ala Phe Leu Leu Gly Phe Arg Phe Asp Leu Val Val Ile Gly Met Thr
    50                  55                  60

Leu Gly Leu Phe Ala Phe Leu Ser Val Leu Pro Tyr Phe Asn Gln Phe
65                  70                  75                  80

Lys Leu Tyr Arg Phe Phe Trp Gly Tyr Thr Pro Leu Leu Gly Ile
            85                  90                  95

Trp Met Ile Ala His Leu Ile Ala Asp Ile Ile Tyr Phe Glu Asn Ala
            100                 105                 110

Asn Lys His Ile Gly Tyr Glu Gly Phe Val Phe Leu Gly Lys Asp Leu
            115                 120                 125

Gly Val Ile Leu Lys Ser Ala Leu Glu Gln Asn Thr Ile Thr Phe Leu
        130                 135                 140

Ile Gly Val Ile Phe Leu Leu Ile Phe Leu Pro Leu Ser Thr Trp Leu
145                 150                 155                 160

Phe Leu Lys Tyr Asn Pro Tyr Arg Tyr Gln Lys Glu Ser Trp Lys Ser
                165                 170                 175

Thr Thr Ile Gln Ile Val Leu Val Ser Ile Ile Thr Ile Ala Ile
            180                 185                 190

Arg Gly Gly Ile Gln Glu Ser Pro Ile Arg Ala Thr Asn Ala Ile Val
        195                 200                 205
```

-continued

Ser Gly Asn Asn Phe Val Asn Ile Ala Leu Asn Gly Val Phe Thr
    210                 215                 220

Ser Ile Met Asp Leu Lys Ser Gln Ser Ile Pro Lys Phe Leu Lys Leu
225                 230                 235                 240

Glu Thr Gln Glu Ala Ile Thr Ile Val Arg Lys Glu Thr Ala Tyr Ala
                245                 250                 255

Gly Ala Glu Phe Ile Ser Asp Lys Tyr Pro Ile Leu Arg Val Gln Lys
                260                 265                 270

Glu Thr Asn Pro Gly Thr Pro Pro Asn Val Val Leu Ile Met Leu Glu
            275                 280                 285

Asn Trp Thr Gly Lys Phe Ser Pro Ile Ser Asn Gly Leu Val Glu
        290                 295                 300

Gly Lys Glu Ile Thr Pro Tyr Phe Asn Gln Leu Leu Lys Lys Gly Arg
305                 310                 315                 320

Phe Tyr Asn Arg Phe Ile Ala Ser Gly Gly Arg Thr Thr Asn Gly Met
                325                 330                 335

Met Ser Ile Leu Thr Gly Ile Pro Asp Arg Pro Gly Leu Thr Val Val
                340                 345                 350

Arg Thr His Gln Val Leu Gly Asn Phe Ser Gly Ile Gly Asn Ile Phe
            355                 360                 365

Lys Arg Met Gly Tyr Asp Thr Tyr Phe Val Thr Gly Gly Asp Leu Ser
370                 375                 380

Phe Asp Asn Lys Ser Thr Leu Met Pro His Trp Gly Phe Asp Thr Val
385                 390                 395                 400

Leu Gly Glu Lys Glu Ile Thr Lys Leu Gly Arg Phe Lys Leu Gly Ala
                405                 410                 415

Trp Gly Tyr Asp Asp Ala Asp Val Leu Gln Leu Leu His Glu Arg Ile
            420                 425                 430

Ser Thr Ser Lys Lys Pro Ile Leu Gly Leu Ala Leu Thr Leu Thr Thr
            435                 440                 445

His Tyr Pro Tyr Arg Thr Pro Ser Glu Lys Phe Arg Ile Phe Asp Pro
    450                 455                 460

Ser Thr Arg Asp Tyr Asp Phe Leu Asn Val Tyr Asn Tyr Ala Asp Trp
465                 470                 475                 480

Ala Val His Asn Phe Ile Thr Gln Ala Glu Lys Ser Gly Tyr Phe Lys
                485                 490                 495

Asn Thr Ile Phe Val Phe Val Ala Asp His Thr His His Arg Tyr Leu
            500                 505                 510

Asp Tyr Tyr Glu Asp Arg Asn Val Pro Phe Leu Ile Tyr Ala Pro Gly
        515                 520                 525

Lys Val Glu Pro Ala Leu Asp Glu Thr Ile Ala Ser Gln Leu Asp Ile
530                 535                 540

Ile Pro Thr Ile Leu Gly Leu Val Gly Lys Lys Ala Tyr Phe Ser Ala
545                 550                 555                 560

Met Gly Arg Asn Leu Leu Ala Pro Glu Arg Thr Lys Thr Ala Tyr Phe
                565                 570                 575

Ala Tyr Gly Asn Leu Phe Gly Trp Ile Glu Lys Glu Leu Phe Tyr Leu
            580                 585                 590

Arg Phe Phe Asp Gly Lys Glu Asp Leu Ser Tyr Asn Ile Asn Pro Pro
        595                 600                 605

Arg Glu Lys Asn Asn Phe Cys Ser Lys Asp Pro Phe Val Cys Glu Glu
    610                 615                 620

```
Met Ser Lys Lys Ala Lys Ala Tyr Leu Asn Leu Ser Tyr Asp Leu Leu
625                 630                 635                 640

Asn Arg Asn Ile Val Phe Pro Ser Asp Ala Glu Leu Gln Lys Ile Met
            645                 650                 655

Ser Pro Asn Thr Thr Pro
            660
```

<210> SEQ ID NO 51
<211> LENGTH: 1392
<212> TYPE: DNA
<213> ORGANISM: Artificial Sequence
<220> FEATURE:
<223> OTHER INFORMATION: LIC10868

<400> SEQUENCE: 51

| | | | | | |
|---|---|---|---|---|---|
| atgaaattga | atttaggttt | cgccgttttt | tatatccttt | tttccgcata | caattgttta | 60 |
| tcgtatgagt | gttactcttt | agattacaca | tgcaatccac | aatcactttt | aatcaactcc | 120 |
| tcatcattga | atgaagataa | cgtcaatcat | tccaatccag | gtgaaacctt | tagcaattct | 180 |
| gggacgagac | aatggacaag | acttttaggg | gtagcgggag | cttccacaac | tgcttatgga | 240 |
| attacatccg | atagtttagg | aaatgtatac | acaaccggaa | tgacttccgg | aaatttagac | 300 |
| ggccaagttc | aaagtggaac | ccaagatcta | tttgtgacaa | agtatgatgg | aaatggaaac | 360 |
| aaacaatgga | caagactttt | aggagtggcg | ggaattcaaa | ctttagcgcg | tggaattacg | 420 |
| tctgataatt | taggaaatgt | gtacacaacc | ggaacgactt | tcggaaattt | agacggtcaa | 480 |
| gccttaagtg | aacccaaga | tctatttgtg | acaaagtatg | acggaagtgg | aaataaacaa | 540 |
| tggaccagac | ttttaggagt | ggcaggagca | acaactcaag | ccaacggaat | tagtcgtgat | 600 |
| attttaata | acttgcatgt | aagtggatac | acgctcggaa | atttagacgg | tcaagcctta | 660 |
| agtggaatcc | aagatctatt | tgtgacaaag | tatgatactg | gcggaaataa | acaatggaca | 720 |
| agacttttgg | gagtggcggg | acaaattact | cagggaaacg | gagttgcatt | tgatagttct | 780 |
| ggaaatatat | atttaacagg | acgaacctcc | ggaaatttag | acggtcaagc | cttaagtgga | 840 |
| atccaagatc | tatttgtgac | aaagtatgat | actggcggaa | acaaacaatg | gacaagactt | 900 |
| ttaggagtag | cgggagtttc | cacaactgct | tatggaatta | catccgatag | tttaggaaat | 960 |
| gtatacacaa | ccggagtgac | ttccggaagt | ttagacggtc | aagccttaag | tggaacccaa | 1020 |
| gatctatttg | tgcaaagta | tgatactggc | gggaacaaac | aatggacaag | acttttagga | 1080 |
| gtagcaggac | aaattactca | ggcaaatgga | attgcatctg | atagttctgg | aaacacatat | 1140 |
| ttaacaggac | gaacatccgg | aagtttagac | ggccaagcct | taagtggaac | ccaagatcta | 1200 |
| tttgtgacaa | agtatgacag | cggcgggaac | aaacaatgga | caagactttt | aggaatagcg | 1260 |
| ggagtttcca | caactgctta | tggaattaca | tccgatagtt | taggagatct | atattcaacc | 1320 |
| ggaattactt | ccggaaattt | agatggtcag | atcctaacag | gaactcaaga | tctatttgtg | 1380 |
| ttaaaatacc | ga | | | | | 1392 |

<210> SEQ ID NO 52
<211> LENGTH: 464
<212> TYPE: PRT
<213> ORGANISM: Artificial Sequence
<220> FEATURE:
<223> OTHER INFORMATION: LIC10868

<400> SEQUENCE: 52

```
Met Lys Leu Asn Leu Gly Phe Ala Val Phe Tyr Ile Leu Phe Ser Ala
1               5                   10                  15
```

```
Tyr Asn Cys Leu Ser Tyr Glu Cys Tyr Ser Leu Asp Tyr Thr Cys Asn
            20                  25                  30

Pro Gln Ser Leu Leu Ile Asn Ser Ser Leu Asn Glu Asp Asn Val
        35                  40                  45

Asn His Ser Asn Pro Gly Glu Thr Phe Ser Asn Ser Gly Thr Arg Gln
    50                  55                  60

Trp Thr Arg Leu Leu Gly Val Ala Gly Ala Ser Thr Thr Ala Tyr Gly
65                  70                  75                  80

Ile Thr Ser Asp Ser Leu Gly Asn Val Tyr Thr Thr Gly Met Thr Ser
                85                  90                  95

Gly Asn Leu Asp Gly Gln Val Gln Ser Gly Thr Gln Asp Leu Phe Val
            100                 105                 110

Thr Lys Tyr Asp Gly Asn Gly Asn Lys Gln Trp Thr Arg Leu Leu Gly
        115                 120                 125

Val Ala Gly Ile Gln Thr Leu Ala Arg Gly Ile Thr Ser Asp Asn Leu
130                 135                 140

Gly Asn Val Tyr Thr Thr Gly Thr Thr Phe Gly Asn Leu Asp Gly Gln
145                 150                 155                 160

Ala Leu Ser Gly Thr Gln Asp Leu Phe Val Thr Lys Tyr Asp Gly Ser
            165                 170                 175

Gly Asn Lys Gln Trp Thr Arg Leu Leu Gly Val Ala Gly Ala Thr Thr
        180                 185                 190

Gln Ala Asn Gly Ile Ser Arg Asp Ile Phe Asn Asn Leu His Val Ser
    195                 200                 205

Gly Tyr Thr Leu Gly Asn Leu Asp Gly Gln Ala Leu Ser Gly Ile Gln
210                 215                 220

Asp Leu Phe Val Thr Lys Tyr Asp Thr Gly Gly Asn Lys Gln Trp Thr
225                 230                 235                 240

Arg Leu Leu Gly Val Ala Gly Gln Ile Thr Gln Gly Asn Gly Val Ala
            245                 250                 255

Phe Asp Ser Ser Gly Asn Ile Tyr Leu Thr Gly Arg Thr Ser Gly Asn
        260                 265                 270

Leu Asp Gly Gln Ala Leu Ser Gly Ile Gln Asp Leu Phe Val Thr Lys
    275                 280                 285

Tyr Asp Thr Gly Gly Asn Lys Gln Trp Thr Arg Leu Leu Gly Val Ala
290                 295                 300

Gly Val Ser Thr Thr Ala Tyr Gly Ile Thr Ser Asp Ser Leu Gly Asn
305                 310                 315                 320

Val Tyr Thr Thr Gly Val Thr Ser Gly Ser Leu Asp Gly Gln Ala Leu
            325                 330                 335

Ser Gly Thr Gln Asp Leu Phe Val Thr Lys Tyr Asp Thr Gly Gly Asn
        340                 345                 350

Lys Gln Trp Thr Arg Leu Leu Gly Val Ala Gly Gln Ile Thr Gln Ala
    355                 360                 365

Asn Gly Ile Ala Ser Asp Ser Ser Gly Asn Thr Tyr Leu Thr Gly Arg
    370                 375                 380

Thr Ser Gly Ser Leu Asp Gly Gln Ala Leu Ser Gly Thr Gln Asp Leu
385                 390                 395                 400

Phe Val Thr Lys Tyr Asp Ser Gly Gly Asn Lys Gln Trp Thr Arg Leu
            405                 410                 415

Leu Gly Ile Ala Gly Val Ser Thr Thr Ala Tyr Gly Ile Thr Ser Asp
        420                 425                 430
```

Ser Leu Gly Asp Leu Tyr Ser Thr Gly Ile Thr Ser Gly Asn Leu Asp
        435                 440                 445

Gly Gln Ile Leu Thr Gly Thr Gln Asp Leu Phe Val Leu Lys Tyr Arg
    450                 455                 460

<210> SEQ ID NO 53
<211> LENGTH: 1380
<212> TYPE: DNA
<213> ORGANISM: Artificial Sequence
<220> FEATURE:
<223> OTHER INFORMATION: LIC10898

<400> SEQUENCE: 53

| | | | | |
|---|---|---|---|---|
| atgaaatcaa | ttttcttaaa | aaggacttca | cttttaatcg | taagtgcggc | cttattactt | 60 |
| tcttctttta | tcaattgtaa | agaagacaaa | aatgataata | gtatgttgtt | acttctcgct | 120 |
| ttgttagcgg | gaggaaatag | cgacgccgga | gccgctatct | gcgacggtgc | ttccgttcaa | 180 |
| ggtggaaaca | cagtcctttc | gggtaacatc | acttctagtc | agagtcttcc | tgcttactct | 240 |
| tcttcttcgc | taaatggaat | cgtaagagta | aaaagtggcg | ccactcttac | ctttgaaaga | 300 |
| ggttccgtaa | ttttcggtac | tgctggttcc | gctttagtta | tcgaacaagg | agctaagatc | 360 |
| gttacaaacg | gagatgctgc | tgcacccgta | tgttttactt | cttctaaagt | ttctggaaat | 420 |
| agagctccgg | gcgattgggg | tggtatttta | atcgtaggag | acggtattgg | ttctagagcc | 480 |
| gctgcacaaa | acacgaaggt | ggaaccggt | cttaataca | atagcggtgc | caatgataac | 540 |
| ggaagttcgg | gtaaccttac | ttatacgatc | gttgagtttg | ctggaaacga | agtttctacc | 600 |
| ggtgacgaat | taaacggact | gtctatgtat | gtggtaggaa | gtggtactac | tttagatcac | 660 |
| attcaagttc | atagacattt | agacgacggt | atcgaagctt | ggggtggcgc | ttggaccggt | 720 |
| aaatatcttt | taatgactgg | tggaatggac | gacgacttag | atttagatga | agctttcact | 780 |
| ggaaaagttc | agttcttaat | cgctcataaa | tatcctacca | gttgtggtgg | taccgcatcc | 840 |
| acagatccac | acggttttga | aatggacgga | actcatagcg | gtggaactgc | atccgtgact | 900 |
| tctaaaccga | ctacaaacgt | aaaactttct | aactttactc | ttcttggaaa | aaatgtatcc | 960 |
| aacggatttg | gagcaagact | aagagaagga | cttcaaggta | aatttttcgaa | cggagtcatc | 1020 |
| tacggttttc | aatccggaaa | tattgattgt | gtagccaatg | gaggtggtgg | aaccgtgacc | 1080 |
| tctcctactt | ttgcaaacgt | cttagtagaa | gcttccaaag | gaaacggtaa | cacagcggcc | 1140 |
| tgtgttttac | ctacaaatgg | acttacttct | actcctgtaa | tttccttagg | ttctggagat | 1200 |
| tcggataatt | gcgaatttgc | gaccaaaccg | gattatcaac | cttccggaga | agccgcggct | 1260 |
| ttagctggtt | ccgcattaag | tgcacagtcc | tcagactcgt | tttttatcga | taacactact | 1320 |
| tacggcggta | tggtaagcgg | tttgaactgg | gctttcggtt | ggaccgttta | tagagcgaga | 1380 |

<210> SEQ ID NO 54
<211> LENGTH: 510
<212> TYPE: PRT
<213> ORGANISM: Artificial Sequence
<220> FEATURE:
<223> OTHER INFORMATION: LIC10898

<400> SEQUENCE: 54

Met Leu Phe Tyr Ile Phe Phe Leu Gln Lys Asn Phe Leu Asn Leu
1               5                   10                  15

Met Lys Val Thr Arg Ile Ile Ser Val Cys Asn Leu Tyr Val Thr Pro
        20                  25                  30

Ser Leu Tyr Leu Cys Phe Arg Pro Ser Thr Val Tyr Phe Ser Arg Ser

```
                35                  40                  45
Tyr Lys Met Lys Ser Ile Phe Leu Lys Arg Thr Ser Leu Leu Ile Val
 50                  55                  60

Ser Ala Ala Leu Leu Leu Ser Ser Phe Ile Asn Cys Lys Glu Asp Lys
 65                  70                  75                  80

Asn Asp Asn Ser Met Leu Leu Leu Leu Ala Leu Leu Ala Gly Gly Asn
                 85                  90                  95

Ser Asp Ala Gly Ala Ile Cys Asp Gly Ala Ser Val Gln Gly Gly
                100                 105                 110

Asn Thr Val Leu Ser Gly Asn Ile Thr Ser Ser Gln Ser Leu Pro Ala
                115                 120                 125

Tyr Ser Ser Ser Leu Asn Gly Ile Val Arg Val Lys Ser Gly Ala
                130                 135                 140

Thr Leu Thr Phe Glu Arg Gly Ser Val Ile Phe Gly Thr Ala Gly Ser
145                 150                 155                 160

Ala Leu Val Ile Glu Gln Gly Ala Lys Ile Val Thr Asn Gly Asp Ala
                165                 170                 175

Ala Ala Pro Val Cys Phe Thr Ser Lys Val Ser Gly Asn Arg Ala
                180                 185                 190

Pro Gly Asp Trp Gly Gly Ile Leu Ile Val Gly Asp Gly Ile Gly Ser
                195                 200                 205

Arg Ala Ala Gln Asn Thr Glu Gly Gly Thr Gly Leu Gln Tyr Asn
210                 215                 220

Ser Gly Ala Asn Asp Asn Gly Ser Ser Gly Asn Leu Thr Tyr Thr Ile
225                 230                 235                 240

Val Glu Phe Ala Gly Asn Glu Val Ser Thr Gly Asp Glu Leu Asn Gly
                245                 250                 255

Leu Ser Met Tyr Val Val Gly Ser Gly Thr Thr Leu Asp His Ile Gln
                260                 265                 270

Val His Arg His Leu Asp Asp Gly Ile Glu Ala Trp Gly Gly Ala Trp
                275                 280                 285

Thr Gly Lys Tyr Leu Leu Met Thr Gly Gly Met Asp Asp Asp Leu Asp
                290                 295                 300

Leu Asp Glu Ala Phe Thr Gly Lys Val Gln Phe Leu Ile Ala His Lys
305                 310                 315                 320

Tyr Pro Thr Ser Cys Gly Gly Thr Ala Ser Thr Asp Pro His Gly Phe
                325                 330                 335

Glu Met Asp Gly Thr His Ser Gly Gly Thr Ala Ser Val Thr Ser Lys
                340                 345                 350

Pro Thr Thr Asn Val Lys Leu Ser Asn Phe Thr Leu Gly Lys Asn
                355                 360                 365

Val Ser Asn Gly Phe Gly Ala Arg Leu Arg Glu Gly Leu Gln Gly Lys
                370                 375                 380

Phe Ser Asn Gly Val Ile Tyr Gly Phe Gln Ser Gly Asn Ile Asp Cys
385                 390                 395                 400

Val Ala Asn Gly Gly Gly Thr Val Thr Ser Pro Thr Phe Ala Asn
                405                 410                 415

Val Leu Val Glu Ala Ser Lys Gly Asn Gly Asn Thr Ala Ala Cys Val
                420                 425                 430

Leu Pro Thr Asn Gly Leu Thr Ser Thr Pro Val Ile Ser Leu Gly Ser
                435                 440                 445

Gly Asp Ser Asp Asn Cys Glu Phe Ala Thr Lys Pro Asp Tyr Gln Pro
450                 455                 460
```

Ser Gly Glu Ala Ala Ala Leu Ala Gly Ser Ala Leu Ser Ala Gln Ser
465                 470                 475                 480

Ser Asp Ser Phe Phe Ile Asp Asn Thr Thr Tyr Gly Gly Met Val Ser
            485                 490                 495

Gly Leu Asn Trp Ala Phe Gly Trp Thr Val Tyr Arg Ala Arg
        500                 505                 510

<210> SEQ ID NO 55
<211> LENGTH: 402
<212> TYPE: DNA
<213> ORGANISM: Artificial Sequence
<220> FEATURE:
<223> OTHER INFORMATION: LIC11299

<400> SEQUENCE: 55
atgactctaa aaacaaaaaa tttgagagga acgaaggtga taagaatttt aaattgtatt     60
cttgtgtttt tacttgcttt cggggcttgt acaaaacaag tcaaagagca tattcacgta    120
gatacgggag tcaccgtaga ggtgttaggc gttcacaaat acaaattgat cgcgattggt    180
ggagcttctt caacctctgt cgaagaaaac gatacattca aaatgaagaa tacttcttgc    240
accgccgcga atctattgc ggcgcgtaaa ttagaagaac ttgaaccgga acaaaaaaac    300
agattatttt ttatggaaac cgtggacacg aaatatatag acgacggggc ttattgtgaa    360
attacgtatc actatgaact tcctgcgcct aagaagcagc ag                       402

<210> SEQ ID NO 56
<211> LENGTH: 134
<212> TYPE: PRT
<213> ORGANISM: Artificial Sequence
<220> FEATURE:
<223> OTHER INFORMATION: LIC11299

<400> SEQUENCE: 56

Met Thr Leu Lys Thr Lys Asn Leu Arg Gly Thr Lys Val Ile Arg Ile
1               5                   10                  15

Leu Asn Cys Ile Leu Val Phe Leu Leu Ala Phe Gly Ala Cys Thr Lys
            20                  25                  30

Gln Val Lys Glu His Ile His Val Asp Thr Gly Val Thr Val Glu Val
        35                  40                  45

Leu Gly Val His Lys Tyr Lys Leu Ile Ala Ile Gly Gly Ala Ser Ser
    50                  55                  60

Thr Ser Val Glu Glu Asn Asp Thr Phe Lys Met Lys Asn Thr Ser Cys
65                  70                  75                  80

Thr Ala Ala Lys Ser Ile Ala Ala Arg Lys Leu Glu Glu Leu Glu Pro
                85                  90                  95

Glu Gln Lys Asn Arg Leu Phe Phe Met Glu Thr Val Asp Thr Lys Tyr
            100                 105                 110

Ile Asp Asp Gly Ala Tyr Cys Glu Ile Thr Tyr His Tyr Glu Leu Pro
        115                 120                 125

Ala Pro Lys Lys Gln Gln
    130

<210> SEQ ID NO 57
<211> LENGTH: 498
<212> TYPE: DNA
<213> ORGANISM: Artificial Sequence
<220> FEATURE:
<223> OTHER INFORMATION: LIC11693

-continued

<400> SEQUENCE: 57

| atgaaaatat tattcggttt attaggaacg atttgtattc ttggtttggt tttttttgggt | 60 |
| ttaggagctt ttgcaaatcc gaatttgaa ggtgacattt cgggaacgat aaatgcgcct | 120 |
| gtgaaaaaag tatttcaaca tctgttaaat ttagaagaga ttccaaaata tagaaagaa | 180 |
| gtggtggatg taattctgga aggaaaaaac acaaaggat atccgatttg aaagaagga | 240 |
| acggatatgg ggggatatat tcatttcgaa atgactgaaa gagaagaaaa ctctcgggtt | 300 |
| cgagttgaaa tgaaagaaag tagttttgga atgaaaggat cttgggatta tagattacaa | 360 |
| cctgatggag acaaaacaaa aattacgatt agtgaggttt cagaagtttc tagtattcca | 420 |
| attcgagcga tttttatgat tgttggaaaa gatgcaaatc tcaagaagga acttgaaatc | 480 |
| ttaaataatg tttttcct | 498 |

<210> SEQ ID NO 58
<211> LENGTH: 166
<212> TYPE: PRT
<213> ORGANISM: Artificial Sequence
<220> FEATURE:
<223> OTHER INFORMATION: LIC11693

<400> SEQUENCE: 58

Met Lys Ile Leu Phe Gly Leu Leu Gly Thr Ile Cys Ile Leu Gly Leu
1               5                   10                  15

Val Phe Leu Gly Leu Gly Ala Phe Ala Asn Pro Lys Phe Glu Gly Asp
            20                  25                  30

Ile Ser Gly Thr Ile Asn Ala Pro Val Lys Lys Val Phe Gln His Leu
        35                  40                  45

Leu Asn Leu Glu Glu Ile Pro Lys Tyr Arg Lys Glu Val Val Asp Val
    50                  55                  60

Ile Leu Glu Gly Lys Asn Thr Lys Gly Tyr Pro Ile Trp Lys Glu Gly
65                  70                  75                  80

Thr Asp Met Gly Gly Tyr Ile His Phe Glu Met Thr Glu Arg Glu Glu
                85                  90                  95

Asn Ser Arg Val Arg Val Glu Met Lys Glu Ser Ser Phe Gly Met Lys
            100                 105                 110

Gly Ser Trp Asp Tyr Arg Leu Gln Pro Asp Gly Asp Lys Thr Lys Ile
        115                 120                 125

Thr Ile Ser Glu Val Ser Glu Val Ser Ser Ile Pro Ile Arg Ala Ile
    130                 135                 140

Phe Met Ile Val Gly Lys Asp Ala Asn Leu Lys Lys Glu Leu Glu Ile
145                 150                 155                 160

Leu Asn Asn Val Phe Pro
                165

<210> SEQ ID NO 59
<211> LENGTH: 1128
<212> TYPE: DNA
<213> ORGANISM: Artificial Sequence
<220> FEATURE:
<223> OTHER INFORMATION: LIC12030

<400> SEQUENCE: 59

| atgaaatcat ctagaatttt cttttatttc cttatgttct ttttttgtct gggtttattt | 60 |
| tcctattgta ataattcatc ttgggataaa ctaaaacctt ctaaaaataa aaacaccgca | 120 |
| gaagagttat taaaaacttt gaccgtctta ttttggggag aattcaatca cgaactttat | 180 |

| | | |
|---|---|---|
| aagttcattc caattcccctt tgtaacttta aaaagtcaat tgagtgcgga tcaatttgct | 240 | |
| gtagccactt cagaatcaaa agaaaataaa ccaaaaattg ttttaattca tggttgggac | 300 | |
| tttcaagaaa aaaactctga ttcccccacg ataaactcg caaaggtaac taatattaga | 360 | |
| gaaacctggg atgacgtatt agaaatgtat tctcaaaata tttcgggggt tcagaactca | 420 | |
| tatgagcttt atacgtttac gtatcgaact tccgattata tagaaaacaa cggaaaaaga | 480 | |
| cttatcgata aactcaattc ggttttttact cccgaagaca aggtaattct actcgctcat | 540 | |
| tctatgggag gtcttgtaag tagatccgct ctttatcact caaacaatac aaaagacgtg | 600 | |
| attgatttta tagtcagttt aggaactcct tatctgggtt ctccttttgc ttctactagt | 660 | |
| taccaaggaa attttggaac gttaggcgaa cttatggcct tcttaaccgg tacggaagga | 720 | |
| ggaaaggact tagcctacac aaatgcgtta ggcacgtttt atcaggttcc gatcaatgaa | 780 | |
| cttatcagcg gagcgttcaa tccatatttta gaaagacttc ttgaagaatc ttctaaagat | 840 | |
| tcaaggataa ctgcgttta cggagaaatg aatgtttgca acaatcatcc aggttcagaa | 900 | |
| tccgtttata ttatcggatg taattttta tccaacggaa gtcctagttt tacaaacaaa | 960 | |
| agcgacggaa ttgtgacttc tacaagcggt aagatgtctt ctaaactccc aggagccaaa | 1020 | |
| caattttcta aaaacttaga tcattcccaa ctttcttttc gtaatcatgt aaatacaact | 1080 | |
| tcaagaaaca cctatttga tgaggtttta tccctaataa actctttg | 1128 | |

<210> SEQ ID NO 60
<211> LENGTH: 376
<212> TYPE: PRT
<213> ORGANISM: Artificial Sequence
<220> FEATURE:
<223> OTHER INFORMATION: LIC12030

<400> SEQUENCE: 60

```
Met Lys Ser Ser Arg Ile Phe Phe Tyr Phe Leu Met Phe Phe Phe Cys
1               5                  10                  15

Leu Gly Leu Phe Ser Tyr Cys Asn Asn Ser Ser Trp Asp Lys Leu Lys
            20                  25                  30

Pro Ser Lys Asn Lys Asn Thr Ala Glu Glu Leu Leu Lys Thr Leu Thr
        35                  40                  45

Val Leu Phe Trp Gly Glu Phe Asn His Glu Leu Tyr Lys Phe Ile Pro
    50                  55                  60

Ile Pro Phe Val Thr Leu Lys Ser Gln Leu Ser Ala Asp Gln Phe Ala
65                  70                  75                  80

Val Ala Thr Ser Glu Ser Lys Glu Asn Lys Pro Lys Ile Val Leu Ile
                85                  90                  95

His Gly Trp Asp Phe Gln Glu Lys Asn Ser Asp Ser Pro Thr Asp Lys
            100                 105                 110

Leu Ala Lys Val Thr Asn Ile Arg Glu Thr Trp Asp Val Leu Glu
        115                 120                 125

Met Tyr Ser Gln Asn Ile Ser Gly Val Gln Asn Ser Tyr Glu Leu Tyr
    130                 135                 140

Thr Phe Thr Tyr Arg Thr Ser Asp Tyr Ile Glu Asn Asn Gly Lys Arg
145                 150                 155                 160

Leu Ile Asp Lys Leu Asn Ser Val Phe Thr Pro Glu Asp Lys Val Ile
                165                 170                 175

Leu Leu Ala His Ser Met Gly Gly Leu Val Ser Arg Ser Ala Leu Tyr
            180                 185                 190

His Ser Asn Asn Thr Lys Asp Val Ile Asp Phe Ile Val Ser Leu Gly
```

```
                195                 200                 205
Thr Pro Tyr Leu Gly Ser Pro Phe Ala Ser Ser Tyr Gln Gly Asn
    210                 215                 220

Phe Gly Thr Leu Gly Glu Leu Met Ala Phe Leu Thr Gly Thr Glu Gly
225                 230                 235                 240

Gly Lys Asp Leu Ala Tyr Thr Asn Ala Leu Gly Thr Phe Tyr Gln Val
                245                 250                 255

Pro Ile Asn Glu Leu Ile Ser Gly Ala Phe Asn Pro Tyr Leu Glu Arg
            260                 265                 270

Leu Leu Glu Glu Ser Ser Lys Asp Ser Arg Ile Thr Ala Phe Tyr Gly
        275                 280                 285

Glu Met Asn Val Cys Asn Asn His Pro Gly Ser Glu Ser Val Tyr Ile
290                 295                 300

Ile Gly Cys Asn Phe Leu Ser Asn Gly Ser Pro Ser Phe Thr Asn Lys
305                 310                 315                 320

Ser Asp Gly Ile Val Thr Ser Thr Ser Gly Lys Met Ser Ser Lys Leu
                325                 330                 335

Pro Gly Ala Lys Gln Phe Ser Lys Asn Leu Asp His Ser Gln Leu Ser
            340                 345                 350

Phe Arg Asn His Val Asn Thr Thr Ser Arg Asn Thr Tyr Phe Asp Glu
        355                 360                 365

Val Leu Ser Leu Ile Asn Ser Leu
    370                 375
```

<210> SEQ ID NO 61
<211> LENGTH: 576
<212> TYPE: DNA
<213> ORGANISM: Artificial Sequence
<220> FEATURE:
<223> OTHER INFORMATION: LIC20153

<400> SEQUENCE: 61

```
atgagaaaaa ttcaaaaatg tataaataca acagtcattt tcagtctgat ttttagtgta      60
ttcttaaatt gtaaagacga caaaaaagac gatatagatc cgttattaat tttggtaggt     120
ttagcttctg gttcacccag ttataactgt tcggcaaccg taaaggggaa agtcgcttct     180
ttgcctgcga tgaccgcaac tacttccatt caaactcttg tttacggtaa ggttccgttt     240
gtgaatcatt ccattgcagc cgtaaaagtg acaggtgcgg tcaacggaac tagaatcgtt     300
tttaccggac gaaacgttgc tgattttgat gaagggactt ccagtaatga aatgcacct      360
ttgatttata atacttcttc ttgcccactt gccgattcta gccaagatac tacaagatcg     420
acttacacaa caagtagcga aggtcaatat ggttctgcag ctggagatgg tccttacact     480
tacactttaa atgctacaaa aggtggggat tactacttcg ttttttatct tgcaagtaga     540
accgcggaat ctcctacgac cacgttccaa ctacag                               576
```

<210> SEQ ID NO 62
<211> LENGTH: 192
<212> TYPE: PRT
<213> ORGANISM: Artificial Sequence
<220> FEATURE:
<223> OTHER INFORMATION: LIC20153

<400> SEQUENCE: 62

```
Met Arg Lys Ile Gln Lys Cys Ile Asn Thr Thr Val Ile Phe Ser Leu
1               5                  10                  15

Ile Phe Ser Val Phe Leu Asn Cys Lys Asp Asp Lys Lys Asp Asp Ile
```

```
            20                  25                  30
Asp Pro Leu Leu Ile Leu Val Gly Leu Ala Ser Gly Ser Pro Ser Tyr
        35                  40                  45

Asn Cys Ser Ala Thr Val Lys Gly Lys Val Ala Ser Leu Pro Ala Met
 50                  55                  60

Thr Ala Thr Thr Ser Ile Gln Thr Leu Val Tyr Gly Lys Val Pro Phe
 65                  70                  75                  80

Val Asn His Ser Ile Ala Ala Val Lys Val Thr Gly Ala Val Asn Gly
                 85                  90                  95

Thr Arg Ile Val Phe Thr Gly Arg Asn Val Ala Asp Phe Asp Glu Gly
                100                 105                 110

Thr Ser Ser Asn Glu Asn Ala Pro Leu Ile Tyr Asn Thr Ser Ser Cys
                115                 120                 125

Pro Leu Ala Asp Ser Ser Gln Asp Thr Thr Arg Ser Thr Tyr Thr Thr
        130                 135                 140

Ser Ser Glu Gly Gln Tyr Gly Ser Ala Ala Gly Asp Gly Pro Tyr Thr
145                 150                 155                 160

Tyr Thr Leu Asn Ala Thr Lys Gly Gly Asp Tyr Tyr Phe Val Phe Tyr
                165                 170                 175

Leu Ala Ser Arg Thr Ala Glu Ser Pro Thr Thr Thr Phe Gln Leu Gln
                180                 185                 190

<210> SEQ ID NO 63
<211> LENGTH: 687
<212> TYPE: DNA
<213> ORGANISM: Artificial Sequence
<220> FEATURE:
<223> OTHER INFORMATION: LIC10672

<400> SEQUENCE: 63
atgaaaaagg tttgcttttt tcaatttttct tcctttatct tgaacgtgga ggaatttatg      60
aaaaaaatca cctggctcac aatcttgttt atcctcctta acgttcctgc atttgcgcag     120
aataaagaga aggacaagc agacctgagt cgttccgacg tattttctga caaggaagt      180 tcttacacaa atcccttca gaaaatagtc agagatctgg aagccacaat caatgaaagg     240
cttacagatt tggagaagaa acattctctt ctcgtaattc tgagaccgga actggaaaag     300
gtgcaaacaa tcgtcacgga agacattcct tttacttttg acgaaggata cgagagcaac     360
ctactcaagt atgttcgttt caggtttgag gctggcaaaa tcaaggaagt tgaacttgcc     420
tcggagaaaa aagaattca atacgaattc gcttttgaaa acaaaagact gattttcact     480
cctccggacg tattggcatc tcaggtcaaa ctcgaaagat tcgacaaaat agagaataca     540
aaagtggctg atatttcttt ggaaaatcag atcaaagcgc ttagactttt agagtctagc     600
ctcagatctt cgatctaccg aattgatatt atgatcgcac tttacaaaga caaaaaagac     660
agaaaaaatc tctatcagat cgacatc                                          687

<210> SEQ ID NO 64
<211> LENGTH: 229
<212> TYPE: PRT
<213> ORGANISM: Artificial Sequence
<220> FEATURE:
<223> OTHER INFORMATION: LIC10672

<400> SEQUENCE: 64

Met Lys Lys Val Cys Phe Phe Gln Phe Ser Ser Phe Ile Leu Asn Val
 1               5                  10                  15
```

```
Glu Glu Phe Met Lys Lys Ile Thr Trp Leu Thr Ile Leu Phe Ile Leu
            20                  25                  30

Leu Asn Val Pro Ala Phe Ala Gln Asn Lys Glu Lys Gly Gln Ala Asp
        35                  40                  45

Leu Ser Arg Ser Asp Val Phe Ser Glu Gln Gly Ser Ser Tyr Thr Lys
    50                  55                  60

Ser Leu Gln Lys Ile Val Arg Asp Leu Glu Ala Thr Ile Asn Glu Arg
65                  70                  75                  80

Leu Thr Asp Leu Glu Lys Lys His Ser Leu Leu Val Ile Leu Arg Pro
                85                  90                  95

Glu Leu Glu Lys Val Gln Thr Ile Val Thr Glu Asp Ile Pro Phe Thr
            100                 105                 110

Phe Asp Glu Gly Tyr Glu Ser Asn Leu Leu Lys Tyr Val Arg Phe Arg
        115                 120                 125

Phe Glu Ala Gly Lys Ile Lys Glu Val Glu Leu Ala Ser Glu Lys Lys
    130                 135                 140

Arg Ile Gln Tyr Glu Phe Ala Phe Glu Asn Lys Arg Leu Ile Phe Thr
145                 150                 155                 160

Pro Pro Asp Val Leu Ala Ser Gln Val Lys Leu Glu Arg Phe Asp Lys
                165                 170                 175

Ile Glu Asn Thr Lys Val Ala Asp Ile Ser Leu Glu Asn Gln Ile Lys
            180                 185                 190

Ala Leu Arg Leu Leu Glu Ser Ser Leu Arg Ser Ser Ile Tyr Arg Ile
        195                 200                 205

Asp Ile Met Ile Ala Leu Tyr Lys Asp Lys Lys Asp Arg Lys Asn Leu
    210                 215                 220

Tyr Gln Ile Asp Ile
225

<210> SEQ ID NO 65
<211> LENGTH: 375
<212> TYPE: DNA
<213> ORGANISM: Artificial Sequence
<220> FEATURE:
<223> OTHER INFORMATION: LIC11966

<400> SEQUENCE: 65
atggaaatca tgaacgcttc tacaaacgat ttagatgcgt taaacgcagc catggaaaag      60
gaagacctta caaacgcaga aaatgttaga aaagcttggg aaacaaagct agtttcttca     120
ctcgataagc ttaaaggaat cagtgatttt aaaggagatt ccagttttaa aaatgcaagc     180
gtccaagctc tcgaaactta tttaaacata gtaagtaaag actacaaacg tttgatcgaa     240
ttacgaggat taggtgacaa agcagactca aatgaaatca accaagttct caatcgtatt     300
aatcaggatt ttgaaaaagc tgtaaatact ctcaatgctg cttctgataa atttgcgaaa     360
gaatacgctt ctcaa                                                     375

<210> SEQ ID NO 66
<211> LENGTH: 125
<212> TYPE: PRT
<213> ORGANISM: Artificial Sequence
<220> FEATURE:
<223> OTHER INFORMATION: LIC11966

<400> SEQUENCE: 66

Met Glu Ile Met Asn Ala Ser Thr Asn Asp Leu Asp Ala Leu Asn Ala
1               5                   10                  15
```

```
Ala Met Glu Lys Glu Asp Leu Thr Asn Ala Glu Asn Val Arg Lys Ala
         20                  25                  30

Trp Glu Thr Lys Leu Val Ser Ser Leu Asp Lys Leu Lys Gly Ile Ser
         35                  40                  45

Asp Phe Lys Gly Asp Ser Ser Phe Lys Asn Ala Ser Val Gln Ala Leu
         50                  55                  60

Glu Thr Tyr Leu Asn Ile Val Ser Lys Asp Tyr Lys Arg Leu Ile Glu
 65                  70                  75                  80

Leu Arg Gly Leu Gly Asp Lys Ala Asp Ser Asn Glu Ile Asn Gln Val
                 85                  90                  95

Leu Asn Arg Ile Asn Gln Asp Phe Glu Lys Ala Val Asn Thr Leu Asn
                100                 105                 110

Ala Ala Ser Asp Lys Phe Ala Lys Glu Tyr Ala Ser Gln
            115                 120                 125

<210> SEQ ID NO 67
<211> LENGTH: 960
<212> TYPE: DNA
<213> ORGANISM: Artificial Sequence
<220> FEATURE:
<223> OTHER INFORMATION: LIC10973

<400> SEQUENCE: 67
atgatccgta acataagtaa ggcattgctc attttagccg tagcattatc ttcggctgca       60
agcctaagtg caaaaacata tgcaattgta ggatttgggt tacagttaga cctaggacaa      120
ttaggaggaa ccatcaccaa agatggttta gacgctgcaa gttattatgg cccggtccga      180
tcaacagata cttgtacagt aggtccaaac gatcctactt gtgtacaaaa tccaggaaaa      240
cctacaggtg aaggaaatta tctaggagtt gctcccagaa aagcgattcc tgctgaaaat      300
aaattgatta ccctcgatag aactactggc ggcttgatca acgcaagaag cactaaaggc      360
gccatggtcg gaggaaactt gatggtaggt tatgagtccg actttggtaa atatttttc      420 tggagagttg ctgcagaata tactcaaaaa atttctggcg gtattacaaa agcagacatc      480
gctggttata acattgtaga tatgacttgg ggttttagtt ctatcgtcat tcctgcaacc      540
gttggtatca aattgaatgt tactgaagac gctgcaatat atatgggagc aggtttaaac      600
tatttcaatg gtggatggag tttaaacgga tcaaacaacc tcaaaggagg tcatgacatt      660
ttagctgcag cgggagcggg aagtgttgca aacttgatcg cagacggaac agatccagtc      720
acgactcgtg aacacgttcg atttagaact tctggaattg ctcctaactt tttaattgga      780
actcaggcca gagtaaccga taaaggacac gttttttctg aattagaaac gatcatgtct      840
gctgcgtatg cagttggtaa aactcaatct gcaggaggag ctacgaacct ttctcctttt      900
cctgcatatc caatcgttgt cggtgggcaa atctacagat cggttataaa acacgaactc      960

<210> SEQ ID NO 68
<211> LENGTH: 320
<212> TYPE: PRT
<213> ORGANISM: Artificial Sequence
<220> FEATURE:
<223> OTHER INFORMATION: LIC10973

<400> SEQUENCE: 68

Met Ile Arg Asn Ile Ser Lys Ala Leu Leu Ile Leu Ala Val Ala Leu
 1               5                  10                  15

Ser Ser Ala Ala Ser Leu Ser Ala Lys Thr Tyr Ala Ile Val Gly Phe
         20                  25                  30
```

Gly Leu Gln Leu Asp Leu Gly Gln Leu Gly Gly Thr Ile Thr Lys Asp
                 35                  40                  45

Gly Leu Asp Ala Ala Ser Tyr Tyr Gly Pro Val Arg Ser Thr Asp Thr
 50                  55                  60

Cys Thr Val Gly Pro Asn Asp Pro Thr Cys Val Gln Asn Pro Gly Lys
 65                  70                  75                  80

Pro Thr Gly Glu Gly Asn Tyr Leu Gly Val Ala Pro Arg Lys Ala Ile
                 85                  90                  95

Pro Ala Glu Asn Lys Leu Ile Thr Leu Asp Arg Thr Thr Gly Gly Leu
                100                 105                 110

Ile Asn Ala Arg Ser Thr Lys Gly Ala Met Val Gly Gly Asn Leu Met
                115                 120                 125

Val Gly Tyr Glu Ser Asp Phe Gly Lys Tyr Phe Phe Trp Arg Val Ala
130                 135                 140

Ala Glu Tyr Thr Gln Lys Ile Ser Gly Gly Ile Thr Lys Ala Asp Ile
145                 150                 155                 160

Ala Gly Tyr Asn Ile Val Asp Met Thr Trp Gly Phe Ser Ser Ile Val
                165                 170                 175

Ile Pro Ala Thr Val Gly Ile Lys Leu Asn Val Thr Glu Asp Ala Ala
                180                 185                 190

Ile Tyr Met Gly Ala Gly Leu Asn Tyr Phe Asn Gly Trp Ser Leu
                195                 200                 205

Asn Gly Ser Asn Asn Leu Lys Gly Gly His Asp Ile Leu Ala Ala Ala
                210                 215                 220

Gly Ala Gly Ser Val Ala Asn Leu Ile Ala Asp Gly Thr Asp Pro Val
225                 230                 235                 240

Thr Thr Arg Glu His Val Arg Phe Arg Thr Ser Gly Ile Ala Pro Asn
                245                 250                 255

Phe Leu Ile Gly Thr Gln Ala Arg Val Thr Asp Lys Gly His Val Phe
                260                 265                 270

Leu Glu Leu Glu Thr Ile Met Ser Ala Ala Tyr Ala Val Gly Lys Thr
                275                 280                 285

Gln Ser Ala Gly Ala Thr Asn Leu Ser Pro Phe Pro Ala Tyr Pro
290                 295                 300

Ile Val Val Gly Gly Gln Ile Tyr Arg Phe Gly Tyr Lys His Glu Leu
305                 310                 315                 320

<210> SEQ ID NO 69
<211> LENGTH: 948
<212> TYPE: DNA
<213> ORGANISM: Artificial Sequence
<220> FEATURE:
<223> OTHER INFORMATION: Lp1118 (also called LA1118)

<400> SEQUENCE: 69
gtgaaacatc caaaaatgaa cctcttggga gcgcttttac ttagctcctt attcttaaat      60
cctttgaatt ccgaccctac gttaggcaac tgtgaagtat ttccaacaaa taatatttgg     120
aatactcccg tagatacact tcccctgcat ccttttttcag aatcttatgt tcgaagtatt    180
ggagcacaaa aaaaattaaa agcggatttc ggctctgggc tttgggaggg aatgccaatt    240
ggaattccat ttatactaac gtctggtgcc aatcctgtcc cagtatcttt tgaatatact    300
gatgaaagtg aacctggacc gtatccaatt ccacataacg cacctataga aggtggagaa    360
acaagcgacg gagacaggca cgttctagtt gtagagcaaa aaacatgcaa gttatatgaa    420
ttgtattccg caaggaaaaa aggaaaatct tggactgctg tgtctggtgc ggtctttgat    480

-continued

```
ttgaagtcca atcaacttcg tccggctaac tggacttctg cggacgcagc cggactacca    540
attttacctg gtttagtgag atacgaagaa atagcttctg gagaaatcaa acacgcaatt    600
cgtttcaccg ctaaaaaaac acaaaaagcg tatctatggc ctgctcgtca ttacgcttct    660
aaaatcacag acaaaaacgt cccaccgatg ggaactcgtt tccgtttaaa agcaagtttt    720
aacatagacg gatttagtaa agaaaaccaa gtaattctac gtgcattaaa aaatatgga    780 atgatacttg ccgacaacgg atcagattgg tttttatccg gagctccaaa cgaaaaatgg    840
aacaatgatc aacttcataa actaggtaag gttttaggag atcagttcga agcagtagat    900
tcagaaagtt taatgatttc gacagattcc ggagaagcca aacaaaac    948
```

<210> SEQ ID NO 70
<211> LENGTH: 316
<212> TYPE: PRT
<213> ORGANISM: Artificial Sequence
<220> FEATURE:
<223> OTHER INFORMATION: Lp1118 (also called LA1118)

<400> SEQUENCE: 70

```
Met Lys His Pro Lys Met Asn Leu Leu Gly Ala Leu Leu Ser Ser
1               5                   10                  15

Leu Phe Leu Asn Pro Leu Asn Ser Asp Pro Thr Leu Gly Asn Cys Glu
                20                  25                  30

Val Phe Pro Thr Asn Asn Ile Trp Asn Thr Pro Val Asp Thr Leu Pro
            35                  40                  45

Leu His Pro Phe Ser Glu Ser Tyr Val Arg Ser Ile Gly Ala Gln Lys
        50                  55                  60

Lys Leu Lys Ala Asp Phe Gly Ser Gly Leu Trp Glu Gly Met Pro Ile
65                  70                  75                  80

Gly Ile Pro Phe Ile Leu Thr Ser Gly Ala Asn Pro Val Pro Val Ser
                85                  90                  95

Phe Glu Tyr Thr Asp Glu Ser Glu Pro Gly Pro Tyr Pro Ile Pro His
            100                 105                 110

Asn Ala Pro Ile Glu Gly Gly Glu Thr Ser Asp Gly Asp Arg His Val
        115                 120                 125

Leu Val Val Glu Gln Lys Thr Cys Lys Leu Tyr Glu Leu Tyr Ser Ala
    130                 135                 140

Arg Lys Lys Gly Lys Ser Trp Thr Ala Val Ser Gly Ala Val Phe Asp
145                 150                 155                 160

Leu Lys Ser Asn Gln Leu Arg Pro Ala Asn Trp Thr Ser Ala Asp Ala
                165                 170                 175

Ala Gly Leu Pro Ile Leu Pro Gly Leu Val Arg Tyr Glu Glu Ile Ala
            180                 185                 190

Ser Gly Glu Ile Lys His Ala Ile Arg Phe Thr Ala Lys Lys Thr Gln
        195                 200                 205

Lys Ala Tyr Leu Trp Pro Ala Arg His Tyr Ala Ser Lys Ile Thr Asp
    210                 215                 220

Lys Asn Val Pro Pro Met Gly Thr Arg Phe Arg Leu Lys Ala Ser Phe
225                 230                 235                 240

Asn Ile Asp Gly Phe Ser Lys Glu Asn Gln Val Ile Leu Arg Ala Leu
                245                 250                 255

Lys Lys Tyr Gly Met Ile Leu Ala Asp Asn Gly Ser Asp Trp Phe Leu
            260                 265                 270

Ser Gly Ala Pro Asn Glu Lys Trp Asn Asn Asp Gln Leu His Lys Leu
```

```
                275                 280                 285
Gly Lys Val Leu Gly Asp Gln Phe Glu Ala Val Asp Ser Glu Ser Leu
            290                 295                 300
Met Ile Ser Thr Asp Ser Gly Glu Ala Lys Gln Asn
305                 310                 315

<210> SEQ ID NO 71
<211> LENGTH: 798
<212> TYPE: DNA
<213> ORGANISM: Artificial Sequence
<220> FEATURE:
<223> OTHER INFORMATION: MceII (also called Lp0607)

<400> SEQUENCE: 71
atgaatcttt ccaaacacac agccgttctc acagggattg ttttcttctt agcattttcc      60
ttaagtatgt atgtctccgt tattgaaaaa gccggaacca agacgaata tccatatacc      120 atgaaaattt attatccccg tttggaagga attcatccag gtgcacccgt tcgaattta      180 ggagtagaaa aaggaattgt acgtagttta gacgtggttc cgattgacga agtagaagat      240
caaagattcc tcaataagga tcaaacgaag gcaatcgaaa ttattgttag actgaaagag      300
ccaatcacac tctgggacaa ttataaaatt acattccaaa ccaacacgat tctctctgga      360
agaaccatcg atatagaccc tggatctttc gataaagaag agacgtcctt ttttcaacct      420
acttacttag aagaagaaca aaaatctcca gacttcttac cttctgcaga ttactttgaa      480
gattttttcg cggcttccac gggagtcatc cgagaaaatc gtgaagacat ccgaacttct      540
tttaataatt tttatgaaat ttcagaaaaa ttgaaatcaa atcgaggaac aattcctcag      600
atcattaact ctccggaaac gtacgataac gtgatagaat tacttacaga tgctagaatt      660
ttcggtaacg atgctcgtcg ttatctggaa gggaaccgta agttggaacg ttctgctccg      720
attccactca cgattaatat gtatcgtaga actactttga tcggaaacgt gagtaatcgg      780
tattatttcg gaaagtta                                                   798

<210> SEQ ID NO 72
<211> LENGTH: 266
<212> TYPE: PRT
<213> ORGANISM: Artificial Sequence
<220> FEATURE:
<223> OTHER INFORMATION: MceII (also called Lp0607)

<400> SEQUENCE: 72

Met Asn Leu Ser Lys His Thr Ala Val Leu Thr Gly Ile Val Phe Phe
1               5                   10                  15

Leu Ala Phe Ser Leu Ser Met Tyr Val Ser Val Ile Glu Lys Ala Gly
            20                  25                  30

Thr Lys Asp Glu Tyr Pro Tyr Thr Met Lys Ile Tyr Tyr Pro Arg Leu
        35                  40                  45

Glu Gly Ile His Pro Gly Ala Pro Val Arg Ile Leu Gly Val Glu Lys
    50                  55                  60

Gly Ile Val Arg Ser Leu Asp Val Val Pro Ile Asp Glu Val Glu Asp
65                  70                  75                  80

Gln Arg Phe Leu Asn Lys Asp Gln Thr Lys Ala Ile Glu Ile Ile Val
                85                  90                  95

Arg Leu Lys Glu Pro Ile Thr Leu Trp Asp Asn Tyr Lys Ile Thr Phe
            100                 105                 110

Gln Thr Asn Thr Ile Leu Ser Gly Arg Thr Ile Asp Ile Asp Pro Gly
        115                 120                 125
```

Ser Phe Asp Lys Glu Glu Thr Ser Phe Phe Gln Pro Thr Tyr Leu Glu
            130                 135                 140

Glu Glu Gln Lys Ser Pro Asp Phe Leu Pro Ser Ala Asp Tyr Phe Glu
145                 150                 155                 160

Asp Phe Ala Ala Ser Thr Gly Val Ile Arg Glu Asn Arg Glu Asp
                165                 170                 175

Ile Arg Thr Ser Phe Asn Asn Phe Tyr Glu Ile Ser Glu Lys Leu Lys
            180                 185                 190

Ser Asn Arg Gly Thr Ile Pro Gln Ile Ile Asn Ser Pro Glu Thr Tyr
            195                 200                 205

Asp Asn Val Ile Glu Leu Leu Thr Asp Ala Arg Ile Phe Gly Asn Asp
            210                 215                 220

Ala Arg Arg Tyr Leu Glu Gly Asn Arg Lys Leu Glu Arg Ser Ala Pro
225                 230                 235                 240

Ile Pro Leu Thr Ile Asn Met Tyr Arg Arg Thr Thr Leu Ile Gly Asn
                245                 250                 255

Val Ser Asn Arg Tyr Tyr Phe Gly Lys Leu
            260                 265

<210> SEQ ID NO 73
<211> LENGTH: 432
<212> TYPE: DNA
<213> ORGANISM: Artificial Sequence
<220> FEATURE:
<223> OTHER INFORMATION: Lsa21

<400> SEQUENCE: 73
acgcaactac tcaataccga ttgtgttact agttcggaag tagtatcaga ctcttataac      60
aaaacaacaa taaccttcga aaataaacct caatattaca attcacccag tggaaatgta    120
gttccaaaag caattatgcc gattttgatt aaaaagggc agacaattca agtatccagt     180
ataacgacta acgttaagta tgaagcgaca aaccaagact taacttttct ttttagaaaa    240
gatggttgtc acggtacaaa ctccgaaatt gcaacctatg caggagctac taatacaaat   300 gttttttag gaaacacaaa tactgttagc ttaactcaat ttaaatttac cgccgactat    360
aatgggatta tactaatcgt tgggaaaaac ctaggtgcaa gtttacctgg agatattcgt   420
gtgaatgtat tt                                                        432

<210> SEQ ID NO 74
<211> LENGTH: 144
<212> TYPE: PRT
<213> ORGANISM: Artificial Sequence
<220> FEATURE:
<223> OTHER INFORMATION: Lsa21

<400> SEQUENCE: 74

Thr Gln Leu Leu Asn Thr Asp Cys Val Thr Ser Ser Glu Val Val Ser
1               5                   10                  15

Asp Ser Tyr Asn Lys Thr Thr Ile Thr Phe Glu Asn Lys Pro Gln Tyr
                20                  25                  30

Tyr Asn Ser Pro Ser Gly Asn Val Val Pro Lys Ala Ile Met Pro Ile
            35                  40                  45

Leu Ile Lys Lys Gly Gln Thr Ile Gln Val Ser Ser Ile Thr Thr Asn
        50                  55                  60

Val Lys Tyr Glu Ala Thr Asn Gln Asp Leu Thr Phe Leu Phe Arg Lys
65                  70                  75                  80

```
Asp Gly Cys His Gly Thr Asn Ser Glu Ile Ala Thr Tyr Ala Gly Ala
            85                  90                  95

Thr Asn Thr Asn Val Phe Leu Gly Asn Thr Thr Val Ser Leu Thr
            100                 105                 110

Gln Phe Lys Phe Thr Ala Asp Tyr Asn Gly Ile Ile Leu Ile Val Gly
        115                 120                 125

Lys Asn Leu Gly Ala Ser Leu Pro Gly Asp Ile Arg Val Asn Val Phe
    130                 135                 140
```

<210> SEQ ID NO 75
<211> LENGTH: 897
<212> TYPE: DNA
<213> ORGANISM: Artificial Sequence
<220> FEATURE:
<223> OTHER INFORMATION: LIC20229

<400> SEQUENCE: 75

```
atgaaactca agtttataat cctagttgca attattctta taggaaattg taaacccaaa      60
gaaacaatca ccgtcacggg ttcggaaacg atgcacgtaa tgcttcagat gatcggcttg     120
gaatatactc gaaagaaatc cggaatccaa gtagtagttc aaggtggtgg atcgatcgaa     180
ggtattgaaa aattatttca aggtaaaact gatattgctg cagccagtag accacttacc     240
gaaacagagc tcaaagaatt tgattccaaa ggcaagtttg aatcacttac catagcctat     300
gatggaattg ccatcatcgt tcatccatcc aatccgatcc gtaaaatcag tttggaaatc     360
gcttctaaaa ttttttcggg agaaatttca gattggtcca agatcggagg taaacccgga     420
aaaatagacg tgatcattag aaacgataaa tctggaaccg catcctatttt tgaaacccac     480
gttctcaaac aaaaagactt aggaagtaaa aattttgaga caaggaaaaa tgtaatatat     540
tcaaaaatgg ctaaaatcgt ctcagataac gactcaatgg cagcggaaat tgattccaat     600
ccaaacgcga tcggttttat gggaatgggg agcgctcttt ttgaaaacaa aggcagagta     660
cgcgctctag aatattctct ttccggtaaa gatccttttg tagtacctag catagaaaac     720
gtgtataatc gaaagtatga actttccaga ggactttatt tattttatct ttccgaccac     780
ggtcaaaaaa tagcgacgtt cattacgtat gttacgggcg aggaaggaca aaagacaatt     840
ctaaaaagtg gatatttaag aggaacactc ccaaccgtag aagtagaagt caaaaag      897
```

<210> SEQ ID NO 76
<211> LENGTH: 299
<212> TYPE: PRT
<213> ORGANISM: Artificial Sequence
<220> FEATURE:
<223> OTHER INFORMATION: LIC20229

<400> SEQUENCE: 76

```
Met Lys Leu Lys Phe Ile Ile Leu Val Ala Ile Ile Leu Ile Gly Asn
1               5                   10                  15

Cys Lys Pro Lys Glu Thr Ile Thr Val Thr Gly Ser Glu Thr Met His
            20                  25                  30

Val Met Leu Gln Met Ile Gly Leu Glu Tyr Thr Arg Lys Lys Ser Gly
        35                  40                  45

Ile Gln Val Val Val Gln Gly Gly Gly Ser Ile Glu Gly Ile Glu Lys
    50                  55                  60

Leu Phe Gln Gly Lys Thr Asp Ile Ala Ala Ala Ser Arg Pro Leu Thr
65                  70                  75                  80

Glu Thr Glu Leu Lys Glu Phe Asp Ser Lys Gly Lys Phe Glu Ser Leu
                85                  90                  95
```

```
Thr Ile Ala Tyr Asp Gly Ile Ala Ile Ile Val His Pro Ser Asn Pro
                100                 105                 110

Ile Arg Lys Ile Ser Leu Glu Ile Ala Ser Lys Ile Phe Ser Gly Glu
            115                 120                 125

Ile Ser Asp Trp Ser Lys Ile Gly Gly Lys Pro Gly Lys Ile Asp Val
        130                 135                 140

Ile Ile Arg Asn Asp Lys Ser Gly Thr Ala Ser Tyr Phe Glu Thr His
145                 150                 155                 160

Val Leu Lys Gln Lys Asp Leu Gly Ser Lys Asn Phe Glu Thr Arg Lys
                165                 170                 175

Asn Val Ile Tyr Ser Lys Met Ala Lys Ile Val Ser Asp Asn Asp Ser
            180                 185                 190

Met Ala Ala Glu Ile Asp Ser Asn Pro Asn Ala Ile Gly Phe Met Gly
        195                 200                 205

Met Gly Ser Ala Leu Phe Glu Asn Lys Gly Arg Val Arg Ala Leu Glu
210                 215                 220

Tyr Ser Leu Ser Gly Lys Asp Pro Phe Val Val Pro Ser Ile Glu Asn
225                 230                 235                 240

Val Tyr Asn Arg Lys Tyr Glu Leu Ser Arg Gly Leu Tyr Leu Phe Tyr
                245                 250                 255

Leu Ser Asp His Gly Gln Lys Ile Asp Asp Phe Ile Thr Tyr Val Thr
            260                 265                 270

Gly Glu Glu Gly Gln Lys Thr Ile Leu Lys Ser Gly Tyr Leu Arg Gly
        275                 280                 285

Thr Leu Pro Thr Val Glu Val Glu Val Lys Lys
        290                 295

<210> SEQ ID NO 77
<211> LENGTH: 1134
<212> TYPE: DNA
<213> ORGANISM: Artificial Sequence
<220> FEATURE:
<223> OTHER INFORMATION: LIC11181

<400> SEQUENCE: 77 atgttttta aaagaagtta tctattctat tttcttttt tgatccttat actttacgga      60
atttggtctt atacggatcg ctcctcttgg aacagactc cggattctag attgaaaaga    120
atagagagtt ttggaaagaa cctaaaaaaa ggaaatcttc taggcattca accctggatg    180
tatcctatcg attattcgaa tgaaatcaat ttttcgaaaa aaattcaatc ttatctcgaa    240
gaagcaagta agaacggtta tcaatccg aaaacgatcg tagtatttcc ggaatattta    300
ggaacttggc ttgtggtcgc aggagaaaaa acttctgtgg tcaagtcgga caaactcgaa    360
gattcgatgc gaacccttat tttgagtaat ccagtaagtt ttattttcaa ttttttcaaa    420
gcacaaggaa aggataaaat cagagacgca ctttttagaa tgaaagcgga aaagatgtta    480
tctatttact cgaatacgtt ctcgggtatg gcaaaaaaat ggggagtaac cattgtagcg    540
ggatcgattc ttcttccgga accctatatt ttagaaggta aaattcaaat aagaaatggg    600
gccttaaaaa acgtttctta cgttttttta ccggatggta gagtagccga aaactctccc    660
gaaaaaatat atccaataga agacgaaaaa tcctttgtgg cagcttctac tctcaaaaat    720
ctaaaaatta tccaaagtcc aatgggtaaa attggagtat tagtctgtgc agattcttgg    780
taccctgaag tttacgaaat attcaaaaaa cagaatgtga attttgtagt cgttccctct    840
tatgtggctc cggatggggc tatgtccgag gtttggaaag gttataacgg ttcaaaaaat    900
```

```
ccaaccgata ttcgtctgga agacgtacat agaatttcgg aaggagaggc ctggcttaaa     960
tatgcacttg ccgggaggat tttaaaatct ggagctactc atgggatgaa cgttttttta    1020 agggatctc tttgggatct gggatccgat ggagaaatca ttttagttca ccggtcgatg    1080
gttcggacct ttccaaaaat ttacggagct agtatcgtaa atctctggtt agat          1134
```

```
<210> SEQ ID NO 78
<211> LENGTH: 378
<212> TYPE: PRT
<213> ORGANISM: Artificial Sequence
<220> FEATURE:
<223> OTHER INFORMATION: LIC11181

<400> SEQUENCE: 78
```

| Met | Phe | Phe | Lys | Arg | Ser | Tyr | Leu | Phe | Tyr | Phe | Leu | Phe | Leu | Ile | Leu |
|---|---|---|---|---|---|---|---|---|---|---|---|---|---|---|---|
| 1 | | | | 5 | | | | | 10 | | | | | 15 | |

| Ile | Leu | Tyr | Gly | Ile | Trp | Ser | Tyr | Thr | Asp | Arg | Ser | Ser | Trp | Glu | Gln |
|---|---|---|---|---|---|---|---|---|---|---|---|---|---|---|---|
| | | | 20 | | | | | 25 | | | | | 30 | | |

| Thr | Pro | Asp | Ser | Arg | Leu | Lys | Arg | Ile | Glu | Ser | Phe | Gly | Lys | Asn | Leu |
|---|---|---|---|---|---|---|---|---|---|---|---|---|---|---|---|
| | | 35 | | | | | 40 | | | | | 45 | | | |

| Lys | Lys | Gly | Asn | Leu | Leu | Gly | Ile | Gln | Pro | Trp | Met | Tyr | Pro | Ile | Asp |
|---|---|---|---|---|---|---|---|---|---|---|---|---|---|---|---|
| 50 | | | | | 55 | | | | | 60 | | | | | |

| Tyr | Ser | Asn | Glu | Ile | Asn | Phe | Ser | Lys | Lys | Ile | Gln | Ser | Tyr | Leu | Glu |
|---|---|---|---|---|---|---|---|---|---|---|---|---|---|---|---|
| 65 | | | | | 70 | | | | | 75 | | | | | 80 |

| Glu | Ala | Ser | Lys | Asn | Gly | Tyr | Ile | Asn | Pro | Lys | Thr | Ile | Val | Val | Phe |
|---|---|---|---|---|---|---|---|---|---|---|---|---|---|---|---|
| | | | | 85 | | | | | 90 | | | | | 95 | |

| Pro | Glu | Tyr | Leu | Gly | Thr | Trp | Leu | Val | Val | Ala | Gly | Glu | Lys | Thr | Ser |
|---|---|---|---|---|---|---|---|---|---|---|---|---|---|---|---|
| | | | 100 | | | | | 105 | | | | | 110 | | |

| Val | Val | Lys | Ser | Asp | Lys | Leu | Glu | Asp | Ser | Met | Arg | Thr | Leu | Ile | Leu |
|---|---|---|---|---|---|---|---|---|---|---|---|---|---|---|---|
| | | 115 | | | | | 120 | | | | | 125 | | | |

| Ser | Asn | Pro | Val | Ser | Phe | Ile | Phe | Asn | Phe | Phe | Lys | Ala | Gln | Gly | Lys |
|---|---|---|---|---|---|---|---|---|---|---|---|---|---|---|---|
| 130 | | | | | 135 | | | | | 140 | | | | | |

| Asp | Lys | Ile | Arg | Asp | Ala | Leu | Phe | Arg | Met | Lys | Ala | Glu | Lys | Met | Leu |
|---|---|---|---|---|---|---|---|---|---|---|---|---|---|---|---|
| 145 | | | | | 150 | | | | | 155 | | | | | 160 |

| Ser | Ile | Tyr | Ser | Asn | Thr | Phe | Ser | Gly | Met | Ala | Lys | Lys | Trp | Gly | Val |
|---|---|---|---|---|---|---|---|---|---|---|---|---|---|---|---|
| | | | | 165 | | | | | 170 | | | | | 175 | |

| Thr | Ile | Val | Ala | Gly | Ser | Ile | Leu | Leu | Pro | Glu | Pro | Tyr | Ile | Leu | Glu |
|---|---|---|---|---|---|---|---|---|---|---|---|---|---|---|---|
| | | | 180 | | | | | 185 | | | | | 190 | | |

| Gly | Lys | Ile | Gln | Ile | Arg | Asn | Gly | Ala | Leu | Lys | Asn | Val | Ser | Tyr | Val |
|---|---|---|---|---|---|---|---|---|---|---|---|---|---|---|---|
| | | 195 | | | | | 200 | | | | | 205 | | | |

| Phe | Leu | Pro | Asp | Gly | Arg | Val | Ala | Glu | Asn | Ser | Pro | Glu | Lys | Ile | Tyr |
|---|---|---|---|---|---|---|---|---|---|---|---|---|---|---|---|
| 210 | | | | | 215 | | | | | 220 | | | | | |

| Pro | Ile | Glu | Asp | Glu | Lys | Ser | Phe | Val | Ala | Ala | Ser | Thr | Leu | Lys | Asn |
|---|---|---|---|---|---|---|---|---|---|---|---|---|---|---|---|
| 225 | | | | | 230 | | | | | 235 | | | | | 240 |

| Leu | Lys | Ile | Ile | Gln | Ser | Pro | Met | Gly | Lys | Ile | Gly | Val | Leu | Val | Cys |
|---|---|---|---|---|---|---|---|---|---|---|---|---|---|---|---|
| | | | | 245 | | | | | 250 | | | | | 255 | |

| Ala | Asp | Ser | Trp | Tyr | Pro | Glu | Val | Tyr | Glu | Ile | Phe | Lys | Lys | Gln | Asn |
|---|---|---|---|---|---|---|---|---|---|---|---|---|---|---|---|
| | | | 260 | | | | | 265 | | | | | 270 | | |

| Val | Asn | Phe | Val | Val | Pro | Ser | Tyr | Val | Ala | Pro | Asp | Gly | Ala | Met |
|---|---|---|---|---|---|---|---|---|---|---|---|---|---|---|
| | | 275 | | | | | 280 | | | | | 285 | | | |

| Ser | Glu | Val | Trp | Lys | Gly | Tyr | Asn | Gly | Ser | Lys | Asn | Pro | Thr | Asp | Ile |
|---|---|---|---|---|---|---|---|---|---|---|---|---|---|---|---|
| | | 290 | | | | | 295 | | | | | 300 | | | |

| Arg | Leu | Glu | Asp | Val | His | Arg | Ile | Ser | Glu | Gly | Glu | Ala | Trp | Leu | Lys |
|---|---|---|---|---|---|---|---|---|---|---|---|---|---|---|---|
| 305 | | | | | 310 | | | | | 315 | | | | | 320 |

Tyr Ala Leu Ala Gly Arg Ile Leu Lys Ser Gly Ala Thr His Gly Met
                    325                 330                 335

Asn Val Phe Leu Arg Gly Ser Leu Trp Asp Leu Gly Ser Asp Gly Glu
            340                 345                 350

Ile Ile Leu Val His Arg Ser Met Val Arg Thr Phe Pro Lys Ile Tyr
        355                 360                 365

Gly Ala Ser Ile Val Asn Leu Trp Leu Asp
    370                 375

<210> SEQ ID NO 79
<211> LENGTH: 693
<212> TYPE: DNA
<213> ORGANISM: Artificial Sequence
<220> FEATURE:
<223> OTHER INFORMATION: LIC13059

<400> SEQUENCE: 79
atgaaattca gtataatcaa aaatttgaat ttagtacttg ccctactcgt tttatcttct      60
tgcaaggatg atagaattaa ataagcgatc taggtgtaaa tcgacaaaga taaaaaaaat     120
caaacagcct tgttcttca accggaaaaa ctactcgtga tggtgcgaac cgattcgaat      180
ctagatggaa aaacgatct atggacttgg gtacgcggag acgataagga tcctaaaaca     240
agtttggttc tatttgaaga actcattcga aaaggaaatc atagtcggac ttggtatggt     300
ccaggaaatc gaaaattaat cgaacaaagt gatttagacg aaaatggaac ttgggaatcc     360
atggtatatt ataatgcgtt tgcagttccc aaagaaacaa tgagaattgt agcacatgta     420
gaagtagatc tttatggaaa aggcaaacca agtttatgga ttttcccgga agctcgaatg     480
gagttagatt caaacgaaga cggaaaaccg gatcaaatat tgaccaatca agatcgtatg     540
ttagaaaatt ttactcaact tcaaaaagga aaacaaattc aagagaagga ttttaatccg     600
atgcctgcaa acagttcttg ggtattaaac ccgaaccaaa ttacaaaccc tcggtatcag     660
gcattgattc gtcaaagtct ctttccagta aat                                  693

<210> SEQ ID NO 80
<211> LENGTH: 231
<212> TYPE: PRT
<213> ORGANISM: Artificial Sequence
<220> FEATURE:
<223> OTHER INFORMATION: LIC13059

<400> SEQUENCE: 80

Met Lys Phe Ser Ile Ile Lys Asn Leu Asn Leu Val Leu Ala Leu Leu
1               5                   10                  15

Val Leu Ser Ser Cys Lys Asp Asp Arg Ile Lys Ile Ser Asp Leu Gly
            20                  25                  30

Val Ile Asp Lys Asp Lys Lys Asn Gln Thr Ala Phe Val Leu Gln Pro
        35                  40                  45

Glu Lys Leu Leu Val Met Val Arg Thr Asp Ser Asn Leu Asp Gly Lys
    50                  55                  60

Thr Asp Leu Trp Thr Trp Val Arg Gly Asp Asp Lys Asp Pro Lys Thr
65                  70                  75                  80

Ser Leu Val Leu Phe Glu Glu Leu Ile Arg Lys Gly Asn His Ser Arg
                85                  90                  95

Thr Trp Tyr Gly Pro Gly Asn Arg Lys Leu Ile Glu Gln Ser Asp Leu
            100                 105                 110

Asp Glu Asn Gly Thr Trp Glu Ser Met Val Tyr Tyr Asn Ala Phe Ala
        115                 120                 125

```
Val Pro Lys Glu Thr Met Arg Ile Val Ala His Val Glu Val Asp Leu
        130                 135                 140

Tyr Gly Lys Gly Lys Pro Ser Leu Trp Ile Phe Pro Glu Ala Arg Met
145                 150                 155                 160

Glu Leu Asp Ser Asn Glu Asp Gly Lys Pro Asp Gln Ile Leu Thr Asn
                165                 170                 175

Gln Asp Arg Met Leu Glu Asn Phe Thr Gln Leu Gln Lys Gly Lys Gln
            180                 185                 190

Ile Gln Glu Lys Asp Phe Asn Pro Met Pro Ala Asn Ser Ser Trp Val
        195                 200                 205

Leu Asn Pro Asn Gln Ile Thr Asn Pro Arg Tyr Gln Ala Leu Ile Arg
    210                 215                 220

Gln Ser Leu Phe Pro Val Asn
225                 230

<210> SEQ ID NO 81
<211> LENGTH: 1404
<212> TYPE: DNA
<213> ORGANISM: Artificial Sequence
<220> FEATURE:
<223> OTHER INFORMATION: LIC10959

<400> SEQUENCE: 81
ttgatttcac gaatgatctc aaagcgcaag gaggatcgaa tgaaatcgaa cgccagagtt      60
tgtgtagtag gtgctggacc aagcggaatt gccgccggaa agaattgtgt cgaatacggt     120
ttggatgtag taattttcga aaaaaacgat aaagttggcg ggaactgggt tttcaacgcc     180
aaaaccggtc attccagcgt ctacgaaaat acccacatca tcagttctaa ggtttggtcc     240
gaatatgaag actttccaat gcccgaagat tatcccgagt acccaaatca aaacaacttt     300
caagcttatt ttgaatctta tgcaaaacac ttcggagtct ataagaaaat tcgatttcat     360
cataccattc aaaagattac caaaacacct aacgaagaat ggaaagtaga atatacaaac     420
gcttctaaaa aaagaaggt agaatttttt gacgtcctta tggttgcaaa cggacatcac     480
tgggatccca aatatccaga atatgaaggc aagtttactg gtaagttttt acattctcac     540
gatttcaaag gtgttacaaa cgaatggaaa ggaaaagata ttttagtcat cggagccggt     600
aattcagctt gtgacgttgc agtcgaatcg gcaagagttg caaacagtgt aaagttatca     660
atgagaagtc ctcaatggtt ttttccgaaa tttcttttg gtatgccttc tgacgtgttt     720
gcggcaaaaa ctccaaattg gattccttct atcattaaac aatttgccct tagtaagtta     780
atttatatat tacaaggttc ttataaaaac tatggccttc cagaaaataa aaatctagcg     840
ctcagtcatc acccaacttt aaattcagac cttctagatt ttatccgtca tggtagaatc     900
aaccctcgtc ctgcgatcaa aaaattacac ggtaaagaag tggaattat agatggaacc     960 aaagaacgtt ttgacatcat ctgcgcttgc accggctttt ggactacgtt tccttttttt    1020
gataaatcgt ttatcgattt tcagcacgtt gaaaaaattc tctctttcg caagatgata    1080 cataacgatt ttcaaaattt atatttcatc ggtttgtttc aacccgtagg ttgtatctgg    1140
ccgatggcag attatcaagc aaaactagct tgtttagaaa ttttaggaaa atataaacgt    1200
ccccaaaatt tgaaggccgc aattcaatac gaaattgatc atcctcactt tacatttgaa    1260
agaggccaaa gacacgctgt agaagtagac tatcactctt tccgtaaaga acttagattg    1320 gaactttaa aagcgggtgt agatattgga aaacctcccg gtggaaataa atctctttat    1380
aaaaattttc caaaagccgc gagt                                            1404
```

<210> SEQ ID NO 82
<211> LENGTH: 468
<212> TYPE: PRT
<213> ORGANISM: Artificial Sequence
<220> FEATURE:
<223> OTHER INFORMATION: LIC10959

<400> SEQUENCE: 82

```
Leu Ile Ser Arg Met Ile Ser Lys Arg Lys Glu Asp Arg Met Lys Ser
1               5                   10                  15

Asn Ala Arg Val Cys Val Val Gly Ala Gly Pro Ser Gly Ile Ala Ala
            20                  25                  30

Gly Lys Asn Cys Val Glu Tyr Gly Leu Asp Val Val Ile Phe Glu Lys
        35                  40                  45

Asn Asp Lys Val Gly Gly Asn Trp Val Phe Asn Ala Lys Thr Gly His
    50                  55                  60

Ser Ser Val Tyr Glu Asn Thr His Ile Ile Ser Ser Lys Val Trp Ser
65                  70                  75                  80

Glu Tyr Glu Asp Phe Pro Met Pro Glu Asp Tyr Pro Glu Tyr Pro Asn
                85                  90                  95

His Lys Gln Leu Gln Ala Tyr Phe Glu Ser Tyr Ala Lys His Phe Gly
            100                 105                 110

Val Tyr Lys Lys Ile Arg Phe His His Thr Ile Gln Lys Ile Thr Lys
        115                 120                 125

Thr Pro Asn Glu Glu Trp Lys Val Glu Tyr Thr Asn Ala Ser Lys Lys
    130                 135                 140

Lys Lys Val Glu Phe Phe Asp Val Leu Met Val Ala Asn Gly His His
145                 150                 155                 160

Trp Asp Pro Lys Tyr Pro Glu Tyr Glu Gly Lys Phe Thr Gly Lys Phe
                165                 170                 175

Leu His Ser His Asp Phe Lys Gly Val Thr Asn Glu Trp Lys Gly Lys
            180                 185                 190

Asp Ile Leu Val Ile Gly Ala Gly Asn Ser Ala Cys Asp Val Ala Val
        195                 200                 205

Glu Ser Ala Arg Val Ala Asn Ser Val Lys Leu Ser Met Arg Ser Pro
    210                 215                 220

Gln Trp Phe Phe Pro Lys Phe Leu Phe Gly Met Pro Ser Asp Val Phe
225                 230                 235                 240

Ala Ala Lys Thr Pro Asn Trp Ile Pro Ser Ile Ile Lys Gln Phe Ala
                245                 250                 255

Leu Ser Lys Leu Ile Tyr Ile Leu Gln Gly Ser Tyr Lys Asn Tyr Gly
            260                 265                 270

Leu Pro Glu Asn Lys Asn Leu Ala Leu Ser His Pro Thr Leu Asn
        275                 280                 285

Ser Asp Leu Leu Asp Phe Ile Arg His Gly Arg Ile Asn Pro Arg Pro
    290                 295                 300

Ala Ile Lys Lys Leu His Gly Lys Glu Val Glu Phe Ile Asp Gly Thr
305                 310                 315                 320

Lys Glu Arg Phe Asp Ile Ile Cys Ala Cys Thr Gly Phe Trp Thr Thr
                325                 330                 335

Phe Pro Phe Phe Asp Lys Ser Phe Ile Asp Phe Gln His Val Glu Lys
            340                 345                 350

Ile Pro Leu Phe Arg Lys Met Ile His Asn Asp Phe Gln Asn Leu Tyr
        355                 360                 365
```

```
Phe Ile Gly Leu Phe Gln Pro Val Gly Cys Ile Trp Pro Met Ala Asp
        370                 375                 380

Tyr Gln Ala Lys Leu Ala Cys Leu Glu Ile Leu Gly Lys Tyr Lys Arg
385                 390                 395                 400

Pro Gln Asn Leu Lys Ala Ala Ile Gln Tyr Glu Ile Asp His Pro His
                405                 410                 415

Phe Thr Phe Glu Arg Gly Gln Arg His Ala Val Glu Val Asp Tyr His
                420                 425                 430

Ser Phe Arg Lys Glu Arg Leu Glu Leu Leu Lys Ala Gly Val Asp
        435                 440                 445

Ile Gly Lys Pro Pro Gly Gly Asn Lys Ser Leu Tyr Lys Asn Phe Pro
        450                 455                 460

Lys Ala Ala Ser
465

<210> SEQ ID NO 83
<211> LENGTH: 2304
<212> TYPE: DNA
<213> ORGANISM: Artificial Sequence
<220> FEATURE:
<223> OTHER INFORMATION: LIC11289

<400> SEQUENCE: 83
atgcaaatca tacagaggaa atggaaaatt cctcacgcgg ccagaaaacc tctcgtattt      60
tttttagttt ttttatttt atctgtacaa tttcgatttt tattttcgga tcaagtaccc      120
gatttcgtat ccttacaaaa ccaatatcta atcgctcagg attatcagat cctatttaag     180
aattttcttt cttctggata cgatcgttcc ttacaagggg gcagtcccat ttttttattc     240
caagcccctt ttttcttttt tttggtttct tttcttcaca cgtttatttt attttttctt     300 cccttttggag tttcttttaa tttaggaatt ttgcttggac tgttttatt tcatacgcg     360 tttttaaaat taggattttt atttcttaca gaaacaaatc tcagtccagg aaatacttta     420
cttactataa ctggacttat gttttatttt ttatatccgg gagaccgtgt tgtaggtgca     480
ggaattgtag gggtttttca aaattcaatt tcgttttcgg taggacttgc gattgcgttg     540
ctttctattt attatctgga aaaatttcgt tataccggaa aagtctcttc cttttttaaa     600
aatctgatcg ctggaactct cgtatttat acacactacg aaacttcttt gttttattg      660 atagcattag gtatctattt tcttttttat aaagacgaat ttgaaattct tgagatctta     720 ttgattttc tagttcctct tctttttgcc tttcctatat tatggaatta ttttgcgtat     780 atttcattc agcaaaatcc tcctgttct tttccgatta acggactttt atctctttta     840
ggagaagagt tttcaaattc aattgcaagg ccagagaaaa ttttagatct aataaaacag     900
attttaatgg atcaatattg gattcatcta ttgtttccaa ttttatttgt gatcggaatt     960
cggctgttgt ttatcagaaa actattacct ccaatttcta gatttctaat atttggagcc    1020
ttgttttttt attggatggc tacggattct tctttatcta tgatttttcc ttggttacat    1080
gcaaaatggc atacggcctt aaacgtatct ttggtctttc tgactctttc ttcacttgta    1140
actgccagat tctttttaaa aaaccttccg cccggaaaat ggaaattatg gagtggtttg    1200
attttattca tattaggatt atatcgattt attgtaacaa ttccggggcc agccactggg    1260
atagaaactt ttacagataa tccttctgta atctggaaac agaaagaaga gtggattcgt    1320 gttttgaaa aacttcttta tggagctttg attgcatccg aagaaatatt agaagaaaaa    1380
gattttgcgg actctcgttg ggcctctgta ctaatccgac aatccattag acgaaatatc    1440
```

```
actttgaaga atcgttttga aaaatcgttt cctgcttcga ttgaagaaat cattagactg    1500
tttccggaac aaggaacaaa gactttttta aacaaagaag agaaacaaat aaattttcat    1560
cctgctcttg aaagagaaaa actttcagaa ttattttcta aattactttc gaaagaggg     1620 gtttcctacg tattgcttgg ttcggattct ttgaatcaat tggcgattgt gtctcctaaa    1680
tatttttata agatagatca aaaaggaaaa tggattttat ggaaattgaa ttcttctcga    1740
tcttttatgg agctacttcc taaaaagccg attgctattt taattgaaga ttttcactt     1800 caaaaactta aattagaatc cgtcttagat ctaaaatttg aacaaaatct cactttgatt    1860
cctgttccca aagaagaatt taaatcagat caaaattctt tttcggacgt ttgcgaagta    1920
tcttcttgtt ttagggaaaa ggtcaaagaa aagaaagtt ttcaaaataa aacaggaact     1980
aaaacagatt tagttggttt acctacagaa atttggccgg ttacttggag cgattccgaa    2040
atcagatggg agatttcaaa agaaaacaa tccgaggtat gttttcctac acttgttcat     2100
tccagttttt tccctctttg gaacttgta tcaggagaaa aagttttatcg actttggaa     2160 gatcaatttt attttgttc taaagaaaga aaaaatgaat tcatattta tgatattcga      2220 acatacttaa ttcgtttgt tcaacttta cttcctcttg ctttttggg agccacattc       2280 ttaacacgta ggaaagtatc taat                                           2304
```

<210> SEQ ID NO 84
<211> LENGTH: 768
<212> TYPE: PRT
<213> ORGANISM: Artificial Sequence
<220> FEATURE:
<223> OTHER INFORMATION: LIC11289

<400> SEQUENCE: 84

Met Gln Ile Ile Gln Arg Lys Trp Lys Ile Pro His Ala Ala Arg Lys
1               5                   10                  15

Pro Leu Val Phe Phe Leu Val Phe Leu Phe Ser Val Gln Phe Arg
            20                  25                  30

Phe Leu Phe Ser Asp Gln Val Pro Asp Phe Val Ser Leu Gln Asn Gln
        35                  40                  45

Tyr Leu Ile Ala Gln Asp Tyr Gln Ile Leu Phe Lys Asn Phe Leu Ser
    50                  55                  60

Ser Gly Tyr Asp Arg Ser Leu Gln Gly Gly Ser Pro Ile Phe Tyr Phe
65                  70                  75                  80

Gln Ala Pro Phe Phe Phe Leu Val Ser Phe Leu His Thr Phe Ile
            85                  90                  95

Leu Phe Phe Leu Pro Phe Gly Val Ser Phe Asn Leu Gly Ile Leu Leu
            100                 105                 110

Gly Leu Phe Leu Phe Ser Tyr Ala Phe Leu Lys Leu Gly Phe Leu Phe
            115                 120                 125

Leu Thr Glu Thr Asn Leu Ser Pro Gly Asn Thr Leu Leu Thr Ile Thr
    130                 135                 140

Gly Leu Met Phe Tyr Phe Leu Tyr Pro Gly Asp Arg Val Val Gly Ala
145                 150                 155                 160

Gly Ile Val Gly Val Phe Gln Asn Ser Ile Ser Phe Ser Val Gly Leu
                165                 170                 175

Ala Ile Ala Leu Leu Ser Ile Tyr Tyr Leu Glu Lys Phe Arg Tyr Thr
            180                 185                 190

Gly Lys Val Ser Ser Phe Phe Lys Asn Leu Ile Ala Gly Thr Leu Val
        195                 200                 205

```
Phe Tyr Thr His Tyr Glu Thr Ser Leu Phe Tyr Leu Ile Ala Leu Gly
        210                 215                 220

Ile Tyr Phe Leu Phe Tyr Lys Asp Glu Phe Glu Ile Leu Glu Ile Leu
225                 230                 235                 240

Leu Ile Phe Leu Val Pro Leu Leu Phe Ala Phe Pro Ile Leu Trp Asn
                245                 250                 255

Tyr Phe Ala Tyr Ile Ser Phe Gln Gln Asn Pro Pro Val Ser Phe Pro
            260                 265                 270

Ile Asn Gly Leu Leu Ser Leu Leu Gly Glu Glu Phe Ser Asn Ser Ile
        275                 280                 285

Ala Arg Pro Glu Lys Ile Leu Asp Leu Ile Lys Gln Ile Leu Met Asp
290                 295                 300

Gln Tyr Trp Ile His Leu Leu Phe Pro Ile Leu Phe Val Ile Gly Ile
305                 310                 315                 320

Arg Leu Leu Phe Ile Arg Lys Leu Leu Pro Pro Ile Ser Arg Phe Leu
                325                 330                 335

Ile Phe Gly Ala Leu Phe Phe Tyr Trp Met Ala Thr Asp Ser Ser Leu
            340                 345                 350

Ser Met Ile Phe Pro Trp Leu His Ala Lys Trp His Thr Ala Leu Asn
        355                 360                 365

Val Ser Leu Val Phe Leu Thr Leu Ser Ser Leu Val Thr Ala Arg Phe
370                 375                 380

Phe Leu Lys Asn Leu Pro Pro Gly Lys Trp Lys Leu Trp Ser Gly Leu
385                 390                 395                 400

Ile Leu Phe Ile Leu Gly Leu Tyr Arg Phe Ile Val Thr Ile Pro Gly
                405                 410                 415

Pro Ala Thr Gly Ile Glu Thr Phe Thr Asp Asn Pro Ser Val Ile Trp
            420                 425                 430

Lys Gln Lys Glu Glu Trp Ile Arg Val Phe Glu Lys Thr Ser Tyr Gly
        435                 440                 445

Ala Leu Ile Ala Ser Glu Glu Ile Leu Glu Glu Lys Asp Phe Ala Asp
450                 455                 460

Ser Arg Trp Ala Ser Val Leu Ile Arg Gln Ser Ile Arg Arg Asn Ile
465                 470                 475                 480

Thr Leu Lys Asn Arg Phe Glu Lys Ser Phe Pro Ala Ser Ile Glu Glu
                485                 490                 495

Ile Ile Arg Leu Phe Pro Glu Gln Gly Thr Lys Thr Phe Leu Asn Lys
            500                 505                 510

Glu Glu Lys Gln Ile Asn Phe His Pro Ala Leu Glu Arg Glu Lys Leu
        515                 520                 525

Ser Glu Leu Phe Ser Lys Leu Leu Ser Glu Arg Gly Val Ser Tyr Val
530                 535                 540

Leu Leu Gly Ser Asp Ser Leu Asn Gln Leu Ala Ile Val Ser Pro Lys
545                 550                 555                 560

Tyr Phe Tyr Lys Ile Asp Gln Lys Gly Lys Trp Ile Leu Trp Lys Leu
                565                 570                 575

Asn Ser Ser Arg Ser Phe Met Glu Leu Leu Pro Lys Lys Pro Ile Ala
            580                 585                 590

Ile Leu Ile Glu Asp Phe Ser Leu Gln Lys Leu Lys Leu Glu Ser Val
        595                 600                 605

Leu Asp Leu Lys Phe Glu Gln Asn Leu Thr Leu Ile Pro Val Ser Lys
610                 615                 620
```

```
Glu Glu Phe Lys Ser Asp Gln Asn Ser Phe Ser Asp Val Cys Glu Val
625                 630                 635                 640

Ser Ser Cys Phe Arg Glu Lys Val Lys Glu Lys Glu Ser Phe Gln Asn
                645                 650                 655

Lys Thr Gly Thr Lys Thr Asp Leu Val Gly Leu Pro Thr Glu Ile Trp
            660                 665                 670

Pro Val Thr Trp Ser Asp Ser Glu Ile Arg Trp Glu Ile Ser Lys Glu
        675                 680                 685

Lys Gln Ser Glu Val Cys Phe Pro Thr Leu Val His Ser Ser Phe Phe
    690                 695                 700

Pro Leu Trp Lys Leu Val Ser Gly Lys Val Tyr Arg Thr Leu Glu
705                 710                 715                 720

Asp Gln Phe Tyr Phe Cys Ser Lys Glu Arg Lys Asn Glu Phe Ile Phe
                725                 730                 735

Tyr Asp Ile Arg Thr Tyr Leu Ile Thr Phe Val Gln Leu Leu Leu Pro
            740                 745                 750

Leu Ala Phe Leu Gly Ala Thr Phe Leu Thr Arg Arg Lys Val Ser Asn
        755                 760                 765
```

<210> SEQ ID NO 85
<211> LENGTH: 1620
<212> TYPE: DNA
<213> ORGANISM: Artificial Sequence
<220> FEATURE:
<223> OTHER INFORMATION: LIC12349

<400> SEQUENCE: 85

```
ttgtcttgga gttccccttt tctggggttg gggatttttt tccctcttgg tgtactcttt      60
gcctttccta aaggtagaga agtccgttcc tccgcttttg gttctttgct ctttcaaatc     120
gcctgttggg tagttcttta tccattggaa gtttcggcga ttttatttcc taccgtagag     180
gcgtttgttc gtaccttcgt tatgaattta agagaatggc tgatcgggtt ttacgttctt     240
gtaggatttg taatcttagt ctctcattct tattttctca aaaacaaag agaacgactg      300
tcgaaacgga gtcttagtgt tttgattccg gaagagaaga tagaaagaat tcattataaa     360
attttagtgc ttttttgttgc agggtatcta acttctaaac tcgtatttca agactcttat    420
cgattggaat atggacagat cggaatttta gaagatagtt ttctctattt cttttcggtt    480
ttaattgctg gggatactct tttaagtaga ggaaaacaat tcttcctatt tagaaggcct    540
tggaaacttt ttgaaaaaca gactcggatc gcgcgttatt ctggctttca aggaaaatgg   600
ggacttctga aacagaaaaa tgcaaagttg agggattgga ttttttccggg ctgggggcat    660
atttacatcg gaaatctttg gaaaggtttt tcgattttat ttttatatct tcttctttta    720
ttatttcttg ctacttcttt tttctcttgg cttgagcctg cagacggaat tcgttttta     780
atgtcgatgg gattaaaacc aggaatccgg gatcaaactt ttttttaagat cacttcgagt    840
gtaattccga tcctaatttt tctaggggga atagcagtag ttcatatcat ttctaagttt    900
ttactcggta ggagctttcg ttcggaaccg gatgatctca ctcctaaaag cacatttatt    960
agtaatttat catatagtat tttacttcat ttaattctaa tatctttgat tttgatcata   1020
ccggtaaccc ttcagagaaa gaacaaacaa aaggaatcgg aaagacaaag aactcatttt    1080
actcccgaga atttggaatt ctattttata gatcctaatc ttccaaacga agtgaaaggt    1140
ctaaacggag gagttgtatc cggaaccgaa acaccaactc agaagaagg agaaaaaagtt   1200
ccagaagata aaccagcgga agaaggaagg gtcaaggaa aagtcaaaca ggttcgagga    1260
```

-continued

```
aaaaaattac ctgccactta ttccaattat atttccgcaa agatgagggg acccgagtct    1320
tttatggaat attggagaag ggctcctaaa aattattctt ccgtagtcgc ttatactgta    1380
actccggatg gagaagttgt ggatgtggat cttgtggaag cctcggatta ccggaacaa    1440 gaccaaatga ctttggaact cattgaaagt ctttctcctc tgatgcctcc gccaggaacg    1500
aagggttatg ttcgagtcac cgaacttttt tggaatggaa gtattgatcc gaatgcaatg    1560
ccaactccac ttcaaaaaga actggttacg atgtatgacg ggcgttatat ggaggagtta    1620
```

<210> SEQ ID NO 86
<211> LENGTH: 540
<212> TYPE: PRT
<213> ORGANISM: Artificial Sequence
<220> FEATURE:
<223> OTHER INFORMATION: LIC12349

<400> SEQUENCE: 86

| Met | Ser | Trp | Ser | Ser | Pro | Phe | Leu | Gly | Leu | Gly | Ile | Phe | Phe | Pro | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Gly Val Leu Phe Ala Phe Pro Lys Gly Arg Glu Val Arg Ser Ser Ala
          20                  25                  30

Phe Gly Ser Leu Leu Phe Gln Ile Ala Cys Trp Val Val Leu Tyr Pro
        35                  40                  45

Leu Glu Val Ser Ala Ile Leu Phe Pro Thr Val Glu Ala Phe Val Arg
    50                  55                  60

Thr Phe Val Met Asn Leu Arg Glu Trp Leu Ile Gly Phe Tyr Val Leu
65                  70                  75                  80

Val Gly Phe Val Ile Leu Val Ser His Ser Tyr Phe Leu Lys Lys Gln
                85                  90                  95

Arg Glu Arg Leu Ser Lys Arg Ser Leu Ser Val Leu Ile Pro Glu Glu
            100                 105                 110

Lys Ile Glu Arg Ile His Tyr Lys Ile Leu Val Leu Phe Val Ala Gly
        115                 120                 125

Tyr Leu Thr Ser Lys Leu Val Phe Gln Asp Ser Tyr Arg Leu Glu Tyr
    130                 135                 140

Gly Gln Ile Gly Ile Leu Glu Asp Ser Phe Leu Tyr Phe Phe Ser Val
145                 150                 155                 160

Leu Ile Ala Gly Asp Thr Leu Leu Ser Arg Gly Lys Gln Phe Phe Leu
                165                 170                 175

Phe Arg Arg Pro Trp Lys Leu Phe Glu Lys Gln Thr Arg Ile Ala Arg
            180                 185                 190

Tyr Ser Gly Phe Gln Gly Lys Trp Gly Leu Leu Lys Gln Lys Asn Ala
        195                 200                 205

Lys Leu Arg Asp Trp Ile Phe Pro Gly Trp Gly His Ile Tyr Ile Gly
    210                 215                 220

Asn Leu Trp Lys Gly Phe Ser Ile Leu Phe Leu Tyr Leu Leu Leu Leu
225                 230                 235                 240

Leu Phe Leu Ala Thr Ser Phe Phe Ser Trp Leu Glu Pro Ala Asp Gly
                245                 250                 255

Ile Arg Phe Leu Met Ser Met Gly Leu Lys Pro Gly Ile Arg Asp Gln
            260                 265                 270

Thr Phe Phe Lys Ile Thr Ser Ser Val Ile Pro Ile Leu Ile Phe Leu
        275                 280                 285

Gly Gly Ile Ala Val Val His Ile Ile Ser Lys Phe Leu Leu Gly Arg
    290                 295                 300

| Ser | Phe | Arg | Ser | Glu | Pro | Asp | Asp | Leu | Thr | Pro | Lys | Ser | Thr | Phe | Ile |
| 305 | | | | 310 | | | | | 315 | | | | | 320 | |

| Ser | Asn | Leu | Ser | Tyr | Ser | Ile | Leu | Leu | His | Leu | Ile | Leu | Ile | Ser | Leu |
| | | | | 325 | | | | | 330 | | | | | 335 | |

| Ile | Leu | Ile | Ile | Pro | Val | Thr | Leu | Gln | Arg | Lys | Asn | Lys | Gln | Lys | Glu |
| | | | 340 | | | | | 345 | | | | | 350 | | |

| Ser | Glu | Arg | Gln | Arg | Thr | His | Phe | Thr | Pro | Glu | Asn | Leu | Glu | Phe | Tyr |
| | | | 355 | | | | | 360 | | | | | 365 | | |

| Phe | Ile | Asp | Pro | Asn | Leu | Pro | Asn | Glu | Val | Lys | Gly | Leu | Asn | Gly | Gly |
| | | 370 | | | | | 375 | | | | | 380 | | | |

| Val | Val | Ser | Gly | Thr | Glu | Thr | Pro | Thr | Gln | Lys | Glu | Gly | Glu | Lys | Val |
| 385 | | | | | 390 | | | | | 395 | | | | | 400 |

| Pro | Glu | Asp | Lys | Pro | Ala | Glu | Glu | Gly | Arg | Val | Lys | Gly | Lys | Val | Lys |
| | | | | 405 | | | | | 410 | | | | | 415 | |

| Gln | Val | Arg | Gly | Lys | Lys | Leu | Pro | Ala | Thr | Tyr | Ser | Asn | Tyr | Ile | Ser |
| | | | 420 | | | | | 425 | | | | | 430 | | |

| Ala | Lys | Met | Arg | Gly | Pro | Glu | Ser | Phe | Met | Glu | Tyr | Trp | Arg | Arg | Ala |
| | | | 435 | | | | | 440 | | | | | 445 | | |

| Pro | Lys | Asn | Tyr | Ser | Ser | Val | Val | Ala | Tyr | Thr | Val | Thr | Pro | Asp | Gly |
| | | | 450 | | | | | 455 | | | | | 460 | | |

| Glu | Val | Val | Asp | Val | Asp | Leu | Val | Glu | Ala | Ser | Asp | Tyr | Pro | Glu | Gln |
| 465 | | | | | 470 | | | | | 475 | | | | | 480 |

| Asp | Gln | Met | Thr | Leu | Glu | Leu | Ile | Glu | Ser | Leu | Ser | Pro | Leu | Met | Pro |
| | | | | 485 | | | | | 490 | | | | | 495 | |

| Pro | Pro | Gly | Thr | Lys | Gly | Tyr | Val | Arg | Val | Thr | Glu | Leu | Phe | Trp | Asn |
| | | | 500 | | | | | 505 | | | | | 510 | | |

| Gly | Ser | Ile | Asp | Pro | Asn | Ala | Met | Pro | Thr | Pro | Leu | Gln | Lys | Glu | Leu |
| | | | 515 | | | | | 520 | | | | | 525 | | |

| Val | Thr | Met | Tyr | Asp | Gly | Arg | Tyr | Met | Glu | Glu | Leu |
| | | | 530 | | | | | 535 | | | | | 540 | | |

<210> SEQ ID NO 87
<211> LENGTH: 1827
<212> TYPE: DNA
<213> ORGANISM: Artificial Sequence
<220> FEATURE:
<223> OTHER INFORMATION: LIC13250

<400> SEQUENCE: 87

```
ttgttgactt ctatttctaa aatcaagata aacgttttat ccatggatac attacatcat    60
cgttttcaac aatttcaaaa aacaatctgg ttcaacatat tctgttatct ttggacagga   120
attttttctt ttttagcgtt tgctcctgtc tctctaactc attttgtatg gatcgcacct   180
tttggatttt tttggctgag tttgaaatac cacggaaagt ataaaaaatt attctttcac   240
ggattgctta taggagttgt cttctatgcg atttcttttc attggatcat tcatatggcg   300
attactttcg gaattttcc gtatgtggtt gcgatactca ttcttttatt tgcgggtcta   360
ttattcggtt taaaatttcc gattttatg atgagttttt cttttctttc gggaaagata   420
ggacgtcatt ccgtttgggt tgctggtttt tgtggacttt atccgagtt gattggacct   480
cagttatttc cttggtattg gggaaactta gccgctggaa atataattct cgcgcagaat   540
gcagaaatta ccggagtgta tggtatcagc ttttagtat tcatagtttc ttatactttg   600
tttcaatcca atccttggca ttggaaagaa attatacatt ctaaagaaaa aagaaaacaa   660
tatcttcgtt ttattacgtt gcccgctctt ttactttaa catttattgt ttcaggcatt   720
```

```
tttcttttta aaaaatggga aaatgtaaaa ccagttaaat ctttaaatgt acttatcgtt      780
caaccagatg ctcctttgag ttttagagat ggaagagaaa ttaaagaatc cattgaagct      840
ctgatggctc gtatcgaaaa actgaccgac gaaggcgcag taaggctggg aaaaaaaccg      900
gatcttatcg tattgcctga ggcaggggtt ccgttttttt ccgcccacaa aacagaaata      960
actacgaagg ttcgtagaat gtattgggat cgatttgatt ctttgatgtt tttacttgcc     1020
aatcgataca aagcgaatgt attttttaac gaaattgacg caggatttaa aggagcccct     1080
agtcctcgta atttaagata ttataataat aatgtattat atgatcctaa tggagatcgc     1140
agggattcgt atcaaaagaa atttcttttg atgttcggag aatatatgcc attcgatttt     1200
ttatatgaac tcagtcaaca aaccggaaga tttgagccgg gactgactca taatttgatt     1260
cgatactaca ctccccgtta ttacactctc gcggaaaaag aaaaatctcc gaaaggccga     1320
catttgggat ggacggatac ggaaactttc aatcacgaag cggtaagatc gtattacgaa     1380
acgacaagaa cggaagtttc agaaaccgga agtttcttc ctttgatttg ttatgaggta     1440
attcttccag agtttgttag agaatttaga accgctggaa acccagaatt tatagtaaat     1500
cttaccaatg ataaatggta tgggcaaca acggaaagtg atcaacacat ggagcttgga     1560
agattacgtt ccatagagtt gagaagatgg atggttcgtt ctaccaattc tggaatttcc     1620
gcaaatatag atcatctcgg tagatttgta ggaaataaaa aaacaggatt gatgacggcg     1680
gaagcgcttt ctgaaacgat agacgtaatt gattctccgc ctacgtttta tactcagtat     1740
ggaaatttaa ttccttggtt gatgcttttt ttaactggaa tttattacct taatcttttg     1800
atcggaatcc gaagaggaaa gtcctcc                                         1827
```

<210> SEQ ID NO 88
<211> LENGTH: 609
<212> TYPE: PRT
<213> ORGANISM: Artificial Sequence
<220> FEATURE:
<223> OTHER INFORMATION: LIC13250

<400> SEQUENCE: 88

```
Met Leu Thr Ser Ile Ser Lys Ile Lys Ile Asn Val Leu Ser Met Asp
1               5                   10                  15

Thr Leu His His Arg Phe Gln Gln Phe Gln Lys Thr Ile Trp Phe Asn
            20                  25                  30

Ile Phe Cys Tyr Leu Trp Thr Gly Ile Phe Ser Phe Leu Ala Phe Ala
        35                  40                  45

Pro Val Ser Leu Thr His Phe Val Trp Ile Ala Pro Phe Gly Phe Phe
    50                  55                  60

Trp Leu Ser Leu Lys Tyr His Gly Lys Tyr Lys Lys Leu Phe Phe His
65                  70                  75                  80

Gly Leu Leu Ile Gly Val Val Phe Tyr Ala Ile Ser Phe His Trp Ile
                85                  90                  95

Ile His Met Ala Ile Thr Phe Gly Asn Phe Pro Tyr Val Val Ala Ile
            100                 105                 110

Leu Ile Leu Leu Phe Ala Gly Leu Leu Phe Gly Leu Lys Phe Pro Ile
        115                 120                 125

Phe Met Met Ser Phe Ser Phe Leu Ser Gly Lys Ile Gly Arg His Ser
    130                 135                 140

Val Trp Val Ala Gly Phe Cys Gly Leu Leu Ser Glu Leu Ile Gly Pro
145                 150                 155                 160

Gln Leu Phe Pro Trp Tyr Trp Gly Asn Leu Ala Ala Gly Asn Ile Ile
```

```
                    165                 170                 175
Leu Ala Gln Asn Ala Glu Ile Thr Gly Val Tyr Gly Ile Ser Phe Leu
                180                 185                 190

Val Phe Ile Val Ser Tyr Thr Leu Phe Gln Ser Asn Pro Trp His Trp
            195                 200                 205

Lys Glu Ile Ile His Ser Lys Glu Lys Arg Lys Gln Tyr Leu Arg Phe
        210                 215                 220

Ile Thr Leu Pro Ala Leu Leu Leu Thr Phe Ile Val Ser Gly Ile
225                 230                 235                 240

Phe Leu Phe Lys Lys Trp Glu Asn Val Lys Pro Val Lys Ser Leu Asn
                245                 250                 255

Val Leu Ile Val Gln Pro Asp Ala Pro Leu Ser Phe Arg Asp Gly Arg
            260                 265                 270

Glu Ile Lys Glu Ser Ile Glu Ala Leu Met Ala Arg Ile Glu Lys Leu
        275                 280                 285

Thr Asp Glu Gly Ala Val Arg Leu Gly Lys Lys Pro Asp Leu Ile Val
    290                 295                 300

Leu Pro Glu Ala Gly Val Pro Phe Phe Ser Ala His Lys Thr Glu Ile
305                 310                 315                 320

Thr Thr Lys Val Arg Arg Met Tyr Trp Asp Arg Phe Asp Ser Leu Met
                325                 330                 335

Phe Leu Leu Ala Asn Arg Tyr Lys Ala Asn Val Phe Phe Asn Glu Ile
            340                 345                 350

Asp Ala Gly Phe Lys Gly Ala Pro Ser Pro Arg Asn Leu Arg Tyr Tyr
        355                 360                 365

Asn Asn Asn Val Leu Tyr Asp Pro Asn Gly Asp Arg Arg Asp Ser Tyr
    370                 375                 380

Gln Lys Lys Phe Leu Leu Met Phe Gly Tyr Met Pro Phe Asp Phe
385                 390                 395                 400

Leu Tyr Glu Leu Ser Gln Gln Thr Gly Arg Phe Glu Pro Gly Leu Thr
                405                 410                 415

His Asn Leu Ile Arg Tyr Tyr Thr Pro Arg Tyr Tyr Thr Leu Ala Glu
            420                 425                 430

Lys Glu Lys Ser Pro Lys Gly Arg His Leu Gly Trp Thr Asp Thr Glu
        435                 440                 445

Thr Phe Asn His Glu Ala Val Arg Ser Tyr Tyr Glu Thr Thr Arg Thr
    450                 455                 460

Glu Val Ser Glu Thr Gly Lys Phe Leu Pro Leu Ile Cys Tyr Glu Val
465                 470                 475                 480

Ile Leu Pro Glu Phe Val Arg Glu Phe Arg Thr Ala Gly Asn Pro Glu
                485                 490                 495

Phe Ile Val Asn Leu Thr Asn Asp Lys Trp Tyr Gly Ala Thr Thr Glu
            500                 505                 510

Ser Asp Gln His Met Glu Leu Gly Arg Leu Arg Ser Ile Glu Leu Arg
        515                 520                 525

Arg Trp Met Val Arg Ser Thr Asn Ser Gly Ile Ser Ala Asn Ile Asp
    530                 535                 540

His Leu Gly Arg Phe Val Gly Asn Lys Lys Thr Gly Leu Met Thr Ala
545                 550                 555                 560

Glu Ala Leu Ser Glu Thr Ile Asp Val Ile Asp Ser Pro Pro Thr Phe
                565                 570                 575

Tyr Thr Gln Tyr Gly Asn Leu Ile Pro Trp Leu Met Leu Phe Leu Thr
            580                 585                 590
```

Gly Ile Tyr Tyr Leu Asn Leu Leu Ile Gly Ile Arg Arg Gly Lys Ser
        595                 600                 605
Ser

<210> SEQ ID NO 89
<211> LENGTH: 1575
<212> TYPE: DNA
<213> ORGANISM: Artificial Sequence
<220> FEATURE:
<223> OTHER INFORMATION: LIC20146

<400> SEQUENCE: 89

| | | | | | |
|---|---|---|---|---|---|
| atgaattctg | aaacccgaat | caaaatcaaa | ataatttgga | tcttttat | cctttactt | 60 |
| ggattttat | ttttagatcg | agttctattt | ccgatcgcac | ttttcgaatt | ccgaatgaa | 120 |
| cttgaatggg | atacttctcc | ttggtataac | tttcttcata | acgaaaaaa | cattcatttt | 180 |
| gaaaaagatg | aaagggaat | tctcataacg | ggaagtagtg | tcgctctcta | ttcctcttat | 240 |
| cctaaacaga | taaccgaaga | aatacgaaat | tctaatataa | aagacggaaa | aaatttaga | 300 |
| gcggaatttt | attctcatcc | tgccttatct | cctacggatc | tttattatta | ctcagatgat | 360 |
| attttatcta | aaaaaccaga | gctggtagta | tacatattaa | atccagcaga | tttacaatta | 420 |
| gattatattc | aaaaattaga | atcttctgaa | gcccgtttcg | acgaacgaac | aagaataaaa | 480 |
| gattataaga | ttcgccacca | gaatcgcttc | atttttccgg | gagagtttct | tgctgatcat | 540 |
| tggagagatt | atacaaaagc | agaaattttt | gctcaattga | caaaaacatt | catactgttg | 600 |
| aatcgcttta | gaagtttctt | atacgatcct | tgggtagaat | acatagaaca | tcataccaga | 660 |
| actatgcgtt | cttatcatta | ctacactggt | tccataccta | aggaagggat | tttctccgc | 720 |
| ggatggaccc | cgccttcatt | tacgatcgaa | tgtgagctca | aagatggaaa | attgtcggaa | 780 |
| gatatttta | ctcagaagcc | gggagttcgg | attcaagttg | aagaaataaa | ttcaagtgca | 840 |
| aaacatttaa | acagagaacc | gatttttat | gatcaaacct | tttctaaatc | cggatggaaa | 900 |
| tcgcttttc | tcgacttcaa | aaagaattca | tccggagaaa | atcctcaatc | agttaccta | 960 |
| aaatttactg | tttctcctac | tacaagttct | gacgaagtgg | atgcgagaat | tttcggaatc | 1020 |
| ccagctaatt | atggaattcg | tcttcctcaa | aattttgta | aaaggaaat | taaaaccaat | 1080 |
| atttcttatg | atagaattca | cggtttagac | gatgatcgga | tcgaaactat | gtccgatgaa | 1140 |
| gattatttga | agactatga | aaaacgcctc | tatttcaatc | cggaaaacga | aggtgccctt | 1200 |
| aatcgtttga | aaaaaattca | agaaacaaa | gaatttttag | gaaactcaac | ttactttact | 1260 |
| tggtctgaaa | ttcaattttt | ggaaaagaca | atctctaagt | ttcaagcaaa | tggtcaaaaa | 1320 |
| tgatcatca | tcaattctcc | tgaaaatcca | attgaaagca | aatattataa | aaatggaaat | 1380 |
| tggtatcgtg | gttatcttaa | atttttaaat | tcttataaaa | atgatacata | tggttttttac | 1440 |
| gatctcaaag | atgcgattcg | ggataaaaga | tcgtttttag | atccgcatca | cctaacattt | 1500 |
| aacgctgcaa | acatagttc | ttctttatat | acaaacgtca | ttctagattt | tttaaacgtt | 1560 |
| tcggagcgaa | aaaaa | | | | | 1575 |

<210> SEQ ID NO 90
<211> LENGTH: 525
<212> TYPE: PRT
<213> ORGANISM: Artificial Sequence
<220> FEATURE:
<223> OTHER INFORMATION: LIC20146

<400> SEQUENCE: 90

```
Met Asn Ser Glu Thr Arg Ile Lys Ile Lys Ile Ile Trp Ile Phe Leu
1               5                   10                  15

Phe Leu Leu Leu Gly Phe Leu Phe Leu Asp Arg Val Leu Phe Pro Ile
            20                  25                  30

Ala Leu Phe Glu Phe Pro Asn Glu Leu Glu Trp Asp Thr Ser Pro Trp
        35                  40                  45

Tyr Asn Phe Leu His Lys Arg Lys Asn Ile His Phe Glu Lys Asp Glu
    50                  55                  60

Lys Gly Ile Leu Ile Thr Gly Ser Ser Val Ala Leu Tyr Ser Ser Tyr
65                  70                  75                  80

Pro Lys Gln Ile Thr Glu Glu Ile Arg Asn Ser Asn Ile Lys Asp Gly
                85                  90                  95

Lys Lys Phe Arg Ala Glu Phe Tyr Ser His Pro Ala Leu Ser Pro Thr
            100                 105                 110

Asp Leu Tyr Tyr Tyr Ser Asp Asp Ile Leu Ser Lys Lys Pro Glu Leu
        115                 120                 125

Val Val Tyr Ile Leu Asn Pro Ala Asp Leu Gln Leu Asp Tyr Ile Gln
    130                 135                 140

Lys Leu Glu Ser Ser Glu Ala Arg Phe Asp Glu Arg Thr Arg Ile Lys
145                 150                 155                 160

Asp Tyr Lys Ile Arg His Gln Asn Arg Phe Ile Phe Pro Gly Glu Phe
                165                 170                 175

Leu Ala Asp His Trp Arg Asp Tyr Thr Lys Ala Glu Ile Phe Ala Gln
            180                 185                 190

Leu Thr Lys Thr Phe Ile Leu Leu Asn Arg Phe Arg Ser Phe Leu Tyr
        195                 200                 205

Asp Pro Trp Val Glu Tyr Ile Glu His His Thr Arg Thr Met Arg Ser
    210                 215                 220

Tyr His Tyr Tyr Thr Gly Ser Ile Pro Lys Glu Gly Ile Phe Leu Arg
225                 230                 235                 240

Gly Trp Thr Pro Pro Ser Phe Thr Ile Glu Cys Glu Leu Lys Asp Gly
                245                 250                 255

Lys Leu Ser Glu Asp Ile Phe Thr Gln Lys Pro Gly Val Arg Ile Gln
            260                 265                 270

Val Glu Glu Ile Asn Ser Ser Ala Lys His Leu Asn Arg Glu Pro Ile
        275                 280                 285

Phe Tyr Asp Gln Thr Phe Ser Lys Ser Gly Trp Lys Ser Leu Phe Leu
    290                 295                 300

Asp Phe Lys Lys Asn Ser Ser Gly Glu Asn Pro Gln Ser Val Thr Leu
305                 310                 315                 320

Lys Phe Thr Val Ser Pro Thr Thr Ser Ser Asp Glu Val Asp Ala Arg
                325                 330                 335

Ile Phe Gly Ile Pro Ala Asn Tyr Gly Ile Arg Leu Pro Gln Asn Phe
            340                 345                 350

Cys Lys Lys Glu Ile Lys Thr Asn Ile Ser Tyr Asp Arg Ile His Gly
        355                 360                 365

Leu Asp Asp Asp Arg Ile Glu Thr Met Ser Asp Glu Asp Tyr Leu Lys
    370                 375                 380

Asp Tyr Glu Lys Arg Leu Tyr Phe Asn Pro Glu Asn Glu Gly Ala Leu
385                 390                 395                 400

Asn Arg Leu Lys Lys Ile Gln Arg Asn Lys Glu Ile Leu Gly Asn Ser
                405                 410                 415
```

```
Thr Tyr Phe Thr Trp Ser Glu Ile Gln Phe Leu Glu Lys Thr Ile Ser
            420                 425                 430

Lys Phe Gln Ala Asn Gly Gln Lys Trp Ile Ile Ile Asn Ser Pro Glu
        435                 440                 445

Asn Pro Ile Glu Ser Lys Tyr Tyr Lys Asn Gly Asn Trp Tyr Arg Gly
    450                 455                 460

Tyr Leu Lys Phe Leu Asn Ser Tyr Lys Asn Asp Thr Tyr Gly Phe Tyr
465                 470                 475                 480

Asp Leu Lys Asp Ala Ile Arg Asp Lys Arg Ser Phe Leu Asp Pro His
                485                 490                 495

His Leu Thr Phe Asn Ala Ala Lys His Ser Ser Ser Leu Tyr Thr Asn
            500                 505                 510

Val Ile Leu Asp Phe Leu Asn Val Ser Glu Arg Lys Lys
        515                 520                 525

<210> SEQ ID NO 91
<211> LENGTH: 2088
<212> TYPE: DNA
<213> ORGANISM: Artificial Sequence
<220> FEATURE:
<223> OTHER INFORMATION: LIC10321

<400> SEQUENCE: 91
atgaccggac tcaagttaag aattgctatt ttaattttat cggtcctttc ttttttttat      60
tatagattta taccgtattt tcctgatgga atatattata aaaacagaat gaattctgct     120
tttactaatc taaacgaaga actccgccat cttgagactg gactaggaca atcaattca      180 atttcggaat tagaaaattt acagttggaa ttcccgatcg tttccggttt aaaatttgta     240
accgaatccg atctatcctc ccgcaaagac ccagaaggaa aactacttaa agaaacctta     300
aaagatggaa ccagccgttt atttttttta aaaccatcct tggtgttttg tcttccccat     360
cctgaaaaaa agaaattgat tctcgcagaa ctcagggagg atttatttag agtctctttt     420
tcaggtgtag aatctatgtt aattccggat ttaaaatttg gaggatatgc ggagccggga     480
ggttttaaca aaggaagaat ctcttttccta ttgatagaag aattgagccg gtccgaaaat     540
gccgtcaatc ggattgaaat cggttcttct ccgtttatcg gatattatta tcgcgacaccc     600 gaaaactcat acggattttt aaaaggaatt ctcatttttaa aacccggaaa cgacggactt     660 ttttctcttat ttctatcagg gttttaaatc ttactattct tgatcgattt catgattcga     720
atcttaagaa tcaaacggaa ttttttcact cataaggaag gaaaagaaat tcaagaaatc     780
attggtcaga tttctaaaag aatcgatgca cttcaaaccg ctaaacaaaa agcaatagaa     840
tctgctcaaa aaagtgaagt agaagaaata cagactttaa cttccgaaga agtagatttc     900
gacctacaaa acgttccgat cccaatgaaa gaagtaaaac aagaagatgg tccctccatt     960
ttcgttttac cattcgaatt gaaaagagaa ggttatgttt ctccagcttt tttaagagat    1020
cctgaaaaat ttaaagagca cgaaccgata gctccagaaa tagaaaagaa acgttccgaa    1080 attttttactc ccgaattgca agacttgatt tccaaggtga acgaacctat tcgcgaaaaa    1140
ccggatatac aaatcgccaa acaagagatc gaaccagaac caatttccac ggatcatacg    1200
gaattaggtc ccggttatat gaaatggtta aatactcttc cgatcagaga acgaagaaaa    1260
atattggaag tattggatga acttcgttat ggattagaat cagaatattc atttatttta    1320
aaatactata tatccgtatt tttagatcta aaacttatg gatttgcaat tcattactac    1380
gacagaagaa acggaagtta tagcccattt gtaacccaag ggcttaggga acgtacatct    1440
```

```
ggaaacatga tttttttata cgatgaccaa tatataggaa agaatccgg aacctattcc    1500 attatagaaa ttacggatga agaaaaatg gatcgttttt tcagaaaaaa gttcgatccg    1560
atcgatcttg aaatttgtac gtctatcctt acaattccat tgtccaattt tggaatccca   1620
tttcgatttt ttctattttt caaagaccca ctaacaaaag aaaacgctca ggaaatagaa   1680
aatttaatct ttcattcttt ggaaccagta attcccgcgt tcgaagaata cgatcgaaaa   1740
attttagggg aactattcag agacaagcga gacgtagttt cttcccgagt tcatttaatg   1800
agaattgcga cagacggaga agaggactg actagatcct ttaaaattga atttcatgga    1860
aaaaatttta aaactctcga atctcttcgc aaaaaaacaa tgtctcaaat ttctgaaatt   1920
atcggtccag aagatatatg tttcggaatc ggagttggtg cctttggttt atatactaga   1980
aaaaatttgg aaaacaaat tcgttcttta atagatcaaa ctggaaatcc ctacgatttt    2040
gtagaagaca tatatcctga aaacggaaaa aacctattca tatatctt                2088
```

<210> SEQ ID NO 92
<211> LENGTH: 696
<212> TYPE: PRT
<213> ORGANISM: Artificial Sequence
<220> FEATURE:
<223> OTHER INFORMATION: LIC10321

<400> SEQUENCE: 92

```
Met Thr Gly Leu Lys Leu Arg Ile Ala Ile Leu Ile Leu Ser Val Leu
1               5                   10                  15

Ser Phe Phe Tyr Tyr Arg Phe Ile Pro Tyr Phe Pro Asp Gly Ile Tyr
                20                  25                  30

Tyr Lys Asn Arg Met Asn Ser Ala Phe Thr Asn Leu Asn Glu Glu Leu
            35                  40                  45

Arg His Leu Glu Thr Gly Leu Gly Gln Ile Asn Ser Ile Ser Glu Leu
        50                  55                  60

Glu Asn Leu Gln Leu Glu Phe Pro Ile Val Ser Gly Leu Lys Phe Val
65                  70                  75                  80

Thr Glu Ser Asp Leu Ser Ser Arg Lys Asp Pro Glu Gly Lys Leu Leu
                85                  90                  95

Lys Glu Thr Leu Lys Asp Gly Thr Ser Arg Leu Phe Phe Leu Lys Pro
            100                 105                 110

Ser Leu Val Phe Cys Leu Pro His Pro Glu Lys Lys Leu Ile Leu
            115                 120                 125

Ala Glu Leu Arg Glu Asp Leu Phe Arg Val Ser Phe Ser Gly Val Glu
        130                 135                 140

Ser Met Leu Ile Pro Asp Leu Lys Phe Gly Gly Tyr Ala Glu Pro Gly
145                 150                 155                 160

Gly Phe Asn Lys Gly Arg Ile Ser Phe Leu Ile Glu Glu Leu Ser
                165                 170                 175

Arg Ser Glu Asn Ala Val Asn Arg Ile Glu Ile Gly Ser Ser Pro Phe
            180                 185                 190

Ile Gly Tyr Tyr Tyr Ala Thr Pro Glu Asn Ser Tyr Gly Phe Leu Lys
        195                 200                 205

Gly Ile Leu Ile Leu Lys Pro Gly Asn Asp Gly Leu Phe Phe Leu Phe
    210                 215                 220

Leu Ser Gly Phe Leu Ile Leu Phe Leu Ile Asp Phe Met Ile Arg
225                 230                 235                 240

Ile Leu Arg Ile Lys Arg Asn Phe Phe Thr His Lys Glu Gly Lys Glu
                245                 250                 255
```

```
Ile Gln Glu Ile Ile Gly Gln Ile Ser Lys Arg Ile Asp Ala Leu Gln
            260                 265                 270
Thr Ala Lys Gln Lys Ala Ile Glu Ser Ala Gln Lys Ser Glu Val Glu
        275                 280                 285
Glu Ile Gln Thr Leu Thr Ser Glu Glu Val Asp Phe Asp Leu Gln Asn
290                 295                 300
Val Pro Ile Pro Met Lys Glu Val Lys Gln Glu Asp Gly Pro Ser Ile
305                 310                 315                 320
Phe Val Leu Pro Phe Glu Leu Lys Arg Glu Gly Tyr Val Ser Pro Ala
                325                 330                 335
Phe Leu Arg Asp Pro Glu Lys Phe Lys Glu His Glu Pro Ile Ala Pro
            340                 345                 350
Glu Ile Glu Lys Lys Arg Ser Glu Ile Phe Thr Pro Glu Leu Gln Asp
        355                 360                 365
Leu Ile Ser Lys Val Asn Glu Pro Ile Arg Glu Lys Pro Asp Ile Gln
370                 375                 380
Ile Ala Lys Gln Glu Ile Glu Pro Glu Pro Ile Ser Thr Asp His Thr
385                 390                 395                 400
Glu Leu Gly Pro Gly Tyr Met Lys Trp Leu Asn Thr Leu Pro Ile Arg
                405                 410                 415
Glu Arg Arg Lys Ile Leu Glu Val Leu Asp Glu Leu Arg Tyr Gly Leu
            420                 425                 430
Glu Ser Glu Tyr Ser Phe Ile Leu Lys Tyr Tyr Ile Ser Val Phe Leu
        435                 440                 445
Asp Leu Lys Leu Tyr Gly Phe Ala Ile His Tyr Tyr Asp Arg Arg Asn
450                 455                 460
Gly Ser Tyr Ser Pro Phe Val Thr Gln Gly Leu Arg Glu Arg Thr Ser
465                 470                 475                 480
Gly Asn Met Ile Phe Leu Tyr Asp Asp Gln Tyr Ile Gly Lys Glu Ser
                485                 490                 495
Gly Thr Tyr Ser Ile Ile Glu Ile Thr Asp Glu Arg Lys Met Asp Arg
            500                 505                 510
Phe Phe Arg Lys Lys Phe Asp Pro Ile Asp Leu Glu Ile Cys Thr Ser
        515                 520                 525
Ile Leu Thr Ile Pro Leu Ser Asn Phe Gly Ile Pro Phe Arg Phe Phe
530                 535                 540
Leu Phe Phe Lys Asp Pro Leu Thr Lys Glu Asn Ala Gln Glu Ile Glu
545                 550                 555                 560
Asn Leu Ile Phe His Ser Leu Glu Pro Val Ile Pro Ala Phe Glu Glu
                565                 570                 575
Tyr Asp Arg Lys Ile Leu Gly Glu Leu Phe Arg Asp Lys Arg Asp Val
            580                 585                 590
Val Ser Ser Arg Val His Leu Met Arg Ile Ala Thr Asp Gly Glu Arg
        595                 600                 605
Gly Leu Thr Arg Ser Phe Lys Ile Glu Phe His Gly Lys Asn Phe Lys
610                 615                 620
Thr Leu Glu Ser Leu Arg Lys Lys Thr Met Ser Gln Ile Ser Glu Ile
625                 630                 635                 640
Ile Gly Pro Glu Asp Ile Cys Phe Gly Ile Gly Val Gly Ala Phe Gly
                645                 650                 655
Leu Tyr Thr Arg Lys Asn Leu Glu Lys Gln Ile Arg Ser Leu Ile Asp
            660                 665                 670
```

Gln Thr Gly Asn Pro Tyr Asp Phe Val Glu Asp Ile Tyr Pro Glu Asn
          675                 680                 685

Gly Lys Asn Leu Phe Ile Tyr Leu
    690                 695

<210> SEQ ID NO 93
<211> LENGTH: 546
<212> TYPE: DNA
<213> ORGANISM: Artificial Sequence
<220> FEATURE:
<223> OTHER INFORMATION: LIC10662

<400> SEQUENCE: 93

```
atgtctaaat caaaaatgat cgttttatca gtgttagctg tatttgcagc tttagttata        60
gggatcatcg cggtcgcttc cacaaaaccg gcagaattcc gttttgaaag aacactaagc       120
ataaaggcac aacccggaaa aattttcact ttcgttaatg attatcataa ttggccgtct       180
tggtctcctt gggaaaaact agatccggga atgaaacggt cttatagcgg tgcgtctatt       240
ggtttaggtt ccgtttacga gtgggaagga aacagcgaag taggaaaagg acgtatggaa       300
attatagaat caaattcgcc ttccaatatc aaaatgaagt tagattttat ttctcctttt       360
gaagcccata ataccgccga atttacgttt gtagccaaag acggtaaaac taacgtcacc       420
tgggcaatgt atggccctaa tgccttcatc tccaaattga tgggactatt ctacgatatg       480
gatcagatga tcggaaaaga ttttgaaacc ggtttaaata atattaaaac gatcgtagag       540
gaaaaa                                                                  546
```

<210> SEQ ID NO 94
<211> LENGTH: 182
<212> TYPE: PRT
<213> ORGANISM: Artificial Sequence
<220> FEATURE:
<223> OTHER INFORMATION: LIC10662

<400> SEQUENCE: 94

Met Ser Lys Ser Lys Met Ile Val Leu Ser Val Leu Ala Val Phe Ala
1               5                   10                  15

Ala Leu Val Ile Gly Ile Ile Ala Val Ala Ser Thr Lys Pro Ala Glu
            20                  25                  30

Phe Arg Phe Glu Arg Thr Leu Ser Ile Lys Ala Gln Pro Gly Lys Ile
        35                  40                  45

Phe Thr Phe Val Asn Asp Tyr His Asn Trp Pro Ser Trp Ser Pro Trp
    50                  55                  60

Glu Lys Leu Asp Pro Gly Met Lys Arg Ser Tyr Ser Gly Ala Ser Ile
65                  70                  75                  80

Gly Leu Gly Ser Val Tyr Glu Trp Glu Gly Asn Ser Glu Val Gly Lys
                85                  90                  95

Gly Arg Met Glu Ile Ile Glu Ser Asn Ser Pro Ser Asn Ile Lys Met
            100                 105                 110

Lys Leu Asp Phe Ile Ser Pro Phe Glu Ala His Asn Thr Ala Glu Phe
        115                 120                 125

Thr Phe Val Ala Lys Asp Gly Lys Thr Asn Val Thr Trp Ala Met Tyr
    130                 135                 140

Gly Pro Asn Ala Phe Ile Ser Lys Leu Met Gly Leu Phe Tyr Asp Met
145                 150                 155                 160

Asp Gln Met Ile Gly Lys Asp Phe Glu Thr Gly Leu Asn Asn Ile Lys
                165                 170                 175

Thr Ile Val Glu Glu Lys
        180

<210> SEQ ID NO 95
<211> LENGTH: 1044
<212> TYPE: DNA
<213> ORGANISM: Artificial Sequence
<220> FEATURE:
<223> OTHER INFORMATION: LIC11183

<400> SEQUENCE: 95

| | | | | |
|---|---|---|---|---|
| ttgagttgtt | tatcaaagag | ttatgaggaa | aaattaagaa | tgaaaatact | taaatggatt | 60 |
| tgggaatca | tcggaacatt | cgctctattt | ttagtcgtca | ccttttatgc | tgaaactcct | 120 |
| aaatatgaat | acaaatctgt | tcccttatat | tcaaacttcg | acagttatta | tcgggaaaaa | 180 |
| cttcaaatca | gtcgatctaa | aaagtaaga | cctggcaacg | aagaaaaatt | agtgagatat | 240 |
| tctgcagata | aaaccgattt | ctcaatcctt | tatatccacg | gctttggagc | atctcgcgca | 300 |
| gaaggagaag | aagttacaga | tcaactcgca | aaagatttca | agcaaatct | ctactatgtt | 360 |
| cgtcttcccg | gtcatggaac | taatttagaa | atcatagag | atacaacttt | tgaagaaatt | 420 |
| ttacaggact | ccgaaacggc | tttttagaa | tgcgaaaaac | taggtaaaaa | aacgattcta | 480 |
| atcggaacta | gtatgggagg | gttgatttct | acataccag | cagccaaata | tcctgaaaaa | 540 |
| gttcacgctt | tagttcttgt | ttcccctttt | tacgattta | caatccatt | tagtgttatt | 600 |
| tatcaatttt | cttggggtaa | agatttgct | aatatagtaa | tgggaaaaat | tcgtaaatct | 660 |
| acagaagaag | aaaaacgaaa | tccagccagc | gctttctggt | atagagatca | atatctcgca | 720 |
| gcggttcaaa | atttatcaga | cttaagagag | ttcatcttgg | gaactgatcc | attttccaaa | 780 |
| atttcctctc | ctattttatt | gttctactat | tataaaaacg | aaaaaaatca | agatgtgtcc | 840 |
| gcttccgtct | catctatgtt | aaacgcattc | aaaaagtaa | atgaaaacgg | aaaggcaagc | 900 |
| ccattgaaca | aagcggtaaa | agtagaattt | ggaaatcacg | tattattttc | caaatacatg | 960 |
| aaaagtgata | agacctgat | tttaaaagaa | acagaaactt | tcatccaaaa | tgtattttct | 1020 |
| ttaaataaaa | atttatccca | caat | | | 1044 |

<210> SEQ ID NO 96
<211> LENGTH: 348
<212> TYPE: PRT
<213> ORGANISM: Artificial Sequence
<220> FEATURE:
<223> OTHER INFORMATION: LIC11183

<400> SEQUENCE: 96

Leu Ser Cys Leu Ser Lys Ser Tyr Glu Glu Lys Leu Arg Met Lys Ile
1               5                   10                  15

Leu Lys Trp Ile Leu Gly Ile Ile Gly Thr Phe Ala Leu Phe Leu Val
            20                  25                  30

Val Thr Phe Tyr Ala Glu Thr Pro Lys Tyr Glu Tyr Lys Ser Val Pro
        35                  40                  45

Leu Tyr Ser Asn Phe Asp Ser Tyr Tyr Arg Glu Lys Leu Gln Ile Ser
    50                  55                  60

Arg Ser Lys Lys Val Arg Pro Gly Asn Glu Glu Lys Leu Val Arg Tyr
65                  70                  75                  80

Ser Ala Asp Lys Thr Asp Phe Ser Ile Leu Tyr Ile His Gly Phe Gly
            85                  90                  95

Ala Ser Arg Ala Glu Gly Glu Glu Val Thr Asp Gln Leu Ala Lys Asp
        100                 105                 110

Phe Lys Ala Asn Leu Tyr Tyr Val Arg Leu Pro Gly His Gly Thr Asn
            115                 120                 125
Leu Glu Asn His Arg Asp Thr Thr Phe Glu Glu Ile Leu Gln Asp Ser
        130                 135                 140
Glu Thr Ala Phe Leu Glu Cys Glu Lys Leu Gly Lys Lys Thr Ile Leu
145                 150                 155                 160
Ile Gly Thr Ser Met Gly Gly Leu Ile Ser Thr Tyr Leu Ala Ala Lys
                165                 170                 175
Tyr Pro Glu Lys Val His Ala Leu Val Leu Val Ser Pro Phe Tyr Asp
            180                 185                 190
Phe Thr Asn Pro Phe Ser Val Ile Tyr Gln Phe Ser Trp Gly Lys Asp
            195                 200                 205
Phe Ala Asn Ile Val Met Gly Lys Ile Arg Lys Ser Thr Glu Glu Glu
            210                 215                 220
Lys Arg Asn Pro Ala Ser Ala Phe Trp Tyr Arg Asp Gln Tyr Leu Ala
225                 230                 235                 240
Ala Val Gln Asn Leu Ser Asp Leu Arg Glu Phe Ile Leu Gly Thr Asp
                245                 250                 255
Pro Phe Ser Lys Ile Ser Ser Pro Ile Leu Leu Phe Tyr Tyr Tyr Lys
            260                 265                 270
Asn Glu Lys Asn Gln Asp Val Ser Ala Ser Val Ser Ser Met Leu Asn
            275                 280                 285
Ala Phe Lys Lys Val Asn Glu Asn Gly Lys Ala Ser Pro Leu Asn Lys
            290                 295                 300
Ala Val Lys Val Glu Phe Gly Asn His Val Leu Phe Ser Lys Tyr Met
305                 310                 315                 320
Lys Ser Asp Lys Asp Leu Ile Leu Lys Glu Thr Glu Thr Phe Ile Gln
                325                 330                 335
Asn Val Phe Ser Leu Asn Lys Asn Leu Ser His Asn
            340                 345

<210> SEQ ID NO 97
<211> LENGTH: 1332
<212> TYPE: DNA
<213> ORGANISM: Artificial Sequence
<220> FEATURE:
<223> OTHER INFORMATION: LIC11489

<400> SEQUENCE: 97
atgtatctgt caatcggacc ggtttctgaa gcgttttttct cacttttctc ctttacagaa      60
atattccttc acagacccct tcagtttatt gatacaatca tggaattaga aaacgtttca     120
ctcaaagaca aaatcattcg cgctgtagtc ggtttttttc tttttatact tgtaggtggt     180
ttgatcgtca cctttctacc cggagacgcc gaaaagagct tttttgacgt aatttccggt     240
aaatccaatg taaacgccgg taaaatcggg gactattcaa tcccaatgga ttattaccaa     300
gccgccaaaa gagaatgtta tttccaatat agaaacatag ccccttctct tgcggaagat     360
ccttctactc ttcaatcctg tgcatttcaa acgattcgca gtttagtagt aacagaacaa     420
attgcaaaag cgactggatt ctccgcttcc gaaactggaa ttcgagagga actttccgat     480
gaagctcgta gaatttatag agaatccgta aatggagccg atattcgga cgacgaagta     540 cgtaaaccgg aagtcattta taaacaaatt ttaaattcag ccccgatgca gtatagaatc     600
gatcgtaaaa acgcgagtat tatctacgac acccttctca actccgattt aaaaaagaca     660
gacggagaaa ttgcagttca aaaggaatct acttctgcca gattccgact tagaatcgtg     720

```
tcttatacag acgatcaact ttctaaactc gcagaaaaag aagctcctat ttccgaagaa    780
attttgcgag ccaaatacga aaacgaaaag aagaaggga aactacctaa aaacacagac    840
ggaaaagaaa tttcttttga agaaagaaaa aatttcctca agagtaaact acttctcgaa    900
atacgttcta agtcccaaga agaatggaaa ggtaaactca aaccatcca acaagaacca    960 gacggacttt ctaaaattgc ttctttgtta ggcgccaata ttcaagaatt gaaagatcaa   1020 tccctttag atttatggga attaaaatcg ggaaatcaaa atatccgact tggaagtaat   1080
actcaattcc ttaaagattt gacaaccgtt gcctttggtt ctaaaaaagt cggtggtcct   1140
tacaaagaat ctgaaaaaaa tatttttgta gaatttgctt cgttggaaat cgattcgtct   1200
aagatcaata attcccaagg acccgatttg agagacaatc caaacctaat gaatgggttt   1260
gttatggaga tcaatcaggc acttcaggaa aaatacccga ttgaacgaag gatcggtcaa   1320
aaggtagaag aa                                                      1332
```

<210> SEQ ID NO 98
<211> LENGTH: 444
<212> TYPE: PRT
<213> ORGANISM: Artificial Sequence
<220> FEATURE:
<223> OTHER INFORMATION: LIC11489

<400> SEQUENCE: 98

```
Met Tyr Leu Ser Ile Gly Pro Val Ser Glu Ala Phe Phe Ser Leu Phe
1               5                   10                  15

Ser Phe Thr Glu Ile Phe Leu His Arg Pro Phe Gln Phe Ile Asp Thr
            20                  25                  30

Ile Met Glu Leu Glu Asn Val Ser Leu Lys Asp Lys Ile Ile Arg Ala
        35                  40                  45

Val Val Gly Phe Phe Leu Phe Ile Leu Val Gly Gly Leu Ile Val Thr
    50                  55                  60

Phe Leu Pro Gly Asp Ala Glu Lys Ser Phe Phe Asp Val Ile Ser Gly
65                  70                  75                  80

Lys Ser Asn Val Asn Ala Gly Lys Ile Gly Asp Tyr Ser Ile Pro Met
                85                  90                  95

Asp Tyr Tyr Gln Ala Ala Lys Arg Glu Cys Tyr Phe Gln Tyr Arg Asn
            100                 105                 110

Ile Ala Pro Ser Leu Ala Glu Asp Pro Ser Thr Leu Gln Ser Cys Ala
        115                 120                 125

Phe Gln Thr Ile Arg Ser Leu Val Val Thr Glu Gln Ile Ala Lys Ala
    130                 135                 140

Thr Gly Phe Ser Ala Ser Glu Thr Gly Ile Arg Glu Glu Leu Ser Asp
145                 150                 155                 160

Glu Ala Arg Arg Ile Tyr Arg Glu Ser Val Asn Gly Ala Gly Tyr Ser
                165                 170                 175

Asp Asp Glu Val Arg Lys Pro Gly Val Ile Tyr Lys Gln Ile Leu Asn
            180                 185                 190

Ser Ala Pro Met Gln Tyr Arg Ile Asp Arg Lys Asn Ala Ser Ile Ile
        195                 200                 205

Tyr Asp Thr Leu Leu Asn Ser Asp Leu Lys Lys Thr Asp Gly Glu Ile
    210                 215                 220

Ala Val Gln Lys Glu Ser Thr Ser Ala Arg Phe Arg Leu Arg Ile Val
225                 230                 235                 240

Ser Tyr Thr Asp Asp Gln Leu Ser Lys Leu Ala Glu Lys Glu Ala Pro
```

|  |  |  |  | 245 |  |  |  | 250 |  |  |  | 255 |  |
|---|---|---|---|---|---|---|---|---|---|---|---|---|---|
| Ile | Ser | Glu | Glu | Ile | Leu | Arg | Ala | Lys | Tyr | Glu | Asn | Glu | Lys | Lys | Glu |
|  |  |  | 260 |  |  |  |  | 265 |  |  |  | 270 |  |  |

Ile Ser Glu Glu Ile Leu Arg Ala Lys Tyr Glu Asn Glu Lys Lys Glu
                260                 265                 270

Gly Lys Leu Pro Lys Asn Thr Asp Gly Lys Glu Ile Ser Phe Glu Glu
            275                 280                 285

Arg Lys Asn Phe Leu Lys Ser Lys Leu Leu Leu Glu Ile Arg Ser Lys
        290                 295                 300

Ser Gln Glu Glu Trp Lys Gly Lys Leu Lys Thr Ile Gln Gln Glu Pro
305                 310                 315                 320

Asp Gly Leu Ser Lys Ile Ala Ser Leu Gly Ala Asn Ile Gln Glu
                325                 330                 335

Leu Lys Asp Gln Ser Leu Leu Asp Leu Trp Glu Leu Lys Ser Gly Asn
                340                 345                 350

Gln Asn Ile Arg Leu Gly Ser Asn Thr Gln Phe Leu Lys Asp Leu Thr
                355                 360                 365

Thr Val Ala Phe Gly Ser Lys Lys Val Gly Pro Tyr Lys Glu Ser
370                 375                 380

Glu Lys Asn Ile Phe Val Glu Phe Ala Ser Leu Glu Ile Asp Ser Ser
385                 390                 395                 400

Lys Ile Asn Asn Ser Gln Gly Pro Asp Leu Arg Asp Asn Pro Asn Leu
                405                 410                 415

Met Asn Gly Phe Val Met Glu Ile Asn Gln Ala Leu Gln Glu Lys Tyr
                420                 425                 430

Pro Ile Glu Arg Arg Ile Gly Gln Lys Val Glu Glu
            435                 440

<210> SEQ ID NO 99
<211> LENGTH: 1449
<212> TYPE: DNA
<213> ORGANISM: Artificial Sequence
<220> FEATURE:
<223> OTHER INFORMATION: LIC12258

<400> SEQUENCE: 99

| atgaatcgga tttttagaaa ctggaactgg attggtttat ggattctgat ctggagttta | 60 |
|---|---|
| tttccgattt ttggagaagg acttagaaat ttacccgagg ctcgaattcc tttagatgaa | 120 |
| ggaaagaaat tagaacctgg tgaacttgca gaaaaaaagg aaggttggta tgtaacagca | 180 |
| attccgttat tgagttcgga tcctgtaagg gggcaaggag gtggtattcg cgcgagttta | 240 |
| ttttttaacg gaaaaaaaac agatttatat tatgaatatg aagcgtatcg aagtaaactt | 300 |
| acacttcaat tgtttcaaac taatcaggga gttaaaaatc atttataca gtttgattct | 360 |
| ccttatatat aaatactgc gtttcgatgg aaaagtagtc ttagcttgga ttacaatcct | 420 |
| aattctcagt attttggaat tggagaatct tctcttcaat ctctttctta tagtcctaga | 480 |
| aatttatctg ggatcggtcg tgtagggaat gtaaattttg acgcttacga aacttctcag | 540 |
| tcatacatcc gtccttctcg tactggttcg gaaattactc caacggtaag tgatcagggt | 600 |
| tataaccagt atctgttcaa ttctactact ttctttaatg gaatcgatta ctttttttgg | 660 |
| aaggcttgga atgggtggt tgcaaatgaa atttccagaa atataattgg tcactcggat | 720 |
| ggagtttggc atccttccaa agatccatat tttgccggaa gtatctggga acaccggtt | 780 |
| ccaaatggag aatcaaagtt gaccgaagat tatagagccg gaaaaatccg aggatacaac | 840 |
| ggaggagata tagtttattt tagagcaggt attgcttatg acacccggga ttttgagcca | 900 |
| gacccggatc gaggtatatt agcagaatta aatgtagcaa acgtttctaa cgcaccggt | 960 |

```
tctgatttta attacaataa gattttttt cagacaaaat atttttataa gattctacca    1020
gatgttttta aagaattggt gtttgctaca agggtcgcgt taggttacac atcttctggt    1080
gctccttttt ctgaagtaag atatatgtgg agtttggacg gacctatgac tggaattggt    1140
ggtcttcaaa cgatgagagg ttatcgccaa gatcgttttg tcgctcctgt ggttggtttt    1200
ggaagtgcgg agtttcgctg gagatttgct acattcaaaa ttttgatga acttttact    1260 ttgagtttag ttccatttgt tgacgtaggt agagtctggg attctgaaaa agaattaat    1320 ttacaaggtt ataaacattc ttggggaagt ggatttagaa tcatctggaa tcaagctact    1380
gtaattttga tagattttgc taaatccaaa gaggattctc agatgtttgt agattttagt    1440
cacgcgttt                                                           1449
```

<210> SEQ ID NO 100
<211> LENGTH: 483
<212> TYPE: PRT
<213> ORGANISM: Artificial Sequence
<220> FEATURE:
<223> OTHER INFORMATION: LIC12258

<400> SEQUENCE: 100

```
Met Asn Arg Ile Phe Arg Asn Trp Asn Trp Ile Gly Leu Trp Ile Leu
1               5                   10                  15

Ile Trp Ser Leu Phe Pro Ile Phe Gly Glu Gly Leu Arg Asn Leu Pro
            20                  25                  30

Glu Ala Arg Ile Pro Leu Asp Glu Gly Lys Lys Leu Glu Pro Gly Glu
        35                  40                  45

Leu Ala Glu Lys Lys Glu Gly Trp Tyr Val Thr Ala Ile Pro Leu Leu
    50                  55                  60

Ser Ser Asp Pro Val Arg Gly Gln Gly Gly Ile Arg Ala Ser Leu
65                  70                  75                  80

Phe Phe Asn Gly Lys Lys Thr Asp Leu Tyr Tyr Glu Tyr Glu Ala Tyr
                85                  90                  95

Arg Ser Lys Leu Thr Leu Gln Leu Phe Gln Thr Asn Gln Gly Val Lys
            100                 105                 110

Asn His Phe Ile Gln Phe Asp Ser Pro Tyr Ile Leu Asn Thr Ala Phe
        115                 120                 125

Arg Trp Lys Ser Ser Leu Ser Leu Asp Tyr Asn Pro Asn Ser Gln Tyr
    130                 135                 140

Phe Gly Ile Gly Glu Ser Ser Leu Gln Ser Leu Ser Tyr Ser Pro Arg
145                 150                 155                 160

Asn Leu Ser Gly Ile Gly Arg Val Gly Asn Val Asn Phe Asp Ala Tyr
                165                 170                 175

Glu Thr Ser Gln Ser Tyr Ile Arg Pro Ser Arg Thr Gly Ser Glu Ile
            180                 185                 190

Thr Pro Thr Val Ser Asp Gln Gly Tyr Asn Gln Tyr Leu Phe Asn Ser
        195                 200                 205

Thr Thr Phe Phe Asn Gly Ile Asp Tyr Thr Phe Trp Lys Ala Trp Lys
    210                 215                 220

Trp Val Val Ala Asn Glu Ile Ser Arg Asn Ile Ile Gly His Ser Asp
225                 230                 235                 240

Gly Val Trp His Pro Ser Lys Asp Pro Tyr Phe Ala Gly Ser Ile Trp
                245                 250                 255

Glu Thr Pro Val Pro Asn Gly Glu Ser Lys Leu Thr Glu Asp Tyr Arg
            260                 265                 270
```

```
Ala Gly Lys Ile Arg Gly Tyr Asn Gly Gly Asp Ile Val Tyr Phe Arg
        275                 280                 285

Ala Gly Ile Ala Tyr Asp Thr Arg Asp Phe Glu Pro Asp Pro Asp Arg
        290                 295                 300

Gly Ile Leu Ala Glu Leu Asn Val Ala Asn Val Ser Lys Arg Thr Gly
305                 310                 315                 320

Ser Asp Phe Asn Tyr Asn Lys Ile Phe Phe Gln Thr Lys Tyr Phe Tyr
                325                 330                 335

Lys Ile Leu Pro Asp Val Phe Lys Glu Leu Val Phe Ala Thr Arg Val
            340                 345                 350

Ala Leu Gly Tyr Thr Ser Ser Gly Ala Pro Phe Ser Glu Val Arg Tyr
        355                 360                 365

Met Trp Ser Leu Asp Gly Pro Met Thr Gly Ile Gly Gly Leu Gln Thr
    370                 375                 380

Met Arg Gly Tyr Arg Gln Asp Arg Phe Val Ala Pro Val Val Gly Phe
385                 390                 395                 400

Gly Ser Ala Glu Phe Arg Trp Arg Phe Ala Thr Phe Lys Ile Phe Asp
                405                 410                 415

Glu Leu Phe Thr Leu Ser Leu Val Pro Phe Val Asp Val Gly Arg Val
            420                 425                 430

Trp Asp Ser Glu Lys Arg Ile Asn Leu Gln Gly Tyr Lys His Ser Trp
        435                 440                 445

Gly Ser Gly Phe Arg Ile Ile Trp Asn Gln Ala Thr Val Ile Leu Ile
    450                 455                 460

Asp Phe Ala Lys Ser Lys Glu Asp Ser Gln Met Phe Val Asp Phe Ser
465                 470                 475                 480

His Ala Phe

<210> SEQ ID NO 101
<211> LENGTH: 1995
<212> TYPE: DNA
<213> ORGANISM: Artificial Sequence
<220> FEATURE:
<223> OTHER INFORMATION: LIC12731

<400> SEQUENCE: 101
atgattttaa gttttttaca aaaacctttt ctatatctat tatttctgat tttatactta      60
tccatcggat caactcattc gcaagataca gttcgaaaaa tccaagaagg agaatctttt     120
cttaaagacc gtaattacac ggctgcttat caatcttttt ccgaagcctc tcgtttaaat     180
cctatgtcca tccgttcttt acttggattt gccgaagcgg cacaacatct tcacaaggat     240
aaggaatccc tagacgctta taacaaagta ttagaattag agccggaaaa caaagctgca     300
atcaaaggag ccgccttagg atacattcga aaaaagaat atcataattc tctaaacctc     360
cttaaacctt ctctagaaac agatccgttt gatccagttc tggccccaat tcaaattcag     420
attcttttag aaatgggaaa ttacgaatcc gcccttaaaa aactggaagc atcaaaatcc     480
agactccaaa attctaagga agttcaaatt ttagaagcga aggtaaatgg caaaaccggc     540
aactttccta atcctatca tctttggaat gcggcgcttg cgtcatcttc agacgatccg     600
gatttattct ttaatatggc tttgttatta atggattggt ccgaaaaaag ttccgatcca     660
gaaaaaaaac aaaaactaga atcgcttcc gaaaaattgg aaagagcaat ttctttatat     720
ccggatttcg aagaagcaat cgattcactt gcaagaatca gaatatggca aggagacttt     780
caatctgcag aatcactttc tcgcaaactc gtttctattt atcctcaaaa cccttatat      840
```

-continued

```
ctttatctaa aagcttttgc ggaagaaaaa aacgcaaata gttcttccaa agatatactt     900
aaaaacgatt taatcgaaat attaaagtta gacgacttag actccatttc aagacaaaaa     960
gcagagtcgg ttgcacgcga tcattttcca gaaaatcatt ctttcagaag aaagttagga    1020
gaatatagaa tgcaacgttt tcgttcttct aaaaattctc ttctctatga tatggcttct    1080
catcatcttt cttgtgcgag agaactcatt ccgggtcaac cagaagttca gtttcaaact    1140
ttatcagaat ataaacgaac tggattttt ccgcgttatc tcaaccttct tttattttg     1200
agaaagaaat atcctgaaaa tcaaaaatat caatatgaaa tcgaaaatct tctgagctcc    1260
accaaacaat caatcgctta tagagaaggt ttaatagaaa ttacaggaga caatcttgtt    1320
gaaaattatg aagaacacc acccgttctt ttgatgtttg atctttttaga taaatccttt    1380
ttaggagatt atccagatct ggcactttta atttcttctt ccgtacgtaa aaatctttct    1440
ttaaatccta cgatcactct ttcagaagtg ttagaatctg ctcgtaacaa cccatctttt    1500
gagatcaaag cagctcctta tactggaacc taccttata ccgaatctac atatcttaaa    1560
attaaagact cttcaaaaaa aagcatcaaa cctagatttc taatttatgg ttctctaaaa    1620
tacgaaaacc attctttgca catagattgg acaatcaaag attccaaaca cgagaaagtg    1680
ttttcgacat ttagaatatt tcaaaaggt agagatttta taccggaagc ggttgttaga    1740
tctgttccta aaattttagc ttctatacct ccgagtggtt ccgtattaaa agtgaaggat    1800
gaagatctga tagtcaacgt aggagccctt gacggcctca aaaaggaag caaaatccag    1860
atctacaaca gctccggaaa atccggagaa gctacgatag aagaaatcga ttactttctt    1920
tccagagccg ttcccaataa tggaattaac ggtttaaaaa cgatttcaga aggagatagg    1980
atattttgga aacgt                                                      1995
```

<210> SEQ ID NO 102
<211> LENGTH: 665
<212> TYPE: PRT
<213> ORGANISM: Artificial Sequence
<220> FEATURE:
<223> OTHER INFORMATION: LIC12731

<400> SEQUENCE: 102

```
Met Ile Leu Ser Phe Leu Gln Lys Pro Phe Leu Tyr Leu Leu Phe Leu
1               5                   10                  15

Ile Leu Tyr Leu Ser Ile Gly Ser Thr His Ser Gln Asp Thr Val Arg
            20                  25                  30

Lys Ile Gln Glu Gly Glu Ser Phe Leu Lys Asp Arg Asn Tyr Thr Ala
        35                  40                  45

Ala Tyr Gln Ser Phe Ser Glu Ala Ser Arg Leu Asn Pro Met Ser Ile
    50                  55                  60

Arg Ser Leu Leu Gly Phe Ala Glu Ala Ala Gln His Leu His Lys Asp
65                  70                  75                  80

Lys Glu Ser Leu Asp Ala Tyr Asn Lys Val Leu Glu Leu Glu Pro Glu
                85                  90                  95

Asn Lys Ala Ala Ile Lys Gly Ala Ala Leu Gly Tyr Ile Arg Lys Lys
            100                 105                 110

Glu Tyr His Asn Ser Leu Asn Leu Lys Pro Ser Leu Glu Thr Asp
        115                 120                 125

Pro Phe Asp Pro Val Leu Ala Pro Ile Gln Ile Gln Ile Leu Leu Glu
    130                 135                 140

Met Gly Asn Tyr Glu Ser Ala Leu Lys Lys Leu Glu Ala Ser Lys Ser
```

```
            145                 150                 155                 160
Arg Leu Gln Asn Ser Lys Glu Val Gln Ile Leu Glu Ala Lys Val Asn
                165                 170                 175
Gly Lys Thr Gly Asn Phe Ser Lys Ser Tyr His Leu Trp Asn Ala Ala
                180                 185                 190
Leu Ala Ser Ser Ser Asp Asp Pro Asp Leu Phe Phe Asn Met Ala Leu
                195                 200                 205
Leu Leu Met Asp Trp Ser Glu Lys Ser Ser Asp Pro Glu Lys Lys Gln
                210                 215                 220
Lys Leu Glu Ile Ala Ser Glu Lys Leu Glu Arg Ala Ile Ser Leu Tyr
225                 230                 235                 240
Pro Asp Phe Glu Glu Ala Ile Asp Ser Leu Ala Arg Ile Arg Ile Trp
                245                 250                 255
Gln Gly Asp Phe Gln Ser Ala Glu Ser Leu Ser Arg Lys Leu Val Ser
                260                 265                 270
Ile Tyr Pro Gln Asn Pro Leu Tyr Leu Tyr Leu Lys Ala Phe Ala Glu
                275                 280                 285
Glu Lys Asn Ala Asn Ser Ser Ser Lys Asp Ile Leu Lys Asn Asp Leu
                290                 295                 300
Ile Glu Ile Leu Lys Leu Asp Asp Leu Asp Ser Ile Ser Arg Gln Lys
305                 310                 315                 320
Ala Glu Ser Val Ala Arg Asp His Phe Pro Glu Asn His Ser Phe Arg
                325                 330                 335
Arg Lys Leu Gly Glu Tyr Arg Met Gln Arg Phe Arg Ser Ser Lys Asn
                340                 345                 350
Ser Leu Leu Tyr Asp Met Ala Ser His His Leu Ser Cys Ala Arg Glu
                355                 360                 365
Leu Ile Pro Gly Gln Pro Glu Val Gln Phe Gln Thr Leu Ser Glu Tyr
                370                 375                 380
Lys Arg Thr Gly Phe Phe Pro Arg Tyr Leu Asn Leu Leu Phe Leu
385                 390                 395                 400
Arg Lys Lys Tyr Pro Glu Asn Gln Lys Tyr Gln Tyr Glu Ile Glu Asn
                405                 410                 415
Leu Leu Ser Ser Thr Lys Gln Ser Ile Ala Tyr Arg Glu Gly Leu Ile
                420                 425                 430
Glu Ile Thr Gly Asp Asn Leu Val Glu Asn Tyr Gly Arg Thr Pro Pro
                435                 440                 445
Val Leu Leu Met Phe Asp Leu Leu Asp Lys Ser Phe Leu Gly Asp Tyr
                450                 455                 460
Pro Asp Leu Ala Leu Leu Ile Ser Ser Val Arg Lys Asn Leu Ser
465                 470                 475                 480
Leu Asn Pro Thr Ile Thr Leu Ser Glu Val Leu Glu Ser Ala Arg Asn
                485                 490                 495
Asn Pro Ser Phe Glu Ile Lys Ala Ala Pro Tyr Thr Gly Thr Leu Pro
                500                 505                 510
Tyr Thr Glu Ser Thr Tyr Leu Lys Ile Lys Asp Ser Ser Lys Lys Ser
                515                 520                 525
Ile Lys Pro Arg Phe Leu Ile Tyr Gly Ser Leu Lys Tyr Glu Asn His
                530                 535                 540
Ser Leu His Ile Asp Trp Thr Ile Lys Asp Ser Lys His Glu Lys Val
545                 550                 555                 560
Phe Ser Thr Phe Arg Ile Phe Ser Lys Gly Arg Asp Phe Ile Pro Glu
                565                 570                 575
```

Ala Val Arg Ser Val Ser Lys Ile Leu Ala Ser Ile Pro Pro Ser
            580                 585                 590

Gly Ser Val Leu Lys Val Lys Asp Glu Asp Leu Ile Val Asn Val Gly
        595                 600                 605

Ala Leu Asp Gly Leu Lys Lys Gly Ser Lys Ile Gln Ile Tyr Asn Ser
    610                 615                 620

Ser Gly Lys Ser Gly Glu Ala Thr Ile Glu Glu Ile Asp Tyr Phe Leu
625                 630                 635                 640

Ser Arg Ala Val Pro Asn Asn Gly Ile Asn Gly Leu Lys Thr Ile Ser
                645                 650                 655

Glu Gly Asp Arg Ile Phe Trp Lys Arg
            660                 665

<210> SEQ ID NO 103
<211> LENGTH: 1080
<212> TYPE: DNA
<213> ORGANISM: Artificial Sequence
<220> FEATURE:
<223> OTHER INFORMATION: LIC12332

<400> SEQUENCE: 103

| | | |
|---|---|---|
| atgggttggt tgaaaaaaat aacggcgata ttaggaattc ttttcggaag tctttttgatt | 60 |
| ttgatttatg taatcacgta tcatccagat caggcggaac ctgcggagat tgtatgtaat | 120 |
| gagaacgctc caatcttaaa agaaaattct aagattaaag tgttggtctg aacgtacaa | 180 |
| tacctcgccg gaaaaaaaag gattttttgg tatgacttac ctaacggaga tgggccggac | 240 |
| acagggcctt ctaaagagga aatcgaagaa acacttaaaa agtagccgg ctacattcat | 300 |
| tcggaagacc cagatgtgat acttttttcag gagcttcatg acggagcaga aaatacgttt | 360 |
| cgtgaagatc agttagaaag aattctttct cggattgggt ccgagtatgt ctgtagaagt | 420 |
| gaggcatttt actggaaatc taattttgtt ccacatccta aaattttggg aagtgtgggt | 480 |
| atgaaactgg caacgattag taaatataaa atttctgatg gaattagaca ctctttgcct | 540 |
| ctaatgccag cagatcctat ttctactcag tttaatttga aaaggcgat tcttcaaaat | 600 |
| gatttaccaa ttgaaggtgg ggataagttt acggtattga atactcatct agatgcgttt | 660 |
| tcacaaggaa ctgatacgat gcataggcag gtggaaacga ttacaggttt attaaaagaa | 720 |
| ctggatcttg caggacatta tgggttttg gggggagatt ttaatcttct ccctcctggg | 780 |
| ttcgatcgaa agtctatgca tcctaatgga gctttctttt attcggacga acaggaaatt | 840 |
| aaacctcttt tgacagatg gaattccgcc gttccattca agattttgaa tggacctgaa | 900 |
| aaagaaaaat attacacata ttatccgaac gatcctgcga ttggaaagcc agatagaact | 960 |
| attgattata tattttattc ttctaatttg aaacagtctg gatataaagt ggatcagaaa | 1020 |
| gatatactct ggacaatctc ggatcatttc cctcagatag aacgtatag aatgtcccaa | 1080 |

<210> SEQ ID NO 104
<211> LENGTH: 360
<212> TYPE: PRT
<213> ORGANISM: Artificial Sequence
<220> FEATURE:
<223> OTHER INFORMATION: LIC12332

<400> SEQUENCE: 104

Met Gly Trp Leu Lys Lys Ile Thr Ala Ile Leu Gly Ile Leu Phe Gly
1               5                   10                  15

Ser Leu Leu Ile Leu Ile Tyr Val Ile Thr Tyr His Pro Asp Gln Ala 20                  25                  30
Glu Pro Ala Glu Ile Val Cys Asn Glu Asn Ala Pro Ile Leu Lys Glu
             35                  40                  45

Asn Ser Lys Ile Lys Val Leu Val Trp Asn Val Gln Tyr Leu Ala Gly
         50                  55                  60

Lys Lys Arg Ile Phe Trp Tyr Asp Leu Pro Asn Gly Asp Gly Pro Asp
 65                  70                  75                  80

Thr Gly Pro Ser Lys Glu Glu Ile Glu Thr Leu Lys Lys Val Ala
                 85                  90                  95

Gly Tyr Ile His Ser Glu Asp Pro Asp Val Ile Leu Phe Gln Glu Leu
                100                 105                 110

His Asp Gly Ala Glu Asn Thr Phe Arg Glu Asp Gln Leu Glu Arg Ile
            115                 120                 125

Leu Ser Arg Ile Gly Ser Glu Tyr Val Cys Arg Ser Glu Ala Phe Tyr
        130                 135                 140

Trp Lys Ser Asn Phe Val Pro His Pro Lys Ile Leu Gly Ser Val Gly
145                 150                 155                 160

Met Lys Leu Ala Thr Ile Ser Lys Tyr Lys Ile Ser Asp Gly Ile Arg
                165                 170                 175

His Ser Leu Pro Leu Met Pro Ala Asp Pro Ile Ser Thr Gln Phe Asn
            180                 185                 190

Leu Lys Arg Ala Ile Leu Gln Asn Asp Leu Pro Ile Glu Gly Asp
        195                 200                 205

Lys Phe Thr Val Leu Asn Thr His Leu Asp Ala Phe Ser Gln Gly Thr
    210                 215                 220

Asp Thr Met His Arg Gln Val Glu Thr Ile Thr Gly Leu Leu Lys Glu
225                 230                 235                 240

Leu Asp Leu Ala Gly His Tyr Trp Val Leu Gly Gly Asp Phe Asn Leu
                245                 250                 255

Leu Pro Pro Gly Phe Asp Arg Lys Ser Met His Pro Asn Gly Ala Phe
            260                 265                 270

Phe Tyr Ser Asp Glu Gln Glu Ile Lys Pro Leu Phe Asp Arg Trp Asn
        275                 280                 285

Ser Ala Val Pro Phe Lys Ile Leu Asn Gly Pro Glu Lys Glu Lys Tyr
    290                 295                 300

Tyr Thr Tyr Tyr Pro Asn Asp Pro Ala Ile Gly Lys Pro Asp Arg Thr
305                 310                 315                 320

Ile Asp Tyr Ile Phe Tyr Ser Ser Asn Leu Lys Gln Ser Gly Tyr Lys
                325                 330                 335

Val Asp Gln Lys Asp Ile Leu Trp Thr Ile Ser Asp His Phe Pro Gln
            340                 345                 350

Ile Gly Thr Tyr Arg Met Ser Gln
        355                 360

<210> SEQ ID NO 105
<211> LENGTH: 1368
<212> TYPE: DNA
<213> ORGANISM: Artificial Sequence
<220> FEATURE:
<223> OTHER INFORMATION: LIC10793

<400> SEQUENCE: 105
ttgaactcga atccaaaaaa aaatcttcta aaacttatca aaattaaatc ggatataatt      60
ctgctaattc ctatattttt gttttagtc tgctgcaaaa gtggagactt ttctttactt     120

```
tcttctccaa tcaatcgaga aaagaacgga accgaaattg ttaagtttag tattcatcct    180
tataaaggaa ccgtaatacg attgggagaa gagattcttc cttttaaggt tttagaaatg    240
gataagaata ttgctttggt cgaaatggca attcccgttt ataaggatga aaggaaatt     300
gaattaaaac tttcttctcc gggttttcaa aattcttctt atcgtattag aaagccagaa    360
gaactaaatg aaaaattgat agctttagat aaagagggca taacgcatcg ttttatctca    420
agatttaaaa caggatttca gcccaaaagc gttcgattca tagacaatac taggcttgcg    480
attcctcttt tagaagatga aggtatggac gttttggata taaattccgg tcagaccgtc    540
agactttctc cccctgaaaa atacaaaaaa aaattgggtt ttgtggaaac gatttcgatt    600
ccagagcata acgaactttg ggtcagtcag atgcaggcaa atgcggttca cgttttcgat    660
ttaaaaactc tcgcgtataa agcgacggtt gatctaacgg gtaaatggtc taaaatcctt    720
ctttatgatc caattcgaga tttggtttat tgctccaatt ggattagtga ggatatttcc    780
gttattgata gaaaaacgaa attagaaatt cgtaaaacag ataagattgg tttacctcgt    840
ggacttctac tttcgaaaga cggtaaagaa ttatatattg ctcaattttc cgcgagcaat    900
caagaatctg gaggtggtag acttggaatc tattctatgg ataaggaaaa actcatcgat    960
acaatcggtc ctccggggaa caaacgtcat atcgtctcgg caatactgaa aataagatt   1020
tatgtttctg atatgtgttg tagcaagatc gaagtttatg atttaaaaga aaaaaaagtt   1080
caaaagtcaa ttcctgtatt cgataaaccg aatacgattg ctctttctcc tgacggaaag   1140
tatctttatg tttcttgtag aggtcctaat catccaaccg aaggttatct caaaaaaggt   1200
ttggtacttg gaaaagttta tgttattgac acaacgacgg acacggttaa ggaattttgg   1260
gaagctggta atcaacctac tggtcttgac gtttcacccg acaatcgtta cctagtgatc   1320
tcggattttt tagatcatca aattcgagtt tatcgtaggg atggtttt               1368
```

<210> SEQ ID NO 106
<211> LENGTH: 456
<212> TYPE: PRT
<213> ORGANISM: Artificial Sequence
<220> FEATURE:
<223> OTHER INFORMATION: LIC10793

<400> SEQUENCE: 106

```
Leu Asn Ser Asn Pro Lys Lys Asn Leu Leu Lys Leu Ile Lys Ile Lys
1               5                   10                  15

Ser Asp Ile Ile Leu Leu Ile Pro Ile Phe Leu Phe Leu Val Cys Cys
            20                  25                  30

Lys Ser Gly Asp Phe Ser Leu Ser Ser Pro Ile Asn Arg Glu Lys
        35                  40                  45

Asn Gly Thr Glu Ile Val Lys Phe Ser Ile His Pro Tyr Lys Gly Thr
    50                  55                  60

Val Ile Arg Leu Gly Glu Glu Ile Leu Pro Phe Lys Val Leu Glu Met
65                  70                  75                  80

Asp Lys Asn Ile Ala Leu Val Glu Met Ala Ile Pro Val Tyr Lys Asp
                85                  90                  95

Glu Lys Glu Ile Glu Leu Lys Leu Ser Ser Pro Gly Phe Gln Asn Ser
            100                 105                 110

Ser Tyr Arg Ile Arg Lys Pro Glu Glu Leu Asn Glu Lys Leu Ile Ala
        115                 120                 125

Leu Asp Lys Glu Gly Ile Thr His Arg Phe Ile Ser Arg Phe Lys Thr
    130                 135                 140
```

Gly Phe Gln Pro Lys Ser Val Arg Phe Ile Asp Asn Thr Arg Leu Ala
145                 150                 155                 160

Ile Pro Leu Leu Glu Asp Glu Gly Met Asp Val Leu Asp Ile Asn Ser
                165                 170                 175

Gly Gln Thr Val Arg Leu Ser Pro Pro Glu Lys Tyr Lys Lys Lys Leu
            180                 185                 190

Gly Phe Val Glu Thr Ile Ser Ile Pro Glu His Asn Glu Leu Trp Val
        195                 200                 205

Ser Gln Met Gln Ala Asn Ala Val His Val Phe Asp Leu Lys Thr Leu
    210                 215                 220

Ala Tyr Lys Ala Thr Val Asp Leu Thr Gly Lys Trp Ser Lys Ile Leu
225                 230                 235                 240

Leu Tyr Asp Pro Ile Arg Asp Leu Val Tyr Cys Ser Asn Trp Ile Ser
                245                 250                 255

Glu Asp Ile Ser Val Ile Asp Arg Lys Thr Lys Leu Glu Ile Arg Lys
                260                 265                 270

Thr Asp Lys Ile Gly Leu Pro Arg Gly Leu Leu Leu Ser Lys Asp Gly
            275                 280                 285

Lys Glu Leu Tyr Ile Ala Gln Phe Ser Ala Ser Asn Gln Glu Ser Gly
        290                 295                 300

Gly Gly Arg Leu Gly Ile Tyr Ser Met Asp Lys Glu Lys Leu Ile Asp
305                 310                 315                 320

Thr Ile Gly Pro Pro Gly Asn Lys Arg His Ile Val Ser Gly Asn Thr
                325                 330                 335

Glu Asn Lys Ile Tyr Val Ser Asp Met Cys Cys Ser Lys Ile Glu Val
                340                 345                 350

Tyr Asp Leu Lys Glu Lys Lys Val Gln Lys Ser Ile Pro Val Phe Asp
            355                 360                 365

Lys Pro Asn Thr Ile Ala Leu Ser Pro Asp Gly Lys Tyr Leu Tyr Val
        370                 375                 380

Ser Cys Arg Gly Pro Asn His Pro Thr Glu Gly Tyr Leu Lys Lys Gly
385                 390                 395                 400

Leu Val Leu Gly Lys Val Tyr Val Ile Asp Thr Thr Thr Asp Thr Val
                405                 410                 415

Lys Glu Phe Trp Glu Ala Gly Asn Gln Pro Thr Gly Leu Asp Val Ser
            420                 425                 430

Pro Asp Asn Arg Tyr Leu Val Ile Ser Asp Phe Leu Asp His Gln Ile
        435                 440                 445

Arg Val Tyr Arg Arg Asp Gly Phe
450                 455

<210> SEQ ID NO 107
<211> LENGTH: 1296
<212> TYPE: DNA
<213> ORGANISM: Artificial Sequence
<220> FEATURE:
<223> OTHER INFORMATION: LIC11884

<400> SEQUENCE: 107
ttgagggatt tttttaaaca aaataggaat tctcggatgc tcaacacaaa aataaagaaa      60
aaattatttc tctcagttat tttttttcta tttctaccat cggtcgcctg tgcggaaaaa     120
agttttcgta acatatcgc ggactcaaaa ctcattcctt ctgaaatcga atttattct      180 aacattcttc ccggactttc cggaaaaaat gtcattctaa ttacaaaccc atccggaatc     240
ggaagaagcc ccgaaaggat tttacgagaa tttaaaaaac acgacgtaaa aatcaaacat     300

```
ctcatcggat tggaacacgg atttttagga ctcgaggagg acttcagtaa atctcccgtt    360
acggtggatg aattttttaa tctcccaatc tatcatatct atcgagtcaa gaacgcagaa    420
cttcctacga ttttgaaagg agccgacgcg attcttttg atgtgcaaga tatggggatg     480
agatgttata cttatctaac cgttttaaaa agaattatgg atggaattcc agatcctaca    540
aatacgagac tgatcgtttt ggatcacgta aaccccgctc tttatttaaa aggaagagga    600
gaaatgatcg ataaacgttt cttaaatttt gcaggagaat tcccttctct tttttttgga   660
ggtttgacct tgggagaatc agcggtttat tataactctg aatatttaga taaaaaggtt    720
cgtttagaag tggtatctcc taaaaacgca aaacgatctt ttgattggga tagagaagga    780
attccttgga ctacaccttc tcctaattta ccaactgtag attctgcgat caattatctg    840
gggcttgttt tgttagaagg agtgaacgtt tctgtgggaa ggggtacaac cgcacccttt    900
gtatatttcg gagcgccttg gatgacagag cccgaaaagt tagcggaaga attaaatcaa    960
aattcaggtg gagaatatta ttatcagact gtgtttttta aacctgtatt tggtccttac   1020
aagaatgaga tttgtagagg attgcgccta acggtagtaa atcgaaagta tgatccttta   1080
aaaatggcat tccagttgat ctccgcttta aaatcgaatt ataaagaatt taaatggaga   1140
tcgtatccgg atggaaccta caatatagat ttcctatggg aacggaatc gtttcgaaaa    1200 acgatcgacg ccggaaaaaa atacgatcaa tatgcggaat acttaagttc cattgagaaa   1260
gaatataatg aaaaaattaa gaaatattat ctctac                            1296

<210> SEQ ID NO 108
<211> LENGTH: 432
<212> TYPE: PRT
<213> ORGANISM: Artificial Sequence
<220> FEATURE:
<223> OTHER INFORMATION: LIC11884

<400> SEQUENCE: 108

Leu Arg Asp Phe Phe Lys Gln Asn Arg Asn Ser Arg Met Leu Asn Thr
1               5                   10                  15

Lys Ile Lys Lys Lys Leu Phe Leu Ser Val Ile Phe Phe Leu Phe Leu
            20                  25                  30

Pro Ser Val Ala Cys Ala Glu Lys Ser Phe Arg Lys His Ile Ala Asp
        35                  40                  45

Ser Lys Leu Ile Pro Ser Glu Ile Glu Phe Tyr Ser Asn Ile Leu Pro
    50                  55                  60

Gly Leu Ser Gly Lys Asn Val Ile Leu Ile Thr Asn Pro Ser Gly Ile
65                  70                  75                  80

Gly Arg Ser Pro Glu Arg Ile Leu Arg Glu Phe Lys Lys His Asp Val
                85                  90                  95

Lys Ile Lys His Leu Ile Gly Leu Glu His Gly Phe Leu Gly Leu Glu
            100                 105                 110

Glu Asp Phe Ser Lys Ser Pro Val Thr Val Asp Glu Phe Phe Asn Leu
        115                 120                 125

Pro Ile Tyr His Ile Tyr Arg Val Lys Asn Ala Glu Leu Pro Thr Ile
    130                 135                 140

Leu Lys Gly Ala Asp Ala Ile Leu Phe Asp Val Gln Asp Met Gly Met
145                 150                 155                 160

Arg Cys Tyr Thr Tyr Leu Thr Val Leu Lys Arg Ile Met Asp Gly Ile
                165                 170                 175

Pro Asp Pro Thr Asn Thr Arg Leu Ile Val Leu Asp His Val Asn Pro
```

180                 185                 190
Ala Leu Tyr Leu Lys Gly Arg Gly Glu Met Ile Asp Lys Arg Phe Leu
            195                 200                 205

Asn Phe Ala Gly Glu Phe Pro Ser Leu Phe Phe Gly Gly Leu Thr Leu
        210                 215                 220

Gly Glu Ser Ala Val Tyr Tyr Asn Ser Glu Tyr Leu Asp Lys Lys Val
225                 230                 235                 240

Arg Leu Glu Val Val Ser Pro Lys Asn Ala Lys Arg Ser Phe Asp Trp
                245                 250                 255

Asp Arg Glu Gly Ile Pro Trp Thr Thr Pro Ser Pro Asn Leu Pro Thr
            260                 265                 270

Val Asp Ser Ala Ile Asn Tyr Leu Gly Leu Val Leu Leu Glu Gly Val
        275                 280                 285

Asn Val Ser Val Gly Arg Gly Thr Thr Ala Pro Phe Val Tyr Phe Gly
        290                 295                 300

Ala Pro Trp Met Thr Glu Pro Glu Lys Leu Ala Glu Glu Leu Asn Gln
305                 310                 315                 320

Asn Ser Gly Gly Glu Tyr Tyr Gln Thr Val Phe Lys Pro Val
                325                 330                 335

Phe Gly Pro Tyr Lys Asn Glu Ile Cys Arg Gly Leu Arg Leu Thr Val
            340                 345                 350

Val Asn Arg Lys Tyr Asp Pro Leu Lys Met Ala Phe Gln Leu Ile Ser
        355                 360                 365

Ala Leu Lys Ser Asn Tyr Lys Glu Phe Lys Trp Arg Ser Tyr Pro Asp
        370                 375                 380

Gly Thr Tyr Asn Ile Asp Phe Leu Trp Gly Thr Glu Ser Phe Arg Lys
385                 390                 395                 400

Thr Ile Asp Ala Gly Lys Lys Tyr Asp Gln Tyr Ala Glu Tyr Leu Ser
                405                 410                 415

Ser Ile Glu Lys Glu Tyr Asn Glu Lys Ile Lys Lys Tyr Tyr Leu Tyr
            420                 425                 430

<210> SEQ ID NO 109
<211> LENGTH: 2085
<212> TYPE: DNA
<213> ORGANISM: Artificial Sequence
<220> FEATURE:
<223> OTHER INFORMATION: LIC12285

<400> SEQUENCE: 109
atgtctattt tggcgatcgt cactgctgtg gtctatacct taaaagtcac ctccatcaaa      60
gtaggtacct taggcggtaa cgaaaaagaa acgaaaaagc ttttagaaat ttcatccgct     120
atctccgaag gagctatggc ctttctcgta aggaatata aagtcatttc cctgtttatt     180
gcctttatgg cagtattgat cgttctattg ttagacaatc ctggatcgga aggatttaac     240
gacggaattt atactgcaat tgcttttgta tcggagcttt gatttcctg tatttccggt     300 tttatcggaa tgaaaattgc aactgcagga acgtaagaa ccgcagaggc cgctaaatct     360
tctatggcaa aggcttttcg ggtagcattt gattctggag ccgtgatggg gttcggactc     420
gtagggcttg caatttttagg aatgatcgtg cttttttcttg tttttactgg aatgtatcca     480
ggtgtagaaa acatttttct tatggaatcc ttggctggtt ttggattagg ggggtctgct     540
gtagcacttt ttggaagagt gggcggcgga atttatacaa aagcagcaga cgtaggagcg     600
gatctagtcg gaaaggtgga aaaaggaatt cctgaagacg atcctagaaa cccggcaacg     660

| | |
|---|---|
| attgcggata acgtaggaga taatgtgggc gatgtggcag gaatgggagc agatttattt | 720 |
| ggttcctgtg cggaagctac ttgtgcggct cttgtaattg gtgctactgc ctccgctctt | 780 |
| tctggatctg tagacgctct attatacccg cttttgattt ctgcatttgg aatcccagct | 840 |
| tctattttaa ccagctttct tgcaagagtc aaagaagatg gaaatgtgga atccgctctt | 900 |
| aaagttcaac tttgggtttc tacacttcta gtcgcgggaa tcatgtattt tgtaacaaaa | 960 |
| actttcatgg tggattcttt tgaaattgcg gggaaaacaa tcacaaaatg gacgtttac | 1020 |
| atttcgatgg tggttggact tttttctgga atgtttatag ggattgtaac tgaatattat | 1080 |
| acttcacatt cttataaacc tgtaagagaa gtggcagaag cgtctaacac aggagcggcg | 1140 |
| acaaatatca tctacggatt gtctcttggt tatcattctt ccgtaattcc agtgatttta | 1200 |
| cttgtgatta caattgtaac ggcaaaccta cttgcgggaa tgtatggaat cgcgattgcg | 1260 |
| gctctgggca tgatttccac gatcgcgatt ggattgacca tagacgctta cggtcctgtt | 1320 |
| tcggataacg cgggcgggat cgcgaaaatg gcggaactcg gaaaagaagt tcgtgataga | 1380 |
| accgatactc tggacgcggc tggaaataca actgcgcgca tcggcaaggg atttgcgatt | 1440 |
| ggaagcgccg ctttgacttc tcttgcgtta tttgcggctt tcatcacaag aactcatacc | 1500 |
| acgagtcttg aggttttaaa tgcggaagtg tttggaggat tgatgtttgg agcgatgctt | 1560 |
| ccttttttat tcaccgcaat gacgatgaag tctgtaggaa aagccgcagt ggatatggtg | 1620 |
| gaagaggttc gcaaacaatt caagagatt ccaggaatta tggaagggaa aaataaaccg | 1680 |
| gactacaaac gttgtgtgga tatatctacg agcgctgctt tgagggaaat gattcttccg | 1740 |
| gggcttctcg ttttattaac tccgatctta gtaggttatc ttttggagt caaaactctt | 1800 |
| gccggagtac ttgcggggc attggttgcg ggtgtggtgc ttgcaatttc tgccgcaaat | 1860 |
| tccggaggag gttgggacaa cgcaaagaaa tacattgaga aaaagcggg cggaaaagga | 1920 |
| tcggatcaac acaaagccgc ggttgtaggt gatactgtag gagatccgtt taaagatact | 1980 |
| tctggaccat ctatcaatat tctaatcaaa ttgatggcga ttacaagttt agttttgct | 2040 |
| gaattttttg tccaacaagg tggattgata tttaaaatat ttcat | 2085 |

<210> SEQ ID NO 110
<211> LENGTH: 695
<212> TYPE: PRT
<213> ORGANISM: Artificial Sequence
<220> FEATURE:
<223> OTHER INFORMATION: LIC12285

<400> SEQUENCE: 110

Met Ser Ile Leu Ala Ile Val Thr Ala Val Val Tyr Thr Leu Lys Val
1               5                   10                  15

Thr Ser Ile Lys Val Gly Thr Leu Gly Gly Asn Glu Lys Glu Thr Lys
            20                  25                  30

Lys Leu Leu Glu Ile Ser Ser Ala Ile Ser Glu Gly Ala Met Ala Phe
        35                  40                  45

Leu Val Arg Glu Tyr Lys Val Ile Ser Leu Phe Ile Ala Phe Met Ala
    50                  55                  60

Val Leu Ile Val Leu Leu Asp Asn Pro Gly Ser Glu Gly Phe Asn
65                  70                  75                  80

Asp Gly Ile Tyr Thr Ala Ile Ala Phe Val Ser Gly Ala Leu Ile Ser
                85                  90                  95

Cys Ile Ser Gly Phe Ile Gly Met Lys Ile Ala Thr Ala Gly Asn Val
            100                 105                 110

-continued

```
Arg Thr Ala Glu Ala Ala Lys Ser Met Ala Lys Ala Phe Arg Val
            115                 120                 125
Ala Phe Asp Ser Gly Ala Val Met Gly Phe Gly Leu Val Gly Leu Ala
        130                 135                 140
Ile Leu Gly Met Ile Val Leu Phe Leu Val Phe Thr Gly Met Tyr Pro
145                 150                 155                 160
Gly Val Glu Lys His Phe Leu Met Glu Ser Leu Ala Gly Phe Gly Leu
                165                 170                 175
Gly Gly Ser Ala Val Ala Leu Phe Gly Arg Val Gly Gly Ile Tyr
            180                 185                 190
Thr Lys Ala Ala Asp Val Gly Ala Asp Leu Val Gly Lys Val Glu Lys
        195                 200                 205
Gly Ile Pro Glu Asp Asp Pro Arg Asn Pro Ala Thr Ile Ala Asp Asn
210                 215                 220
Val Gly Asp Asn Val Gly Asp Val Ala Gly Met Gly Ala Asp Leu Phe
225                 230                 235                 240
Gly Ser Cys Ala Glu Ala Thr Cys Ala Ala Leu Val Ile Gly Ala Thr
                245                 250                 255
Ala Ser Ala Leu Ser Gly Ser Val Asp Ala Leu Leu Tyr Pro Leu Leu
            260                 265                 270
Ile Ser Ala Phe Gly Ile Pro Ala Ser Ile Leu Thr Ser Phe Leu Ala
        275                 280                 285
Arg Val Lys Glu Asp Gly Asn Val Glu Ser Ala Leu Lys Val Gln Leu
    290                 295                 300
Trp Val Ser Thr Leu Leu Val Ala Gly Ile Met Tyr Phe Val Thr Lys
305                 310                 315                 320
Thr Phe Met Val Asp Ser Phe Glu Ile Ala Gly Lys Thr Ile Thr Lys
                325                 330                 335
Trp Asp Val Tyr Ile Ser Met Val Val Gly Leu Phe Ser Gly Met Phe
            340                 345                 350
Ile Gly Ile Val Thr Glu Tyr Tyr Thr Ser His Ser Tyr Lys Pro Val
        355                 360                 365
Arg Glu Val Ala Glu Ala Ser Asn Thr Gly Ala Ala Thr Asn Ile Ile
    370                 375                 380
Tyr Gly Leu Ser Leu Gly Tyr His Ser Ser Val Ile Pro Val Ile Leu
385                 390                 395                 400
Leu Val Ile Thr Ile Val Thr Ala Asn Leu Leu Ala Gly Met Tyr Gly
                405                 410                 415
Ile Ala Ile Ala Ala Leu Gly Met Ile Ser Thr Ile Ala Ile Gly Leu
            420                 425                 430
Thr Ile Asp Ala Tyr Gly Pro Val Ser Asp Asn Ala Gly Gly Ile Ala
        435                 440                 445
Glu Met Ala Glu Leu Gly Lys Glu Val Arg Asp Arg Thr Asp Thr Leu
    450                 455                 460
Asp Ala Ala Gly Asn Thr Thr Ala Ala Ile Gly Lys Gly Phe Ala Ile
465                 470                 475                 480
Gly Ser Ala Ala Leu Thr Ser Leu Ala Leu Phe Ala Ala Phe Ile Thr
                485                 490                 495
Arg Thr His Thr Thr Ser Leu Glu Val Leu Asn Ala Glu Val Phe Gly
            500                 505                 510
Gly Leu Met Phe Gly Ala Met Leu Pro Phe Leu Phe Thr Ala Met Thr
        515                 520                 525
Met Lys Ser Val Gly Lys Ala Ala Val Asp Met Val Glu Glu Val Arg
```

```
              530              535                 540
Lys Gln Phe Lys Glu Ile Pro Gly Ile Met Glu Gly Lys Asn Lys Pro
545                  550                 555                 560

Asp Tyr Lys Arg Cys Val Asp Ile Ser Thr Ser Ala Ala Leu Arg Glu
                565                 570                 575

Met Ile Leu Pro Gly Leu Leu Val Leu Leu Thr Pro Ile Leu Val Gly
            580                 585                 590

Tyr Leu Phe Gly Val Lys Thr Leu Ala Gly Val Leu Ala Gly Ala Leu
        595                 600                 605

Val Ala Gly Val Val Leu Ala Ile Ser Ala Ala Asn Ser Gly Gly Gly
    610                 615                 620

Trp Asp Asn Ala Lys Lys Tyr Ile Glu Lys Lys Ala Gly Lys Gly
625                 630                 635                 640

Ser Asp Gln His Lys Ala Ala Val Val Gly Asp Thr Val Gly Asp Pro
                645                 650                 655

Phe Lys Asp Thr Ser Gly Pro Ser Ile Asn Ile Leu Ile Lys Leu Met
            660                 665                 670

Ala Ile Thr Ser Leu Val Phe Ala Glu Phe Val Gln Gln Gly Gly
        675                 680                 685

Leu Ile Phe Lys Ile Phe His
    690                 695
```

<210> SEQ ID NO 111
<211> LENGTH: 1080
<212> TYPE: DNA
<213> ORGANISM: Artificial Sequence
<220> FEATURE:
<223> OTHER INFORMATION: LIC10509

<400> SEQUENCE: 111

```
atgggttggt tgaaaaaaat aacggcgata ttaggaattc ttttcggaag tcttttgatt      60
ttgatttatg taatcacgta tcatccagat caggcggaac ctgcggagat tgtatgtaat     120
gagaacgctc caatcttaaa agaaaattct aagattaaag tgttggtctg aacgtacaa     180
tacctcgccg gaaaaaaaag gatttttttgg tatgacttac ctaacggaga tgggccggac     240
acagggcctt ctaaagagga atcgaagaa acacttaaaa agtagccgg ctacattcat     300
tcggaagacc cagatgtgat acttttttcag gagcttcatg acggagcaga aaatacgttt     360
cgtgaagatc agttagaaag aattctttct cggattgggt ccgagtatgt ctgtagaagt     420
gaggcatttt actggaaatc taattttgtt ccacatccta aaattttggg aagtgtgggt     480
atgaaactgg caacgattag taaatataaa atttctgatg gaattagaca ctctttgcct     540
ctaatgccag cagatcctat ttctactcag tttaatttga aaagggcgat tcttcaaaat     600
gatttaccaa ttgaaggtgg ggataagttt acggtattga atactcatct agatgcgttt     660
tcacaaggaa ctgatacgat gcataggcag gtggaaacga ttacaggttt attaaaagaa     720
ctggatcttg caggacatta tgggttttg ggggagatt taatcttct ccctcctggg     780
ttcgatcgaa agtctatgca tcctaatgga gctttctttt attcggacga acaggaaatt     840
aaacctcttt tgacagatg gaattccgcc gttccattca agattttgaa tggacctgaa     900
aaagaaaat attacacata ttatccgaac gatcctgcga ttggaaagcc agatagaact     960
attgattata tattttattc ttctaattg aaacagtctg gatataaagt ggatcagaaa    1020
gatatactct ggacaatctc ggatcatttc cctcagatag gaacgtatag aatgtcccaa    1080
```

```
<210> SEQ ID NO 112
<211> LENGTH: 360
<212> TYPE: PRT
<213> ORGANISM: Artificial Sequence
<220> FEATURE:
<223> OTHER INFORMATION: LIC10509

<400> SEQUENCE: 112

Met Gly Trp Leu Lys Lys Ile Thr Ala Ile Leu Gly Ile Leu Phe Gly
1               5                   10                  15

Ser Leu Leu Ile Leu Ile Tyr Val Ile Thr Tyr His Pro Asp Gln Ala
            20                  25                  30

Glu Pro Ala Glu Ile Val Cys Asn Glu Asn Ala Pro Ile Leu Lys Glu
        35                  40                  45

Asn Ser Lys Ile Lys Val Leu Val Trp Asn Val Gln Tyr Leu Ala Gly
    50                  55                  60

Lys Lys Arg Ile Phe Trp Tyr Asp Leu Pro Asn Gly Asp Gly Pro Asp
65                  70                  75                  80

Thr Gly Pro Ser Lys Glu Glu Ile Glu Glu Thr Leu Lys Lys Val Ala
                85                  90                  95

Gly Tyr Ile His Ser Glu Asp Pro Asp Val Ile Leu Phe Gln Glu Leu
            100                 105                 110

His Asp Gly Ala Glu Asn Thr Phe Arg Glu Asp Gln Leu Glu Arg Ile
        115                 120                 125

Leu Ser Arg Ile Gly Ser Glu Tyr Val Cys Arg Ser Glu Ala Phe Tyr
    130                 135                 140

Trp Lys Ser Asn Phe Val Pro His Pro Lys Ile Leu Gly Ser Val Gly
145                 150                 155                 160

Met Lys Leu Ala Thr Ile Ser Lys Tyr Lys Ile Ser Asp Gly Ile Arg
                165                 170                 175

His Ser Leu Pro Leu Met Pro Ala Asp Pro Ile Ser Thr Gln Phe Asn
            180                 185                 190

Leu Lys Arg Ala Ile Leu Gln Asn Asp Leu Pro Ile Glu Gly Gly Asp
        195                 200                 205

Lys Phe Thr Val Leu Asn Thr His Leu Asp Ala Phe Ser Gln Gly Thr
    210                 215                 220

Asp Thr Met His Arg Gln Val Glu Thr Ile Thr Gly Leu Leu Lys Glu
225                 230                 235                 240

Leu Asp Leu Ala Gly His Tyr Trp Val Leu Gly Asp Phe Asn Leu
                245                 250                 255

Leu Pro Pro Gly Phe Asp Arg Lys Ser Met His Pro Asn Gly Ala Phe
            260                 265                 270

Phe Tyr Ser Asp Glu Gln Glu Ile Lys Pro Leu Phe Asp Arg Trp Asn
        275                 280                 285

Ser Ala Val Pro Phe Lys Ile Leu Asn Gly Pro Glu Lys Glu Lys Tyr
    290                 295                 300

Tyr Thr Tyr Tyr Pro Asn Asp Pro Ala Ile Gly Lys Pro Asp Arg Thr
305                 310                 315                 320

Ile Asp Tyr Ile Phe Tyr Ser Ser Asn Leu Lys Gln Ser Gly Tyr Lys
                325                 330                 335

Val Asp Gln Lys Asp Ile Leu Trp Thr Ile Ser Asp His Phe Pro Gln
            340                 345                 350

Ile Gly Thr Tyr Arg Met Ser Gln
        355                 360
```

<210> SEQ ID NO 113
<211> LENGTH: 762
<212> TYPE: DNA
<213> ORGANISM: Artificial Sequence
<220> FEATURE:
<223> OTHER INFORMATION: LIC10596

<400> SEQUENCE: 113

```
atgaaccaat ttaaatttct tttaattgcg atccttttag ttttatccat tgtcaactgc    60
aataaaaaag agcctatttc cattttggaa attagagatc tcatcgaaaa acaaaatctt   120
gtagaagaac ttcgaaaagc ggaagaagat ctcaggttga aggcgacaa tgcagcatta    180
ctttatgttc gaggttggat tcgttattta caaaaaaacc aagacgctgc catgagcgat   240
tttaaaaaat gtctgggatt tgaccctaaa tccttggatt gcaaagagg acttggtctc    300
atatacgagt ccaacaaaga atataaagaa gccgaattgg tttataaaga agctcttttct  360
ttcgcaaaag aaaagggggc agactcagaa gctctcattc atgagaatat tggaatactt   420
tatctcagac aaaatcttag aaaagaaagt ttagaagaat ccaaaaagc aatttcactt    480
tctgataaag gggatgctta ttacggtttc agtttgtgta tgattatgga aggaaattca   540
gaaggtgcaa tttcttcttt agaaaaaggt atttctaaat cgtttcgttc taaagcgttt   600
caatcagaat cacactttt attatctaaa ttctactttg aaaaagaaa agacccagta    660
aaagcagaat cagaaatcaa aaggcaatc gaattttttc cccttcataa ggaatatcta    720
gacgcattac aaatttacat aaagaaaga attaagaatt cg                       762
```

<210> SEQ ID NO 114
<211> LENGTH: 254
<212> TYPE: PRT
<213> ORGANISM: Artificial Sequence
<220> FEATURE:
<223> OTHER INFORMATION: LIC10596

<400> SEQUENCE: 114

```
Met Asn Gln Phe Lys Phe Leu Leu Ile Ala Ile Leu Leu Val Leu Ser
1               5                   10                  15

Ile Val Asn Cys Asn Lys Lys Glu Pro Ile Ser Ile Leu Glu Ile Arg
            20                  25                  30

Asp Leu Ile Glu Lys Gln Asn Leu Val Glu Glu Leu Arg Lys Ala Glu
        35                  40                  45

Glu Asp Leu Arg Leu Lys Gly Asp Asn Ala Ala Leu Leu Tyr Val Arg
    50                  55                  60

Gly Trp Ile Arg Tyr Leu Gln Lys Asn Gln Asp Ala Ala Met Ser Asp
65                  70                  75                  80

Phe Lys Lys Cys Leu Gly Phe Asp Pro Lys Ser Leu Asp Cys Lys Arg
                85                  90                  95

Gly Leu Gly Leu Ile Tyr Glu Ser Asn Lys Glu Tyr Lys Glu Ala Glu
            100                 105                 110

Leu Val Tyr Lys Glu Ala Leu Ser Phe Ala Lys Glu Lys Gly Ala Asp
        115                 120                 125

Ser Glu Ala Leu Ile His Glu Asn Ile Gly Ile Leu Tyr Leu Arg Gln
    130                 135                 140

Asn Leu Arg Lys Glu Ser Leu Glu Glu Phe Gln Lys Ala Ile Ser Leu
145                 150                 155                 160

Ser Asp Lys Gly Asp Ala Tyr Tyr Gly Phe Ser Leu Cys Met Ile Met
                165                 170                 175

Glu Gly Asn Ser Glu Gly Ala Ile Ser Ser Leu Glu Lys Gly Ile Ser
```

```
                180               185                 190
Lys Ser Phe Arg Ser Lys Ala Phe Gln Ser Glu Ser His Phe Leu Leu
                195                 200                 205

Ser Lys Phe Tyr Phe Glu Lys Arg Lys Asp Pro Val Lys Ala Glu Ser
            210                 215                 220

Glu Ile Lys Lys Ala Ile Glu Ile Phe Pro Leu His Lys Glu Tyr Leu
225                 230                 235                 240

Asp Ala Leu Gln Ile Tyr Ile Lys Glu Arg Ile Lys Asn Ser
                245                 250

<210> SEQ ID NO 115
<211> LENGTH: 7764
<212> TYPE: DNA
<213> ORGANISM: Artificial Sequence
<220> FEATURE:
<223> OTHER INFORMATION: LIC11028

<400> SEQUENCE: 115
```

| | | | | | |
|---|---|---|---|---|---|
| atggttcgat | ttggaatctg | cttctttagt | tttttctttt | tttatcattg | ttctattttt |   60 |
| cgagcggctt | ccagaattaa | acctttggaa | ttcaattata | cttctatcgc | cgtaaattat |  120 |
| tttactcctg | aaaatgaaaa | accgttttcct | cttactgtgc | agcgaggaaa | taatttatac |  180 |
| aattctacca | cggcagacgg | aagttatctt | ttttatacaa | ccggtcaaaa | gggaaactac |  240 |
| gatatttggt | ttagggattt | gaaaagttcg | attacggttc | cggttactac | tcatcccgct |  300 |
| cctgaatata | aacctgcaat | cagtccagac | ggaagaagt | tggtcttcgt | gtccgaacaa |  360 |
| tacgattctt | cggggagattt | aattttactt | aaaatgaatc | cgggtttgtg | ggcggataag |  420 |
| atccttcaag | gaaaaagatt | tataaattcg | gactttataa | tattaacaaa | ttctaattt |  480 |
| tctgatacag | gtaaaaaga | ttcttatgta | gatacggatc | ctttttttgc | accggatggg |  540 |
| cgtcatttgg | tgttttccac | ggatcgtctg | actccaggaa | ttcagaattt | agtcgttttg |  600 |
| gatacggaag | gcaaggagcc | gatgaaattg | ctgactcaaa | agggagggc | ttctccgttt |  660 |
| tggtccaaag | acggtaaatc | gatcgtttat | atttcgtatc | aagacggagt | ttttggagat |  720 |
| gtgtatcttt | ggatcttttc | ttctggtaaa | aacgaaagac | ttaccaaaga | ttcttatcta |  780 |
| aatttttctc | cgtctctttc | ggaggataaa | cggtatttgt | attatacttc | aattcaaaac |  840 |
| gatacaaatc | gcaatggtcg | tttggacgaa | agagacaata | gtttaatcgt | aagaaaggat |  900 |
| ctaaaaacgg | gtgtggttcg | taggttgacg | tctggtaatg | attctttatt | tgattctaga |  960 |
| ttttctgcgt | ttaatggcgg | ttctatttta | tttactgcag | catattatga | tactctaaat | 1020 |
| atctatttta | ttccggcgtc | tggttctgta | tccaaagaaa | aggatatcat | ttctcaatac | 1080 |
| gaacttgctt | tgaaatacaa | ggaaaaacag | agttttgaag | attttctttt | ggctatagac | 1140 |
| gcgatcgaat | tttatttttc | gcaagatcct | atttatcctt | tgatcttttc | taaggcgctt | 1200 |
| cttttaaaat | acgaggaagc | aaaaaattcc | ggaagaacca | taattgcaga | aaacgcaaag | 1260 |
| aaagaaattc | tatcttctcg | tttaaacccg | gtttatggac | tggcttatgg | tttattctt | 1320 |
| tctaatgaaa | aaaaacttac | tgtttctatt | caggaattga | ggaaatacta | cgaacaaatt | 1380 |
| cgcgtcattt | cagataccgg | aaaaaattta | ttggcttctc | ttttggaaga | agaggggac | 1440 |
| ttggctcgaa | agtcggagga | ctctcaacat | tcttaaaag | tatatgatga | aattataatt | 1500 |
| cattatccag | attattatag | gattcgagat | gtttatcgaa | agtcgggaga | tctacagtat | 1560 |
| aaaaacgctc | atctaaatca | ttataaaatt | ccggaaccgt | tttcagggt | agcaaatgat | 1620 |
| ttgagcgctg | ggaaagagga | tttaaaactt | ttatacgaac | ggattgatgg | agaagtggtc | 1680 |

```
gtaggaaaaa gttttcgga aaaataaac gcctccgaaa tttcgatcga atctaattct   1740
cttgaaaata aatctcctag gttgtttcaa tatttttat atattaaatc tctaggctta   1800
aacggaaaag gttctttcga agaaagtaat tctttattga atacgttttt gtccaaggtt   1860
gccaaaagtg atccactttt tttaaaaata catcttctaa aatcgaataa ttttaaagga   1920
ttgggagaag ttcaaaaatc ctttgacgaa cttagaattt atttggaaga atacgatcct   1980
cttttaggcg tagacttaga agaaaaagag atagaacgtt cttttattta ttttgaaaat   2040
aaagcgaggg atcacgatcg aagaggaaac cttcaagacg ctgcatttca ttacttttat   2100
aataccgaaa atatgttttt agtaaaaagc agaaacctat ttctggaaag cctttataag   2160
gaatttgcgg tttattatca aaggatgatg gtggatgcgg tatttaaatt gtctggttct   2220
ctaagtgaag aaagaaaaaa agcccttttg aatcaattgg atgtgattga tattgctaag   2280
gtcgacccgc ttgctgaaga aggccttgtt tatatcaatc aatactataa ggaagccgtt   2340
cctagagcca gacccgtttt ggatctagct acgttatacg gctattcgta ttatttgatc   2400
aaccgaagtg taattcgcga aacgtattac aattctacta aatcgatgac ttcttctaaa   2460
aaagaagaga tcctaagaga ttttaaacaa gctgaatatg agttacgatg gattattttt   2520
gcagacccga ggtattacga ggcttatcaa cttttaggtt ggatgtatca gtatgtggat   2580
atattaaaaa atagaaagtc cggagaagat caaccaagcg atgaagagaa gtatataagt   2640
gtttatgaaa atatttttcc cgaaaagaat ttcgaagaaa acatagaatt atacagccag   2700
gttctggaac ttttaggaga taattttgaa aataaaaagg ctctttccga tctgagattg   2760
aatcttggaa ataattattt tctactgaaa aattatccta aagcaaacga acagtattcc   2820
aaagtggatt cactttcgga ttatattatt tctaaaacac agttcgaaga ttatcgtcaa   2880
aaggcgatct ttcttttaa ctctgcgagg tcttccattt atgtggccga ttataaatcc   2940
gcgattcaaa aattaaaagc ggcttctgat atctacttta gaaacgagtc taaaaaaacg   3000
atcgttggaa aagacagcgc agaaaaacta gaacagtata aactcaaact tgctctttta   3060
ttcacgttaa ccggtctttc ctatatggaa gcaggagaat attctaacgc gattccttat   3120
tataaggatg cactttcttt aaatggagaa aatggatgga tcgatccggt taatcttcat   3180
aatggtctgg cgcttgtta tcaaaaatta ggaaagtata aattatcaga attgcattta   3240
accaaagccg ataaaattgt cgacgatcga gtcggaactg gttggattcc gagaggagtt   3300
aaactcgctt tttgggatta ttttggac tgggtttggg aagttgctct gccggatgga   3360
gttcggattt ctggggaagg aagatttccg gaagctattt ctcctaagtt tcaacctttg   3420
atgacaagtg gaattcgagt aaataattta atcgcctcga tggaaatcga tggagctatt   3480
aaagaaatta attccagact tgcttatgtg aaatctaaga gttaggaac cacgttagct   3540
ggttctttga ttggagccaa ttcttaaat gatttagggt atttacattt taaagggat   3600
gaattcaaaa atgctattga tgtttatgaa caggccgaaa aatttgaaac cgaaaaagga   3660
tttgcagcta aagctagaac ttcctttaaa agaaaacttt attcctactt tggtcattta   3720
gaaaatacaa acgaggatcc agagcttgaa ttgagaactt taggttctgc ggccgaacgt   3780
attcttttcct ctaaatctga ttttatcaaa ggttgtttgg gggatgttca gtatcaagaa   3840
gagttaatat attccgaaac taaaaaatgt atattaaaat tttataattc cttttcggat   3900
cacgatccta ctttggctct gatttattac tatcagggg aacaattttt tagaatgggg   3960
aactttgtag ccgcttttga atttttggga aaatctgcag ggcttttaga aaatccgtcc   4020
```

```
ttggttccta aagaagtagt aggtctagcc gatgacccgt attctagaaa agaaagactt    4080
tcttattcga tcagcagagc caatctttac gttcgattgg aagactcaca aaaagcaatc    4140
tctcttttag agctggcatc cgaaaccgca aacgaatttt attatattca agaatggatc    4200
gaggcattgg tgacccaagc ggagattttc agaaaagaaa aaaatgattt taaagctaaa    4260
gaaaaaatcg ataaagctag tgctctttta ttgtctcatc ctcatttaat aagtgaactt    4320
aagtatttta gaatatataa acttttttaaa attcagtctg agcttaactt tcaatctgga    4380
aagttttcgg acggatttaa aagtttggat cgactccata aattaaaact ctatcgtcaa    4440
tttattaaga ttcctcacga atcagaggat ccaaatttta cggaagacat aacaaaacta    4500
cagaacttga tcaaaaaaca gaagttttac tattctgcga tccaaaatgc gttagaaaaa    4560
aaggaaaagt ccgaaagttt acttaaaaaa tacgttcaac tttctaagga tttagaaaaa    4620
gaattagggg ttatcagtcg taaaaaccag gacttggacg gttatttggg aatatttatc    4680
gaagaacctt ctgtaacttc tttgttggat gtaaatgaag ttatcttag aattgagtct    4740 gcggaagata agataagaat ctatcgagca acttcgtaca ctgaagaata tttggtgaat    4800
actgggaagt tggaagaagt tttgaatcag attccaact ctggaaaaat tccttttgtc    4860
tctaaaaaaa tttggtttgt tcagcttggg gatcgtattg actttgaaaa aattcgaaat    4920
tttcttccag aaaaatttc tctagttttt agaccttctc atttgaagcc agttcgggaa    4980
aaggatcgaa gaacaacgcg taacgttgca atcgtagatg gatcacctaa ttttaaatct    5040
tctctttctg taaaaagat tactccaaat cagatatttt ctatacattt agatacggat    5100
atgcttgtat ctccatttcc aaatataaac gaagataatt cttttgggga agtttatcc    5160 gaaaaaaatc ttgcagttcg tgatcttttt cacaatcaaa atgaaatttc ttcggcactc    5220
ttttatgaac aaacaaaacc acatcttgga aaaattccg aactttacga ggtgttaaat    5280
gcatcaggaa ttcgtaatgt tgcaatttgt aatgcgagtg attcttgtgc caccgctttt    5340
cccgaaaaga tattttccgg agaaatttct ggaagtttat ttttgggttc cagtgtatta    5400
agaaaaaaag atgtgtttat atctttggaa aatctgagtt tgttggttcg ggaaaatgaa    5460
aggaaagaca atgtaagaga ggcgtataca cacgcttttt cgtatcgctc ttttttaaaa    5520
aaggaagata tgttttggc cgcggaattg gatgttcttc gtctaaagtg gaaactttcc    5580
ccccaagtta cgatggaaga aatctacggt gatcttttgc agaatacaaa gttggaaaca    5640
gtaaaagatt cgatttttatt ttccgcgctt ttgaactgtt atctagataa aaatctttct    5700
gattgtaatt cttattcttt cgaagatata accgattttc aaaaagaaa tttattaaaa    5760 aatttgtatc tattgaaaaa tggtatttct gtagaaccct tatccttaaa agtttcggat    5820
aaaaccgttt tttcttttta cgacccttat ttatattata agaatattct aaaaattgca    5880
agagctaatt acgagccgga actaggggag tttgccggta gactcgcgct tgaatttact    5940
catgatccag acgaaataat agctgtagaa gaaatccttc aaggattgta cgctcagaag    6000 tatttttttac aaggaagtgc acttctaaa aatcaaattc gtagaaaaga agaattatat    6060
ttgattcttt ccggaaactg gaaagaagcg cttagaattt taaagaaaa agaagccgaa    6120 gaagatactg gaaaatttag agaaagatta tttcgaaatt ggagaagaga attacggga    6180 gcttggtttt ctccttattc tctttattca gaggtctacg gaaattcttc taaattgttc    6240
gagtctttgg atgcggaaga aagaagtctt ttatatcatt tgatttttata ttctattccg    6300 tttcaagaaa acgaagagtt ggacttactc accgaatcct tggtgaaata cgagtggaat    6360
accggagcaa aatctagggc tctacgtatg gtgcttggtt attctcaagc cctgttttcg    6420
```

-continued

```
aggggagagt tatctaaaag taaggattgg atggataaaa tagattctcg ttataagacg    6480
gaatcaaaaa gtatattcag agataagaat attctaaata ataaattact ttttcatttg    6540
ggtaagattt cttccgttgc cgaaggagat gaaaaaacgg aatggctttt actctacgaa    6600
aaggcggctt ctaaacctcc gaatgaattt gtagaatttc taaattctac gatcagatcc    6660
aaacgtggaa atcgttttag ttctaaggaa aggacggagc tgttggattg gatcgtgtat    6720
ttacaaaaac tttgttttaa gaaaaataat tcagaagtat tctttgattt agttttggca    6780
aaagatctct tatctcttac tcgtcccgtg gtattaaatt caattcccga ttataaagac    6840
attcctactt ttgttgccgt tgctgacaaa cttaaagaaa aacttcccgc ggatcaagaa    6900
tttcttgcag tgacagattt ggggcttgaa accttttata tccgtttttt aaaaggaaaa    6960
tctaaaggag atcttgcgtt taagacaac cgtaaactca gggcttcttt gtttcaatat    7020
ttagaagagg cggcgaaagg tggttacgag gttttactta gggaagaact tgaaaacgaa    7080
tatagaagaa acgttaaact tgcaaaaaat aaacttaccr atctctattt gagttcgtat    7140
cattttagga ttcctttggt tccaagaacg gaggataaat tttatctggt aaatgatcct    7200
cagtctttag tttccaatcc aattgtttct acaaaggaag aatttagtcc tgaatatcga    7260
attcaatttt tagaaaattc taaacttcca gaaagttgga agaagtcttt aaaagaactt    7320
gaagttttg aggcgggttc cggtaaatta ggttccgatt ctaaaagtcg tctttatatt    7380
ctacaagatc ctttagaaat tgttgatcag gtgcatttaa gtttaggtgg aaaggcgctt    7440
gcagattctt atggctctcc gaaaaaagga aattggattt ttacttcttc ttttttagat    7500
gatgaatatt atgatattat aaattatagg gattcttttt attggatctc tcaaaatttt    7560
caaagtccgg gtgtaatatt tattggagaa cagactgata cggcccacgt ggatttttta    7620
aaacgtttta cgaaacggag cttgtccaag gtcccacttt atattcggtt ccaagaaacg    7680
ttagatgcaa ttaaagaagc atatccattg gatcgaattt ggaacggtta taggctttat    7740
acgaatagta ttatattaga agaa                                          7764
```

<210> SEQ ID NO 116
<211> LENGTH: 2588
<212> TYPE: PRT
<213> ORGANISM: Artificial Sequence
<220> FEATURE:
<223> OTHER INFORMATION: LIC11028

<400> SEQUENCE: 116

```
Met Val Arg Phe Gly Ile Cys Phe Phe Ser Phe Phe Phe Tyr His
1               5                   10                  15

Cys Ser Ile Phe Arg Ala Ala Ser Arg Ile Lys Pro Leu Glu Phe Asn
                20                  25                  30

Tyr Thr Ser Ile Ala Val Asn Tyr Phe Thr Pro Glu Asn Glu Lys Pro
            35                  40                  45

Phe Pro Leu Thr Val Gln Arg Gly Asn Asn Leu Tyr Asn Ser Thr Thr
        50                  55                  60

Ala Asp Gly Ser Tyr Leu Phe Tyr Thr Thr Gly Gln Lys Gly Asn Tyr
65                  70                  75                  80

Asp Ile Trp Phe Arg Asp Leu Lys Ser Ser Ile Thr Val Pro Val Thr
                85                  90                  95

Thr His Pro Ala Pro Glu Tyr Lys Pro Ala Ile Ser Pro Asp Gly Lys
            100                 105                 110

Lys Leu Val Phe Val Ser Glu Gln Tyr Asp Ser Ser Gly Asp Leu Ile
```

```
            115                 120                 125
Leu Leu Lys Met Asn Pro Gly Leu Trp Ala Asp Lys Ile Leu Gln Gly
    130                 135                 140

Lys Arg Phe Ile Asn Ser Asp Phe Ile Ile Leu Thr Asn Ser Asn Phe
145                 150                 155                 160

Ser Asp Thr Gly Lys Lys Asp Ser Tyr Val Asp Thr Asp Pro Phe Phe
                165                 170                 175

Ala Pro Asp Gly Arg His Leu Val Phe Ser Thr Asp Arg Leu Thr Pro
            180                 185                 190

Gly Ile Gln Asn Leu Val Val Leu Asp Thr Glu Gly Lys Glu Pro Met
        195                 200                 205

Lys Leu Leu Thr Gln Lys Gly Gly Ala Ser Pro Phe Trp Ser Lys Asp
210                 215                 220

Gly Lys Ser Ile Val Tyr Ile Ser Tyr Gln Asp Gly Val Phe Gly Asp
225                 230                 235                 240

Val Tyr Leu Leu Asp Leu Ser Ser Gly Lys Asn Glu Arg Leu Thr Lys
                245                 250                 255

Asp Ser Tyr Leu Asn Phe Ser Pro Ser Leu Ser Glu Asp Lys Arg Tyr
            260                 265                 270

Leu Tyr Tyr Thr Ser Ile Gln Asn Asp Thr Asn Arg Asn Gly Arg Leu
        275                 280                 285

Asp Glu Arg Asp Asn Ser Leu Ile Val Arg Lys Asp Leu Lys Thr Gly
    290                 295                 300

Val Val Arg Arg Leu Thr Ser Gly Asn Asp Ser Leu Phe Asp Ser Arg
305                 310                 315                 320

Phe Ser Ala Phe Asn Gly Gly Ser Ile Leu Phe Thr Ala Ala Tyr Tyr
                325                 330                 335

Asp Thr Leu Asn Ile Tyr Phe Ile Pro Ala Ser Gly Ser Val Ser Lys
            340                 345                 350

Glu Lys Asp Ile Ile Ser Gln Tyr Glu Leu Ala Leu Lys Tyr Lys Glu
        355                 360                 365

Lys Gln Ser Phe Glu Asp Phe Leu Leu Ala Ile Asp Ala Ile Glu Phe
    370                 375                 380

Tyr Phe Ser Gln Asp Pro Ile Tyr Pro Leu Ile Phe Ser Lys Ala Leu
385                 390                 395                 400

Leu Leu Lys Tyr Glu Glu Ala Lys Asn Ser Gly Arg Thr Ile Ile Ala
                405                 410                 415

Glu Asn Ala Lys Lys Glu Ile Leu Ser Ser Arg Leu Asn Pro Val Tyr
            420                 425                 430

Gly Leu Ala Tyr Gly Leu Phe Leu Ser Asn Glu Lys Lys Leu Thr Val
        435                 440                 445

Ser Ile Gln Glu Leu Arg Lys Tyr Tyr Glu Gln Ile Arg Val Ile Ser
    450                 455                 460

Asp Thr Gly Lys Asn Leu Leu Ala Ser Leu Leu Glu Glu Gly Asp
465                 470                 475                 480

Leu Ala Arg Lys Ser Gly Asp Ser Gln His Ser Leu Lys Val Tyr Asp
                485                 490                 495

Glu Ile Ile Ile His Tyr Pro Asp Tyr Arg Ile Arg Asp Val Tyr
            500                 505                 510

Arg Lys Ser Gly Asp Leu Gln Tyr Lys Asn Ala His Leu Asn His Tyr
        515                 520                 525

Lys Ile Pro Glu Pro Phe Phe Arg Val Ala Asn Asp Leu Ser Ala Gly
    530                 535                 540
```

```
Lys Glu Asp Leu Lys Leu Leu Tyr Glu Arg Ile Asp Gly Glu Val Val
545                 550                 555                 560

Val Gly Lys Ser Phe Ser Glu Lys Ile Asn Ala Ser Glu Ile Ser Ile
                565                 570                 575

Glu Ser Asn Ser Leu Glu Asn Lys Ser Pro Arg Leu Phe Gln Tyr Phe
            580                 585                 590

Leu Tyr Ile Lys Ser Leu Gly Leu Asn Gly Lys Gly Ser Phe Glu Glu
                595                 600                 605

Ser Asn Ser Leu Leu Asn Thr Phe Leu Ser Lys Val Ala Lys Ser Asp
            610                 615                 620

Pro Leu Phe Leu Lys Ile His Leu Leu Lys Ser Asn Asn Phe Lys Gly
625                 630                 635                 640

Leu Gly Glu Val Gln Lys Ser Phe Asp Glu Leu Arg Ile Tyr Leu Glu
                645                 650                 655

Glu Tyr Asp Pro Leu Leu Gly Val Asp Leu Glu Glu Lys Glu Ile Glu
            660                 665                 670

Arg Ser Phe Ile Tyr Phe Glu Asn Lys Ala Arg Asp His Asp Arg Arg
                675                 680                 685

Gly Asn Leu Gln Asp Ala Ala Phe His Tyr Phe Asn Thr Glu Asn
            690                 695                 700

Met Phe Leu Val Lys Ser Arg Asn Leu Phe Leu Glu Ser Leu Tyr Lys
705                 710                 715                 720

Glu Phe Ala Val Tyr Tyr Gln Arg Met Met Val Asp Ala Val Phe Lys
                725                 730                 735

Leu Ser Gly Ser Leu Ser Glu Glu Arg Lys Lys Ala Leu Leu Asn Gln
            740                 745                 750

Leu Asp Val Ile Asp Ile Ala Lys Val Asp Pro Leu Ala Glu Glu Gly
                755                 760                 765

Leu Val Tyr Ile Asn Gln Tyr Tyr Lys Glu Ala Val Pro Arg Ala Arg
            770                 775                 780

Pro Val Leu Asp Leu Ala Thr Leu Tyr Gly Tyr Ser Tyr Tyr Leu Ile
785                 790                 795                 800

Asn Arg Ser Val Ile Arg Glu Thr Tyr Tyr Asn Ser Thr Lys Ser Met
                805                 810                 815

Thr Ser Ser Lys Lys Glu Glu Ile Leu Arg Asp Phe Lys Gln Ala Glu
            820                 825                 830

Tyr Glu Leu Arg Trp Ile Ile Phe Ala Asp Pro Arg Tyr Tyr Glu Ala
                835                 840                 845

Tyr Gln Leu Leu Gly Trp Met Tyr Gln Tyr Val Asp Ile Leu Lys Asn
            850                 855                 860

Arg Lys Ser Gly Glu Asp Gln Pro Ser Asp Glu Lys Tyr Ile Ser
865                 870                 875                 880

Val Tyr Glu Lys Tyr Phe Pro Glu Lys Asn Phe Glu Asn Ile Glu
                885                 890                 895

Leu Tyr Ser Gln Val Leu Glu Leu Leu Gly Asp Asn Phe Glu Asn Lys
            900                 905                 910

Lys Ala Leu Ser Asp Leu Arg Leu Asn Leu Gly Asn Asn Tyr Phe Leu
                915                 920                 925

Leu Lys Asn Tyr Pro Lys Ala Asn Glu Gln Tyr Ser Lys Val Asp Ser
            930                 935                 940

Leu Ser Asp Tyr Ile Ile Ser Lys Thr Gln Phe Glu Asp Tyr Arg Gln
945                 950                 955                 960
```

```
Lys Ala Ile Phe Leu Phe Asn Ser Ala Arg Ser Ile Tyr Val Ala
            965                 970                 975
Asp Tyr Lys Ser Ala Ile Gln Lys Leu Lys Ala Ser Asp Ile Tyr
            980                 985                 990
Phe Arg Asn Glu Ser Lys Lys Thr Ile Val Gly Lys Asp Ser Ala Glu
            995                1000                1005
Lys Leu Glu Gln Tyr Lys Leu Lys Leu Ala Leu Leu Phe Thr Leu
           1010                1015                1020
Thr Gly Leu Ser Tyr Met Glu Ala Gly Glu Tyr Ser Asn Ala Ile
           1025                1030                1035
Pro Tyr Tyr Lys Asp Ala Leu Ser Leu Asn Gly Glu Asn Gly Trp
           1040                1045                1050
Ile Asp Pro Val Asn Leu His Asn Gly Leu Ala Leu Cys Tyr Gln
           1055                1060                1065
Lys Leu Gly Lys Tyr Lys Leu Ser Glu Leu His Leu Thr Lys Ala
           1070                1075                1080
Asp Lys Ile Val Asp Asp Arg Val Gly Thr Gly Trp Ile Pro Arg
           1085                1090                1095
Gly Val Lys Leu Ala Phe Trp Asp Tyr Phe Trp Asp Trp Val Trp
           1100                1105                1110
Glu Val Ala Leu Pro Asp Gly Val Arg Ile Ser Gly Glu Gly Arg
           1115                1120                1125
Phe Pro Glu Ala Ile Ser Pro Lys Phe Gln Pro Leu Met Thr Ser
           1130                1135                1140
Gly Ile Arg Val Asn Asn Leu Ile Ala Ser Met Glu Ile Asp Gly
           1145                1150                1155
Ala Ile Lys Glu Ile Asn Ser Arg Leu Ala Tyr Val Lys Ser Lys
           1160                1165                1170
Ser Leu Gly Thr Thr Leu Ala Gly Ser Leu Ile Gly Ala Asn Ser
           1175                1180                1185
Leu Asn Asp Leu Gly Tyr Leu His Phe Lys Arg Asp Glu Phe Lys
           1190                1195                1200
Asn Ala Ile Asp Val Tyr Glu Gln Ala Glu Lys Phe Glu Thr Glu
           1205                1210                1215
Lys Gly Phe Ala Ala Lys Ala Arg Thr Ser Phe Lys Arg Lys Leu
           1220                1225                1230
Tyr Ser Tyr Phe Gly His Leu Glu Asn Thr Asn Glu Asp Pro Glu
           1235                1240                1245
Leu Glu Leu Arg Thr Leu Gly Ser Ala Ala Glu Arg Ile Leu Ser
           1250                1255                1260
Ser Lys Ser Asp Phe Ile Lys Gly Cys Leu Gly Asp Val Gln Tyr
           1265                1270                1275
Gln Glu Glu Leu Ile Tyr Ser Glu Thr Lys Lys Cys Ile Leu Lys
           1280                1285                1290
Phe Tyr Asn Ser Phe Ser Asp His Asp Pro Thr Leu Ala Leu Ile
           1295                1300                1305
Tyr Tyr Tyr Gln Gly Glu Gln Phe Phe Arg Met Gly Asn Phe Val
           1310                1315                1320
Ala Ala Phe Glu Phe Phe Gly Lys Ser Ala Gly Leu Leu Glu Asn
           1325                1330                1335
Pro Ser Leu Val Pro Lys Glu Val Val Gly Leu Ala Asp Asp Pro
           1340                1345                1350
Tyr Ser Arg Lys Glu Arg Leu Ser Tyr Ser Ile Ser Arg Ala Asn
```

```
           1355                1360                1365

Leu Tyr Val Arg Leu Glu Asp Ser Gln Lys Ala Ile Ser Leu Leu
        1370                1375                1380

Glu Leu Ala Ser Glu Thr Ala Asn Glu Phe Tyr Tyr Ile Gln Glu
        1385                1390                1395

Trp Ile Glu Ala Leu Val Thr Gln Ala Glu Ile Phe Arg Lys Glu
        1400                1405                1410

Lys Asn Asp Phe Lys Ala Lys Glu Lys Ile Asp Lys Ala Ser Ala
        1415                1420                1425

Leu Leu Leu Ser His Pro His Leu Ile Ser Glu Leu Lys Tyr Phe
        1430                1435                1440

Arg Ile Tyr Lys Leu Phe Lys Ile Gln Ser Glu Leu Asn Phe Gln
        1445                1450                1455

Ser Gly Lys Phe Ser Asp Gly Phe Lys Ser Leu Asp Arg Leu His
        1460                1465                1470

Lys Leu Lys Leu Tyr Arg Gln Phe Ile Lys Ile Pro His Glu Ser
        1475                1480                1485

Glu Asp Pro Asn Phe Thr Glu Asp Ile Thr Lys Leu Gln Asn Leu
        1490                1495                1500

Ile Lys Lys Gln Lys Phe Tyr Tyr Ser Ala Ile Gln Asn Ala Leu
        1505                1510                1515

Glu Lys Lys Glu Lys Ser Glu Ser Leu Leu Lys Lys Tyr Val Gln
        1520                1525                1530

Leu Ser Lys Asp Leu Glu Lys Glu Leu Gly Val Ile Ser Arg Lys
        1535                1540                1545

Asn Gln Asp Leu Asp Gly Tyr Leu Gly Ile Phe Ile Glu Glu Pro
        1550                1555                1560

Ser Val Thr Ser Leu Leu Asp Val Asn Glu Gly Tyr Leu Arg Ile
        1565                1570                1575

Glu Ser Ala Glu Asp Lys Ile Arg Ile Tyr Arg Ala Thr Ser Tyr
        1580                1585                1590

Thr Glu Glu Tyr Leu Val Asn Thr Gly Lys Leu Glu Glu Val Leu
        1595                1600                1605

Asn Gln Ile Ser Asn Ser Gly Lys Ile Pro Phe Val Ser Lys Lys
        1610                1615                1620

Ile Trp Phe Val Gln Leu Gly Asp Arg Ile Asp Phe Glu Lys Ile
        1625                1630                1635

Arg Asn Phe Leu Pro Glu Lys Phe Ser Leu Val Phe Arg Pro Ser
        1640                1645                1650

His Leu Lys Pro Val Arg Glu Lys Asp Arg Arg Thr Thr Arg Asn
        1655                1660                1665

Val Ala Ile Val Asp Gly Ser Pro Asn Phe Lys Ser Ser Leu Ser
        1670                1675                1680

Val Lys Lys Ile Thr Pro Asn Gln Ile Phe Ser Ile His Leu Asp
        1685                1690                1695

Thr Asp Met Leu Val Ser Pro Phe Pro Asn Ile Asn Glu Asp Asn
        1700                1705                1710

Ser Phe Gly Glu Ser Leu Ser Glu Lys Asn Leu Ala Val Arg Asp
        1715                1720                1725

Leu Phe His Asn Gln Asn Glu Ile Ser Ser Ala Leu Phe Tyr Glu
        1730                1735                1740

Gln Thr Lys Pro His Leu Gly Lys Ile Ser Glu Leu Tyr Glu Val
        1745                1750                1755
```

```
Leu Asn Ala Ser Gly Ile Arg Asn Val Ala Ile Cys Asn Ala Ser
    1760            1765            1770

Asp Ser Cys Ala Thr Ala Phe Pro Glu Lys Ile Phe Ser Gly Glu
    1775            1780            1785

Ile Ser Gly Ser Leu Phe Leu Gly Ser Ser Val Leu Arg Lys Lys
    1790            1795            1800

Asp Val Phe Ile Ser Leu Glu Asn Leu Ser Leu Leu Val Arg Glu
    1805            1810            1815

Asn Glu Arg Lys Asp Asn Val Arg Glu Ala Tyr Thr His Ala Phe
    1820            1825            1830

Ser Tyr Arg Ser Phe Leu Lys Lys Glu Asp Met Phe Leu Ala Ala
    1835            1840            1845

Glu Leu Asp Val Leu Arg Leu Lys Trp Lys Leu Ser Pro Gln Val
    1850            1855            1860

Thr Met Glu Glu Ile Tyr Gly Asp Leu Leu Gln Asn Thr Lys Leu
    1865            1870            1875

Glu Thr Val Lys Asp Ser Ile Leu Phe Ser Ala Leu Leu Asn Cys
    1880            1885            1890

Tyr Leu Asp Lys Asn Leu Ser Asp Cys Asn Ser Tyr Ser Phe Glu
    1895            1900            1905

Asp Ile Thr Asp Phe Gln Lys Arg Asn Leu Leu Lys Asn Leu Tyr
    1910            1915            1920

Leu Leu Lys Asn Gly Ile Ser Val Glu Pro Leu Ser Leu Lys Val
    1925            1930            1935

Ser Asp Lys Thr Val Phe Ser Phe Tyr Asp Pro Tyr Leu Tyr Tyr
    1940            1945            1950

Lys Asn Ile Leu Lys Ile Ala Arg Ala Asn Tyr Glu Pro Glu Leu
    1955            1960            1965

Gly Glu Phe Ala Gly Arg Leu Ala Leu Glu Phe Thr His Asp Pro
    1970            1975            1980

Asp Glu Ile Ile Ala Val Glu Glu Ile Leu Gln Gly Leu Tyr Ala
    1985            1990            1995

Gln Lys Tyr Phe Leu Gln Gly Ser Ala Leu Ser Lys Asn Gln Ile
    2000            2005            2010

Arg Arg Lys Glu Glu Leu Tyr Leu Ile Leu Ser Gly Asn Trp Lys
    2015            2020            2025

Glu Ala Leu Arg Ile Leu Lys Glu Lys Glu Ala Glu Glu Asp Thr
    2030            2035            2040

Gly Lys Phe Arg Glu Arg Leu Phe Arg Asn Trp Arg Arg Glu Ile
    2045            2050            2055

Thr Gly Ala Trp Phe Ser Pro Tyr Ser Leu Tyr Ser Glu Val Tyr
    2060            2065            2070

Gly Asn Ser Ser Lys Leu Phe Glu Ser Leu Asp Ala Glu Glu Arg
    2075            2080            2085

Ser Leu Leu Tyr His Leu Ile Leu Tyr Ser Ile Pro Phe Gln Glu
    2090            2095            2100

Asn Glu Glu Leu Asp Leu Leu Thr Glu Ser Leu Val Glu Tyr Glu
    2105            2110            2115

Trp Asn Thr Gly Ala Lys Ser Arg Ala Leu Arg Met Val Leu Gly
    2120            2125            2130

Tyr Ser Gln Ala Leu Phe Ser Arg Gly Glu Leu Ser Lys Ser Lys
    2135            2140            2145
```

-continued

| | | | | | | | | | | | |
|---|---|---|---|---|---|---|---|---|---|---|---|
|Asp|Trp|Met|Asp|Lys|Ile|Asp|Ser|Arg|Tyr|Lys|Thr|Glu|Ser|Lys|
|2150| | | | |2155| | | | |2160| | | | |

Ser Ile Phe Arg Asp Lys Asn Ile Leu Asn Asn Lys Leu Leu Phe
2165                     2170                    2175

His Leu Gly Lys Ile Ser Ser Val Ala Glu Gly Asp Glu Lys Thr
2180                     2185                    2190

Glu Trp Leu Leu Leu Tyr Glu Lys Ala Ala Ser Lys Pro Pro Asn
2195                     2200                    2205

Glu Phe Val Glu Phe Leu Asn Ser Thr Ile Arg Ser Lys Arg Gly
2210                     2215                    2220

Asn Arg Phe Ser Ser Lys Glu Arg Thr Glu Leu Leu Asp Trp Ile
2225                     2230                    2235

Val Tyr Leu Gln Lys Leu Cys Phe Lys Lys Asn Asn Ser Glu Val
2240                     2245                    2250

Phe Phe Asp Leu Val Leu Ala Lys Asp Leu Leu Ser Leu Thr Arg
2255                     2260                    2265

Pro Val Val Leu Asn Ser Ile Pro Asp Tyr Lys Asp Ile Pro Thr
2270                     2275                    2280

Phe Val Ala Val Ala Asp Lys Leu Lys Glu Lys Leu Pro Ala Asp
2285                     2290                    2295

Gln Glu Phe Leu Ala Val Thr Asp Leu Gly Leu Glu Thr Phe Tyr
2300                     2305                    2310

Ile Arg Phe Leu Lys Gly Lys Ser Lys Gly Asp Leu Ala Phe Lys
2315                     2320                    2325

Asp Asn Arg Lys Leu Arg Ala Ser Leu Phe Gln Tyr Leu Glu Glu
2330                     2335                    2340

Ala Ala Lys Gly Gly Tyr Glu Val Leu Leu Arg Glu Glu Leu Glu
2345                     2350                    2355

Asn Glu Tyr Arg Arg Asn Val Lys Leu Ala Lys Asn Lys Leu Thr
2360                     2365                    2370

Tyr Leu Tyr Leu Ser Ser Tyr His Phe Arg Ile Pro Leu Val Pro
2375                     2380                    2385

Arg Thr Glu Asp Lys Phe Tyr Leu Val Asn Asp Pro Gln Ser Leu
2390                     2395                    2400

Val Ser Asn Pro Ile Val Ser Thr Lys Glu Glu Phe Ser Pro Glu
2405                     2410                    2415

Tyr Arg Ile Gln Phe Leu Glu Asn Ser Lys Leu Pro Glu Ser Trp
2420                     2425                    2430

Lys Lys Ser Leu Lys Glu Leu Glu Val Phe Glu Ala Gly Ser Gly
2435                     2440                    2445

Lys Leu Gly Ser Asp Ser Lys Ser Arg Leu Tyr Ile Leu Gln Asp
2450                     2455                    2460

Pro Leu Glu Ile Val Asp Gln Val His Leu Ser Leu Gly Gly Lys
2465                     2470                    2475

Ala Leu Ala Asp Ser Tyr Gly Ser Pro Lys Lys Gly Asn Trp Ile
2480                     2485                    2490

Phe Thr Ser Ser Phe Leu Asp Asp Glu Tyr Tyr Asp Ile Ile Asn
2495                     2500                    2505

Tyr Arg Asp Ser Phe Tyr Trp Ile Ser Gln Asn Phe Gln Ser Pro
2510                     2515                    2520

Gly Val Ile Phe Ile Gly Glu Gln Thr Asp Thr Ala His Val Asp
2525                     2530                    2535

Phe Leu Lys Arg Phe Thr Lys Arg Ser Leu Ser Lys Val Pro Leu

Tyr Ile Arg Phe Gln Glu Thr Leu Asp Ala Ile Lys Glu Ala Tyr
            2555                2560                2565

Pro Leu Asp Arg Ile Trp Asn Gly Tyr Arg Leu Tyr Thr Asn Ser
    2570                2575                2580

Ile Ile Leu Glu Glu
    2585

<210> SEQ ID NO 117
<211> LENGTH: 666
<212> TYPE: DNA
<213> ORGANISM: Artificial Sequence
<220> FEATURE:
<223> OTHER INFORMATION: LIC11874

<400> SEQUENCE: 117
atgagccatt tttcaggcca aatttttaag ttttttcgttt ttgtcctaat tttattactt      60
tccaattgtt tcgactatga ggaaacactt acaatcaatc atgattttc tgggacatta      120 gaaattgctt atgtggttcc tactcgtaga aattcagatg aatctctcat caaattcctt     180
cccactcaaa aagatgaaat tttaggaaga ttgaataagg ttttttctc tagaaatatt     240 tcgttaaaag actatacata tcaaaaaatc gtaattccag aaacggaccc gagtttattt     300
cgcgaaaaag cgaaggtcta ttataaggtg aatttcaag atctttccca aattgaagat     360
gcgatgcttg gaaaggttca ggttcgtaaa aaggaaata ctctttatgt taaaagagaa     420
attcctatga ttagtcgttc acctgaaacc ctcaagaaag atggggaaaa aaagatttat     480
tcggaaactc ttcgtttatt acgtacaagt tctattttat ttaaggtaaa ttttccgatc     540
gcttctattt gtagatctaa tcgaggagac gtaaatttgg gaaaactcag ttatcgttta     600
cctcttgcgg aaacgattga gaggacggga ataattctt gggattatag gatcactgta     660
atttat                                                                666

<210> SEQ ID NO 118
<211> LENGTH: 222
<212> TYPE: PRT
<213> ORGANISM: Artificial Sequence
<220> FEATURE:
<223> OTHER INFORMATION: LIC11874

<400> SEQUENCE: 118

Met Ser His Phe Ser Gly Gln Ile Phe Lys Phe Phe Val Phe Val Leu
1               5                   10                  15

Ile Leu Leu Ser Asn Cys Phe Asp Tyr Glu Glu Thr Leu Thr Ile
            20                  25                  30

Asn His Asp Phe Ser Gly Thr Leu Glu Ile Ala Tyr Val Val Pro Thr
            35                  40                  45

Arg Arg Asn Ser Asp Glu Ser Leu Ile Lys Phe Leu Pro Thr Gln Lys
    50                  55                  60

Asp Glu Ile Leu Gly Arg Leu Asn Lys Gly Phe Ser Arg Asn Ile
65                  70                  75                  80

Ser Leu Lys Asp Tyr Thr Tyr Gln Lys Ile Val Ile Pro Glu Thr Asp
                85                  90                  95

Pro Ser Leu Phe Arg Glu Lys Ala Lys Val Tyr Tyr Lys Val Glu Phe
            100                 105                 110

Gln Asp Leu Ser Gln Ile Glu Asp Ala Met Leu Gly Lys Val Gln Val
        115                 120                 125

```
Arg Lys Lys Gly Asn Thr Leu Tyr Val Lys Arg Glu Ile Pro Met Ile
            130                 135                 140

Ser Arg Ser Pro Glu Thr Leu Lys Lys Asp Gly Glu Lys Lys Ile Tyr
145                 150                 155                 160

Ser Glu Thr Leu Arg Leu Leu Arg Thr Ser Ser Ile Leu Phe Lys Val
                165                 170                 175

Asn Phe Pro Ile Ala Ser Ile Cys Arg Ser Asn Arg Gly Asp Val Asn
            180                 185                 190

Leu Gly Lys Leu Ser Tyr Arg Leu Pro Leu Ala Glu Thr Ile Glu Arg
            195                 200                 205

Thr Gly Asn Asn Ser Trp Asp Tyr Arg Ile Thr Val Ile Tyr
210                 215                 220
```

<210> SEQ ID NO 119
<211> LENGTH: 3111
<212> TYPE: DNA
<213> ORGANISM: Artificial Sequence
<220> FEATURE:
<223> OTHER INFORMATION: LIC13090

<400> SEQUENCE: 119

| | | | | |
|---|---|---|---|---|
| atgaaatcac | tcatagaatc | ttttattcaa | aatcgacttt | ttatgtattt | agggatggtc | 60 |
| tttatctttt | tatccggagt | tgtttcactg | atcggattac | gaagagatgc | atttcctaat | 120 |
| gtggacttaa | agcaaatggt | gatctctaca | aaatttcctg | gggcttctcc | cgccgatgta | 180 |
| gaacttagag | tcacttatcc | tatagaagaa | aagctcaaag | aaatagatgg | aatcgatgag | 240 |
| attcgttctt | tttctagaaa | ttccgtttcg | gacattgacg | ttcgtgttag | tctggaagaa | 300 |
| aaagatccgg | aaaaagtttt | aaatgaaatt | cgaagagccg | tagacaatgc | gatgggagag | 360 |
| ctaccggctc | aagttaccga | aaagcctaaa | atgacggagc | gcaagtcagg | gtcttttccg | 420 |
| attcttgaat | ttctattttt | tggaggaaag | gacgaaatcg | aactacatac | caccgccgaa | 480 |
| tttgtagaac | gagaacttga | aaaaattcaa | ggtgtggcta | gggtagacgt | ttttggtaaa | 540 |
| agagatagag | aatggcatat | tttagtaaat | gctaataaac | taaagcaata | ttctttagac | 600 |
| ttaaacgata | ttatcaatac | gattcggaac | agaaacatta | atcttcctgc | cggttccgtg | 660 |
| gattcggaaa | ctgcgttcga | tttgagaatt | gatggagaat | ttaaaaaccc | ttccgaaatt | 720 |
| gggaaaatcc | ctacaaggac | taacgaaatt | ttttccacgg | ttaaactaga | agatattgca | 780 |
| agggtggaag | atacttttga | atatcctaga | tttcttgcga | ttgcaaatgg | gaaacaggga | 840 |
| ctaattcttt | ctgtgatcaa | aaaagaaaga | tcggatgcga | ttgaggttgc | agataacgtt | 900 |
| cacaaaagac | taaacgaact | tccaaaaact | tatccttctg | gaatgaaaac | ttttgtgtta | 960 |
| aacgacgagg | ccaaaaggac | taaaaacaga | ctcaacgtag | tttcttctaa | cgctttgatc | 1020 |
| ggatttacga | tcgtattcgg | gatttttattt | ctattttttgg | attttagaac | ggctacattg | 1080 |
| acttctcttt | cattaccgtt | ctcgatgttg | atgacttttt | cggttcttcc | atttttcgac | 1140 |
| gtatcgttta | acatgatttc | tatgatgggt | ttgatcatct | ctcttggaat | gttggtggat | 1200 |
| aactcgattg | taatttcgga | aaatatatat | acatatcttg | ctgaaaaaaa | tgattctgtc | 1260 |
| gctgcgtcgt | tacgcggaac | cgtggaaatg | atcgttccta | ttttttggatc | ttatcttaca | 1320 |
| actgtaaccg | cgttcttgcc | catgttgttt | atgactggaa | ttatgggaaa | attcatttgg | 1380 |
| gaaattcctt | tagtagtgat | tgtggcgctt | acagcgagtc | ttatagaatc | gttttattt | 1440 |
| ttgccggcga | ggattgctgc | gtttgcaaaa | actccaaacc | agatgaagat | caaaagtaaa | 1500 |
| tttcgtctca | agatggattc | gatttttcac | tctatcgaaa | caaatttttc | taaattagtt | 1560 |

```
tcttttaata ttcgacataa gaaatcttcg tttgcggtca ttttattgtt ggtctttggt    1620
tcttgtggag ccttgtctca gatggacttt gtacttttc caaaagaaga tatagaaatc    1680
atcatgatca aagccgaatt tccacctact tccagaattt ttcaaaccag agaaaaaatg    1740
aaatatatgg aaagtattgt gcagaaaatt cctaaagaag aattggtcag ctattccaca    1800
aagatagggg tgcaacaaac cgatccagat gatcctttat ctcgttttgg tgaaaacttg    1860
ggagtgattt taatttatct gactcctgaa gtaaaacgcg aaagaaaggc gactgaaatt    1920
cttcgttcga tcgaaccgga tcttaaaaaa actccaggtt taaacgaaat cttttagaa     1980 gaatttggaa atgctcctcc aattggtgct ccgattacta tttctattca aggcaaagat    2040
tatgaaactc taagaacat ttcgaatgag ttacaatcgt ttttaaagtc gattcccgga    2100
gttttttctg ttcgagatga ctatcgatat ggtcgtaagc agatgtatat tcaactcgac    2160
gagggattgg aaagttttac tggggtatcc actttgtccg cagcgaacgg tctgcgtgct    2220
gcgtatgatg agaaagggc gggaaccgtt cgaaaaggaa gaacaaaaat atacttaaga    2280
gttctttacg atagagactt tcggaaaaat cctaatgaaa ttaagacgat tccattacgt    2340
aataaggcgg gaaacattac aaatcttgca aagatttcta aaatggattt gatcgaatct    2400
cctgaacttc tcgcgcataa agactttgaa cgcgccatta ccgttaacgg agatgtaaag    2460
ttagacgaaa ttacggctca cgacgcaaac caaagagtag ccacggagtt taaaccgcta    2520
atcgaaaaac aatatcccgg aattatgatt acgtttggag gagaagaaaa ggatacacaa    2580
agatctatgg cctctcttgc aaaagcgggg atcattgcta tatttggcat ttttggaatt    2640
ttggctctta caatcaaaag ttttggaag cctgtcttga tactcagcac tattcctttg    2700
ggaattatag gtattgtgat tggttttcct ctttctggaa agtctattag cttttttagca    2760 atgatcggta ttattggttt agctggggtt ttggtaaacg cttcgattgt tttagtggat    2820
tgtatcgatt ctatccgaaa agattccaag gcaagtatgg acgatatttt aatcgaagca    2880
agtcaaagaa gatttaggcc gattcttta acgactctga ctacggtagc gggtttgtta    2940
cctaccgctt atagtcttgg tggttccgat ccggttctta ttcctatgac acttgctttg    3000
ggttggggtt tgggttttgg aacattagga agtctttat atgttccggt caccttatca    3060
gtgtttaatg atcttactac tcgattcaaa gaaaaaaggt caaaaaagaa g             3111
```

<210> SEQ ID NO 120
<211> LENGTH: 1037
<212> TYPE: PRT
<213> ORGANISM: Artificial Sequence
<220> FEATURE:
<223> OTHER INFORMATION: LIC13090

<400> SEQUENCE: 120

```
Met Lys Ser Leu Ile Glu Ser Phe Ile Gln Asn Arg Leu Phe Met Tyr
1               5                   10                  15

Leu Gly Met Val Phe Ile Phe Leu Ser Gly Val Ser Leu Ile Gly
            20                  25                  30

Leu Arg Arg Asp Ala Phe Pro Asn Val Asp Leu Lys Gln Met Val Ile
        35                  40                  45

Ser Thr Lys Phe Pro Gly Ala Ser Pro Ala Asp Val Glu Leu Arg Val
    50                  55                  60

Thr Tyr Pro Ile Glu Glu Lys Leu Lys Glu Ile Asp Gly Ile Asp Glu
65                  70                  75                  80

Ile Arg Ser Phe Ser Arg Asn Ser Val Ser Asp Ile Asp Val Arg Val
```

```
            85                  90                  95
Ser Leu Glu Glu Lys Asp Pro Glu Lys Val Leu Asn Glu Ile Arg Arg
            100                 105                 110

Ala Val Asp Asn Ala Met Gly Glu Leu Pro Ala Gln Val Thr Glu Lys
            115                 120                 125

Pro Lys Met Thr Glu Arg Lys Ser Gly Ser Phe Pro Ile Leu Glu Phe
130                 135                 140

Ser Ile Phe Gly Gly Lys Asp Glu Ile Glu Leu His Thr Thr Ala Glu
145                 150                 155                 160

Phe Val Glu Arg Glu Leu Glu Lys Ile Gln Gly Val Ala Arg Val Asp
                165                 170                 175

Val Phe Gly Lys Arg Asp Arg Glu Trp His Ile Leu Val Asn Ala Asn
                180                 185                 190

Lys Leu Lys Gln Tyr Ser Leu Asp Leu Asn Asp Ile Ile Asn Thr Ile
                195                 200                 205

Arg Asn Arg Asn Ile Asn Leu Pro Ala Gly Ser Val Asp Ser Glu Thr
            210                 215                 220

Ala Phe Asp Leu Arg Ile Asp Gly Glu Phe Lys Asn Pro Ser Glu Ile
225                 230                 235                 240

Gly Lys Ile Pro Thr Arg Thr Asn Glu Ile Phe Ser Thr Val Lys Leu
                245                 250                 255

Glu Asp Ile Ala Arg Val Glu Asp Thr Phe Glu Tyr Pro Arg Phe Leu
                260                 265                 270

Ala Ile Ala Asn Gly Lys Gln Gly Leu Ile Leu Ser Val Ile Lys Lys
                275                 280                 285

Glu Arg Ser Asp Ala Ile Glu Val Ala Asp Asn Val His Lys Arg Leu
            290                 295                 300

Asn Glu Leu Ser Lys Thr Tyr Pro Ser Gly Met Lys Thr Phe Val Leu
305                 310                 315                 320

Asn Asp Glu Ala Lys Arg Thr Lys Asn Arg Leu Asn Val Val Ser Ser
                325                 330                 335

Asn Ala Leu Ile Gly Phe Thr Ile Val Phe Gly Ile Leu Phe Leu Phe
                340                 345                 350

Leu Asp Phe Arg Thr Ala Thr Leu Thr Ser Leu Ser Leu Pro Phe Ser
                355                 360                 365

Met Leu Met Thr Phe Ser Val Leu Pro Phe Phe Asp Val Ser Phe Asn
            370                 375                 380

Met Ile Ser Met Met Gly Leu Ile Ile Ser Leu Gly Met Leu Val Asp
385                 390                 395                 400

Asn Ser Ile Val Ile Ser Glu Asn Ile Tyr Thr Tyr Leu Ala Glu Lys
                405                 410                 415

Asn Asp Ser Val Ala Ala Ser Leu Arg Gly Thr Val Glu Met Ile Val
                420                 425                 430

Pro Ile Phe Gly Ser Tyr Leu Thr Thr Val Thr Ala Phe Leu Pro Met
                435                 440                 445

Leu Phe Met Thr Gly Ile Met Gly Lys Phe Ile Trp Glu Ile Pro Leu
            450                 455                 460

Val Val Ile Val Ala Leu Thr Ala Ser Leu Ile Glu Ser Phe Leu Phe
465                 470                 475                 480

Leu Pro Ala Arg Ile Ala Ala Phe Ala Lys Thr Pro Asn Gln Met Lys
                485                 490                 495

Ile Lys Ser Lys Phe Arg Leu Lys Met Asp Ser Ile Phe His Ser Ile
                500                 505                 510
```

```
Glu Thr Asn Phe Ser Lys Leu Val Ser Phe Asn Ile Arg His Lys Lys
        515                 520                 525
Ser Ser Phe Ala Val Ile Leu Leu Val Phe Gly Ser Cys Gly Ala
530                 535                 540
Leu Ser Gln Met Asp Phe Val Leu Phe Pro Lys Glu Asp Ile Glu Ile
545                 550                 555                 560
Ile Met Ile Lys Ala Glu Phe Pro Pro Thr Ser Arg Ile Phe Gln Thr
                565                 570                 575
Arg Glu Lys Met Lys Tyr Met Glu Ser Ile Val Gln Lys Ile Pro Lys
                580                 585                 590
Glu Glu Leu Val Ser Tyr Ser Thr Lys Ile Gly Val Gln Gln Thr Asp
            595                 600                 605
Pro Asp Asp Pro Leu Ser Arg Phe Gly Glu Asn Leu Gly Val Ile Leu
        610                 615                 620
Ile Tyr Leu Thr Pro Glu Val Lys Arg Glu Lys Ala Thr Glu Ile
625                 630                 635                 640
Leu Arg Ser Ile Glu Pro Asp Leu Lys Lys Thr Pro Gly Leu Asn Glu
                645                 650                 655
Ile Phe Leu Glu Glu Phe Gly Asn Ala Pro Pro Ile Gly Ala Pro Ile
            660                 665                 670
Thr Ile Ser Ile Gln Gly Lys Asp Tyr Glu Thr Leu Lys Asn Ile Ser
        675                 680                 685
Asn Glu Leu Gln Ser Phe Leu Lys Ser Ile Pro Gly Val Phe Ser Val
        690                 695                 700
Arg Asp Asp Tyr Arg Tyr Gly Arg Lys Gln Met Tyr Ile Gln Leu Asp
705                 710                 715                 720
Glu Gly Leu Glu Ser Phe Thr Gly Val Ser Thr Leu Ser Ala Ala Asn
                725                 730                 735
Gly Leu Arg Ala Ala Tyr Asp Gly Glu Arg Ala Gly Thr Val Arg Lys
            740                 745                 750
Gly Arg Thr Lys Ile Tyr Leu Arg Val Leu Tyr Asp Arg Asp Phe Arg
        755                 760                 765
Lys Asn Pro Asn Glu Ile Lys Thr Ile Pro Leu Arg Asn Lys Ala Gly
        770                 775                 780
Asn Ile Thr Asn Leu Ala Lys Ile Ser Lys Met Asp Leu Ile Glu Ser
785                 790                 795                 800
Pro Glu Leu Leu Ala His Lys Asp Phe Glu Arg Ala Ile Thr Val Asn
                805                 810                 815
Gly Asp Val Lys Leu Asp Glu Ile Thr Ala His Asp Ala Asn Gln Arg
            820                 825                 830
Val Ala Thr Glu Phe Lys Pro Leu Ile Glu Lys Gln Tyr Pro Gly Ile
        835                 840                 845
Met Ile Thr Phe Gly Gly Glu Glu Lys Asp Thr Gln Arg Ser Met Ala
850                 855                 860
Ser Leu Ala Lys Ala Gly Ile Ile Ala Ile Phe Gly Ile Phe Gly Ile
865                 870                 875                 880
Leu Ala Leu Thr Ile Lys Ser Phe Trp Lys Pro Val Leu Ile Leu Ser
                885                 890                 895
Thr Ile Pro Leu Gly Ile Ile Gly Ile Val Ile Gly Phe Pro Leu Ser
            900                 905                 910
Gly Lys Ser Ile Ser Phe Leu Ala Met Ile Gly Ile Ile Gly Leu Ala
        915                 920                 925
```

Gly Val Leu Val Asn Ala Ser Ile Val Leu Val Asp Cys Ile Asp Ser
            930                 935                 940

Ile Arg Lys Asp Ser Lys Ala Ser Met Asp Asp Ile Leu Ile Glu Ala
945                 950                 955                 960

Ser Gln Arg Arg Phe Arg Pro Ile Leu Leu Thr Thr Leu Thr Thr Val
                965                 970                 975

Ala Gly Leu Leu Pro Thr Ala Tyr Ser Leu Gly Gly Ser Asp Pro Val
            980                 985                 990

Leu Ile Pro Met Thr Leu Ala Leu Gly Trp Gly Leu Gly Phe Gly Thr
                995                1000                1005

Leu Gly Ser Leu Leu Tyr Val Pro Val Thr Leu Ser Val Phe Asn
           1010                1015                1020

Asp Leu Thr Thr Arg Phe Lys Glu Lys Arg Ser Lys Lys Lys
           1025                1030                1035

<210> SEQ ID NO 121
<211> LENGTH: 1920
<212> TYPE: DNA
<213> ORGANISM: Artificial Sequence
<220> FEATURE:
<223> OTHER INFORMATION: LIC10318

<400> SEQUENCE: 121
atgatttcaa atacttaaa aaaatatagt gattttcaca aattaagtag tgttgcatac     60
aacgttttga tgtttgtaga ccatgtattc gttgttagct gctctgtttt acatcaaaat    120
tctggtttta gtaataactc ttatgtccta aaactttgga ataaaatcaa aattgtcttt    180
ttgttaacaa ttttattttt ttacccttt tcacttttta cagagaccaa aacttttccg     240
ctagatgatt tacaaaaaaa cggattggaa ctttccggaa ataattctga aaataaagtt    300
ctaaaactgc aaactaaaaa tcgaagtttc ggttccgaac tttatctaga ttttgaatct    360
ggaaatccgt ctgatctaaa ggatgcatca ggaaattata aaattctcat gtcctcttat    420
ttacctgatt cagaaaacgt ttttcattct aaaagaagcg cacgttttc gggtaaaagg    480 actgggatca agattgcaca ttcttattca ggtctcttga cctccaaaga tctgacaaaa    540
gaattttaca tttctttag ttttcttcct ggaacggttg aaaaggatgc gactctaatt    600
tctaaactct atgaaacatc cggaaatagt tacggttggg atttaaagat cgcggacgat    660
cgactcaaag caggtttta ttctttttt gaaacggagg aaaagcggtt tctttctta    720 tatctgactt ctaacacgac tctgaaaaaa atcaatgga atcgggttct tctttatttc    780
aaccctaacg atcgagaaat tgtactttat ctcaatggaa agaatcggc aagagctgct    840 gttcctgcca gccaaaattt gactcgaatc ggttttcatg ctgatgatac tacttcgttt    900
cgaatcgcga gctcttatta tggctggatg gaaaattttt ctgttttcc aggaaaacca    960 aatcctagtt ccgaagacac ttcttttcca ggccaaaatt ttgattcgga aactcatact   1020
tccgaatcca gttcggaat aggaatttct cctgtctata aagcaagta ttccagttct    1080 ttttttggaag aagttcaatt gaaggccgta gttccgactt cttccgcttt ggaactttat   1140
ctgagagtgt ctccagttcc gtttactcca aattctgaat cccccgcctg gattggtgtt    1200
gacttaagaa aattagaaaa ttctaaaata gattctcttg aaccagatac ctataggatc    1260
cctttgaaat attctctaaa aaaattttg ggaattacgg aagataaaac ggatcttctt    1320
ccatttcgat attatcagtg gagagttaaa tttaaatccg atcccagcgg aaataaaact    1380
ccggaattaa aaaatatatc tctgaccttt agagaaacaa atcctcctgt acgtcctctc    1440

```
ggtctaaaag ttgctgaaaa tggtgttgac gatagcggcc cgagtatatg tctaaattgg    1500
aaatccaatc cagaaaaaga tgttattaac ggaggtggat atttcattca ttatggaatt    1560
catccggatc gaatggttgg gattgttcga ggaactttgg gtgaatcggg tgaaacgcct    1620
aataaaaaaa accgtcctaa acatccggct tcggattatc tagatccgat ttccggactt    1680
cctcccggaa aaaattacat tcatattcaa gaatattata ataaactttc tacttgtata    1740
gataatagaa tcatttcttt gaattcggaa atccttttgg aaaaaaatca gctgttttta    1800
aaaaaaggaa ccacttattt ttttaggatt agcgcttata ataaattcta tcatttccaa    1860
aatgggaaag atcaggtttc cacattaagt gatcccgttg aagtttattt tttgagcgag    1920
```

<210> SEQ ID NO 122
<211> LENGTH: 640
<212> TYPE: PRT
<213> ORGANISM: Artificial Sequence
<220> FEATURE:
<223> OTHER INFORMATION: LIC10318

<400> SEQUENCE: 122

```
Met Ile Ser Lys Tyr Leu Lys Lys Tyr Ser Asp Phe His Lys Leu Ser
1               5                   10                  15

Ser Val Ala Tyr Asn Val Leu Met Phe Val Asp His Val Phe Val Val
                20                  25                  30

Ser Cys Ser Val Leu His Gln Asn Ser Gly Phe Ser Asn Asn Ser Tyr
            35                  40                  45

Val Leu Lys Leu Trp Asn Lys Ile Lys Ile Val Phe Leu Leu Thr Ile
        50                  55                  60

Leu Phe Phe Tyr Pro Phe Ser Leu Phe Thr Glu Thr Lys Thr Phe Pro
65                  70                  75                  80

Leu Asp Asp Leu Gln Lys Asn Gly Leu Glu Leu Ser Gly Asn Asn Ser
                85                  90                  95

Glu Asn Lys Val Leu Lys Leu Gln Thr Lys Asn Arg Ser Phe Gly Ser
            100                 105                 110

Glu Leu Tyr Leu Asp Phe Glu Ser Gly Asn Pro Ser Asp Leu Lys Asp
        115                 120                 125

Ala Ser Gly Asn Tyr Lys Ile Leu Met Ser Ser Tyr Leu Pro Asp Ser
    130                 135                 140

Glu Asn Val Phe His Ser Lys Arg Ser Ala Arg Phe Ser Gly Lys Arg
145                 150                 155                 160

Thr Gly Ile Lys Ile Ala His Ser Tyr Ser Gly Leu Leu Thr Ser Lys
                165                 170                 175

Asp Leu Thr Lys Glu Phe Tyr Ile Ser Phe Ser Phe Leu Pro Gly Thr
            180                 185                 190

Val Glu Lys Asp Ala Thr Leu Ile Ser Lys Leu Tyr Glu Thr Ser Gly
        195                 200                 205

Asn Ser Tyr Gly Trp Asp Leu Lys Ile Ala Asp Asp Arg Leu Lys Ala
    210                 215                 220

Gly Phe Tyr Ser Phe Phe Glu Thr Glu Glu Lys Arg Phe Leu Ser Leu
225                 230                 235                 240

Tyr Leu Thr Ser Asn Thr Thr Leu Lys Lys Asn Gln Trp Asn Arg Val
                245                 250                 255

Leu Leu Tyr Phe Asn Pro Asn Asp Arg Glu Ile Val Leu Tyr Leu Asn
            260                 265                 270

Gly Lys Glu Ser Ala Arg Ala Ala Val Pro Ala Ser Gln Asn Leu Thr
        275                 280                 285
```

Arg Ile Gly Phe His Ala Asp Asp Thr Thr Ser Phe Arg Ile Ala Ser
            290                 295                 300

Ser Tyr Tyr Gly Trp Met Glu Asn Phe Ser Val Phe Pro Gly Lys Pro
305                 310                 315                 320

Asn Pro Ser Ser Glu Asp Thr Ser Phe Pro Gly Gln Asn Phe Asp Ser
                325                 330                 335

Glu Thr His Thr Ser Glu Ser Lys Phe Gly Ile Gly Ile Ser Pro Val
            340                 345                 350

Tyr Lys Ser Lys Tyr Ser Ser Phe Leu Glu Val Gln Leu Lys
        355                 360                 365

Ala Val Val Pro Thr Ser Ser Ala Leu Glu Leu Tyr Leu Arg Val Ser
370                 375                 380

Pro Val Pro Phe Thr Pro Asn Ser Glu Ser Pro Ala Trp Ile Gly Val
385                 390                 395                 400

Asp Leu Arg Lys Leu Glu Asn Ser Lys Ile Asp Ser Leu Glu Pro Asp
                405                 410                 415

Thr Tyr Arg Ile Pro Leu Lys Tyr Ser Leu Lys Lys Phe Leu Gly Ile
            420                 425                 430

Thr Glu Asp Lys Thr Asp Leu Leu Pro Phe Arg Tyr Tyr Gln Trp Arg
        435                 440                 445

Val Lys Phe Lys Ser Asp Pro Ser Gly Asn Lys Thr Pro Glu Leu Lys
450                 455                 460

Asn Ile Ser Leu Thr Phe Arg Glu Thr Asn Pro Pro Val Arg Pro Leu
465                 470                 475                 480

Gly Leu Lys Val Ala Glu Asn Gly Val Asp Asp Ser Gly Pro Ser Ile
                485                 490                 495

Cys Leu Asn Trp Lys Ser Asn Pro Glu Lys Asp Val Ile Asn Gly Gly
            500                 505                 510

Gly Tyr Phe Ile His Tyr Gly Ile His Pro Asp Arg Met Val Gly Ile
        515                 520                 525

Val Arg Gly Thr Leu Gly Glu Ser Gly Glu Thr Pro Asn Lys Lys Asn
530                 535                 540

Arg Pro Lys His Pro Ala Ser Asp Tyr Leu Asp Pro Ile Ser Gly Leu
545                 550                 555                 560

Pro Pro Gly Lys Asn Tyr Ile His Ile Gln Glu Tyr Tyr Asn Lys Leu
                565                 570                 575

Ser Thr Cys Ile Asp Asn Arg Ile Ile Ser Leu Asn Ser Glu Ile Leu
            580                 585                 590

Leu Glu Lys Asn Gln Leu Phe Leu Lys Lys Gly Thr Thr Tyr Phe Phe
        595                 600                 605

Arg Ile Ser Ala Tyr Asn Lys Phe Tyr His Phe Gln Asn Gly Lys Asp
610                 615                 620

Gln Val Ser Thr Leu Ser Asp Pro Val Glu Val Tyr Phe Leu Ser Glu
625                 630                 635                 640

<210> SEQ ID NO 123
<211> LENGTH: 387
<212> TYPE: DNA
<213> ORGANISM: Artificial Sequence
<220> FEATURE:
<223> OTHER INFORMATION: LIC10655

<400> SEQUENCE: 123 tttttttataa atactaaaat cataaaatct caaagtgaca cttctatttc tactttctgg    60

```
aaggaattta aagatgcagt tcttaaaaat gattcagaaa aattggcgag tttgtctcga    120
tttccaatta aaatgccgta tggatatact caaattaaga ataagaaaga gttcttaaaa    180
cgttatgatg aaatttttc tcggcaagct gatgcaaaag aatgttttca aaagaaaaa    240 caaccggttg cagattcgga aagaaccaaa gaatatattg ttagttgtaa atgagaaac    300 ggagcaccgg acgaagagcc tgttgtttac ggatttacat atactaaaac tggctggaaa    360
ttaatttacc ttgataatat caatgag                                       387
```

<210> SEQ ID NO 124
<211> LENGTH: 149
<212> TYPE: PRT
<213> ORGANISM: Artificial Sequence
<220> FEATURE:
<223> OTHER INFORMATION: LIC10655

<400> SEQUENCE: 124

```
Met Asn Gln Asn Lys Thr Lys Asn Lys Trp Phe Phe Ile Phe Ile
1               5                   10                  15

Leu Leu Gly Val Phe Phe Ile Asn Thr Lys Ile Ile Lys Ser Gln Ser
            20                  25                  30

Asp Thr Ser Ile Ser Thr Phe Trp Lys Glu Phe Lys Asp Ala Val Leu
        35                  40                  45

Lys Asn Asp Ser Glu Lys Leu Ala Ser Leu Ser Arg Phe Pro Ile Lys
    50                  55                  60

Met Pro Tyr Gly Tyr Thr Gln Ile Lys Asn Lys Lys Glu Phe Leu Lys
65                  70                  75                  80

Arg Tyr Asp Glu Ile Phe Ser Arg Gln Ala Asp Ala Lys Glu Cys Phe
                85                  90                  95

Gln Lys Glu Lys Gln Pro Val Ala Asp Ser Glu Arg Thr Lys Glu Tyr
            100                 105                 110

Ile Val Ser Cys Lys Met Arg Asn Gly Ala Pro Asp Glu Glu Pro Val
        115                 120                 125

Val Tyr Gly Phe Thr Tyr Thr Lys Thr Gly Trp Lys Leu Ile Tyr Leu
    130                 135                 140

Asp Asn Ile Asn Glu
145
```

<210> SEQ ID NO 125
<211> LENGTH: 993
<212> TYPE: DNA
<213> ORGANISM: Artificial Sequence
<220> FEATURE:
<223> OTHER INFORMATION: LIC11553

<400> SEQUENCE: 125

```
gtgaatcaag agcaaattag agaaaagtat cttccaatcg gaggttatgt tttattctta     60
gcggtgggtc ttctattatt ttttagtgca gccttcttag tagtattcgt aagaactaaa    120
agtactgcaa aggtaattgt tcctgatctg atcggaaaat cttatccgga agttcataat    180
gaattaggtc gtcttcaatt gaaagtgcgt ctggaaaaca aacgttatcc ggataagacg    240
gatggaatta ttttatatca atctatacga cctgggagag aaatagaagc gggaagtaaa    300
attgtactta ccgtaaatac tggattggat cgagtcattg ttccagacgt aagagggcaa    360
tcaattgatt ccgcaaaagc aaatcttcaa aaagttcttt ctgaagaaac ttatgtagaa    420
atgcagattg tggaattac ttacattgag ccacaagcag atcaacttcc gaatactgtt     480
atcgatcaaa ttccagaacc tggaaaaaat acttctgcaa gagaaaaagt atttttactc    540
```

```
gtaactaagg ttccaagtaa aactaaggaa gaatttctc ctacttcttt tcaaggtgca       600
tcttttccac tcgttcaaaa aagtttaatt cgttccggaa tcaaaagtag agtggaagaa       660
attataaata ctagagttcg ttctgaaaac ggacttatat cttctgcaag attagaagga       720
gatgaggttc gttttaaagt acttactttt gagccagagc ttgcggtaga aagtggttac       780
gaattatttt cttatgaagt cggaaatgat ggaaattata aagcggtatt aaaatcttct       840
aatcaagtag aaacggatgt tttaactctt cctatttcac ttaaggatgg agaaaaattt       900
caaactgtgt tttatcgaaa aggaagtgta aaacttactc ttttagatgc ttccgattcc       960
aagataaaat ccaaatctta tgagagtgaa ctt                                   993

<210> SEQ ID NO 126
<211> LENGTH: 331
<212> TYPE: PRT
<213> ORGANISM: Artificial Sequence
<220> FEATURE:
<223> OTHER INFORMATION: LIC11553

<400> SEQUENCE: 126
```

Met Asn Gln Glu Gln Ile Arg Glu Lys Tyr Leu Pro Ile Gly Gly Tyr
1               5                   10                  15

Val Leu Phe Leu Ala Val Gly Leu Leu Leu Phe Phe Ser Ala Ala Phe
            20                  25                  30

Leu Val Val Phe Val Arg Thr Lys Ser Thr Ala Lys Val Ile Val Pro
        35                  40                  45

Asp Leu Ile Gly Lys Ser Tyr Pro Glu Val His Asn Glu Leu Gly Arg
    50                  55                  60

Leu Gln Leu Lys Val Arg Leu Glu Asn Lys Arg Tyr Pro Asp Lys Thr
65                  70                  75                  80

Asp Gly Ile Ile Leu Tyr Gln Ser Ile Arg Pro Gly Arg Glu Ile Glu
                85                  90                  95

Ala Gly Ser Lys Ile Val Leu Thr Val Asn Thr Gly Leu Asp Arg Val
            100                 105                 110

Ile Val Pro Asp Val Arg Gly Gln Ser Ile Asp Ser Ala Lys Ala Asn
        115                 120                 125

Leu Gln Lys Val Leu Ser Glu Glu Thr Tyr Val Glu Met Gln Ile Gly
    130                 135                 140

Gly Ile Thr Tyr Ile Glu Pro Gln Ala Asp Gln Leu Pro Asn Thr Val
145                 150                 155                 160

Ile Asp Gln Ile Pro Glu Pro Gly Lys Asn Thr Ser Ala Arg Glu Lys
                165                 170                 175

Val Phe Leu Leu Val Thr Lys Val Pro Ser Lys Thr Lys Glu Glu Phe
            180                 185                 190

Ser Pro Thr Ser Phe Gln Gly Ala Ser Phe Pro Leu Val Gln Lys Ser
        195                 200                 205

Leu Ile Arg Ser Gly Ile Lys Ser Arg Val Glu Glu Ile Ile Asn Thr
    210                 215                 220

Arg Val Arg Ser Glu Asn Gly Leu Ile Ser Ser Ala Arg Leu Glu Gly
225                 230                 235                 240

Asp Glu Val Arg Phe Lys Val Leu Tyr Phe Glu Pro Glu Leu Ala Val
                245                 250                 255

Glu Ser Gly Tyr Glu Leu Phe Ser Tyr Glu Val Gly Asn Asp Gly Asn
            260                 265                 270

Tyr Lys Ala Val Leu Lys Ser Ser Asn Gln Val Glu Thr Asp Val Leu

```
              275                 280                 285
Thr Leu Pro Ile Ser Leu Lys Asp Gly Glu Lys Phe Gln Thr Val Phe
    290                 295                 300

Tyr Arg Lys Gly Ser Val Lys Leu Thr Leu Leu Asp Ala Ser Asp Ser
305                 310                 315                 320

Lys Ile Lys Ser Lys Ser Tyr Glu Ser Glu Leu
                325                 330
```

<210> SEQ ID NO 127
<211> LENGTH: 678
<212> TYPE: DNA
<213> ORGANISM: Artificial Sequence
<220> FEATURE:
<223> OTHER INFORMATION: LIC11637

<400> SEQUENCE: 127

```
ttgaaatacg aaatattatt aaaacctgat tttccaattg ttcaagttca gttgaatgat    60
ggagaatcga tacgcgcgga atcgggtgcg atggttgcaa tgagtcccac tgtcaaaatg   120
attacaaaag cagaaggtgg agttttgct tccgcaaaac gcgcgttatt gggtggtgag   180
tcttttttc aaaatacatt taaatcggaa ggtggaaccg gaactctttt tttgacaagc   240
gcaactcaag gagatattga atatcgtaaa atgaacggag aagatctgat cctaagccga   300
ggagcttatg tggctggctc tgaatctatt acgattgata gtaaatgggg aggatttaaa   360
ggttttttt ccggggaagg tttgttcttt ttaaaagttg gtggaactgg ggatttattt   420
ttttcgagtt ttggcgcgat tcatacgatt gacgtaaacg gcaatatgt ggtggacact   480
gggcatatcg tagggtttga aggaactttg gattatacga ttcaaaaagt aggggattg   540
aagtctcttt tcttagtgg agaaggttta gtagcggtgt tttccggaag cggtaaatta   600
tacattcaat ctagaaaatca aaattcgttt gtatcttggg ccaatcaatg gagaagagtg   660
gaaaaatctt cttctgac                                                 678
```

<210> SEQ ID NO 128
<211> LENGTH: 226
<212> TYPE: PRT
<213> ORGANISM: Artificial Sequence
<220> FEATURE:
<223> OTHER INFORMATION: LIC11637

<400> SEQUENCE: 128

```
Met Lys Tyr Glu Ile Leu Leu Lys Pro Asp Phe Pro Ile Val Gln Val
1               5                   10                  15

Gln Leu Asn Asp Gly Glu Ser Ile Arg Ala Glu Ser Gly Ala Met Val
            20                  25                  30

Ala Met Ser Pro Thr Val Lys Met Ile Thr Lys Ala Glu Gly Gly Val
        35                  40                  45

Phe Ala Ser Ala Lys Arg Ala Leu Leu Gly Gly Glu Ser Phe Phe Gln
    50                  55                  60

Asn Thr Phe Lys Ser Glu Gly Gly Thr Gly Thr Leu Phe Leu Thr Ser
65                  70                  75                  80

Ala Thr Gln Gly Asp Ile Glu Tyr Arg Lys Met Asn Gly Glu Asp Leu
                85                  90                  95

Ile Leu Ser Arg Gly Ala Tyr Val Ala Gly Ser Glu Ser Ile Thr Ile
            100                 105                 110

Asp Ser Lys Trp Gly Gly Phe Lys Gly Phe Phe Ser Gly Glu Gly Leu
        115                 120                 125
```

Phe Phe Leu Lys Val Gly Gly Thr Gly Asp Leu Phe Phe Ser Ser Phe
130                 135                 140

Gly Ala Ile His Thr Ile Asp Val Asn Gly Gln Tyr Val Val Asp Thr
145                 150                 155                 160

Gly His Ile Val Gly Phe Glu Gly Thr Leu Asp Tyr Thr Ile Gln Lys
                165                 170                 175

Val Gly Gly Leu Lys Ser Leu Phe Leu Ser Gly Glu Gly Leu Val Ala
                180                 185                 190

Val Phe Ser Gly Ser Gly Lys Leu Tyr Ile Gln Ser Arg Asn Gln Asn
                195                 200                 205

Ser Phe Val Ser Trp Ala Asn Gln Trp Arg Arg Val Glu Lys Ser Ser
210                 215                 220

Ser Asp
225

<210> SEQ ID NO 129
<211> LENGTH: 1077
<212> TYPE: DNA
<213> ORGANISM: Artificial Sequence
<220> FEATURE:
<223> OTHER INFORMATION: LIC12100

<400> SEQUENCE: 129

```
atgagactgt tatctgtagt tggattcggt ttatttttt  taatattgtt ttttattt      60
ctggggaatc cgtatcctac agccatagga atacagaaag tatgggcgtt ttctaaatcg    120
gctcatgcgg gaatggctcc cgatccaaga ttttttatgga atccggaaga agagatcaac   180
ggatataaat atgaaaattc ttactataca ctatcttctt caaatggagt tgtatttgat    240
gatataataa aaattgaata tcctctaaat acaaaaggat atagaata caaaaaaata     300
ggatccgagg tgaattttta ttctccttcg agagagatac tctggactaa agaatataga    360
agttatccaa gggtctcccc ttctggaaat cttgtgttac tcattgcagg agatcataac    420
caagttctac tttctgacat caatggaaat accactggag cggggaaaat agacggacga    480
tttttgacgg actatacatt tgcatccgta tctttgataa ctggagtttt attttcagga    540
ggggaattgt tcgttttaga ttcgaaaggt gcaattcaaa tcaagaaaaa tctaggttcc    600
gaaaaaaatc cagtatttgc caaaagtgta tccttatcgc cggatggaag taaaattgcg    660
attcatcttt tgaatacaaa ccgagatagt gtgatcgttt ttggggaaaa gggagaagag    720
attttttcct ttgatttaga tacgattat ccgcataaac ttaatttagc aatttctaat     780
acgggagaaa tacttgtttc gactcccaat agtatagaat tttacgacgt ttccgggaaa    840
aaaattctga atttaaaacg aacttctaac aacggtgtat atcaagcggt atatcacaat    900
ggaaattggt ttactgccga gttaaatcaa gaaatccttt ttattgatga agtagggaaa    960
attctaaaaa agaaaagat ccgtggttct gatttgcccg tgcgattttt tccttccggc    1020
aaaaacgctt cggtagtctt agagacaaaa aagaactat ttctctatcg aaatctt      1077
```

<210> SEQ ID NO 130
<211> LENGTH: 359
<212> TYPE: PRT
<213> ORGANISM: Artificial Sequence
<220> FEATURE:
<223> OTHER INFORMATION: LIC12100

<400> SEQUENCE: 130

Met Arg Leu Leu Ser Val Val Gly Phe Gly Leu Phe Phe Leu Ile Leu
1               5                   10                  15

Phe Phe Tyr Phe Leu Gly Asn Pro Tyr Pro Thr Ala Ile Gly Ile Gln
                20                  25                  30

Lys Val Trp Ala Phe Ser Lys Ser Ala His Ala Gly Met Ala Pro Asp
            35                  40                  45

Pro Arg Phe Leu Trp Asn Pro Glu Glu Ile Asn Gly Tyr Lys Tyr
50                  55                  60

Glu Asn Ser Tyr Tyr Thr Leu Ser Ser Asn Gly Val Val Phe Asp
65                  70                  75                  80

Asp Ile Ile Lys Ile Glu Tyr Pro Leu Asn Thr Lys Gly Tyr Ile Glu
                85                  90                  95

Tyr Lys Lys Ile Gly Ser Glu Val Asn Phe Tyr Ser Pro Ser Arg Glu
                100                 105                 110

Ile Leu Trp Thr Lys Glu Tyr Arg Ser Tyr Pro Arg Val Ser Pro Ser
            115                 120                 125

Gly Asn Leu Val Leu Leu Ile Ala Gly Asp His Asn Gln Val Leu Leu
    130                 135                 140

Ser Asp Ile Asn Gly Asn Thr Thr Gly Ala Gly Lys Ile Asp Gly Arg
145                 150                 155                 160

Phe Leu Thr Asp Tyr Thr Phe Ala Ser Val Ser Leu Ile Thr Gly Val
                165                 170                 175

Leu Phe Ser Gly Gly Glu Leu Phe Val Leu Asp Ser Lys Gly Ala Ile
            180                 185                 190

Gln Ile Lys Lys Asn Leu Gly Ser Glu Lys Asn Pro Val Phe Ala Lys
        195                 200                 205

Ser Val Ser Leu Ser Pro Asp Gly Ser Lys Ile Ala Ile His Leu Leu
210                 215                 220

Asn Thr Asn Arg Asp Ser Val Ile Val Phe Gly Glu Lys Gly Glu Glu
225                 230                 235                 240

Ile Phe Ser Phe Asp Leu Asp Thr Ile Tyr Pro His Lys Leu Asn Leu
                245                 250                 255

Ala Ile Ser Asn Thr Gly Glu Ile Leu Val Ser Thr Pro Asn Ser Ile
            260                 265                 270

Glu Phe Tyr Asp Val Ser Gly Lys Lys Ile Leu Asn Leu Lys Arg Thr
        275                 280                 285

Ser Asn Asn Gly Val Tyr Gln Ala Val Tyr His Asn Gly Asn Trp Phe
290                 295                 300

Thr Ala Glu Leu Asn Gln Glu Ile Leu Phe Ile Asp Glu Val Gly Lys
305                 310                 315                 320

Ile Leu Lys Lys Glu Lys Ile Arg Gly Ser Asp Leu Pro Val Arg Phe
                325                 330                 335

Phe Pro Ser Gly Lys Asn Ala Ser Val Val Leu Glu Thr Lys Lys Glu
            340                 345                 350

Leu Phe Leu Tyr Arg Asn Leu
        355

<210> SEQ ID NO 131
<211> LENGTH: 282
<212> TYPE: DNA
<213> ORGANISM: Artificial Sequence
<220> FEATURE:
<223> OTHER INFORMATION: LIC12784

<400> SEQUENCE: 131
atgaatccaa aaagaactat tattcttttt ttatatcttt tacctttcgt ttcctgccag    60

-continued

```
gaatatgttc aacaaaaatg taattccgct tgtaaattct ttgttcagtg tgcgatgaac      120
gactttaaac atgtaaaagt tacagagttg gaaaaaaatc aaatgatgat cgattgtgaa      180
agtggttgta tccgtgaaca gggttttgtt cttccttgtt ttgaatctga aaccacatgc      240
aaaggtttta atacttgcgt gatggaatcc ggatttatgg at                        282
```

<210> SEQ ID NO 132
<211> LENGTH: 94
<212> TYPE: PRT
<213> ORGANISM: Artificial Sequence
<220> FEATURE:
<223> OTHER INFORMATION: LIC12784

<400> SEQUENCE: 132

```
Met Asn Pro Lys Arg Thr Ile Ile Leu Phe Leu Tyr Leu Leu Pro Phe
1               5                   10                  15

Val Ser Cys Gln Glu Tyr Val Gln Gln Lys Cys Asn Ser Ala Cys Lys
            20                  25                  30

Phe Phe Val Gln Cys Ala Met Asn Asp Phe Lys His Val Lys Val Thr
        35                  40                  45

Glu Leu Glu Lys Asn Gln Met Met Ile Asp Cys Glu Ser Gly Cys Ile
    50                  55                  60

Arg Glu Gln Gly Phe Val Leu Pro Cys Phe Glu Ser Glu Thr Thr Cys
65                  70                  75                  80

Lys Gly Phe Asn Thr Cys Val Met Glu Ser Gly Phe Met Asp
                85                  90
```

<210> SEQ ID NO 133
<211> LENGTH: 1419
<212> TYPE: DNA
<213> ORGANISM: Artificial Sequence
<220> FEATURE:
<223> OTHER INFORMATION: LIC13002

<400> SEQUENCE: 133

```
atgagaattc tattcaatcg aatccaaaaa agcacacttc caatctttat cggtctggga      60 gttttttattt cttttccatc cctctgggca gttgcaagta acagtagaaa tgcgattaac    120
gcaagatacg aaggtatggc cggcgttaac tttgcgttag gcggctctcc tatggacgtt    180
gcactcaatc ccgcaaattt atatttaatg aaaggaaaaa aatagaatt cggcttagga     240 atgtcgcacg cccaaataag actgaaggat cagttttttag attcggaccc aagtttaaat   300
tatacgaatt ccaaatctag aaccggagca ggtgcagctc catacatggc agttaaactt    360
ccagtaacgg atacgatcga ctatggattt gcggcgtatg tgttcggagt tgtaaatggg    420
gccgcggaaa aaatcaaccg taatacacct acaggagaaa ccgtaaatca atgggcgggt    480
ttacctggta tttttggaga tggtaaaaga atccaagaga ctaccgaaaa tcagggaatt    540
tttattaagg ctgtaaatgg tttatctatt aagtttggaa atctttctttt aggcgctagt    600 ttagaattaa actatggtgc tcaaaatcgc aatataagat attacgacgc ctttggaatt    660
cgggaaattc ctggacaggg atttcattac gaaagcagaa agaacgctct tgcattgagc    720
ggaattatag gttccaatta tacggttaca gattggttca gaattgcata cgtatatcaa    780
tcgagcgcga actttccgtt tgatggtagt tatacgatcg gggtcaatga tcctacctat    840
tatcgatcta caggagtttc ctataatttc cgttcgccgg agaaacacgg tcttggatttt    900 gcagttggtc cagaaaatct aaaagtagcg atcgactttc tttacataaa ttatggttcc    960
tacttaaaaa acgcccgaca aaatttagaa gatccttggt atcctaatcc tcaaggacga   1020
```

```
agttcagaaa caattgcaca tttgaattat cgaaatcaat gggcggtgtt aatcggactc    1080
gaacataaaa ttacaaaaga atggacctat cgtttcggat atagttacaa ttctccgatt    1140
gtttccagta acgctttaaa cggagcacaa gggatcttat taactctcaa ccacgtaatt    1200
gcaggaggat ttagttattc ttccggacct tggagttttg actttggagc aagttgtttt    1260
attcccggaa gacaaatcga aggtggtaaa gatacagact gggcaataag tcacggaatt    1320
tttggtccga caaccaaaa caatatcgta ggatattctt acagtgccca agcgcttcat    1380
tcgattggaa tcaatttttgg tgtaactcgt tcttttgat    1419
```

<210> SEQ ID NO 134
<211> LENGTH: 473
<212> TYPE: PRT
<213> ORGANISM: Artificial Sequence
<220> FEATURE:
<223> OTHER INFORMATION: LIC13002

<400> SEQUENCE: 134

```
Met Arg Ile Leu Phe Asn Arg Ile Gln Lys Ser Thr Leu Pro Ile Phe
1               5                   10                  15

Ile Gly Leu Gly Val Phe Ile Ser Phe Pro Ser Leu Trp Ala Val Ala
            20                  25                  30

Ser Asn Ser Arg Asn Ala Ile Asn Ala Arg Tyr Glu Gly Met Ala Gly
        35                  40                  45

Val Asn Phe Ala Leu Gly Gly Ser Pro Met Asp Val Ala Leu Asn Pro
    50                  55                  60

Ala Asn Leu Tyr Leu Met Lys Gly Lys Lys Ile Glu Phe Gly Leu Gly
65                  70                  75                  80

Met Ser His Ala Gln Ile Arg Leu Lys Asp Gln Phe Leu Asp Ser Asp
                85                  90                  95

Pro Ser Leu Asn Tyr Thr Asn Ser Lys Ser Arg Thr Gly Ala Gly Ala
            100                 105                 110

Ala Pro Tyr Met Ala Val Lys Leu Pro Val Thr Asp Thr Ile Asp Tyr
        115                 120                 125

Gly Phe Ala Ala Tyr Val Phe Gly Val Val Asn Gly Ala Ala Glu Lys
    130                 135                 140

Ile Asn Arg Asn Thr Pro Thr Gly Glu Thr Val Asn Gln Trp Ala Gly
145                 150                 155                 160

Leu Pro Gly Ile Phe Gly Asp Gly Lys Arg Ile Gln Glu Thr Thr Glu
                165                 170                 175

Asn Gln Gly Ile Phe Ile Lys Ala Val Asn Gly Leu Ser Ile Lys Phe
            180                 185                 190

Gly Asn Leu Ser Leu Gly Ala Ser Leu Glu Leu Asn Tyr Gly Ala Gln
        195                 200                 205

Asn Arg Asn Ile Arg Tyr Tyr Asp Ala Phe Gly Ile Arg Glu Ile Pro
    210                 215                 220

Gly Gln Gly Phe His Tyr Glu Ser Arg Lys Asn Ala Leu Ala Leu Ser
225                 230                 235                 240

Gly Ile Ile Gly Ser Asn Tyr Thr Val Thr Asp Trp Phe Arg Ile Ala
                245                 250                 255

Tyr Val Tyr Gln Ser Ser Ala Asn Phe Pro Phe Asp Gly Ser Tyr Thr
            260                 265                 270

Ile Gly Val Asn Asp Pro Thr Tyr Tyr Arg Ser Thr Gly Val Ser Tyr
        275                 280                 285
```

```
Asn Phe Arg Ser Pro Glu Lys His Gly Leu Gly Phe Ala Val Gly Pro
    290                 295                 300

Glu Asn Leu Lys Val Ala Ile Asp Phe Leu Tyr Ile Asn Tyr Gly Ser
305                 310                 315                 320

Tyr Leu Lys Asn Ala Arg Gln Asn Leu Glu Asp Pro Trp Tyr Pro Asn
                325                 330                 335

Pro Gln Gly Arg Ser Ser Glu Thr Ile Ala His Leu Asn Tyr Arg Asn
            340                 345                 350

Gln Trp Ala Val Leu Ile Gly Leu Glu His Lys Ile Thr Lys Glu Trp
        355                 360                 365

Thr Tyr Arg Phe Gly Tyr Ser Tyr Asn Ser Pro Ile Val Ser Ser Asn
    370                 375                 380

Ala Leu Asn Gly Ala Gln Gly Ile Leu Leu Thr Leu Asn His Val Ile
385                 390                 395                 400

Ala Gly Gly Phe Ser Tyr Ser Ser Gly Pro Trp Ser Phe Asp Phe Gly
                405                 410                 415

Ala Ser Cys Phe Ile Pro Gly Arg Gln Ile Glu Gly Gly Lys Asp Thr
            420                 425                 430

Asp Trp Ala Ile Ser His Gly Ile Phe Gly Pro Asn Asn Gln Asn Asn
        435                 440                 445

Ile Val Gly Tyr Ser Tyr Ser Ala Gln Ala Leu His Ser Ile Gly Ile
    450                 455                 460

Asn Phe Gly Val Thr Arg Ser Phe Asp
465                 470
```

<210> SEQ ID NO 135
<211> LENGTH: 1320
<212> TYPE: DNA
<213> ORGANISM: Artificial Sequence
<220> FEATURE:
<223> OTHER INFORMATION: LIC13023

<400> SEQUENCE: 135

```
atgatcaaaa atcaaaaaat tgtaatgaag cagaaaacat tgttgtatt tttacttctt      60
tttattcttc caacagcctt atttccctgg ggaactcact acctcattat ggatcaaata     120
ttagaacatc cttctatgaa atttatatcc ggagaagtag aatctgaatc cttggattct     180
ttcgtaaaaa aagaaaagaa ttctctaaaa gttttatttg acgagtttgc agtttgggaa     240
gaatccagag atcaaaacg atttaaaaaa attgaatttc atccagaaac cgcatcggtt     300
atagaatttt taaaagcggc aagactaaac cccgctactc gattttttgga agtggaaaga     360
attcttcccg gttctaaacc aatgattgga aacgttccag tttcctcaat cactccttat     420
cttttagatc attccgaact tccagcaagg tttcaatcta cactcggaaa aaaagtcaaa     480
cttagaaaca ttctctatac atttatcgat gaaccagatt ggggaatgga tcatgacctt     540
tggaatcttc aagaatatgg atatggaaaa caaccttatg aaaagcaga aggagaaggt     600
agtaaagctc ttttcatat gcaattccaa aatgaaaatt ggattctttc ccttttttgtt     660
cccgaagttg taaaggtgg aatgatctta gatcggatcg agttgttttc tcgcctttttcc     720
aaattggcgg gaaaaacggg acacaattat tggcagtatc gttttgctac ttgggcttgt     780
cattatatcc aagacatagg acaaccgtat cattccaagg cagttcccga cgcagacttc     840
tcgtattacg cccgttatat cttttcatca aagaaacaa aaaagatat gaaagccaaa     900
gctactcaac ttgtaaccaa tcgccatttt ttgtacgaag attttatctc ttacaatttg     960
atagatttt acaagaaccc cactactcgg accttaaccg aatttttagt acaaaattca    1020
```

```
aaagattttc cttcgttttc gtctaacgaa gatttgatga aattcgtagg caaagaggct    1080
tccgttcacg cctttcaaat caaccaatcg atcatagata cttttggaga aaaatataca    1140
atgaaacctg aatatgatct ggaaaaggaa cttgggacca aaatgaagga aatcattccc    1200
acattaaatt cggaaaaaag aaatcttctt ttaaaagaag cgggtagaga tttttctcta    1260
acaggtttcg caaccagaga aatgttacat ttgattttac aagattcaaa tcataaaaat    1320
```

<210> SEQ ID NO 136
<211> LENGTH: 440
<212> TYPE: PRT
<213> ORGANISM: Artificial Sequence
<220> FEATURE:
<223> OTHER INFORMATION: LIC13023

<400> SEQUENCE: 136

```
Met Ile Lys Asn Gln Lys Ile Val Met Lys Gln Lys Thr Phe Val Val
1               5                   10                  15

Phe Leu Leu Phe Ile Leu Pro Thr Ala Leu Phe Pro Trp Gly Thr
            20                  25                  30

His Tyr Leu Ile Met Asp Gln Ile Leu Glu His Pro Ser Met Lys Phe
            35                  40                  45

Ile Ser Gly Glu Val Glu Ser Glu Ser Leu Asp Ser Phe Val Lys Lys
    50                  55                  60

Glu Lys Asn Ser Leu Lys Val Leu Phe Asp Glu Phe Ala Val Trp Glu
65                  70                  75                  80

Glu Ser Arg Gly Ser Lys Arg Phe Lys Lys Ile Glu Phe His Pro Glu
                85                  90                  95

Thr Ala Ser Val Ile Glu Phe Leu Lys Ala Ala Arg Leu Asn Pro Ala
            100                 105                 110

Thr Arg Phe Leu Glu Val Glu Arg Ile Leu Pro Gly Ser Lys Pro Met
        115                 120                 125

Ile Gly Asn Val Pro Val Ser Ser Ile Thr Pro Tyr Leu Leu Asp His
    130                 135                 140

Ser Glu Leu Pro Ala Arg Phe Gln Ser Thr Leu Gly Lys Lys Val Lys
145                 150                 155                 160

Leu Arg Asn Ile Leu Tyr Thr Phe Ile Asp Glu Pro Asp Trp Gly Met
                165                 170                 175

Asp His Asp Leu Trp Asn Leu Gln Glu Tyr Gly Tyr Gly Lys Gln Pro
            180                 185                 190

Tyr Gly Lys Ala Glu Gly Glu Gly Ser Lys Ala Pro Phe His Met Gln
        195                 200                 205

Phe Gln Asn Glu Asn Trp Ile Leu Ser Leu Phe Val Pro Glu Val Val
    210                 215                 220

Lys Gly Gly Met Ile Leu Asp Arg Ile Glu Leu Phe Ser Arg Leu Ser
225                 230                 235                 240

Lys Leu Ala Gly Lys Thr Gly His Asn Tyr Trp Gln Tyr Arg Phe Ala
                245                 250                 255

Thr Trp Ala Cys His Tyr Ile Gln Asp Ile Gly Gln Pro Tyr His Ser
            260                 265                 270

Lys Ala Val Pro Asp Ala Asp Phe Ser Tyr Tyr Ala Arg Tyr Ile Phe
        275                 280                 285

Ser Ser Lys Glu Thr Lys Lys Asp Met Lys Ala Lys Ala Thr Gln Leu
    290                 295                 300

Val Thr Asn Arg His Phe Leu Tyr Glu Asp Phe Ile Ser Tyr Asn Leu
```

```
                305                 310                 315                 320
Ile Asp Phe Tyr Lys Asn Pro Thr Thr Arg Thr Leu Thr Glu Phe Leu
                    325                 330                 335

Val Gln Asn Ser Lys Asp Phe Pro Ser Phe Ser Ser Asn Glu Asp Leu
                    340                 345                 350

Met Lys Phe Val Gly Lys Glu Ala Ser Val His Ala Phe Gln Ile Asn
                    355                 360                 365

Gln Ser Ile Ile Asp Thr Phe Gly Glu Lys Tyr Thr Met Lys Pro Glu
                    370                 375                 380

Tyr Asp Leu Glu Lys Glu Leu Gly Thr Lys Met Lys Glu Ile Ile Pro
385                 390                 395                 400

Thr Leu Asn Ser Glu Lys Arg Asn Leu Leu Leu Lys Glu Ala Gly Arg
                    405                 410                 415

Asp Phe Ser Leu Thr Gly Phe Ala Thr Arg Glu Met Leu His Leu Ile
                    420                 425                 430

Leu Gln Asp Ser Asn His Lys Asn
                    435                 440

<210> SEQ ID NO 137
<211> LENGTH: 3249
<212> TYPE: DNA
<213> ORGANISM: Artificial Sequence
<220> FEATURE:
<223> OTHER INFORMATION: LIC13017

<400> SEQUENCE: 137
atgcttctta ccggttgggt ggctatggga agaatgggag tggatctttt tccggatgtt      60
aacattccag ttgtttcagt tgctacgatc tatccaggag ctggcccgga gaaaattgaa     120
gaactgattt ctaaacccttt agaggaagaa ttgtcttcaa tctctggtct aaaaaaaatt     180
tcttccagaa accaagaagg tgtctctgtg gtattcggag aattcactct cgatacggac     240
attaaatacg cggaacaaca attccgagat aaagttggcc ttgtaaaacc gaaacttccc     300
acaggaatca agaacctaa agtagtccgt tttgatcctg cagaccaacc gatcgttcgt     360
ctggcattgt ttgctgattt ggatcaggct aagttatatg acctcgccaa gaaaacggta     420
aaagcgagat tagaacaggt gcaaggagtt ggttcggtaa aactaatcgg tggaactagg     480
agagaaattc agatcgaatt ggatcggaat aaactcattt cttatcaaat gcctactgta     540
gttatcgcca atcgtttgaa actgctggc ttgaacgttc agttggaaa gtttgaatct     600 ggttctaaag aaacttctta tcgaactttta ggcaggtatg aatctctttc tcaaatcgaa     660
aatacaatcg tttcttttag cggtgaagta ggaaatgcag ttttaattaa acaattggga     720
accgttcgag acggaaccga agacgaagaa acgatcggtt atctttgggc ttcccaagga     780
gaaggagtag aagaaaaagt ttcttttctt actaaaatcg gaattttttt caaaggcaaa     840
aaagaaaact ccgcaactgc aattaaagaa actaaacccg ctttatttat agatgtttat     900
aaacaatcag gtgcaaatac ggtttccgtt gcagacgaag tgcttaaaag aattggtaaa     960
cttaacgaag gaattcagaa cttagaagga aaaccaaaaa tccgtttgat tcgagatgga    1020
tcaaagtgga ttcgttataa cgtagaagac gtaactgaag cgatcgtaat aggaatctta    1080
ctcgccgtta ttactgttta tttcttttta ggaaattttc gttccacggt cattacggga    1140
cttgcacttc ctaactctat gttaggtgca tttgttctta tgtggacgat gggttttaca    1200
atcaacgtta tgactctttt ggctctttct ttggcagtag gttactcgt agacgatgcg    1260 atcgtggttc gggaaaatat attccgaaaa ctggaagaag gaaagggggt gatggaagcg    1320
```

```
gcggaaaccg gaaccacaga agtaacgtta gccgttattg gtacgtcttt aactgtaatt    1380
gccgtatttt taccagtggg atttctttcc ggaatcgtag gacaattctt taaacaattt    1440
ggtttaacag tagtgtttgc gatgctcatt tcgctctttg atggtcttgc ggttgcacct    1500
atgctttccg cttactttgc gggcaagatc gatcataatg caaaaccgaa taaggcagtg    1560
gaacttttcg ataaattcca gacttggttg gaaagacagt atgggaaagt gatgaaggtg    1620
gctttaaaaa gacccggaat cgttctttta ctctctcttg gaattttttat tctttcgatc    1680 ttatctttga agttggtaaa aagtaccttt ttacctgcaa acgatcaggg agaattttta    1740
gttaccttag atttacctcc tggaactagt ttgaacggaa ccaaacaagt agcagatcaa    1800
gttttagaag ttttgaaaaa aattccggaa atggaaatga ttgcggtgac catcggtaaa    1860
ccggatggag gagaacctaa cgcgggaact cttgcgatta cattagtaga ttctaaaaaa    1920
cgaaaactta ctacaaccca agttaaggat caaatcagag aacttttaaa accttttgaa    1980
tatgcaaggc ccgccgtatc tgattatagc gccgtgggag gtgggattca atatccgttc    2040
caacttgtga tcaaagggga aaatctcggg gagatggaag cctattctaa aaaggtactc    2100
acaaaattaa agtccttatc cgatctagct gacttagata cggattatag agcagggaaa    2160
ccggaatacc aaattcattt ggacaatatg aaaatgcagc ttgtaggagt tcttccaggg    2220
gttgctggtt ctgaacttcg gtatcagatt gcgggagacg aggttagtaa attttacgat    2280
cgaggaattg aatacgtagt taagatgagg cttcgtcctg atcaaagaaa cctgagaatg    2340
gcttatgacc aaacgaaggt tccgaatatc gcaaacaaat taattccgct ttctgcgatt    2400
agtgtaggta agaaacagc tggaccttct agaatcaaca ggattgaccg tgctagaacg    2460
atcgtgatca atgcaaactt agcgccggga ggtgcggttc aagatgcgac tcggattgcg    2520
gatgaaattc tcagaaaaga gttacctcct ccacccggaa ttcgatacaa ttttcaaggg    2580
caatcggaag acttcaaaga acttttagcg aacatagttc tcgcgttcgg attggctctt    2640
gtgttcattt atctcgtctt agcttcgtta tatgaatcct ttatcactcc ggtcacgatt    2700
ttgtttgcaa ttccacctgc gatttcggga gcgttttttg cactcgcact tacaagagaa    2760
atgctcaatc tcttttcgat gatcggtttg attctactta tgggtcttgt tgcaaagaac    2820
tctattcttc ttgtggatta tgcgatgcaa gcgagccgag aaaaaggtat gtctagaaat    2880
gacgcgatct atgaggcggg gcttgttcga ctcagaccaa ttttaatgac ttctctcgct    2940
atgattatgg gaacggtccc aattgcactt ggatttggag aagctgcaaa atctagaacc    3000
gcgatgggga ttgcgattat aggagggttg atactttcca cagtggtgac tctcgttgta    3060
gtaccttcta ttttcggatt tatcgatcga tttagagaat ggatcgaaag taaatttcgt    3120
cctgaatatg atatgaacgc atctatggtt caacatgcac cttcgaccaa caaacagaag    3180
ttttacgaaa aagaatgggc ttccatgcaa gaagaagtag aagtagaact tcctaaaaag    3240
agtaaaaaa                                                            3249
```

<210> SEQ ID NO 138
<211> LENGTH: 1083
<212> TYPE: PRT
<213> ORGANISM: Artificial Sequence
<220> FEATURE:
<223> OTHER INFORMATION: LIC13017

<400> SEQUENCE: 138

Met Leu Leu Thr Gly Trp Val Ala Met Gly Arg Met Gly Val Asp Leu
1               5                   10                  15

```
Phe Pro Asp Val Asn Ile Pro Val Ser Val Ala Thr Ile Tyr Pro
             20                  25                  30
Gly Ala Gly Pro Glu Glu Ile Glu Glu Leu Ile Ser Lys Pro Leu Glu
         35                  40                  45
Glu Glu Leu Ser Ser Ile Ser Gly Leu Lys Lys Ile Ser Ser Arg Asn
 50                  55                  60
Gln Glu Gly Val Ser Val Val Phe Gly Glu Phe Thr Leu Asp Thr Asp
 65                  70                  75                  80
Ile Lys Tyr Ala Glu Gln Gln Phe Arg Asp Lys Val Gly Leu Val Lys
                 85                  90                  95
Pro Lys Leu Pro Thr Gly Ile Lys Glu Pro Lys Val Val Arg Phe Asp
             100                 105                 110
Pro Ala Asp Gln Pro Ile Val Arg Leu Ala Leu Phe Ala Asp Leu Asp
             115                 120                 125
Gln Ala Lys Leu Tyr Asp Leu Ala Lys Glu Thr Val Lys Ala Arg Leu
130                 135                 140
Glu Gln Val Gln Gly Val Gly Ser Val Lys Leu Ile Gly Gly Thr Arg
145                 150                 155                 160
Arg Glu Ile Gln Ile Glu Leu Asp Arg Asn Lys Leu Ile Ser Tyr Gln
                 165                 170                 175
Met Pro Thr Val Val Ile Ala Asn Arg Leu Lys Thr Ala Gly Leu Asn
             180                 185                 190
Val Pro Val Gly Lys Phe Glu Ser Gly Ser Lys Glu Thr Ser Tyr Arg
             195                 200                 205
Thr Leu Gly Arg Tyr Glu Ser Leu Ser Gln Ile Glu Asn Thr Ile Val
             210                 215                 220
Ser Phe Ser Gly Glu Val Gly Asn Ala Val Leu Ile Lys Gln Leu Gly
225                 230                 235                 240
Thr Val Arg Asp Gly Thr Glu Asp Glu Thr Ile Gly Tyr Leu Trp
             245                 250                 255
Ala Ser Gln Gly Glu Gly Val Glu Glu Lys Val Ser Phe Leu Thr Lys
             260                 265                 270
Ile Gly Asn Phe Phe Lys Gly Lys Lys Glu Asn Ser Ala Thr Ala Ile
             275                 280                 285
Lys Glu Thr Lys Pro Ala Leu Phe Ile Asp Val Tyr Lys Gln Ser Gly
290                 295                 300
Ala Asn Thr Val Ser Val Ala Asp Glu Val Leu Lys Arg Ile Gly Lys
305                 310                 315                 320
Leu Asn Glu Gly Ile Gln Asn Leu Glu Gly Lys Pro Lys Ile Arg Leu
                 325                 330                 335
Ile Arg Asp Gly Ser Lys Trp Ile Arg Tyr Asn Val Glu Asp Val Thr
             340                 345                 350
Glu Ala Ile Val Ile Gly Ile Leu Leu Ala Val Ile Thr Val Tyr Phe
             355                 360                 365
Phe Leu Gly Asn Phe Arg Ser Thr Val Ile Thr Gly Leu Ala Leu Pro
             370                 375                 380
Asn Ser Met Leu Gly Ala Phe Val Leu Met Trp Thr Met Gly Phe Thr
385                 390                 395                 400
Ile Asn Val Met Thr Leu Leu Ala Leu Ser Leu Ala Val Gly Leu Leu
                 405                 410                 415
Val Asp Asp Ala Ile Val Val Arg Glu Asn Ile Phe Arg Lys Leu Glu
             420                 425                 430
```

```
Glu Gly Lys Gly Val Met Glu Ala Ala Glu Thr Gly Thr Glu Val
            435                 440                 445
Thr Leu Ala Val Ile Gly Thr Ser Leu Thr Val Ile Ala Val Phe Leu
    450                 455                 460
Pro Val Gly Phe Leu Ser Gly Ile Val Gly Gln Phe Phe Lys Gln Phe
465                 470                 475                 480
Gly Leu Thr Val Val Phe Ala Met Leu Ile Ser Leu Phe Asp Gly Leu
                485                 490                 495
Ala Val Ala Pro Met Leu Ser Ala Tyr Phe Ala Gly Lys Ile Asp His
            500                 505                 510
Asn Ala Lys Pro Asn Lys Ala Val Glu Leu Phe Asp Lys Phe Gln Thr
        515                 520                 525
Trp Leu Glu Arg Gln Tyr Gly Lys Val Met Lys Val Ala Leu Lys Arg
    530                 535                 540
Pro Gly Ile Val Leu Leu Leu Ser Leu Gly Ile Phe Ile Leu Ser Ile
545                 550                 555                 560
Leu Ser Leu Lys Leu Val Lys Ser Thr Phe Leu Pro Ala Asn Asp Gln
                565                 570                 575
Gly Glu Phe Leu Val Thr Leu Asp Leu Pro Pro Gly Thr Ser Leu Asn
            580                 585                 590
Gly Thr Lys Gln Val Ala Asp Gln Val Leu Glu Val Leu Lys Lys Ile
        595                 600                 605
Pro Glu Met Glu Met Ile Ala Val Thr Ile Gly Lys Pro Asp Gly Gly
    610                 615                 620
Glu Pro Asn Ala Gly Thr Leu Ala Ile Thr Leu Val Asp Ser Lys Lys
625                 630                 635                 640
Arg Lys Leu Thr Thr Thr Gln Val Lys Asp Gln Ile Arg Glu Leu Leu
                645                 650                 655
Lys Pro Phe Glu Tyr Ala Arg Pro Ala Val Ser Asp Tyr Ser Ala Val
            660                 665                 670
Gly Gly Gly Ile Gln Tyr Pro Phe Gln Leu Val Ile Lys Gly Glu Asn
        675                 680                 685
Leu Gly Glu Met Glu Ala Tyr Ser Lys Lys Val Leu Thr Lys Leu Lys
    690                 695                 700
Ser Leu Ser Asp Leu Ala Asp Leu Asp Thr Asp Tyr Arg Ala Gly Lys
705                 710                 715                 720
Pro Glu Tyr Gln Ile His Leu Asp Asn Met Lys Met Gln Leu Val Gly
                725                 730                 735
Val Leu Pro Gly Val Ala Gly Ser Glu Leu Arg Tyr Gln Ile Ala Gly
            740                 745                 750
Asp Glu Val Ser Lys Phe Tyr Asp Arg Gly Ile Glu Tyr Val Val Lys
        755                 760                 765
Met Arg Leu Arg Pro Asp Gln Arg Asn Leu Arg Met Ala Tyr Asp Gln
    770                 775                 780
Thr Lys Val Pro Asn Ile Ala Asn Lys Leu Ile Pro Leu Ser Ala Ile
785                 790                 795                 800
Ser Val Gly Lys Glu Thr Ala Gly Pro Ser Arg Ile Asn Arg Ile Asp
                805                 810                 815
Arg Ala Arg Thr Ile Val Ile Asn Ala Asn Leu Ala Pro Gly Gly Ala
            820                 825                 830
Val Gln Asp Ala Thr Arg Ile Ala Asp Glu Ile Leu Arg Lys Glu Leu
        835                 840                 845
Pro Pro Pro Pro Gly Ile Arg Tyr Asn Phe Gln Gly Gln Ser Glu Asp
```

Phe Lys Glu Leu Leu Ala Asn Ile Val Leu Ala Phe Gly Leu Ala Leu
865                 870                 875                 880

Val Phe Ile Tyr Leu Val Leu Ala Ser Leu Tyr Glu Ser Phe Ile Thr
            885                 890                 895

Pro Val Thr Ile Leu Phe Ala Ile Pro Pro Ala Ile Ser Gly Ala Phe
        900                 905                 910

Phe Ala Leu Ala Leu Thr Arg Glu Met Leu Asn Leu Phe Ser Met Ile
            915                 920                 925

Gly Leu Ile Leu Leu Met Gly Leu Val Ala Lys Asn Ser Ile Leu Leu
        930                 935                 940

Val Asp Tyr Ala Met Gln Ala Ser Arg Glu Lys Gly Met Ser Arg Asn
945                 950                 955                 960

Asp Ala Ile Tyr Glu Ala Gly Leu Val Arg Leu Arg Pro Ile Leu Met
            965                 970                 975

Thr Ser Leu Ala Met Ile Met Gly Thr Val Pro Ile Ala Leu Gly Phe
        980                 985                 990

Gly Glu Ala Ala Lys Ser Arg Thr Ala Met Gly Ile Ala Ile Ile Gly
            995                 1000                1005

Gly Leu Ile Leu Ser Thr Val Val Thr Leu Val Val Val Pro Ser
        1010                1015                1020

Ile Phe Gly Phe Ile Asp Arg Phe Arg Glu Trp Ile Glu Ser Lys
        1025                1030                1035

Phe Arg Pro Glu Tyr Asp Met Asn Ala Ser Met Val Gln His Ala
        1040                1045                1050

Pro Ser Thr Asn Lys Gln Lys Phe Tyr Glu Lys Glu Trp Ala Ser
        1055                1060                1065

Met Gln Glu Glu Val Glu Val Glu Leu Pro Lys Lys Ser Lys Lys
        1070                1075                1080

<210> SEQ ID NO 139
<211> LENGTH: 543
<212> TYPE: DNA
<213> ORGANISM: Artificial Sequence
<220> FEATURE:
<223> OTHER INFORMATION: LIC10380

<400> SEQUENCE: 139
atgaaaattt ttgcactgag tattttagtt ttagtagttt tacttgtagc gttcttgttt      60
tatatgggcg cttttaatcg ggttttggtt caagaggaaa tgaaaggacc gttttacgtt     120
ctttcgcatg aaaggattgg agattataga aacgttgggc ttacgtttga agcccttcaa     180
aaagaactgc ctgaaaaagg aattcgaaat tttaaattgt tctcaatata tttggataat     240
ccaaatgagg ttcctaaaga aaaactacga tgtgaagtag gagctctttt ttcggaacca     300
ttagaaaaaa ttccaaatgg actttcttta gagttaaaaa taagaaccat tccttctaaa     360
aaatatctta ccgcggaatt tccattgaga aattttcttt ctattttct tggaatttat     420 aaggtttatc cgaaactttt cagagcctgt gaagaaagag gttgtgatct taaaggaagg     480
gcatccattg aaatttatga acctcttacg aacataaga ctacatatct tctgcctta     540 gat                                                                  543

<210> SEQ ID NO 140
<211> LENGTH: 181
<212> TYPE: PRT
<213> ORGANISM: Artificial Sequence

<220> FEATURE:
<223> OTHER INFORMATION: LIC10380

<400> SEQUENCE: 140

Met Lys Ile Phe Ala Leu Ser Ile Leu Val Leu Val Leu Leu Val
1               5                   10                  15

Ala Phe Leu Phe Tyr Met Gly Ala Phe Asn Arg Val Leu Val Gln Glu
                20                  25                  30

Glu Met Lys Gly Pro Phe Tyr Val Leu Ser His Glu Arg Ile Gly Asp
            35                  40                  45

Tyr Arg Asn Val Gly Leu Thr Phe Glu Ala Leu Gln Lys Glu Leu Pro
        50                  55                  60

Glu Lys Gly Ile Arg Asn Phe Lys Leu Phe Ser Ile Tyr Leu Asp Asn
65                  70                  75                  80

Pro Asn Glu Val Pro Lys Glu Lys Leu Arg Cys Glu Val Gly Ala Leu
                85                  90                  95

Phe Ser Glu Pro Leu Glu Lys Ile Pro Asn Gly Leu Ser Leu Glu Leu
            100                 105                 110

Lys Ile Arg Thr Ile Pro Ser Lys Lys Tyr Leu Thr Ala Glu Phe Pro
        115                 120                 125

Leu Arg Asn Phe Leu Ser Ile Phe Leu Gly Ile Tyr Lys Val Tyr Pro
    130                 135                 140

Lys Leu Phe Arg Ala Cys Glu Glu Arg Gly Cys Asp Leu Lys Gly Arg
145                 150                 155                 160

Ala Ser Ile Glu Ile Tyr Glu Pro Leu Thr Glu His Lys Thr Thr Tyr
                165                 170                 175

Leu Leu Pro Leu Asp
            180

<210> SEQ ID NO 141
<211> LENGTH: 1113
<212> TYPE: DNA
<213> ORGANISM: Artificial Sequence
<220> FEATURE:
<223> OTHER INFORMATION: LIC10551

<400> SEQUENCE: 141
gtgccaatga tgggaaaaaa aatcggatat gtcgcgcttg gaatttttatt tttactactg    60
ttactgtatt ggatcggaca aggtcctaga gtttctatac ccaaggatat aaaacctgga   120
gcggaatttg ttttttccagg agaggaaaag actacagaag aaactctttc tcttttgatt   180
tcgtctctca agaaaaaata ccaacccggt ggagtaaaac gagatgcaca tccatttgca   240
cacggttgtg ttaaagcaag ttttacggtt tcttcttcta ttccagaaga atttaaattt   300
ggaatattca aatcttctaa aacgtatcca gcttggattc gattttcaaa cggttccatt   360
acgaaaaaat cggatcaaga aggagatatt agaggaatgg gaattaaaact tttaggtgtg   420
gacggaccta aattgtctgc ggacgaaaat agaacccaag atttttttact gatcaatcat   480
cccgttcttc ctgtgggtgc acccgatgag tatttggctc ttttttcaagc tgcatttgct   540
aaaaagccta tgtcttactt tttgggagga atgccttgga actggaagtt aactgctttg   600
caggaatcta tttcgattcg aagaaaaaaa attccagacg ttttagaaat tcgttattgg   660
agtacaactc catatcgttt ggggaatgaa accagcgccg taaatattc tgcaatacct   720
tgcgaaacaa aaaaattgga agttccaaaa aatccagcgg acgattatct tcgccaaacg   780
atgatttctc atcttaaaga aaagtctgct tgttttgaat ttatgattca gaaacaagga   840

```
aatccgatct ctatgccgat tgaagatccg gctgttcatt ggaacgaaaa agattctcct    900
ttcattgcgg ttgctaaaat agaaatccct aaacaagagt ttgcaactcc agaacaggat    960
cgttttgcg aaaatctttc attaaatcct tggcattctt tggccgagca ccgacctcta   1020
ggagggatta atcgtattcg aaaagttgca tatgaaacga tcgcaaaata tagacacgag   1080
cagaatggga taaacaatt agaaccgacc gaa                                 1113
```

<210> SEQ ID NO 142
<211> LENGTH: 371
<212> TYPE: PRT
<213> ORGANISM: Artificial Sequence
<220> FEATURE:
<223> OTHER INFORMATION: LIC10551

<400> SEQUENCE: 142

```
Met Pro Met Met Gly Lys Lys Ile Gly Tyr Val Ala Leu Gly Ile Leu
1               5                   10                  15

Phe Leu Leu Leu Leu Tyr Trp Ile Gly Gln Gly Pro Arg Val Ser
            20                  25                  30

Ile Pro Lys Asp Ile Lys Pro Gly Ala Glu Phe Val Phe Pro Gly Glu
        35                  40                  45

Glu Lys Thr Thr Glu Glu Thr Leu Ser Leu Leu Ile Ser Ser Leu Lys
    50                  55                  60

Glu Lys Tyr Gln Pro Gly Gly Val Lys Arg Asp Ala His Pro Phe Ala
65                  70                  75                  80

His Gly Cys Val Lys Ala Ser Phe Thr Val Ser Ser Ile Pro Glu
                85                  90                  95

Glu Phe Lys Phe Gly Ile Phe Lys Ser Ser Lys Thr Tyr Pro Ala Trp
            100                 105                 110

Ile Arg Phe Ser Asn Gly Ser Ile Thr Lys Lys Ser Asp Gln Glu Gly
        115                 120                 125

Asp Ile Arg Gly Met Gly Ile Lys Leu Leu Gly Val Asp Gly Pro Lys
    130                 135                 140

Leu Ser Ala Asp Glu Asn Arg Thr Gln Asp Phe Leu Leu Ile Asn His
145                 150                 155                 160

Pro Val Leu Pro Val Gly Ala Pro Asp Glu Tyr Leu Ala Leu Phe Gln
                165                 170                 175

Ala Ala Phe Ala Lys Lys Pro Met Ser Tyr Phe Leu Gly Gly Met Pro
            180                 185                 190

Trp Asn Trp Lys Leu Thr Ala Leu Gln Glu Ser Ile Ser Ile Arg Arg
        195                 200                 205

Lys Lys Ile Pro Asp Val Leu Glu Ile Arg Tyr Trp Ser Thr Thr Pro
    210                 215                 220

Tyr Arg Leu Gly Asn Glu Thr Ser Ala Val Lys Tyr Ser Ala Ile Pro
225                 230                 235                 240

Cys Glu Thr Lys Lys Leu Glu Val Pro Lys Asn Pro Ala Asp Asp Tyr
                245                 250                 255

Leu Arg Gln Thr Met Ile Ser His Leu Lys Glu Lys Ser Ala Cys Phe
            260                 265                 270

Glu Phe Met Ile Gln Lys Gln Gly Asn Pro Ile Ser Met Pro Ile Glu
        275                 280                 285

Asp Pro Ala Val His Trp Asn Glu Lys Asp Ser Pro Phe Ile Ala Val
    290                 295                 300

Ala Lys Ile Glu Ile Pro Lys Gln Glu Phe Ala Thr Pro Glu Gln Asp
305                 310                 315                 320
```

Arg Phe Cys Glu Asn Leu Ser Leu Asn Pro Trp His Ser Leu Ala Glu
            325                 330                 335

His Arg Pro Leu Gly Gly Ile Asn Arg Ile Arg Lys Val Ala Tyr Glu
            340                 345                 350

Thr Ile Ala Lys Tyr Arg His Glu Gln Asn Gly Ile Lys Gln Leu Glu
            355                 360                 365

Pro Thr Glu
    370

<210> SEQ ID NO 143
<211> LENGTH: 789
<212> TYPE: DNA
<213> ORGANISM: Artificial Sequence
<220> FEATURE:
<223> OTHER INFORMATION: LIC10740

<400> SEQUENCE: 143
gtggatatga attggcaaaa cattaaagaa tctgcaaata cgattaaaga tacaatttgg    60
gaagcggccc taagagcggt agaaaaaatc aatcaaggat acctttggct ttttcgtact   120
gcgagcgagg acgagtttc tcgtaaaacc ttatttctca cttattcgtg gatcggggtc    180
gttttatttt ttacttcgtt tatactttcg ggtaacagtc cttttgtcac tttagtccca   240
ttttcacttt atgagttagg taaccgggat cataggaccg aaataacaat ttacgtttct   300
gatggagaac gccaggtctt tccggttcgt agaaaagttc ttttggagga tgaagagttt   360
cgtcataaaa cgatgatact catcggagaa attagcgaat cttcttattt tgataaaacc   420
ttagagggag gaaaaggaga acattataaa aatctaaagc gtcttcccga atccaatac    480 gcggtaaaag cgatttggaa aaacggagga acattgattt tagattttag aaaatccact   540
cttcaggaaa ttctttctgg aatgaaattt agaatcgatt atacttatgc tcgaaggatg   600
aacgacgaag aaaaacaaaa ggaaatcgct cgaaaaaaaa tggcactttt ggattctacc   660
tttctagctt tggaaaaaac cgtttttcgag aattttcaag acattcagag cgtggaatat   720
aggttagacg ggttatccga aaacatctcc ggaatggaat attctctcga tttatcacat   780
aaaaggaat                                                           789

<210> SEQ ID NO 144
<211> LENGTH: 263
<212> TYPE: PRT
<213> ORGANISM: Artificial Sequence
<220> FEATURE:
<223> OTHER INFORMATION: LIC10740

<400> SEQUENCE: 144

Met Asp Met Asn Trp Gln Asn Ile Lys Glu Ser Ala Asn Thr Ile Lys
1               5                   10                  15

Asp Thr Ile Trp Glu Ala Ala Leu Arg Ala Val Glu Lys Ile Asn Gln
            20                  25                  30

Gly Tyr Leu Trp Leu Phe Arg Thr Ala Ser Glu Asp Gly Val Ser Arg
        35                  40                  45

Lys Thr Leu Phe Leu Thr Tyr Ser Trp Ile Gly Val Val Leu Phe Phe
    50                  55                  60

Thr Ser Phe Ile Leu Ser Gly Asn Ser Pro Phe Val Thr Leu Val Pro
65                  70                  75                  80

Phe Ser Leu Tyr Glu Leu Gly Asn Arg Asp His Arg Thr Glu Ile Thr
                85                  90                  95

```
Ile Tyr Val Ser Asp Gly Glu Arg Gln Val Phe Pro Val Arg Arg Lys
                100                 105                 110

Val Leu Leu Glu Asp Glu Glu Phe Arg His Lys Thr Met Ile Leu Ile
            115                 120                 125

Gly Glu Ile Ser Glu Ser Ser Tyr Phe Asp Lys Thr Leu Glu Gly Gly
        130                 135                 140

Lys Gly Glu His Tyr Lys Asn Leu Lys Arg Leu Pro Glu Ile Gln Tyr
145                 150                 155                 160

Ala Val Lys Ala Ile Trp Lys Asn Gly Gly Thr Leu Ile Leu Asp Phe
                165                 170                 175

Arg Lys Ser Thr Leu Gln Glu Ile Leu Ser Gly Met Lys Phe Arg Ile
            180                 185                 190

Asp Tyr Thr Tyr Ala Arg Arg Met Asn Asp Glu Glu Lys Gln Lys Glu
        195                 200                 205

Ile Ala Arg Lys Lys Met Ala Leu Leu Asp Ser Thr Phe Leu Ala Leu
210                 215                 220

Glu Lys Thr Val Phe Glu Asn Phe Gln Asp Ile Gln Ser Val Glu Tyr
225                 230                 235                 240

Arg Leu Asp Gly Leu Ser Glu Asn Ile Ser Gly Met Glu Tyr Ser Leu
                245                 250                 255

Asp Leu Ser His Lys Arg Asn
            260
```

<210> SEQ ID NO 145
<211> LENGTH: 939
<212> TYPE: DNA
<213> ORGANISM: Artificial Sequence
<220> FEATURE:
<223> OTHER INFORMATION: LIC11580

<400> SEQUENCE: 145

| | | | | | |
|---|---|---|---|---|---|
| atgaaaaaag | aaaaagagtt | tccggaagaa | actgcgctga | ccccagaaga | agaagagttt | 60 |
| ttgactctgg | agcttcagga | agaggaagaa | gctgtttctc | gttttacgtt | caaacaaaaa | 120 |
| ttaattctga | tcggaaccgg | aattttttcg | tttctcattt | ttacggtttg | gcttttcct | 180 |
| ttagatgaga | ttgtacgtag | ttctttgtat | tcttcatccg | taaaaacggg | aacgattatt | 240 |
| aattttagag | atctgagtat | ttccgttttg | ggaaatgtaa | ctttagattc | tctcgaagtt | 300 |
| acaacttctt | ccaatctcaa | aatcaaagcg | aagaagcgg | ttctaaagac | ttctttgttt | 360 |
| ggtttgatta | agaaaaaatt | cgatgggaaa | tttaaattgg | tttccttaaa | aatcgatacc | 420 |
| gaaaatggac | ctttagcaaa | gatacgtaac | tttgaaggca | aaggaaaatt | tgataactta | 480 |
| gaccaaggta | tttctagaat | aaatggtgcg | ttggatttgg | aaattcctgc | agggccttct | 540 |
| tcgggaatga | ttcaggagct | tccggaaatt | ccactttag | gtgaactgaa | aaatataacg | 600 |
| attaaaaaat | ttcttacaaa | agtgaatctt | caaggtggaa | atctgatttt | caacgatttt | 660 |
| acgttagata | catcgattgc | acgttttgat | attactggaa | atattcgatt | atcggaaaat | 720 |
| atgtcttttt | ctcaactgaa | tcttagaatt | tgtctagaac | tcgatcgcaa | ctttgctttg | 780 |
| gaaagacaag | atatagcgga | tatgttgact | cttttagaaa | acaaagtgg | aagtaaatgt | 840 |
| attcctgtga | tgggaacctt | tggtaaaccg | gatgtaaaaa | ttccaggact | tactggaccg | 900 |
| cctgcgctgc | cgggaactcc | gccagttcct | ggaagtccg | | | 939 |

<210> SEQ ID NO 146
<211> LENGTH: 313
<212> TYPE: PRT

<213> ORGANISM: Artificial Sequence
<220> FEATURE:
<223> OTHER INFORMATION: LIC11580

<400> SEQUENCE: 146

Met Lys Lys Glu Lys Glu Phe Pro Glu Thr Ala Leu Thr Pro Glu
1               5                   10                  15

Glu Glu Glu Phe Leu Thr Leu Glu Leu Gln Glu Glu Glu Ala Val
            20                  25                  30

Ser Arg Phe Thr Phe Lys Gln Lys Leu Ile Leu Ile Gly Thr Gly Ile
        35                  40                  45

Phe Ser Phe Leu Ile Phe Thr Val Trp Leu Phe Pro Leu Asp Glu Ile
    50                  55                  60

Val Arg Ser Ser Leu Tyr Ser Ser Ser Val Lys Thr Gly Thr Ile Ile
65                  70                  75                  80

Asn Phe Arg Asp Leu Ser Ile Ser Val Leu Gly Asn Val Thr Leu Asp
                85                  90                  95

Ser Leu Glu Val Thr Thr Ser Ser Asn Leu Lys Ile Lys Ala Glu Glu
            100                 105                 110

Ala Val Leu Lys Thr Ser Leu Phe Gly Leu Ile Lys Lys Lys Phe Asp
        115                 120                 125

Gly Lys Phe Lys Leu Val Ser Leu Lys Ile Asp Thr Glu Asn Gly Pro
    130                 135                 140

Leu Ala Lys Ile Arg Asn Phe Glu Gly Lys Gly Lys Phe Asp Asn Leu
145                 150                 155                 160

Asp Gln Gly Ile Ser Arg Ile Asn Gly Ala Leu Asp Leu Glu Ile Pro
                165                 170                 175

Ala Gly Pro Ser Ser Gly Met Ile Gln Glu Leu Pro Glu Ile Pro Leu
            180                 185                 190

Leu Gly Glu Leu Lys Asn Ile Thr Ile Lys Lys Phe Leu Thr Lys Val
        195                 200                 205

Asn Leu Gln Gly Gly Asn Leu Ile Phe Asn Asp Phe Thr Leu Asp Thr
    210                 215                 220

Ser Ile Ala Arg Phe Asp Ile Thr Gly Asn Ile Arg Leu Ser Glu Asn
225                 230                 235                 240

Met Ser Phe Ser Gln Leu Asn Leu Arg Ile Cys Leu Glu Leu Asp Arg
                245                 250                 255

Asn Phe Ala Leu Glu Arg Gln Asp Ile Ala Asp Met Leu Thr Leu Leu
            260                 265                 270

Glu Lys Gln Ser Gly Ser Lys Cys Ile Pro Val Met Gly Thr Phe Gly
        275                 280                 285

Lys Pro Asp Val Lys Ile Pro Gly Leu Thr Gly Pro Ala Leu Pro
    290                 295                 300

Gly Thr Pro Pro Val Pro Gly Ser Pro
305                 310

<210> SEQ ID NO 147
<211> LENGTH: 3597
<212> TYPE: DNA
<213> ORGANISM: Artificial Sequence
<220> FEATURE:
<223> OTHER INFORMATION: LIC11990

<400> SEQUENCE: 147
atggctgagg cgaattctac cccattgagc gaagctgaat tagagcaagt tcgttctatt      60
ctacagcctc tatccaaaaa tccggacatt tcggaagaac tcaatccgat gctttccgta     120

-continued

```
ttccgccaaa aaatgggata cggaactcag atgtcttctc acgacgatga agacatagag    180
gaagaaacag aatctaattc tgactttgaa gaagggaag aagaattcgc acaatctgaa     240
agtcctcaaa gacccccac taaagttttc gaagacgacg atatagattt agacgaactc     300
ttagcagaac caggacaagc tccgacggca agcccgccga ctgatgattt ttcttttgaa    360
gaagaaccca gcgcagactc aggtgatcca tttgcagatt ttggaatgga ttccgaacca    420
gcttctgatt cgttggatga tttcggattg cccgaaactt ctccgacaag tgactccgat    480
gatttctctt tgggggaaga atcgacccaa aacgcagata cgtccgatcc ttttggcgat    540
ttagcagaat caacatccga agatccattc agtggaaccg actttagttc ggagccgata    600
gatgattttt cttcaacacc aactacatct tccgacttag atccattcgc ggatacattc    660
acttctactc cggacacgtc tggagatcca tttgcggaca tgggaagctt agaaacttca    720
agttcgggag aagacgattt tggactttct ggatcagggt ctgacaatga agttacgtct    780
tccgaaccgt ccccaaccga cgatgatttt tttagccagc caatagattc tgaaccttct    840
tcgacggaaa ccgatccttt tgcagacttt ggcgatctag gttctccggc aagtggagga    900
caggatccat tttcagatct ttcttcttcg gctacagttt cggaagatcc ttttgcagac    960
tttgttcctt ccaccgaaga agacacgtta tccgacattg tcacaggcgc agatgcgtcc   1020
ttcgacacct ttagtcccga tttagaatcg gatacaggag gaggagaaga ttttgattcc   1080
ggaagttctt tcggtctgga agcagaccta caaggacttg caagtgaaga aaaagaagaa   1140
atagacaaag gactcaaaga cgaagaactc gcaatcattc aaaaagaaat tctaagatac   1200
cctcctacac ttcgtcgtgc ggtgatagac gcaatcgttc aagataaact caccccctagg  1260
gatcaaaaag gtcttttaga attaatcaaa attgaaagtt cacctgaaga aatcgcggac   1320
ttcctctccg gcgttttagg agaacccgtt tctgtttctc aaagaatgag tggattttcc   1380
aaagacggag ttccgatcat ttctacagat cctgtttata caaagaagg acttcaaaga   1440
caaaaaaaat taattcgaag aacgatttta ggaatcgccg ctaccatctt tattgtagta   1500
ggtggaacct tattttatag aaattttatt gttcccaaac aagcggccca atactacgat   1560
caaggtttaa ctttaattcg agaagctggc gcttatccta aaaatagtga acaagaaaa    1620
agaaaatttt tcgaagcaga gaatctttc gcgagaggtg agaacatttt accaaaccac    1680
ctcaaatacc tgaatctcta tggaatcgaa tacacacgag ttgaggaata cgatcgggct   1740
tttgaaaaat tattcggcaa ggtaagtccc gattttggag caggaggaga agaaccttct   1800
tctaacgctt gggataaaag agaaaaagta cctatcatca cacttgccaa aggccaagtt   1860
tgggacaaca gtaaacttcc aattgcaggt aaagtcggaa gtgaaaatcg tatgactta    1920
atcgcccaag acggaattca aagaaaaatt ctgaaagcgg gcgcgtatat cgtaatgcgt   1980
ttggaaaaac aaactcacga taatcctaca tataaaaatc ttggaaggtt ccattcttcc   2040
atcatgcctt cgttcaccga atcttcgtta ggtggtggaa agtataaaaa cgatcagtta   2100
gcgatcaatt tttacaaaca ggtttataca gatggcaacg aaccctacga cgaagaatct   2160
accgctggaa tcgcaaaaat ttattacaac cgtagagaat tcggtaaagc cgcatccttt   2220
tataataaaa ttgtagaaat cgatccatca agtccaatgg acaaggcgg tttactttcc   2280
acttatatag agatgtggaa agaagatgga atcctcaat tgtcatcaa tcatcataga    2340
caaatcaaaa ataacttgga gatagaaaaa aaactttctc ttcacgttct ttctaaactc   2400
gcttcctttt acacaaatct gaacaaaaaa gaattaagaa ttcgttataa tatcaatccg   2460
```

```
atagatcagg tttccggaat ggaagttaac gataacgctc ttgaaatttt agatttgatt   2520
tatcataaaa ctgaaaaaga tccaatcacc ggcacagaaa tcgaaggttc taattacgcg   2580
gaaggatatt accaaagagg aagatatttt gcctcgatca agaatcaat  ccaagctaga   2640 agattttttg aaaaagcggc tacactggat ccagcacatt atttagcttc tatggaactt   2700
ggggaaaacg caattcgttt ggcaaacttt ggagaagcgg ataaattatt aaacgaatct   2760
cttaaacgtt ttgaaaactt caaacaaagt tacggtgcaa gagaagaaga cgaaacttta   2820
atccaaggaa acgttggccg tatctatttt gacaaagcga aatacaata  tttatctgca   2880 gcaggaatcc acgaaaagga taagatcaca gaatttccag gccgtaaaat ttatccattc   2940
cgagcaaggg ccgccatgga tacagtcgct aaaaccaggt cgatggaact caaaaattct   3000
ttggaaggtt tttctaaagc ggaatcggtt caaactgacg aaaacgaata tactctgatc   3060
cgcagatgga gaacccctct tcctcccgaa attcaaagag aacttcgtta ttttaaaggt   3120
tgggtggatt atatgagcgg tgattttgcc gcttctttaa atgaatggtc cggttttgaa   3180
gacgaagaag aatacaatca ttccaccttg ctcatgggca aagcaaatgc cttttttat    3240 accggccaat acaaagcaag tttaggaaac taccttaaag ttcaagacga tatggaagaa   3300
aaacttttga atatgggact tcctaaaccg gacgatccat atcaccaaga agtatatcaa   3360
acgttagtcg cagcttacaa taacattggc gccgtttatg aaaaacaagg aaacacttcg   3420
gaagctctaa acactattg  gaaagcaatc gaaaccgcaa gaaaaattaa cgaagtttct   3480
gaaattgcaa tgtcaaacaa agatcttatg ttcaaaaaag aagccatcgg acaagacccc   3540
cttttggaag actggctttc tcctacgtta gacagcatta aaaaattaac aagagaa      3597
```

<210> SEQ ID NO 148
<211> LENGTH: 1199
<212> TYPE: PRT
<213> ORGANISM: Artificial Sequence
<220> FEATURE:
<223> OTHER INFORMATION: LIC11990

<400> SEQUENCE: 148

```
Met Ala Glu Ala Asn Ser Thr Pro Leu Ser Glu Ala Glu Leu Glu Gln
1               5                   10                  15

Val Arg Ser Ile Leu Gln Pro Leu Ser Lys Asn Pro Asp Ile Ser Glu
            20                  25                  30

Glu Leu Asn Pro Met Leu Ser Val Phe Arg Gln Lys Met Gly Tyr Gly
        35                  40                  45

Thr Gln Met Ser Ser His Asp Asp Glu Asp Ile Glu Glu Glu Thr Glu
    50                  55                  60

Ser Asn Ser Asp Phe Glu Glu Gly Glu Glu Phe Ala Gln Ser Glu
65                  70                  75                  80

Ser Pro Gln Arg Pro Pro Thr Lys Val Phe Glu Asp Asp Ile Asp
                85                  90                  95

Leu Asp Glu Leu Leu Ala Glu Pro Gly Gln Ala Pro Thr Ala Ser Pro
            100                 105                 110

Pro Thr Asp Asp Phe Ser Phe Glu Glu Glu Pro Ser Ala Asp Ser Gly
        115                 120                 125

Asp Pro Phe Ala Asp Phe Gly Met Asp Ser Glu Pro Ala Ser Asp Ser
    130                 135                 140

Leu Asp Asp Phe Gly Leu Pro Glu Thr Ser Pro Thr Ser Asp Ser Asp
145                 150                 155                 160

Asp Phe Ser Phe Gly Glu Glu Ser Thr Gln Asn Ala Asp Thr Ser Asp
```

-continued

```
                165                 170                 175
Pro Phe Gly Asp Leu Ala Glu Ser Thr Ser Glu Asp Pro Phe Ser Gly
                180                 185                 190
Thr Asp Phe Ser Ser Glu Pro Ile Asp Asp Phe Ser Ser Thr Pro Thr
                195                 200                 205
Thr Ser Ser Asp Leu Asp Pro Phe Ala Asp Thr Phe Thr Ser Thr Pro
                210                 215                 220
Asp Thr Ser Gly Asp Pro Phe Ala Asp Met Gly Ser Leu Glu Thr Ser
225                 230                 235                 240
Ser Ser Gly Glu Asp Asp Phe Gly Leu Ser Gly Ser Gly Ser Asp Asn
                245                 250                 255
Glu Val Thr Ser Ser Glu Pro Ser Pro Thr Asp Asp Phe Phe Ser
                260                 265                 270
Gln Pro Ile Asp Ser Glu Pro Ser Ser Thr Glu Thr Asp Pro Phe Ala
                275                 280                 285
Asp Phe Gly Asp Leu Gly Ser Pro Ala Ser Gly Gln Asp Pro Phe
                290                 295                 300
Ser Asp Leu Ser Ser Ser Ala Thr Val Ser Glu Asp Pro Phe Ala Asp
305                 310                 315                 320
Phe Val Pro Ser Thr Glu Glu Asp Thr Leu Ser Asp Ile Val Thr Gly
                325                 330                 335
Ala Asp Ala Ser Phe Asp Thr Phe Ser Pro Asp Leu Glu Ser Asp Thr
                340                 345                 350
Gly Gly Gly Glu Asp Phe Asp Ser Gly Ser Ser Phe Gly Leu Glu Ala
                355                 360                 365
Asp Leu Gln Gly Leu Ala Ser Glu Glu Lys Glu Ile Asp Lys Gly
                370                 375                 380
Leu Lys Asp Glu Glu Leu Ala Ile Ile Gln Lys Glu Ile Leu Arg Tyr
385                 390                 395                 400
Pro Pro Thr Leu Arg Arg Ala Val Ile Asp Ala Ile Val Gln Asp Lys
                405                 410                 415
Leu Thr Pro Arg Asp Gln Lys Gly Leu Leu Glu Leu Ile Lys Ile Glu
                420                 425                 430
Ser Ser Pro Glu Glu Ile Ala Asp Phe Leu Ser Gly Val Leu Gly Glu
                435                 440                 445
Pro Val Ser Val Ser Gln Arg Met Ser Gly Phe Ser Lys Asp Gly Val
                450                 455                 460
Pro Ile Ile Ser Thr Asp Pro Val Tyr Thr Lys Glu Gly Leu Gln Arg
465                 470                 475                 480
Gln Lys Lys Leu Ile Arg Arg Thr Ile Leu Gly Ile Ala Ala Thr Ile
                485                 490                 495
Phe Ile Val Val Gly Gly Thr Leu Phe Tyr Arg Asn Phe Ile Val Pro
                500                 505                 510
Lys Gln Ala Ala Gln Tyr Tyr Asp Gln Gly Leu Thr Leu Ile Arg Glu
                515                 520                 525
Ala Gly Ala Tyr Pro Lys Asn Ser Glu Thr Arg Lys Arg Lys Phe Phe
                530                 535                 540
Glu Ala Glu Glu Ser Phe Ala Arg Gly Glu Asn Ile Leu Pro Asn His
545                 550                 555                 560
Leu Lys Tyr Leu Asn Leu Tyr Gly Ile Glu Tyr Thr Arg Val Glu Glu
                565                 570                 575
Tyr Asp Arg Ala Phe Glu Lys Leu Phe Gly Lys Val Ser Pro Asp Phe
                580                 585                 590
```

Gly Ala Gly Gly Glu Glu Pro Ser Ser Asn Ala Trp Asp Lys Arg Glu
        595                 600                 605

Lys Val Pro Ile Ile Thr Leu Ala Lys Gly Gln Val Trp Asp Asn Ser
    610                 615                 620

Lys Leu Pro Ile Ala Gly Lys Val Gly Ser Glu Asn Arg Met Thr Leu
625                 630                 635                 640

Ile Ala Gln Asp Gly Ile Gln Arg Lys Ile Leu Lys Ala Gly Ala Tyr
                645                 650                 655

Ile Val Met Arg Leu Glu Lys Gln Thr His Asp Asn Pro Thr Tyr Lys
            660                 665                 670

Asn Leu Gly Arg Phe His Ser Ser Ile Met Pro Ser Phe Thr Glu Ser
        675                 680                 685

Ser Leu Gly Gly Gly Lys Tyr Lys Asn Asp Gln Leu Ala Ile Asn Phe
    690                 695                 700

Tyr Lys Gln Val Tyr Thr Asp Gly Asn Glu Pro Tyr Asp Glu Glu Ser
705                 710                 715                 720

Thr Ala Gly Ile Ala Lys Ile Tyr Tyr Asn Arg Arg Glu Phe Gly Lys
                725                 730                 735

Ala Ala Ser Phe Tyr Asn Lys Ile Val Glu Ile Asp Pro Ser Ser Pro
            740                 745                 750

Met Gly Gln Gly Gly Leu Leu Ser Thr Tyr Ile Glu Met Trp Lys Glu
        755                 760                 765

Asp Gly Asn Pro Gln Phe Val Ile Asn His His Arg Gln Ile Lys Asn
    770                 775                 780

Asn Leu Glu Ile Glu Lys Lys Leu Ser Leu His Val Leu Ser Lys Leu
785                 790                 795                 800

Ala Ser Phe Tyr Thr Asn Leu Asn Lys Lys Glu Leu Arg Ile Arg Tyr
                805                 810                 815

Asn Ile Asn Pro Ile Asp Gln Val Ser Gly Met Glu Val Asn Asp Asn
            820                 825                 830

Ala Leu Glu Ile Leu Asp Leu Ile Tyr His Lys Thr Glu Lys Asp Pro
        835                 840                 845

Ile Thr Gly Thr Glu Ile Glu Gly Ser Asn Tyr Ala Glu Gly Tyr Tyr
    850                 855                 860

Gln Arg Gly Arg Tyr Phe Ala Ser Ile Lys Glu Ser Ile Gln Ala Arg
865                 870                 875                 880

Arg Phe Phe Glu Lys Ala Ala Thr Leu Asp Pro Ala His Tyr Leu Ala
                885                 890                 895

Ser Met Glu Leu Gly Glu Asn Ala Ile Arg Leu Ala Asn Phe Gly Glu
            900                 905                 910

Ala Asp Lys Leu Leu Asn Glu Ser Leu Lys Arg Phe Glu Asn Phe Lys
        915                 920                 925

Gln Ser Tyr Gly Ala Arg Glu Glu Asp Glu Thr Leu Ile Gln Gly Asn
    930                 935                 940

Val Gly Arg Ile Tyr Phe Asp Lys Ala Arg Ile Gln Tyr Leu Ser Ala
945                 950                 955                 960

Ala Gly Ile His Glu Lys Asp Lys Ile Thr Glu Phe Pro Gly Arg Lys
                965                 970                 975

Ile Tyr Pro Phe Arg Ala Arg Ala Ala Met Asp Thr Val Ala Lys Thr
            980                 985                 990

Arg Ser Met Glu Leu Lys Asn Ser  Leu Glu Gly Phe Ser  Lys Ala Glu
        995                 1000                 1005

| | | | | | | | | | | | | |
|---|---|---|---|---|---|---|---|---|---|---|---|---|
| Ser | Val | Gln | Thr | Asp | Glu | Asn | Glu | Tyr | Thr | Leu | Ile | Arg Arg Trp |
| | 1010 | | | | 1015 | | | | 1020 | | | |
| Arg | Thr | Pro | Leu | Pro | Pro | Glu | Ile | Gln | Arg | Glu | Leu | Arg Tyr Phe |
| 1025 | | | | | 1030 | | | | | 1035 | | |
| Lys | Gly | Trp | Val | Asp | Tyr | Met | Ser | Gly | Asp | Phe | Ala | Ala Ser Leu |
| 1040 | | | | | 1045 | | | | | 1050 | | |
| Asn | Glu | Trp | Ser | Gly | Phe | Glu | Asp | Glu | Glu | Tyr | Asn | His Ser |
| 1055 | | | | | 1060 | | | | | 1065 | | |
| Thr | Leu | Leu | Met | Gly | Lys | Ala | Asn | Ala | Phe | Phe | Tyr | Thr Gly Gln |
| | 1070 | | | | 1075 | | | | | 1080 | | |
| Tyr | Lys | Ala | Ser | Leu | Gly | Asn | Tyr | Leu | Lys | Val | Gln | Asp Asp Met |
| | 1085 | | | | 1090 | | | | | 1095 | | |
| Glu | Glu | Lys | Leu | Leu | Asn | Met | Gly | Leu | Pro | Lys | Pro | Asp Asp Pro |
| | 1100 | | | | 1105 | | | | | 1110 | | |
| Tyr | His | Gln | Glu | Val | Tyr | Gln | Thr | Leu | Val | Ala | Ala | Tyr Asn Asn |
| | 1115 | | | | 1120 | | | | | 1125 | | |
| Ile | Gly | Ala | Val | Tyr | Glu | Lys | Gln | Gly | Asn | Thr | Ser | Glu Ala Leu |
| | 1130 | | | | 1135 | | | | | 1140 | | |
| Lys | His | Tyr | Trp | Lys | Ala | Ile | Glu | Thr | Ala | Arg | Lys | Ile Asn Glu |
| | 1145 | | | | 1150 | | | | | 1155 | | |
| Val | Ser | Glu | Ile | Ala | Met | Ser | Asn | Lys | Asp | Leu | Met | Phe Lys Lys |
| | 1160 | | | | 1165 | | | | | 1170 | | |
| Glu | Ala | Ile | Gly | Gln | Asp | Pro | Leu | Leu | Glu | Asp | Trp | Leu Ser Pro |
| | 1175 | | | | 1180 | | | | | 1185 | | |
| Thr | Leu | Asp | Ser | Ile | Lys | Lys | Leu | Thr | Arg | Glu | | |
| | 1190 | | | | 1195 | | | | | | | |

<210> SEQ ID NO 149
<211> LENGTH: 1923
<212> TYPE: DNA
<213> ORGANISM: Artificial Sequence
<220> FEATURE:
<223> OTHER INFORMATION: LIC12339

<400> SEQUENCE: 149

| | | |
|---|---|---|
| atgggtaatt ggaaaaatct cgtagtagtt tgttagtttt cgattggggt tggattcggg | 60 |
| tatcatacac ttatccacgc ttcttcatca aaagctaatt attcgatcgc tcaaaaaccc | 120 |
| actgatcctc caaaagataa acctattaac atcgttacgc atgatgggaa aacgtattgt | 180 |
| tattctcctg tctttagtaa aggtgaaggt tatgtttgga ttgaaaagtg tggggataat | 240 |
| actgctaaag caagatacga tgtgtttcaa agaatttcgt ataacatcaa taatacatgg | 300 |
| ttatgtatta ctgctccgga gccggtagtt aaaggaaatg caaggtgggg ttatgtgaat | 360 |
| cttagacctt gtactatcaa tgatcctcta caaagatgga tcgtaaaaga aaattccttt | 420 |
| tggactgctg acggaaagta tcgttttaaaa gatacaaatt ggtacggtta tatttctaaa | 480 |
| acctctggag ataactacaa tcatacatta aattcttcga tggataattg ggttaaaaca | 540 |
| gtggctaccc ctggaaatat cagtattcgg acttccattt cttggaattc aggttgggga | 600 |
| gatggaattt gggatatcaa tatggcacct agcgcctact ttattcattc caaaggttcc | 660 |
| agtaaagaag atattatacc tttgtactac aatcctgaaa gtggacatat tgcacagtat | 720 |
| gatccttcaa gtggtcttct cagttgtatg tattctaaga tgacagataa atatgattgg | 780 |
| aattgggttc aatggggaaa atgtagtgac gcacctatta aaaagagaa tccagctttt | 840 |
| tggaacgttt attttgtagc aaatgcagga gggatgatta cagattataa aggaaatatt | 900 |

-continued

```
ttgagagtta ccaaggaggg acccaattgg ggcgttgcct atactgctaa accttcttat    960
ttagaaaagg atactactca tagccctact tctgtgttta ctgtcgatgt agatttactg   1020
aaatggatac gttatactac tagtaatctt ggaaagacgg atcaatattg tccagctggc   1080
aagaaagaaa gtcgtatata tcaaagagta aaaaggaact taccgtctga ttttcaattg   1140
agtgttgctt gggttcaaag actttatgat atagcgagat cagccacatt tgaatctgcg   1200
aaccccggtg cgattccgca gagacatgga gcatgtggtg tttgtttgct tcatagtttt   1260
caaatgatag cagaattaat ggagtatcat tctagagagc ctcttacgag tggaggatat   1320
tttttcaata cagcttctaa tagggatccc tttctttcgt ttagccaacg ttatccggaa   1380
ttggacagat tggtgacaaa tgtacctgtc gattacgcta acagaggtag agtgctcgca   1440
tttgcatctg ctatgattat gttacctcag tatgaatggg agtcctcttc tccgcttact   1500
actcggtctg atatacaatc tcacattaga tcgcttatca attctcctcc tggaagcatt   1560
tggttgggat tattaagaag gcaacgtgca aacggatcta tttcggggca tgccgttcct   1620
attttgagaa cttctgaagg gttagtagta attccaacaa atatgcctac ggcatcgttg   1680
aatacctata ttcaatcttt agcacctact atggatccaa acgaggtaat caataggtta   1740
gaaaatggaa ggactttgac aacacttaca accatacggc cggtaggtac ttatgaaact   1800
cctttagtc tcacggtttc aagtagggat tgtactggag atggggatga cagaagaggt   1860
tcaggaagat atccaatcag ttcattgata aaccaatgtt cgggaggtag atgtattctg   1920
cag                                                                1923
```

<210> SEQ ID NO 150
<211> LENGTH: 641
<212> TYPE: PRT
<213> ORGANISM: Artificial Sequence
<220> FEATURE:
<223> OTHER INFORMATION: LIC12339

<400> SEQUENCE: 150

```
Met Gly Asn Trp Lys Asn Leu Val Val Leu Leu Val Ser Ile Gly
1               5                   10                  15

Val Gly Phe Gly Tyr His Thr Leu Ile His Ala Ser Ser Ser Lys Ala
            20                  25                  30

Asn Tyr Ser Ile Ala Gln Lys Pro Thr Asp Pro Pro Lys Asp Lys Pro
        35                  40                  45

Ile Asn Ile Val Thr His Asp Gly Lys Thr Tyr Cys Tyr Ser Pro Val
    50                  55                  60

Phe Ser Lys Gly Glu Gly Tyr Val Trp Ile Glu Lys Cys Gly Asp Asn
65                  70                  75                  80

Thr Ala Lys Ala Arg Tyr Asp Val Phe Gln Arg Ile Ser Tyr Asn Ile
                85                  90                  95

Asn Asn Thr Trp Leu Cys Ile Thr Ala Pro Glu Pro Val Val Lys Gly
            100                 105                 110

Asn Ala Arg Trp Gly Tyr Val Asn Leu Arg Pro Cys Thr Ile Asn Asp
        115                 120                 125

Pro Leu Gln Arg Trp Ile Val Lys Glu Asn Ser Phe Trp Thr Ala Asp
    130                 135                 140

Gly Lys Tyr Arg Leu Lys Asp Thr Asn Trp Tyr Gly Tyr Ile Ser Lys
145                 150                 155                 160

Thr Ser Gly Asp Asn Tyr Asn His Thr Leu Asn Ser Ser Met Asp Asn
                165                 170                 175
```

Trp Val Lys Thr Val Ala Thr Pro Gly Asn Ile Ser Ile Arg Thr Ser
            180                 185                 190

Ile Ser Trp Asn Ser Gly Trp Gly Asp Gly Ile Trp Asp Ile Asn Met
            195                 200                 205

Ala Pro Ser Ala Tyr Phe Ile His Ser Lys Gly Ser Ser Lys Glu Asp
210                 215                 220

Ile Ile Pro Leu Tyr Tyr Asn Pro Glu Ser Gly His Ile Ala Gln Tyr
225                 230                 235                 240

Asp Pro Ser Ser Gly Leu Leu Ser Cys Met Tyr Ser Lys Met Thr Asp
            245                 250                 255

Lys Tyr Asp Trp Asn Trp Val Gln Trp Gly Lys Cys Ser Asp Ala Pro
            260                 265                 270

Ile Lys Lys Glu Asn Pro Ala Phe Trp Asn Val Tyr Phe Val Ala Asn
            275                 280                 285

Ala Gly Gly Met Ile Thr Asp Tyr Lys Gly Asn Ile Leu Arg Val Thr
            290                 295                 300

Lys Glu Gly Pro Asn Trp Gly Val Ala Tyr Thr Ala Lys Pro Ser Tyr
305                 310                 315                 320

Leu Glu Lys Asp Thr Thr His Ser Pro Thr Ser Val Phe Thr Val Asp
            325                 330                 335

Val Asp Leu Leu Lys Trp Ile Arg Tyr Thr Thr Ser Asn Leu Gly Lys
            340                 345                 350

Thr Asp Gln Tyr Cys Pro Ala Gly Lys Lys Glu Ser Arg Ile Tyr Gln
            355                 360                 365

Arg Val Lys Arg Asn Leu Pro Ser Asp Phe Gln Leu Ser Val Ala Trp
            370                 375                 380

Val Gln Arg Leu Tyr Asp Ile Ala Arg Ser Ala Thr Phe Glu Ser Ala
385                 390                 395                 400

Asn Pro Gly Ala Ile Pro Gln Arg His Gly Ala Cys Gly Val Cys Leu
            405                 410                 415

Leu His Ser Phe Gln Met Ile Ala Glu Leu Met Glu Tyr His Ser Arg
            420                 425                 430

Glu Pro Leu Thr Ser Gly Gly Tyr Phe Phe Asn Thr Ala Ser Asn Arg
            435                 440                 445

Asp Pro Phe Leu Ser Phe Ser Gln Arg Tyr Pro Glu Leu Asp Arg Leu
450                 455                 460

Val Thr Asn Val Pro Val Asp Tyr Ala Asn Arg Gly Arg Val Leu Ala
465                 470                 475                 480

Phe Ala Ser Ala Met Ile Met Leu Pro Gln Tyr Glu Trp Glu Ser Ser
            485                 490                 495

Ser Pro Leu Thr Thr Arg Ser Asp Ile Gln Ser His Ile Arg Ser Leu
            500                 505                 510

Ile Asn Ser Pro Pro Gly Ser Ile Trp Leu Gly Leu Arg Arg Gln
            515                 520                 525

Arg Ala Asn Gly Ser Ile Ser Gly His Ala Val Pro Ile Leu Arg Thr
            530                 535                 540

Ser Glu Gly Leu Val Val Ile Pro Thr Asn Met Pro Thr Ala Ser Leu
545                 550                 555                 560

Asn Thr Tyr Ile Gln Ser Leu Ala Pro Thr Met Asp Pro Asn Glu Val
            565                 570                 575

Ile Asn Arg Leu Glu Asn Gly Arg Thr Leu Thr Thr Leu Thr Thr Ile
            580                 585                 590

Arg Pro Val Gly Thr Tyr Glu Thr Pro Phe Ser Leu Thr Val Ser Ser

```
                    595                 600                 605
Arg Asp Cys Thr Gly Asp Gly Asp Arg Arg Gly Ser Gly Arg Tyr
    610                 615                 620

Pro Ile Ser Ser Leu Ile Asn Gln Cys Ser Gly Arg Cys Ile Leu
625                 630                 635                 640

Gln

<210> SEQ ID NO 151
<211> LENGTH: 540
<212> TYPE: DNA
<213> ORGANISM: Artificial Sequence
<220> FEATURE:
<223> OTHER INFORMATION: LIC12691

<400> SEQUENCE: 151
atgaaaattt tatcatatat tctaggtgga tttgtggcat tgataataat ccttgcgatc     60
atttctccca aggaatttaa attagaaaga gaagttatca tcaatcaacc caaaaacgta    120 gttttacag aacttagatt tctgaaaaat cacgaacagt ggaacgcatg gtctaaaaaa    180
gatcctcaga tgaaaaaaca atttaaagga acagatggca agtcggatt tatttcttct    240 tgggaaagtg aacatccaga gtaggaacg gcagaacaag aaattacaaa catcgtagat    300
ggggaaagac tcgatactca aatccgtttt caaaaacctt ttgaaggaag ttttaattcc    360
tatattacga ctcaatctgt aaatgaaaaa caaacaaaag ttttgatcgg catgtcagat    420
aagatgtcct ttcctatgac agtgattagt tttatagtta atgtttgttt tgatcagcaa    480
cagaaaatca ttcagaactt ggatgatagt ctaaataatc tgaaagttct tctggaaaaa    540

<210> SEQ ID NO 152
<211> LENGTH: 180
<212> TYPE: PRT
<213> ORGANISM: Artificial Sequence
<220> FEATURE:
<223> OTHER INFORMATION: LIC12691

<400> SEQUENCE: 152

Met Lys Ile Leu Ser Tyr Ile Leu Gly Gly Phe Val Ala Leu Ile Ile
1               5                   10                  15

Ile Leu Ala Ile Ile Ser Pro Lys Glu Phe Lys Leu Glu Arg Glu Val
            20                  25                  30

Ile Ile Asn Gln Pro Lys Asn Val Val Phe Thr Glu Leu Arg Phe Leu
        35                  40                  45

Lys Asn His Glu Gln Trp Asn Ala Trp Ser Lys Lys Asp Pro Gln Met
    50                  55                  60

Lys Lys Gln Phe Lys Gly Thr Asp Gly Lys Val Gly Phe Ile Ser Ser
65                  70                  75                  80

Trp Glu Ser Glu His Pro Glu Val Gly Thr Ala Glu Gln Glu Ile Thr
                85                  90                  95

Asn Ile Val Asp Gly Glu Arg Leu Asp Thr Gln Ile Arg Phe Gln Lys
            100                 105                 110

Pro Phe Glu Gly Ser Phe Asn Ser Tyr Ile Thr Thr Gln Ser Val Asn
        115                 120                 125

Glu Lys Gln Thr Lys Val Leu Ile Gly Met Ser Asp Lys Met Ser Phe
    130                 135                 140

Pro Met Thr Val Ile Ser Phe Ile Val Asn Val Cys Phe Asp Gln Gln
145                 150                 155                 160

Gln Lys Ile Ile Gln Asn Leu Asp Asp Ser Leu Asn Asn Leu Lys Val
```

Leu Leu Glu Lys
        180

<210> SEQ ID NO 153
<211> LENGTH: 1005
<212> TYPE: DNA
<213> ORGANISM: Artificial Sequence
<220> FEATURE:
<223> OTHER INFORMATION: LIC12805

<400> SEQUENCE: 153

```
atgttgtatc aatccggtct gaaaagctac aaaaagaaaa ccagttataa accctatatt      60
tttattgccc ttttgctgat tttaagcggg actggatttt tttttcgcca agggattaaa     120
aatctatttg caggtgatag aaaaattctt ctcgaaaaag aaagaaaaaa catccaacaa     180
cagattcgct ccggagctct ggaagaaacc tctgtaaaaa attttcaaaa cgccgccaaa     240
gattatattc acgccaatcc ttcggacgaa ttaggatatt tttatatcgc attaggaaat     300
tataattcgt ttttactcaa cggatttca ttcgattccg gaactctaat aaaactcgcc     360
tattctgggt caacgactt tctcaaagaa gacgagtcgt atcttcccat tttagaagaa     420
atgtatcgca atgcacttcg cgcaaaagca attgatccct ctatgaatga aaatccggac     480
aacgaagtga tgattgcgtt tggagagacg gtcaaacaac atctttctag aaaatctctc     540
acacaacttt tgaactctat tccatacgat aaaattagcg ccgaattcaa aacgactat      600
atctggattt ctattttagg agcatctctt tcaggagata cagatttttt aaaacgaaat     660
ttggcaagtc cagaatccag ccaatcgatt cttctcacag aaagagaggc aaacttttta     720
accggacttt ccgaattccg tgcaggccag tatgtttctt cactcaattt aattcgtaag     780
gtcagaaacg aaaacgaaga ttttatcaca actgggtcct ggattttaga ggcgaaaatt     840
ttcagacttc aaaatttaca tcttaaatcg atcgccattt tagaagagtt gtatccaaaa     900
tcggaagata aagagaaga gatcgtaaaa ctggcaaaag aaattataga ggaaaaacct     960
actctcaaaa caaaactcaa cttggaattg actactaccg atcag                   1005
```

<210> SEQ ID NO 154
<211> LENGTH: 335
<212> TYPE: PRT
<213> ORGANISM: Artificial Sequence
<220> FEATURE:
<223> OTHER INFORMATION: LIC12805

<400> SEQUENCE: 154

Met Leu Tyr Gln Ser Gly Leu Lys Ser Tyr Lys Lys Thr Ser Tyr
1               5                   10                  15

Lys Pro Tyr Ile Phe Ile Ala Leu Leu Ile Leu Ser Gly Thr Gly
            20                  25                  30

Phe Phe Phe Arg Gln Gly Ile Lys Asn Leu Phe Ala Gly Asp Arg Lys
        35                  40                  45

Ile Leu Leu Glu Lys Glu Arg Lys Asn Ile Gln Gln Ile Arg Ser
    50                  55                  60

Gly Ala Leu Glu Glu Thr Ser Val Lys Asn Phe Gln Asn Ala Ala Lys
65                  70                  75                  80

Asp Tyr Ile His Ala Asn Pro Ser Asp Glu Leu Gly Tyr Phe Tyr Ile
                85                  90                  95

Ala Leu Gly Asn Tyr Asn Ser Phe Leu Leu Asn Gly Phe Ser Phe Asp
            100                 105                 110

```
Ser Gly Thr Leu Ile Lys Leu Ala Tyr Ser Gly Phe Asn Asp Phe Leu
        115                 120                 125

Lys Glu Asp Glu Ser Tyr Leu Pro Ile Leu Glu Glu Met Tyr Arg Asn
    130                 135                 140

Ala Leu Arg Ala Lys Ala Ile Asp Pro Ser Met Asn Glu Asn Pro Asp
145                 150                 155                 160

Asn Glu Val Met Ile Ala Phe Gly Glu Thr Val Lys Gln His Leu Ser
                165                 170                 175

Arg Lys Ser Leu Thr Gln Leu Leu Asn Ser Ile Pro Tyr Asp Lys Ile
            180                 185                 190

Ser Ala Glu Phe Lys Thr Thr Tyr Ile Trp Ile Ser Ile Leu Gly Ala
        195                 200                 205

Ser Leu Ser Gly Asp Thr Asp Phe Leu Lys Arg Asn Leu Ala Ser Pro
    210                 215                 220

Glu Ser Ser Gln Ser Ile Leu Leu Thr Glu Arg Glu Ala Asn Phe Leu
225                 230                 235                 240

Thr Gly Leu Ser Glu Phe Arg Ala Gly Gln Tyr Val Ser Ser Leu Asn
                245                 250                 255

Leu Ile Arg Lys Val Arg Asn Glu Asn Glu Asp Phe Ile Thr Thr Gly
            260                 265                 270

Ser Trp Ile Leu Glu Ala Lys Ile Phe Arg Leu Gln Asn Leu His Leu
        275                 280                 285

Lys Ser Ile Ala Ile Leu Glu Glu Leu Tyr Pro Lys Ser Glu Asp Arg
    290                 295                 300

Arg Glu Glu Ile Val Lys Leu Ala Lys Glu Ile Ile Glu Glu Lys Pro
305                 310                 315                 320

Thr Leu Lys Thr Lys Leu Asn Leu Glu Leu Thr Thr Thr Asp Gln
                325                 330                 335

<210> SEQ ID NO 155
<211> LENGTH: 1566
<212> TYPE: DNA
<213> ORGANISM: Artificial Sequence
<220> FEATURE:
<223> OTHER INFORMATION: LIC13195

<400> SEQUENCE: 155
atgtcaaaag ataatactcg ttacgacgca atcgttattg ctctggatt tggtggttcc      60 atcagcgcct taagactttc agaaaaaggc caaagggttt tagtattaga aagaggaaaa     120
aaatattctc ccggagattt tccaagggac gtacgtaaaa tagacaatct tctctggcgt     180
tatcccaaaa agaaaaagtc tttgggttta tacgaactca ttttttttag tggactcgga     240
accgtaaccg cttccggttt aggcggaggt tccttgatct acgcgaatat tcatatccgt     300
cccgatcata aggttttttga agatcctcgc tggccagctc cgtttaacag agattatttg     360
gatccctatt ttgataaagt tgcctctaaa tttgatgtaa aaccggttcc accagaatgg     420
gatcttccaa aagaaatag atttaaagcc gctgcggatt taaacagaca tactcatttt     480
gatccggatg cagctgcaag ttggctaaaa ccttccagac caggacaatc tacttgcata     540
cgttgtgcgg aatgtgagtt cggatgtaat cacggagcta aaaacacatt agattttaat     600
tatattgcag acgccgaaaa aaacggtgcc gtgtttcaaa ccaattccct agcatctcat     660
atagccccag atagtcaaaa cggttacgta gttattatg aaaatacgga aaccggagaa     720
aaaaaatcgg tatatgctaa aagggtcata ctttccgcag gaacgttagg tacaaatagg     780
```

-continued

```
attctttta   acagcagaga   cagatacaaa   accctaccaa   atctaagcaa   acaacttgga     840
aaaggatatt  ctggaaatgg   ggactttta    ggcggaattg   aatcgagtaa   aagtgaactc     900
ataccttggg  acggaccgga   cgtaactacc   gtaatcaatt   attttccaca   aggatttcaa     960
tttacaatgg  cagcgcctac   gttcagtcaa   ccggtaatgt   cagtacttgc   ttcattagga    1020
attgctaaac  cgaattggtt   tttaaagctg   attggtccta   tcttttggaa   aagtttgaaa    1080
tggattcttc  cttttgtatt   taaaaaagga   ttactttcca   aacctctacc   acctggtctt    1140
ccgggagcgg  gtaatccaaa   ctatatgaca   aatctatttg   ccataggaag   agacaatgca    1200
aatgggaaaa  tcgtacgtcg   tggcaaaaac   atagacgtga   agtggaagta   ttctaaagaa    1260
aaccaaaccc  tcattcagaa   catgactgct   tctatgcagc   agataggaga   cgcatacggc    1320
ggacagttcg  gtccgttagc   tacctttttg   ttattcaatc   ggatcatctc   agttcattct    1380
ttaggaggtt  gtattctttc   cgccaatccg   gacaaaggag   ttgtatccga   aacgggaaaa    1440
gtattcggtt  ataaaaatct   attcattgcc   gatggatctg   taattccttc   ttcaatcgga    1500
tttcatcctg  tgatgacaat   ttccgccgtg   gccgaacata   ctgcagcttc   catctgtgcc    1560
ggatta                                                                        1566
```

<210> SEQ ID NO 156
<211> LENGTH: 522
<212> TYPE: PRT
<213> ORGANISM: Artificial Sequence
<220> FEATURE:
<223> OTHER INFORMATION: LIC13195

<400> SEQUENCE: 156

```
Met Ser Lys Asp Asn Thr Arg Tyr Asp Ala Ile Val Ile Gly Ser Gly
1               5                   10                  15

Phe Gly Gly Ser Ile Ser Ala Leu Arg Leu Ser Glu Lys Gly Gln Arg
            20                  25                  30

Val Leu Val Leu Glu Arg Gly Lys Lys Tyr Ser Pro Gly Asp Phe Pro
        35                  40                  45

Arg Asp Val Arg Lys Ile Asp Asn Leu Leu Trp Arg Tyr Pro Lys Lys
    50                  55                  60

Lys Lys Ser Leu Gly Leu Tyr Glu Leu Asn Phe Ser Gly Leu Gly
65                  70                  75                  80

Thr Val Thr Ala Ser Gly Leu Gly Gly Gly Ser Leu Ile Tyr Ala Asn
                85                  90                  95

Ile His Ile Arg Pro Asp His Lys Val Phe Glu Asp Pro Arg Trp Pro
            100                 105                 110

Ala Pro Phe Asn Arg Asp Tyr Leu Asp Pro Tyr Phe Asp Lys Val Ala
        115                 120                 125

Ser Lys Phe Asp Val Lys Pro Val Pro Pro Glu Trp Asp Leu Pro Lys
    130                 135                 140

Arg Asn Arg Phe Lys Ala Ala Ala Asp Leu Asn Arg His Thr His Phe
145                 150                 155                 160

Asp Pro Asp Ala Ala Ala Ser Trp Leu Lys Pro Ser Arg Pro Gly Gln
                165                 170                 175

Ser Thr Cys Ile Arg Cys Ala Glu Cys Glu Phe Gly Cys Asn His Gly
            180                 185                 190

Ala Lys Asn Thr Leu Asp Phe Asn Tyr Ile Ala Asp Ala Glu Lys Asn
        195                 200                 205

Gly Ala Val Phe Gln Thr Asn Ser Leu Ala Ser His Ile Ala Pro Asp
    210                 215                 220
```

Ser Gln Asn Gly Tyr Val Val Tyr Glu Asn Thr Glu Thr Gly Glu
225                 230                 235                 240

Lys Lys Ser Val Tyr Ala Lys Arg Val Ile Leu Ser Ala Gly Thr Leu
            245                 250                 255

Gly Thr Asn Arg Ile Leu Phe Asn Ser Arg Asp Arg Tyr Lys Thr Leu
                260                 265                 270

Pro Asn Leu Ser Lys Gln Leu Gly Lys Gly Tyr Ser Gly Asn Gly Asp
            275                 280                 285

Phe Leu Gly Gly Ile Glu Ser Ser Lys Ser Glu Leu Ile Pro Trp Asp
290                 295                 300

Gly Pro Asp Val Thr Thr Val Ile Asn Tyr Phe Pro Gln Gly Phe Gln
305                 310                 315                 320

Phe Thr Met Ala Ala Pro Thr Phe Ser Gln Pro Val Met Ser Val Leu
                325                 330                 335

Ala Ser Leu Gly Ile Ala Lys Pro Asn Trp Phe Leu Lys Leu Ile Gly
                340                 345                 350

Pro Ile Phe Trp Lys Ser Leu Lys Trp Ile Leu Pro Phe Val Phe Lys
            355                 360                 365

Lys Gly Leu Leu Ser Lys Pro Leu Pro Pro Gly Leu Pro Gly Ala Gly
            370                 375                 380

Asn Pro Asn Tyr Met Thr Asn Leu Phe Ala Ile Gly Arg Asp Asn Ala
385                 390                 395                 400

Asn Gly Lys Ile Val Arg Arg Gly Lys Asn Ile Asp Val Lys Trp Lys
                405                 410                 415

Tyr Ser Lys Glu Asn Gln Thr Leu Ile Gln Asn Met Thr Ala Ser Met
                420                 425                 430

Gln Gln Ile Gly Asp Ala Tyr Gly Gly Gln Phe Gly Pro Leu Ala Thr
            435                 440                 445

Phe Leu Leu Phe Asn Arg Ile Ile Ser Val His Ser Leu Gly Gly Cys
450                 455                 460

Ile Leu Ser Ala Asn Pro Asp Lys Gly Val Val Ser Glu Thr Gly Glu
465                 470                 475                 480

Val Phe Gly Tyr Lys Asn Leu Phe Ile Ala Asp Gly Ser Val Ile Pro
                485                 490                 495

Ser Ser Ile Gly Phe His Pro Val Met Thr Ile Ser Ala Val Ala Glu
            500                 505                 510

His Thr Ala Ala Ser Ile Cys Ala Gly Leu
            515                 520

<210> SEQ ID NO 157
<211> LENGTH: 1101
<212> TYPE: DNA
<213> ORGANISM: Artificial Sequence
<220> FEATURE:
<223> OTHER INFORMATION: LIC13313

<400> SEQUENCE: 157
ttgaaacgtt ggcttgtttt attttcgcg ttagtcgcac ttgtgctcag ttttttcttt      60
ttagaagaaa aaaagagga acgttcggag gtttcctttt gggagattga tatagacgaa     120
attgaatacc aaccgcctac gaattttggg acggggaag tttctatttt ttataaatct     180
tctatttttc ttaaaaaaag aaagggtatt agtgaaagtg gaactttct tacgatcgaa     240 tccaaagact tagaaactgg agatacgatt gtatttgaag gtgggtataa ttctgaaaac     300
attttcagag aactttcggt tttaaaagta aaaggagtgg aaccgattca aggagagaag     360

```
atttccacct cactacaatt aaacgaaaat tccccaaaga tttatttaaa atcttctggt    420
aagatcctga aaacaatttg gatcggaaaa aagaaaactg gagattcaac cagaattgta    480
aaagaaggaa acgaaatttt aatcatccag gcaaatacta tagatcgttt tacaagagga    540
attggagaat ttagacaaaa acaactcatc aatttaaaag acgagtccgt cgttgaaacg    600
atttgggaag aagagggaaa aaccattcgt ctggataatc acccgtttaa agaaaaaacg    660
ataaagaaaa atttttggag aagactttcc ggtaaactta aactttggga acaaccttaa    720
ggagattctt ggaacaacca agttgtaggt caacttgtag aattgtatcc ggacgatccg    780
aatggggcgg gttatgcgat tgctaaacgt ttgacagcgg ttcctgcaga cgcctcatta    840
aaaattcgaa tctccaatgg ggattggatc acgttacgtt attatccgaa acgaatatc     900 aattcaatcg attatagacc tgcaattcga atcgtaaatg ataaattttc agaacctcct    960
ttttatattc gagaagatag tttcttgcga ttaaagaag ttgtgggaa tttggagaaa     1020 gcggaacaga aaaagaacc cgtaaatcag aacgaccaga acgggcttcc taaaaatcta    1080
accccaaaaa atgatcgcag a                                             1101
```

<210> SEQ ID NO 158
<211> LENGTH: 367
<212> TYPE: PRT
<213> ORGANISM: Artificial Sequence
<220> FEATURE:
<223> OTHER INFORMATION: LIC13313

<400> SEQUENCE: 158

```
Met Lys Arg Trp Leu Val Leu Phe Phe Ala Leu Val Ala Leu Val Leu
1               5                   10                  15

Ser Phe Phe Leu Glu Glu Lys Lys Glu Glu Arg Ser Glu Val Ser
            20                  25                  30

Phe Trp Glu Ile Asp Ile Asp Glu Ile Glu Tyr Gln Pro Pro Thr Asn
        35                  40                  45

Phe Trp Asp Gly Glu Val Ser Ile Phe Tyr Lys Ser Ser Ile Phe Leu
    50                  55                  60

Lys Lys Arg Lys Gly Ile Ser Glu Ser Gly Asn Phe Leu Thr Ile Glu
65                  70                  75                  80

Ser Lys Asp Leu Glu Thr Gly Asp Thr Ile Val Phe Glu Gly Gly Tyr
                85                  90                  95

Asn Ser Glu Asn Ile Phe Arg Glu Leu Ser Val Leu Lys Val Lys Gly
            100                 105                 110

Val Glu Pro Ile Gln Gly Glu Lys Ile Ser Thr Ser Leu Gln Leu Asn
        115                 120                 125

Glu Asn Ser Pro Lys Ile Tyr Leu Lys Ser Ser Gly Lys Ile Leu Lys
    130                 135                 140

Thr Ile Trp Ile Gly Lys Lys Thr Gly Asp Ser Thr Arg Ile Val
145                 150                 155                 160

Lys Glu Gly Asn Glu Ile Leu Ile Ile Gln Ala Asn Thr Ile Asp Arg
                165                 170                 175

Phe Thr Arg Gly Ile Gly Glu Phe Arg Gln Lys Gln Leu Ile Asn Leu
            180                 185                 190

Lys Asp Glu Ser Val Val Glu Thr Ile Trp Glu Glu Gly Lys Thr
        195                 200                 205

Ile Arg Leu Asp Asn His Pro Phe Lys Glu Lys Thr Ile Lys Lys Asn
    210                 215                 220
```

| | | | | | | | | | | | | |
|---|---|---|---|---|---|---|---|---|---|---|---|---|
| Phe | Trp | Arg | Arg | Leu | Ser | Gly | Lys | Leu | Ile | Thr | Leu | Glu | Gln | Thr | Leu |
| 225 | | | | | 230 | | | | | 235 | | | | | 240 |

| Gly | Asp | Ser | Trp | Asn | Asn | Gln | Val | Val | Gly | Gln | Leu | Val | Glu | Leu | Tyr |
|---|---|---|---|---|---|---|---|---|---|---|---|---|---|---|---|
| | | | | 245 | | | | | 250 | | | | | 255 | |

| Pro | Asp | Asp | Pro | Asn | Gly | Ala | Gly | Tyr | Ala | Ile | Ala | Lys | Arg | Leu | Thr |
|---|---|---|---|---|---|---|---|---|---|---|---|---|---|---|---|
| | | | 260 | | | | | 265 | | | | | 270 | | |

| Ala | Val | Pro | Ala | Asp | Ala | Ser | Leu | Lys | Ile | Arg | Ile | Ser | Asn | Gly | Asp |
|---|---|---|---|---|---|---|---|---|---|---|---|---|---|---|---|
| | | 275 | | | | | 280 | | | | | 285 | | | |

| Trp | Ile | Thr | Leu | Arg | Tyr | Tyr | Pro | Lys | Thr | Asn | Ile | Asn | Ser | Ile | Asp |
|---|---|---|---|---|---|---|---|---|---|---|---|---|---|---|---|
| | 290 | | | | | 295 | | | | | 300 | | | | |

| Tyr | Arg | Pro | Ala | Ile | Arg | Ile | Val | Asn | Asp | Lys | Phe | Ser | Glu | Pro | Pro |
|---|---|---|---|---|---|---|---|---|---|---|---|---|---|---|---|
| 305 | | | | | 310 | | | | | 315 | | | | | 320 |

| Phe | Tyr | Ile | Arg | Glu | Asp | Ser | Phe | Leu | Arg | Leu | Lys | Glu | Val | Val | Gly |
|---|---|---|---|---|---|---|---|---|---|---|---|---|---|---|---|
| | | | | 325 | | | | | 330 | | | | | 335 | |

| Asn | Leu | Glu | Lys | Ala | Glu | Gln | Lys | Lys | Glu | Pro | Val | Asn | Gln | Asn | Asp |
|---|---|---|---|---|---|---|---|---|---|---|---|---|---|---|---|
| | | | 340 | | | | | 345 | | | | | 350 | | |

| Gln | Asn | Gly | Leu | Pro | Lys | Asn | Leu | Thr | Pro | Lys | Asn | Asp | Arg | Arg |
|---|---|---|---|---|---|---|---|---|---|---|---|---|---|---|
| | | 355 | | | | | 360 | | | | | 365 | | |

<210> SEQ ID NO 159
<211> LENGTH: 2079
<212> TYPE: DNA
<213> ORGANISM: Artificial Sequence
<220> FEATURE:
<223> OTHER INFORMATION: LIC13386

<400> SEQUENCE: 159

```
gtgccatttt ccaatagatt agatttgatg aaattttca aacgaattca agaattctta      60
tatacttatc gaattagatt tcttgcaata attttgattc aaattattgc ggttatatcc     120
ttcacgttag ttcctcttct aattcgtgag gactttaca aagatttcat tctcactgca     180
atcgagcaaa agacaggttt agaagtcaaa gtaggttctt cagatttagt tctgtttccg     240
tttccaggaa tcgaattgaa agaagttcag attcgtaaag aggaattggt cattgggatc     300
agcgatcgta ttaaggtaga catttcttgg tttggtttgt taggtcagaa agtagaaatc     360
agagacgttt atatttcagg tggaaaaatc aatcttcata aaaacaaaga cggctctgtg     420
gatctaattg agttctttca gcaagataca gaagattccg aaaactcaaa ccataatcat     480
acgatcagaa tttttgatcc ctcttccact gtcgaaagtt cttcgtttat cagccccaaa     540
gaaatttta agttggatt aaaaaacgtt gagattgaaa attttacat tcactatcaa     600
gacgatactc atcgaaaaac gtatgaaatt tatctttcaa attctgcatt gaacatttct     660
ttttacggaa acaattttgt tctaacctta caaggtaaat tggatggtca gagttttcaa     720
atttatggaa gtactaactt agacgagttt cctacaactt acgaaaattc taaatttcaa     780
tctacgatta gtttagataa atgttctctt tcgatttta gggatttatt gacaattttt     840
ccaaacgccg attttttcaaa gacaatccta aatggaacaa tcaaaatcga taagttcct     900
aatcgatcga ttaactttaa cgttattgca caagcaaaaa attttgctta caaggaggg     960
aatccgttcg gagacattaa agtaaatatg gaattcagat tggatcttcc aaataaaaaa    1020
ctggaatttc cttacatctc aattctttgg cctggaattg cggaaggaaa tgcaaaagga    1080
acggttttat ggaattacaa aacgaacgtt tcctttcaag tcacggcaaa ttatttagat    1140
tatcacagcg cacttcgatt aggaaaactt tttgagttca ctaaaaaatt tgacgaccca    1200
aatagaccta atggagtttt ttatttcagt gtagacctca aaaacgtata cgcattgaaa    1260
```

```
catagaatcc cagtttaaa agcagaattg aaatatagct atccttggat tcacatacct      1320
agttttcatg cctatatata caacggagaa atattaggaa atctaaaat tgacccttc       1380 aaatccaagt tcgaagtgca aggtgaagct tatagaattc aatccgatcg aattctaatg    1440
ccttacgtaa acgatccaat catcaatgga gatatgttta gtaggttcaa cttcgttacg    1500
gaagtacata accgttcttc cgattttact accgagtttt tcagaaatat ggaaggttct    1560
ggaaatcttc aagttctcaa tgagaatta ctcggttatg caatttcat gattccggtt      1620 ttaaacactc ttggaaagat catctcattt aacggaatcg atggtagaaa agtagaattt    1680
tcttctttaa aatcggattt tacaatcgaa ataatcacc ttcactttca gaatctaaaa    1740
ctgcagggca agggtttaga agcagatgga aaggaaata tcagttttga aaaaatata     1800 gatgtactta tcaattaag acttggtgga aatatagttg gtagggtttt aaaattcct     1860 atcatttaca aaggagttt taaacaatcg attccttata tagatccgat ctggttgggt    1920 tcagttttg cgggaagtac aattcttgct ccgtttttta ctttcgcagg tggaccatac    1980
ggaggaggaa tcgctggttc ggtcgtatcg aatacgttca gagatgcttg ggaaggacta   2040
aaaggtttat tttcatctaa agaagataaa aaaagaaa                          2079
```

<210> SEQ ID NO 160
<211> LENGTH: 693
<212> TYPE: PRT
<213> ORGANISM: Artificial Sequence
<220> FEATURE:
<223> OTHER INFORMATION: LIC13386

<400> SEQUENCE: 160

```
Met Pro Phe Ser Asn Arg Leu Asp Leu Met Lys Phe Phe Lys Arg Ile
1               5                   10                  15

Gln Glu Phe Leu Tyr Thr Tyr Arg Ile Arg Phe Leu Ala Ile Ile Leu
            20                  25                  30

Ile Gln Ile Ile Ala Val Ile Ser Phe Thr Leu Val Pro Leu Leu Ile
        35                  40                  45

Arg Glu Asp Phe Tyr Lys Asp Phe Ile Leu Thr Ala Ile Glu Gln Lys
    50                  55                  60

Thr Gly Leu Glu Val Lys Val Gly Ser Ser Asp Leu Val Leu Phe Pro
65                  70                  75                  80

Phe Pro Gly Ile Glu Leu Lys Glu Val Gln Ile Arg Lys Glu Leu
                85                  90                  95

Val Ile Gly Ile Ser Asp Arg Ile Lys Val Asp Ile Ser Trp Phe Gly
            100                 105                 110

Leu Leu Gly Gln Lys Val Glu Ile Arg Asp Val Tyr Ile Ser Gly Gly
        115                 120                 125

Lys Ile Asn Leu His Lys Asn Lys Asp Gly Ser Val Asp Leu Ile Glu
    130                 135                 140

Phe Phe Gln Gln Asp Thr Glu Asp Ser Glu Asn Ser Asn His Asn His
145                 150                 155                 160

Thr Ile Arg Ile Phe Asp Pro Ser Ser Thr Val Glu Ser Ser Phe
                165                 170                 175

Ile Ser Pro Lys Glu Ile Phe Val Gly Leu Lys Asn Val Glu Ile
            180                 185                 190

Glu Asn Phe Tyr Ile His Tyr Gln Asp Asp Thr His Arg Lys Thr Tyr
        195                 200                 205

Glu Ile Tyr Leu Ser Asn Ser Ala Leu Asn Ile Ser Phe Tyr Gly Asn
    210                 215                 220
```

```
Asn Phe Val Leu Thr Leu Gln Gly Lys Leu Asp Gly Gln Ser Phe Gln
225                 230                 235                 240

Ile Tyr Gly Ser Thr Asn Leu Asp Glu Phe Pro Thr Thr Tyr Glu Asn
            245                 250                 255

Ser Lys Phe Gln Ser Thr Ile Ser Leu Asp Lys Cys Ser Leu Ser Ile
                260                 265                 270

Phe Arg Asp Leu Leu Thr Ile Phe Pro Asn Ala Asp Phe Ser Lys Thr
            275                 280                 285

Ile Leu Asn Gly Thr Ile Lys Ile Asp Lys Val Pro Asn Arg Ser Ile
290                 295                 300

Asn Phe Asn Val Ile Ala Gln Ala Lys Asn Phe Ala Tyr Lys Gly Gly
305                 310                 315                 320

Asn Pro Phe Gly Asp Ile Lys Val Asn Met Glu Phe Arg Leu Asp Leu
                325                 330                 335

Pro Asn Lys Lys Leu Glu Phe Pro Tyr Ile Ser Ile Leu Trp Pro Gly
            340                 345                 350

Ile Ala Glu Gly Asn Ala Lys Gly Thr Val Leu Trp Asn Tyr Lys Thr
            355                 360                 365

Asn Val Ser Phe Gln Val Thr Ala Asn Tyr Leu Asp Tyr His Ser Ala
370                 375                 380

Leu Arg Leu Gly Lys Leu Phe Glu Phe Thr Lys Lys Phe Asp Asp Pro
385                 390                 395                 400

Asn Arg Pro Asn Gly Val Phe Tyr Phe Ser Val Asp Leu Lys Asn Val
            405                 410                 415

Tyr Ala Leu Lys His Arg Ile Pro Val Leu Lys Ala Glu Leu Lys Tyr
            420                 425                 430

Ser Tyr Pro Trp Ile His Ile Pro Ser Phe His Ala Tyr Ile Tyr Asn
            435                 440                 445

Gly Glu Ile Leu Gly Lys Ser Lys Ile Asp Pro Phe Lys Ser Lys Phe
450                 455                 460

Glu Val Gln Gly Glu Ala Tyr Arg Ile Gln Ser Asp Arg Ile Leu Met
465                 470                 475                 480

Pro Tyr Val Asn Asp Pro Ile Ile Asn Gly Asp Met Phe Ser Arg Phe
            485                 490                 495

Asn Phe Val Thr Glu Val His Asn Arg Ser Ser Asp Phe Thr Thr Glu
                500                 505                 510

Phe Phe Arg Asn Met Glu Gly Ser Gly Asn Leu Gln Val Leu Asn Gly
            515                 520                 525

Glu Leu Leu Gly Tyr Ala Asn Phe Met Ile Pro Val Leu Asn Thr Leu
530                 535                 540

Gly Lys Ile Ile Ser Phe Asn Gly Ile Asp Gly Arg Lys Val Glu Phe
545                 550                 555                 560

Ser Ser Leu Lys Ser Asp Phe Thr Ile Glu Asn Asn His Leu His Phe
            565                 570                 575

Gln Asn Leu Lys Leu Gln Gly Lys Gly Leu Glu Ala Asp Gly Lys Gly
            580                 585                 590

Asn Ile Ser Phe Glu Lys Asn Ile Asp Val Leu Ile Asn Leu Arg Leu
            595                 600                 605

Gly Gly Asn Ile Val Gly Arg Val Leu Lys Ile Pro Ile Ile Tyr Lys
            610                 615                 620

Gly Val Phe Lys Gln Ser Ile Pro Tyr Ile Asp Pro Ile Trp Leu Gly
625                 630                 635                 640
```

Ser Val Phe Ala Gly Ser Thr Ile Leu Ala Pro Phe Phe Thr Phe Ala
            645                 650                 655

Gly Gly Pro Tyr Gly Gly Gly Ile Ala Gly Ser Val Val Ser Glu Tyr
        660                 665                 670

Val Arg Asp Ala Trp Glu Gly Leu Lys Gly Leu Phe Ser Ser Lys Glu
    675                 680                 685

Asp Lys Lys Lys Lys
    690

<210> SEQ ID NO 161
<211> LENGTH: 1446
<212> TYPE: DNA
<213> ORGANISM: Artificial Sequence
<220> FEATURE:
<223> OTHER INFORMATION: LIC13491

<400> SEQUENCE: 161

| | | | | | |
|---|---|---|---|---|---|
| atgaattgga | aaaaaatcgt | cttcggcttt | ttaggagctt | tggttttatt | tttactctat | 60 |
| acgattttg | ttacagaaaa | agggatccag | tcgataaacc | ccaccacaaa | gtttaaacga | 120 |
| gattatggaa | aaattgccga | agaagcttcg | aaagatttac | aaacgtatct | taaaattcaa | 180 |
| acggttcgag | gaaatgaaaa | acaggcggtt | ttatttttaa | aaagtctctt | tgataaacga | 240 |
| ggaattaaaa | ccagaatatt | tgaagttcct | ggaaaaccgg | aaagagcgag | tatcatggcg | 300 |
| gagatcaaag | gaacagatcc | agaaggtggt | ttgatactta | caaatcatat | cgatgtagta | 360 |
| gaagccgatc | caagtgagtg | ggatgaggcg | ccgttttcag | gagtaagaaa | aggagataga | 420 |
| atttacggaa | gaggggccgt | ggatatgaaa | ggtctgggaa | tcatggagtt | atatgctttc | 480 |
| ttttttgattc | atgattctgg | aatgaaactt | aagaaaaatc | taatgtatct | tgcagttgcc | 540 |
| gacgaagaaa | gtcgttccga | atttgggatg | aggttttttga | tcgcaaatca | taagaaaatt | 600 |
| tttaacggtt | atgagtttgt | tcacaatgag | ggaggaatcg | gaaccaaaga | cgtagttgta | 660 |
| aagggaagta | aaatctttaa | tattcaacac | gcagaaaaag | gaattatctg | ttggatctg | 720 |
| aaatcagaag | atatttccgg | acacggaagt | actccgccaa | tacaatatgc | agctttgaat | 780 |
| ctcatcgact | ttctcagtga | gcttaagaag | atgaacgaag | ttgttattat | caaagacgag | 840 |
| accgcttcgt | tcttttatca | aatgggagaa | gtaagcccct | tccccaattc | atttgtatta | 900 |
| aaaagatctc | ggaatccgtt | attaggaatc | gttctaaatg | gagtgattcg | atcaaacaaa | 960 |
| catctaagag | ctatgactag | taataccgta | agtataaccg | gaattgatac | tcatcaagca | 1020 |
| ggtataaacg | taatcacttc | aaaaacagaa | ggaatggtcg | acataagaat | cttacctggt | 1080 |
| tttagtgaaa | atgagatctt | tgaaaaaata | aaaaaactcg | ctgaaaaata | tagagtgaaa | 1140 |
| gtcagtgcga | gacatttaga | acctggaacg | atttcgccag | tggattcaaa | atattttcaa | 1200 |
| attttatctg | gagttgttca | acaagtggtt | ccaggttcga | tcgtaactcc | tttttatct | 1260 |
| cctggaacta | cggactcatc | ttatttaaga | atggccggat | ttaaatgtta | cggtttgatt | 1320 |
| ccagcgctca | tgacttcgga | agaaatagat | ggaatacatg | gtaaaaatga | agtactacg | 1380 |
| attgaacatt | taaaaacagg | aattgaaatt | ctacatagaa | cggttttaga | attcaataat | 1440 |
| gctcct | | | | | | 1446 |

<210> SEQ ID NO 162
<211> LENGTH: 482
<212> TYPE: PRT
<213> ORGANISM: Artificial Sequence
<220> FEATURE:
<223> OTHER INFORMATION: LIC13491

<400> SEQUENCE: 162

```
Met Asn Trp Lys Lys Ile Val Phe Gly Phe Leu Gly Ala Leu Val Leu
1               5                   10                  15

Phe Leu Leu Tyr Thr Ile Phe Val Thr Glu Lys Gly Ile Gln Ser Ile
            20                  25                  30

Asn Pro Thr Thr Lys Phe Lys Arg Asp Tyr Gly Lys Ile Ala Glu Glu
        35                  40                  45

Ala Ser Lys Asp Leu Gln Thr Tyr Leu Lys Ile Gln Thr Val Arg Gly
    50                  55                  60

Asn Glu Lys Gln Ala Val Leu Phe Leu Lys Ser Leu Phe Asp Lys Arg
65                  70                  75                  80

Gly Ile Lys Thr Arg Ile Phe Glu Val Pro Gly Lys Pro Glu Arg Ala
                85                  90                  95

Ser Ile Met Ala Glu Ile Lys Gly Thr Asp Pro Glu Gly Leu Ile
                100                 105                 110

Leu Thr Asn His Ile Asp Val Val Glu Ala Asp Pro Ser Glu Trp Asp
            115                 120                 125

Glu Ala Pro Phe Ser Gly Val Arg Lys Gly Asp Arg Ile Tyr Gly Arg
        130                 135                 140

Gly Ala Val Asp Met Lys Gly Leu Gly Ile Met Glu Leu Tyr Ala Phe
145                 150                 155                 160

Phe Leu Ile His Asp Ser Gly Met Lys Leu Lys Lys Asn Leu Met Tyr
                165                 170                 175

Leu Ala Val Ala Asp Glu Glu Ser Arg Ser Glu Phe Gly Met Arg Phe
            180                 185                 190

Leu Ile Ala Asn His Lys Glu Ile Phe Asn Gly Tyr Glu Phe Val His
        195                 200                 205

Asn Glu Gly Gly Ile Gly Thr Lys Asp Val Val Lys Gly Ser Lys
    210                 215                 220

Ile Phe Asn Ile Gln His Ala Glu Lys Gly Ile Ile Trp Leu Asp Leu
225                 230                 235                 240

Lys Ser Glu Asp Ile Ser Gly His Gly Ser Thr Pro Pro Ile Gln Tyr
                245                 250                 255

Ala Ala Leu Asn Leu Ile Asp Phe Leu Ser Glu Leu Lys Lys Met Asn
            260                 265                 270

Glu Val Val Ile Ile Lys Asp Glu Thr Ala Ser Phe Phe Tyr Gln Met
        275                 280                 285

Gly Glu Val Ser Pro Phe Pro Asn Ser Phe Val Leu Lys Arg Ser Arg
290                 295                 300

Asn Pro Leu Leu Gly Ile Val Leu Asn Gly Val Ile Arg Ser Asn Lys
305                 310                 315                 320

His Leu Arg Ala Met Thr Ser Asn Thr Val Ser Ile Thr Gly Ile Asp
                325                 330                 335

Thr His Gln Ala Gly Ile Asn Val Ile Thr Ser Lys Thr Glu Gly Met
            340                 345                 350

Val Asp Ile Arg Ile Leu Pro Gly Phe Ser Glu Asn Glu Ile Phe Glu
        355                 360                 365

Lys Ile Lys Lys Leu Ala Glu Lys Tyr Arg Val Lys Val Ser Ala Arg
370                 375                 380

His Leu Glu Pro Gly Thr Ile Ser Pro Val Asp Ser Lys Tyr Phe Gln
385                 390                 395                 400

Ile Leu Ser Gly Val Val Gln Gln Val Val Pro Gly Ser Ile Val Thr
```

```
            405                 410                 415
Pro Phe Leu Ser Pro Gly Thr Thr Asp Ser Ser Tyr Leu Arg Met Ala
            420                 425                 430

Gly Phe Lys Cys Tyr Gly Leu Ile Pro Ala Leu Met Thr Ser Glu Glu
            435                 440                 445

Ile Asp Gly Ile His Gly Lys Asn Glu Ser Thr Thr Ile Glu His Leu
    450                 455                 460

Lys Thr Gly Ile Glu Ile Leu His Arg Thr Val Leu Glu Phe Asn Asn
465                 470                 475                 480

Ala Pro

<210> SEQ ID NO 163
<211> LENGTH: 1158
<212> TYPE: DNA
<213> ORGANISM: Artificial Sequence
<220> FEATURE:
<223> OTHER INFORMATION: LIC20165

<400> SEQUENCE: 163
atgaaagaat atattgcatt tatcaaagat tctaagtttt ggattccggt tttgattcta      60
gttggactcg aaatcgtaat gcagtttggt tgttatagac ctttttttaaa aaagaattca    120
tacgcggcta acgtttctag aattacagat cacgttcttg aaaaacaaaa ggaatttgat    180
cccgacgttt tagttgtagg aacatcggtc gcatatcaag gttgtccat tccaattttg     240
aatcaggaac tttcttcttt aggaaaaaaa gttcagtcta ttgcaattcc aggaaccgag    300
ttgatcgtac aagatctggc catttttaaa actcttcctc atttcaaaaa tgtaaaaaca    360
gtaattcatg tatttgaaat aacaactcct tgggttggtc aaaaaatttt gaacctacct    420
actcttgcga tgatttccga atttaatcgt ctggaagtat atcctagaat ttacgatttc    480
ggttaccaag tgaatgtgaa tgatcttatt tacatcactt tgaagtctat cgcttacaga    540
agagacgttc aagatctaat cttaagtcct tctaaaagaa tcaaagatat aggaaaacgt    600
tttaaaatag aaaatccaaa tccttgggac tatgagaatt catatctaga aagaatcagc    660
atgtatccta ttcaagatat ttccgattgt atagaaaaga ccaaccctgc aacggccag     720
ccaattccaa aaggttcgga tcgatttcat aaaaaggcaa tctttgatac ttgcattatt    780
gcaaatcata tagtgacgca tgcagaagaa gacaaagtta caaacagta tttcgaccgt    840
cttaagattt tacacgacga aattagaagg atcggaaaag aaaacggtca agatatacaa    900
ataatcggag tagtagcacc ttacagtcaa ctcatacaaa agtggaggct tacagaaaga    960
aacgaagttt ggaaaagaga actaagaaga attcatcctt ctaatccggt tccactactt   1020
gattatcagg acatgttgga cggtccggat aacgggaatt actattacga tctaattcat   1080
ctcaattcga ttggaatgaa aaaattaaca ttcacatttg cgaaagattt caaagcaatt   1140
ctggaaaagg aaaccaaa                                                  1158

<210> SEQ ID NO 164
<211> LENGTH: 386
<212> TYPE: PRT
<213> ORGANISM: Artificial Sequence
<220> FEATURE:
<223> OTHER INFORMATION: LIC20165

<400> SEQUENCE: 164

Met Lys Glu Tyr Ile Ala Phe Ile Lys Asp Ser Lys Phe Trp Ile Pro
1               5                   10                  15
```

Val Leu Ile Leu Val Gly Leu Glu Ile Val Met Gln Phe Gly Cys Tyr
                20                  25                  30

Arg Pro Phe Leu Lys Lys Asn Ser Tyr Ala Ala Asn Val Ser Arg Ile
            35                  40                  45

Thr Asp His Val Leu Glu Lys Gln Lys Glu Phe Asp Pro Asp Val Leu
        50                  55                  60

Val Val Gly Thr Ser Val Ala Tyr Gln Gly Leu Ser Ile Pro Ile Leu
65                  70                  75                  80

Asn Gln Glu Leu Ser Ser Leu Gly Lys Lys Val Gln Ser Ile Ala Ile
                85                  90                  95

Pro Gly Thr Glu Leu Ile Val Gln Asp Leu Ala Ile Leu Lys Thr Leu
            100                 105                 110

Pro His Phe Lys Asn Val Lys Thr Val Ile His Val Phe Glu Ile Thr
        115                 120                 125

Thr Pro Trp Val Gly Gln Lys Ile Leu Asn Leu Pro Thr Leu Ala Met
    130                 135                 140

Ile Ser Glu Phe Asn Arg Leu Glu Val Tyr Pro Arg Ile Tyr Asp Phe
145                 150                 155                 160

Gly Tyr Gln Val Asn Val Asn Asp Leu Ile Tyr Ile Thr Leu Lys Ser
                165                 170                 175

Ile Ala Tyr Arg Arg Asp Val Gln Asp Leu Ile Leu Ser Pro Ser Lys
            180                 185                 190

Arg Ile Lys Asp Ile Gly Lys Arg Phe Lys Ile Glu Asn Pro Asn Pro
        195                 200                 205

Trp Asp Tyr Glu Asn Ser Tyr Leu Glu Arg Ile Ser Met Tyr Pro Ile
    210                 215                 220

Gln Asp Ile Ser Asp Cys Ile Glu Lys Thr Asn Pro Ala Asn Gly Gln
225                 230                 235                 240

Pro Ile Pro Lys Gly Ser Asp Arg Phe His Lys Lys Ala Ile Phe Asp
                245                 250                 255

Thr Cys Ile Ile Ala Asn His Ile Val Thr His Ala Glu Glu Asp Lys
            260                 265                 270

Val Thr Lys Gln Tyr Phe Asp Arg Leu Lys Ile Leu His Asp Glu Ile
        275                 280                 285

Arg Arg Ile Gly Lys Glu Asn Gly Gln Asp Ile Gln Ile Ile Gly Val
    290                 295                 300

Val Ala Pro Tyr Ser Gln Leu Ile Gln Lys Trp Arg Leu Thr Glu Arg
305                 310                 315                 320

Asn Glu Val Trp Lys Arg Glu Leu Arg Arg Ile His Pro Ser Asn Pro
                325                 330                 335

Val Pro Leu Leu Asp Tyr Gln Asp Met Leu Asp Gly Pro Asp Asn Gly
            340                 345                 350

Asn Tyr Tyr Tyr Asp Leu Ile His Leu Asn Ser Ile Gly Met Lys Lys
        355                 360                 365

Leu Thr Phe Thr Phe Ala Lys Asp Phe Lys Ala Ile Leu Glu Lys Glu
    370                 375                 380

Thr Lys
385

<210> SEQ ID NO 165
<211> LENGTH: 21
<212> TYPE: DNA
<213> ORGANISM: Artificial Sequence
<220> FEATURE:
<223> OTHER INFORMATION: primer

```
<400> SEQUENCE: 165
agcaaacaac gactcagaac g                                              21

<210> SEQ ID NO 166
<211> LENGTH: 20
<212> TYPE: DNA
<213> ORGANISM: Artificial Sequence
<220> FEATURE:
<223> OTHER INFORMATION: Primer

<400> SEQUENCE: 166
gtttttgcgg catcggtgat                                                20

<210> SEQ ID NO 167
<211> LENGTH: 20
<212> TYPE: DNA
<213> ORGANISM: Artificial Sequence
<220> FEATURE:
<223> OTHER INFORMATION: Primer

<400> SEQUENCE: 167
cactgaacac gccgctaaac                                                20

<210> SEQ ID NO 168
<211> LENGTH: 20
<212> TYPE: DNA
<213> ORGANISM: Artificial Sequence
<220> FEATURE:
<223> OTHER INFORMATION: Primer

<400> SEQUENCE: 168
gagtcgtaga cgctggatgg                                                20

<210> SEQ ID NO 169
<211> LENGTH: 20
<212> TYPE: DNA
<213> ORGANISM: Artificial Sequence
<220> FEATURE:
<223> OTHER INFORMATION: Primer

<400> SEQUENCE: 169
atctggtaac gacagtgcgg                                                20

<210> SEQ ID NO 170
<211> LENGTH: 20
<212> TYPE: DNA
<213> ORGANISM: Artificial Sequence
<220> FEATURE:
<223> OTHER INFORMATION: Primer

<400> SEQUENCE: 170
agtcttgcac cacctgcaaa                                                20

<210> SEQ ID NO 171
<211> LENGTH: 19
<212> TYPE: DNA
<213> ORGANISM: Artificial Sequence
<220> FEATURE:
<223> OTHER INFORMATION: Primer

<400> SEQUENCE: 171
aacaaccggt gggattaca                                                 19

<210> SEQ ID NO 172
```

```
<211> LENGTH: 20
<212> TYPE: DNA
<213> ORGANISM: Artificial Sequence
<220> FEATURE:
<223> OTHER INFORMATION: Primer

<400> SEQUENCE: 172
tcgttcgttc cactgattgg                                              20

<210> SEQ ID NO 173
<211> LENGTH: 20
<212> TYPE: DNA
<213> ORGANISM: Artificial Sequence
<220> FEATURE:
<223> OTHER INFORMATION: Primer

<400> SEQUENCE: 173
ctgttgctct aacggcatgt                                              20

<210> SEQ ID NO 174
<211> LENGTH: 21
<212> TYPE: DNA
<213> ORGANISM: Artificial Sequence
<220> FEATURE:
<223> OTHER INFORMATION: Primer

<400> SEQUENCE: 174
gcagcctgat aggatgcttt a                                            21

<210> SEQ ID NO 175
<211> LENGTH: 20
<212> TYPE: DNA
<213> ORGANISM: Artificial Sequence
<220> FEATURE:
<223> OTHER INFORMATION: Primer

<400> SEQUENCE: 175
gcccacttct ggcaaagaga                                              20

<210> SEQ ID NO 176
<211> LENGTH: 21
<212> TYPE: DNA
<213> ORGANISM: Artificial Sequence
<220> FEATURE:
<223> OTHER INFORMATION: Primer

<400> SEQUENCE: 176
tcccagtctt ccgatttgac g                                            21

<210> SEQ ID NO 177
<211> LENGTH: 22
<212> TYPE: DNA
<213> ORGANISM: Artificial Sequence
<220> FEATURE:
<223> OTHER INFORMATION: Primer

<400> SEQUENCE: 177
acgtaactcc ttccctctat ct                                           22

<210> SEQ ID NO 178
<211> LENGTH: 20
<212> TYPE: DNA
<213> ORGANISM: Artificial Sequence
<220> FEATURE:
<223> OTHER INFORMATION: Primer

<400> SEQUENCE: 178
```

```
agcccagttc aaaccgctta                                            20

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
accttcagat tggctcaccg                                            20

<210> SEQ ID NO 180
<211> LENGTH: 21
<212> TYPE: DNA
<213> ORGANISM: Artificial Sequence
<220> FEATURE:
<223> OTHER INFORMATION: Primer

<400> SEQUENCE: 180
actcagtatc cgtttccgct c                                          21
```

LEPTOSPIRA IMMUNOPROTECTIVE PROTEINS AND METHODS OF IDENTIFICATION AND USE THEREOF

CROSS-REFERENCE TO RELATED APPLICATIONS

This application claims priority to U.S. Provisional Application Ser. No. 62/118,790, which was filed on 20 Feb. 2015, and is herein incorporated by reference in its entirety.

INCORPORATION BY REFERENCE

All references cited herein are incorporated by reference herein in their entirety.

FIELD OF THE INVENTION

The present invention relates generally to immunogenic (including immunoprotective) Leptospira spp. proteins, which are capable of eliciting broad protective immune responses in animals, particularly canine animals. The invention further relates to methods of providing animals, especially canine animals in need of protection thereof, with broad protective immune responses against multiple Leptospira spp.

SUMMARY OF THE INVENTION

Leptospira are spirochete bacteria classified into saprophytic intermediary or pathogenic species inhabiting soil and fresh water reservoirs, predominately in regions of the world with tropical climates (1). Pathogenic species can be transmitted to wild and domesticated animals and to humans through direct or indirect contact with an abraded epidermal lining. Disease manifests as leptospirosis in susceptible hosts with symptoms ranging from a mild febrile illness to fatal kidney, liver or respiratory failure. Asymptomatic hosts include, mice, rats, raccoons and others and in these animals the bacteria colonize the renal tubules resulting in expulsion of the bacteria back into the environment, in the urine. Pathogenic Leptospira can survive for long periods in water (2, 3), providing an opportunity for the bacteria to infect a new host.

Leptospira resemble the hallmarks of Gram negative bacteria in that they contain an inner membrane, a periplasmic space with peptidoglycan and an outer membrane where the lipopolysaccharide is anchored. However, the bacteria are referred to as "Gram negative-like" because unlike other Gram negative bacteria the peptidoglycan is associated with cytoplasmic membrane (4) and not the outer membrane. The components of the envelope of Leptospira have been extensively characterized in previous studies, including the protein compositions of the cytoplasmic and outer membranes. However, protein transport from the cytoplasm to the extracellular space and therefore secretion systems have not been experimentally characterized in Leptospira.

Leptospira have the ability to rapidly disseminate in targets organs (kidneys and liver) where they are generally observed in the interstitial space (8, 9) but they have also been demonstrated to transiently exist intracellular in macrophages (10-12). During both extracellular and intracellular survival, Leptospira likely utilize various outer membrane and extracellular proteins to remain viable during infection. It follows that numerous studies have focused on identification (13-18) and characterization (19-32) of outer membrane proteins and a few studies have begun to characterize extracellular proteins in Leptospira. Previous studies focusing on Leptospiral extracellular proteins have combined to identify a hemolysin (33), an immunoglobulin-like protein (LigA) (34) and a sphingomyelinase (Sph2) (23). On a global scale, one proteomic study has identified Leptospira interrogans proteins in culture supernatants (35) while another study utilized a bioinformatics approach to identify potential outer membrane and extracellular proteins (15). It has also been demonstrated that culture supernatants of Leptospira contain proteases which can interfere with host complement defense against Leptospira (36), that an extracellular enolase interacts with host plasminogen (37) and that an extracellular collagenase can degrade host collagen (38). Lastly, comparison of the transcriptomes of a Leptospira mutant inactivated in a putative regulatory locus (lb139) versus the parent wild type (wt) strain revealed, amongst others, reduced transcript levels of 20 genes which encoded extracellular proteins, in the mutant strain (39) and this mutant displayed virulence attenuation in hamsters. Combined, these studies implicated extracellular proteins in the Leptospiral infection process.

Current vaccines against Leptospira primarily consist of inactivated bacterin preparations, which induce a largely humoral immune response, and are primarily serovar-specific ("Leptospirosis Fact Sheet," WHO, Regional Office for South-East Asia, 2009). Further, the NOBIBAC® (Merck Animal Health) label claim indicates that there is little if any evidence for cross-protection. The observed lack of cross-protection is not surprising, particularly in view of the significant genetic/genomic differences among, for example, the gene organization in the lipopolysaccharide biosynthetic (rfb) locus (Pena-Moctezuma, A. et al.., 2001 FEMS Immunology and Medical Microbiology 31 (2001) 73-81). Leptospira lipopolysaccharides are thus serovar-specific, and as antigenic epitopes, tend to elicit T-cell-independent immune responses. As such, the current strategy for achieving broad protection against different Leptospira serovar(s) has been to include many different inactivated Leptospira serovar(s) in a vaccine formulation. This approach has significant drawbacks, including the need to grow multiple different serovars to achieve complete protection and an increasing potential for interference with other Leptospira serovars or other vaccine components.

Accordingly, it would be useful to provide simplified compositions, perhaps containing only one or more conserved immunogenic proteins, for eliciting broad immunoprotective responses against multiple Leptospira serovar(s). It would be further useful to provide Leptospira vaccine compositions that activate both humoral and cellular immune responses, to provide vaccinates with broader and longer lasting protection against subsequent exposure to Leptospira. Until the instant disclosure, methods for providing such protection against multiple Leptospira serovar(s) using one or more conserved immunoprotective proteins was not known.

REFERENCES

1. Ko A I, Goarant C, & Picardeau M (2009) Leptospira: the dawn of the molecular genetics era for an emerging zoonotic pathogen. Nat. Rev. Micro. 7:736-747.
2. Trueba G, Zapata S, Madrid K, Cullen P, & Haake D (2004) Cell aggregation: a mechanism of pathogenic Leptospira to survive in fresh water. International Microbiology 7(1):35-40.

3. Barragan V A, et al. (2011) Interactions of *Leptospira* with environmental bacteria from surface water. *Current Microbiology* 62(6):1802-1806.
4. Slamti L, de Pedro M A, Guichet E, & Picardeau M (2011) Deciphering morphological determinants of the helix-shaped *Leptospira*. *J Bacteriol* 193(22):6266-6275.
5. Masi M & Wandersman C (2010) Multiple signals direct the assembly and function of a type 1 secretion system. *Journal of Bacteriology* 192(15):3861-3869.
6. Delepelaire P (2004) Type I secretion in gram-negative bacteria. *Biochimica et Biophysica Acta* 1694(1-3):149-161.
7. Sandkvist M (2001) Biology of type II secretion. *Molecular Microbiology* 40(2):271-283.
8. Eshghi A, Cullen P A, Cowen L, Zuerner R L, & Cameron C E (2009) Global proteome analysis of *Leptospira interrogans*. *J Proteome Res* 8(10):4564-4578.
9. Eshghi A, et al. (2012) Methylation and in vivo expression of the surface-exposed *Leptospira interrogans* outer-membrane protein OmpL32. *Microbiology* 158(Pt 3):622-635.
10. Toma C, Okura N, Takayama C, & Suzuki T (2011) Characteristic features of intracellular pathogenic *Leptospira* in infected murine macrophages. *Cell Microbiol* 13(11):1783-1792.
11. Davis J M, Haake D A, & Ramakrishnan L (2009) *Leptospira interrogans* stably infects zebrafish embryos, altering phagocyte behavior and homing to specific tissues. *PLoS Neglected Tropical Diseases* 3(6):e463.
12. Toma C, et al. (2014) Leptospiral outer membrane protein LMB216 is involved in enhancement of phagocytic uptake by macrophages. *Cell Microbiol*.
13. Nally J E, et al. (2005) Purification and proteomic analysis of outer membrane vesicles from a clinical isolate of *Leptospira interrogans* serovar Copenhageni. *Proteomics* 5(1):144-152.
14. Cullen P A, et al. (2005) Surfaceome of *Leptospira* spp. *Infect Immun* 73:4853-4863.
15. Viratyosin W, Ingsriswang S, Pacharawongsakda E, & Palittapongarnpim P (2008) Genome-wide subcellular localization of putative outer membrane and extracellular proteins in *Leptospira interrogans* serovar Lai genome using bioinformatics approaches. *BMC Genomics* 9:181.
16. Pinne M & Haake D A (2009) A comprehensive approach to identification of surface-exposed, outer membrane-spanning proteins of *Leptospira interrogans*. *PLoS One* 4(6):e6071.
17. Lo M, Cordwell S J, Bulach D M, & Adler B (2009) Comparative transcriptional and translational analysis of Leptospiral outer membrane protein expression in response to temperature. *PLoS Negl Trop Dis* 3(12):e560.
18. Pinne M, Matsunaga J, & Haake D A (2012) Leptospiral Outer Membrane Protein Microarray, a Novel Approach to Identification of Host Ligand-Binding Proteins. *Journal of Bacteriology* 194(22):6074-6087.
19. Barbosa A S, et al. (2006) A newly identified Leptospiral adhesin mediates attachment to laminin. *Infect Immun* 74(11):6356-6364.
20. Nally J E, Whitelegge J P, Bassilian S, Blanco D R, & Lovett M A (2007) Characterization of the outer membrane proteome of *Leptospira interrogans* expressed during acute lethal infection. *Infect Immun* 75:766-773.
21. Matsunaga J, Werneid K, Zuerner R L, Frank A, & Haake D A (2006) LipL46 is a novel surface-exposed lipoprotein expressed during Leptospiral dissemination in the mammalian host. *Microbiology* 152:3777-3786.
22. Ristow P, et al. (2007) The OmpA-like protein Loa22 is essential for Leptospiral virulence. *PLoS Pathog* 3:e97.
23. Matsunaga J, Medeiros M A, Sanchez Y, Werneid K F, & Ko A I (2007) Osmotic regulation of expression of two extracellular matrix-binding proteins and a haemolysin of *Leptospira interrogans*: differential effects on LigA and Sph2 extracellular release. *Microbiology* 153(10):3390-3398.
24. Stevenson B, et al. (2007) *Leptospira interrogans* endostatin-like outer membrane proteins bind host fibronectin, laminin and regulators of complement. *PLoS ONE* 2(11):e1188.
25. Murray G L, et al. (2009) Major surface protein LipL32 is not required for either acute or chronic infection with *Leptospira interrogans*. *Infect. Immun.* 77(3):952-958.
26. Atzingen M V, et al. (2009) Lp95, a novel Leptospiral protein that binds extracellular matrix components and activates e-selectin on endothelial cells. *J Infect* 59(4):264-276.
27. Barbosa A S, et al. (2010) Functional characterization of LcpA, a surface-exposed protein of *Leptospira* spp. that binds the human complement regulator C4BP. *Infection and immunity* 78(7):3207-3216.
28. Pinne M, Choy H A, & Haake D A (2011) The OmpL37 surface-exposed protein is expressed by pathogenic *Leptospira* during infection and binds skin and vascular elastin. *PLoS Negl Trop Dis* 4(9):e815.
29. Mendes R S, et al. (2011) The novel Leptospiral surface adhesin Lsa20 binds laminin and human plasminogen and is probably expressed during infection. *Infect Immun* 79(11):4657-4667.
30. Souza N M, et al. (2012) Lsa30, a novel adhesin of *Leptospira interrogans* binds human plasminogen and the complement regulator C4bp. *Microb Pathog* 53(3-4):125-134.
31. Fernandes L G, et al. (2012) OmpL1 is an extracellular matrix- and plasminogen-interacting protein of *Leptospira* spp. *Infect Immun* 80(10):3679-3692.
32. King A M, et al. (2013) Leptospiral outer membrane protein LipL41 is not essential for acute leptospirosis but requires a small chaperone protein, lep, for stable expression. *Infect Immun* 81(8):2768-2776.
33. Zuerner R L, Knudtson W, Bolin C A, & Trueba G (1991) Characterization of outer membrane and secreted proteins of *Leptospira interrogans* serovar pomona. *Microb Pathog* 10(4):311-322.
34. Matsunaga J, Sanchez Y, Xu X, & Haake D A (2005) Osmolarity, a key environmental signal controlling expression of Leptospiral proteins LigA and LigB and the extracellular release of LigA. *Infect. Immun.* 73(1):70-78.
35. Zeng L, et al. (2013) Extracellular proteome analysis of *Leptospira interrogans* serovar Lai. *OMICS* 17(10):527-535.
36. Fraga T R, et al. (2014) Immune evasion by pathogenic *Leptospira* strains: the secretion of proteases that directly cleave complement proteins. *J Infect Dis* 209(6):876-886.
37. Nogueira S V, et al. (2013) *Leptospira interrogans* enolase is secreted extracellularly and interacts with plasminogen. *PLoS One* 8(10):e78150.
38. Kassegne K, et al. (2014) Identification of collagenase as a critical virulence factor for invasiveness and transmission of pathogenic *Leptospira* species. *J Infect Dis* 209(7):1105-1115.
39. Eshghi A, et al. (2014) A putative regulatory genetic locus modulates virulence in the pathogen *Leptospira interrogans*. *Infect Immun* 82(6):2542-2552.

40. Armengaud J, Christie-Oleza J A, Clair G, Malard V, & Duport C (2012) Exoproteomics: exploring the world around biological systems. *Expert Review of Proteomics* 9(5):561-575.
41. Griffin N M, et al. (2010) Label-free, normalized quantification of complex mass spectrometry data for proteomic analysis. *Nature Biotechnology* 28(1):83-89.
42. Trudgian D C, et al. (2010) CPFP: a central proteomics facilities pipeline. *Bioinformatics* 26(8):1131-1132.
43. Trudgian D C, et al. (2011) Comparative evaluation of label-free SINQ normalized spectral index quantitation in the central proteomics facilities pipeline. *Proteomics* 11(14):2790-2797.
44. Ellinghausen H C, Jr. & McCullough W G (1965) Nutrition of *Leptospira pomona* and growth of 13 other serotypes: Fractionation of oleic albumin complex and a medium of bovine albumin and polysorbate 80. *Am J Vet Res* 26:45-51.
45. Johnson R C & Harris V G (1967) Differentiation of pathogenic and saprophytic leptospires. Growth at low temperatures. *J Bacteriol* 94:27-31.
46. Murray G L, Morel V, & Cerqueira G M (2009) Genome-wide transposon mutagenesis in pathogenic *Leptospira* spp. *Infect Immun* 77:810-816.
47. Picardeau M (2008) Conjugative transfer between *Escherichia coli* and *Leptospira* spp. as a new genetic tool. *Applied and Environmental Microbiology* 74(1): 319-322.
48. Bourhy P, Louvel H, Saint Girons I, & Picardeau M (2005) Random insertional mutagenesis of *Leptospira interrogans*, the agent of leptospirosis, using a mariner transposon. *J Bacteriol* 187:3255-3258.
49. Trueba G A, Bolin C A, & Zuerner R L (1992) Characterization of the periplasmic flagellum proteins of *Leptospira interrogans*. J Bacteriol 174:4761-4768.
50. Matsunaga J, et al. (2003) Pathogenic *Leptospira* species express surface-exposed proteins belonging to the bacterial immunoglobulin superfamily. *Molecular Microbiology* 49(4):929-946.
51. Eshghi A, et al. (2012) *Leptospira interrogans* catalase is required for resistance to $H_2O_2$ and for virulence. *Infection and Immunity* 80(11):3892-3899.
52. Chambers M C, et al. (2012) A cross-platform toolkit for mass spectrometry and proteomics. *Nature Biotechnology* 30(10):918-920.
53. Vallenet D, et al. (2009) MicroScope: a platform for microbial genome annotation and comparative genomics. *Database (Oxford)* 2009:bap021.
54. Stamm L V, Gherardini F C, Parrish E A, & Moomaw C R (1991) Heat shock response of spirochetes. *Infection and Immunity* 59(4):1572-1575.
55. Kall L, Krogh A, & Sonnhammer E L (2004) A combined transmembrane topology and signal peptide prediction method. *J. Mol. Biol.* 338(5):1027-1036.
56. Bendtsen J D, Kiemer L, Fausbøll A, & Brunak S (2005) Non-classical protein secretion in bacteria. *BMC Microbiol* 5:58.
57. Mani M, et al. (2015) MoonProt: a database for proteins that are known to moonlight. *Nucleic Acids Research* 43(Database issue):D277-282.
58. Sukumaran S K, et al. (2010) A soluble form of the pilus protein FimA targets the VDAC-hexokinase complex at mitochondria to suppress host cell apoptosis. *Molecular Cell* 37(6):768-783.
59. Blau K, et al. (2007) Flamingo cadherin: a putative host receptor for *Streptococcus pneumoniae*. *Journal of Infectious Disease* 195(12):1828-1837.
60. Ling E, et al. (2004) Glycolytic enzymes associated with the cell surface of *Streptococcus pneumoniae* are antigenic in humans and elicit protective immune responses in the mouse. *Clinical & Experimental Immunology* 138 (2):290-298.
61. Kinnby B, Booth N A, & Svensäter G (2008) Plasminogen binding by oral streptococci from dental plaque and inflammatory lesions. *Microbiology* 154(Pt 3):924-931.
62. Picardeau M, et al. (2008) Genome sequence of the saprophyte *Leptospira biflexa* provides insights into the evolution of *Leptospira* and the pathogenesis of leptospirosis. *PLoS One* 3(2):e1607.
63. Wolff D G, et al. (2013) Interaction of *Leptospira* elongation factor Tu with plasminogen and complement factor H: a metabolic Leptospiral protein with moonlighting activities. *PLoS One* 8(11):e81818.
64. Crowe J D, et al. (2003) *Candida albicans* binds human plasminogen: identification of eight plasminogen-binding proteins. *Molecular Microbiology* 47(6):1637-1651.
65. Sakolvaree Y, et al. (2007) Proteome and immunome of pathogenic *Leptospira* spp. revealed by 2DE and 2DE-immunoblotting with immune serum. *Asian Pac J Allergy Immunol* 25:53-73.
66. Domingos R, et al. (2015) The novel *Leptospira interrogans* protein Lsa32 is expressed during infection and binds laminin and plasminogen. *Microbiology*.
67. King A M, et al. (2014) High-Temperature Protein G Is an Essential Virulence Factor of *Leptospira interrogans*. *Infect Immun* 82(3):1123-1131.
68. Verma A, Kumar P, Babb K, Timoney J F, & Stevenson B (2010) Cross-reactivity of antibodies against Leptospiral recurrent uveitis-associated proteins A and B (LruA and LruB) with eye proteins. *PLoS Neglected Tropical Diseases* 4(8):e778.
69. Verma A, et al. (2008) LruA and LruB antibodies in sera of humans with Leptospiral uveitis. *Clinical Vaccine Immunology* 15(6): 1019-1023.
70. Verma A, Artiushin S, Matsunaga J, Haake D A, & Timoney J F (2005) LruA and LruB, novel lipoproteins of pathogenic *Leptospira interrogans* associated with equine recurrent uveitis. *Infection and Immunity* 73(11):7259-7266.
71. Xu Q, et al. (2011) Structural and sequence analysis of imelysin-like proteins implicated in bacterial iron uptake. *PLoS One* 6(7):e21875.
72. Hullo M F, et al. (2007) Conversion of methionine to cysteine in *Bacillus subtilis* and its regulation. *Journal of Bacteriology* 189(1):187-197.

It is thus an object of this disclosure is to provide a rational, high throughput method for identifying immunoprotective *Leptospira* spp. proteins, which are broadly protective against at least two virulent serovars of *Leptospira*. In a particular embodiment, broad protection is provided by cross-serovar conserved surface proteins, which may not be expressed during the normal culture conditions present during typical lepto bacterin vaccine manufacturing. In another particular embodiment, the broad protection includes both a humoral and cellular immune response.

In an embodiment, the method for identifying immunoprotective *Leptospira* spp. proteins comprises the steps of:
(a) identifying likely membrane-localizing genes, which are conserved between pathogenic *Leptospira* serovars;
(b) identifying conserved *Leptospira* membrane proteins that are expressed in vivo or in vivo-like conditions; and
(c) correlating the results of the genetic (a) and protein (b) studies to identify pan-protective *Leptospira* proteins; thereby identifying the immunoprotective *Leptospira* spp.

proteins, which may be used in formulating broadly immunoprotective *Leptospira* vaccines.

In an embodiment of the identification method, analyses may be carried out using any of the following or equivalents or superiors thereof: CLC GENOMICS WORKBENCH and GENOSTAR SUITE 4.0 (software for assembly annotation); WALLGENE GENOSTAR 1.3.1.2 (software for comparative genomics); and SIGNALP, LIPOP, SPLIP, TMHMM and MCMBB (software for prediction of membrane localization).

In a particular embodiment, an overview of the method and results are presented in FIGS. 1 and 2.

In another embodiment of the identification method, outer membrane proteins may be extracted (e.g. by routine triton or proteinase K methods) and then identified by LC-MS-MS. Peptide sequences may then be aligned against any suitable *Leptospira* (or more general) protein database.

A further object of this disclosure is to provide broadly immunoprotective *Leptospira* spp. proteins, which are suitable for use in single and multi-valent vaccine formulations.

Another object of this disclosure is to provide immunoprotective compositions comprising the immunoprotective *Leptospira* spp. proteins.

Yet another object of this disclosure is to provide methods for eliciting safe and protective immune response, in an animal in need thereof, against multiple *Leptospira* spp., comprising the step of administering at least one immunoprotective *Leptospira* spp. protein according to the instant disclosure to animals in need of protection against the multiple *Leptospira* spp.

In an embodiment, the immunoprotective proteins or compositions comprising or consisting essentially of, or consisting of at least one or more immunogenic (including Immunoprotective) *Leptospira* spp. proteins elicits protection against subsequent experimental or natural challenge by virulent *Leptospira canicola*, *Leptospira grippotyphosa*, *Leptospira icterohaemorrhagiae*, *Leptospira pomona* *Leptospira bratislava* and any other *Leptospira* serovars known now, or future determined, to cause disease or illness in animals, including human animals In an embodiment, the broadly protective immunogenic composition may comprise, consist essentially of, or consist of at least one live attenuated *Leptospira* spp., at least one subunit (e.g. a peptide, protein, or immunoprotective portion thereof), at least one bacterin enriched in surface antigens, or any combination of the preceding.

In another embodiment, the immunoprotective proteins are surface antigens that are relatively more highly expressed in vivo, but relatively less expressed in vitro. As used herein, "in vivo" means the *Leptospira* spp., for example, the pathogenic *Leptospira* spp., is growing and/or infecting an animal host. As used herein, "in vitro" means the *Leptospira* spp. is growing in the context of routine culture conditions, for example, those used to manufacture *Leptospira* spp. for use in bacterin-based vaccines.

Until this disclosure, no one had appreciated this possibility, nor conceived of the disclosed methods for exploiting this phenomenon to generate a broadly effective *Leptospira* vaccine.

Accordingly, another object of the invention is to provide methods for culturing *Leptospira* spp. that mimics in vivo conditions. This method may facilitate the identification of broadly immunoprotective *Leptospira* spp. proteins because it allows relatively higher expression of such proteins relative to when the *Leptospira* spp. are grown under traditional manufacturing or in vitro conditions.

In a particular embodiment of the in vivo culturing method, *Leptospira* spp. may be grown in conditions that mimic the in vivo conditions, including relatively higher osmolarity, relatively higher temperature and relatively lower levels of iron (e.g. by chelation). In an embodiment, *L. interrogans australis* strain 700 may be grown under three conditions: 1) EMJH at 29° C. (in vitro control culture); 2) add to #1 40 µM bipyridil and 120 mM NaCl (in vivo-like conditions); and 3) two or more passages in hamster liver and spleen (actual in vivo conditions).

Surprisingly, when the osmolarity and temperature were raised as disclosed herein, the expression of cross-immunoprotective proteins increased significantly relative to their expression levels in standard culture conditions (see Table 1 below). Development and exploitation of this inventive method has allowed Applicants to produce heretofore unknown vaccine compositions, which are highly safe and effective in eliciting in an animal in need thereof protective immunity against at least two pathogenic *Leptospira* spp.

TABLE 1

*Leptospira* antigens induced by passage, or increasing osmolarity or iron chelation

| ID | fold change for in vivo over-expression (pvalue < 0.05) | fold change for in vivo like (NaCl) over-expression (p < 0.05) | fold change for in vivo like (iron chelation) over-expression (p < 0.05) | Efficacy | Peptide SEQ ID | DNA SEQ ID |
|---|---|---|---|---|---|---|
| LIC10879 | 6 | 19 | | Testing | 10 | 9 |
| LIC13050 | 34 | 50 | | Testing | 4 | 3 |
| LIC10411 | no change | 5 | no change | Testing | 34 | 33 |
| LIC13314 | no change | 15 | no change | 60% protection against australis | 6 | 5 |
| LIC10117 | 5 | 13 | 4 | Testing | 8 | 7 |
| LIC11088 | 10 | no change | no change | Testing | 40 | 39 |
| LIC11089 | 3 | no change | no change | Testing | 42 | 41 |
| LIC13074 | 5 | 9 | no change | Testing | 2 | 1 |
| LIC20229 | 14 | 6 | no change | Testing | 76 | 75 |
| LIC11181 | 6 | 30 | 3 | Testing | 78 | 77 |
| LIC13059 | no change | 5 | no change | Testing | 80 | 79 |
| LIC10959 | 4 | 17 | 3 | Testing | 82 | 81 |
| LIC11289 | 5 | 26 | 4 | Testing | 84 | 83 |
| LIC12349 | 4 | 13 | 3 | Testing | 86 | 85 |
| LIC13250 | 6 | 23 | 7 | Testing | 88 | 87 |

TABLE 1-continued

Leptospira antigens induced by passage, or increasing osmolarity or iron chelation

| ID | fold change for in vivo over-expression (pvalue < 0.05) | fold change for in vivo like (NaCl) over-expression (p < 0.05) | fold change for in vivo like (iron chelation) over-expression (p < 0.05) | Efficacy | Peptide SEQ ID | DNA SEQ ID |
|---|---|---|---|---|---|---|
| LIC20146 | 24 | 146 | 3 | Testing | 90 | 89 |
| LIC10321 | 12 | 12 | no change | Testing | 92 | 91 |
| LIC10662 | 10 | 17 | no change | Testing | 94 | 93 |
| LIC11183 | 7 | 3 | no change | Testing | 96 | 95 |
| LIC11489 | 14 | 50 | no change | Testing | 98 | 97 |
| LIC12258 | 10 | 4 | no change | Testing | 100 | 99 |
| LIC12731 | no change | 6 | no change | Testing | 102 | 101 |
| LIC12332 | no change | 15 | no change | Testing | 104 | 103 |
| LIC10793 | 4 | 2 | no change | Testing | 106 | 105 |
| LIC11884 | no change | 7 | no change | Testing | 108 | 107 |
| LIC20197 | 5 | no change | no change | Testing | 38 | 37 |
| LIC11224 | 3 | 5 | no change | Testing | 28 | 27 |
| LIC11693 | 3 | 9 | no change | Testing | 58 | 57 |
| LIC12285 | no change | 5 | no change | Testing | 110 | 109 |
| LIC10672 | 6 | 4 | no change | Testing | 64 | 63 |
| LIC10509 | 12 | 5 | 6 | Testing | 112 | 111 |
| LIC10596 | 3 | 53 | 8 | Testing | 114 | 113 |
| LIC11028 | 11 | 3 | 4 | Testing | 116 | 115 |
| LIC11874 | 4 | 23 | 2 | Testing | 118 | 117 |
| LIC13090 | 4 | 11 | 2 | Testing | 120 | 119 |
| LIC10318 | 5 | 13 | no change | Testing | 122 | 121 |
| LIC10655 | 10 | 19 | no change | Testing | 124 | 123 |
| LIC11553 | 11 | 10 | no change | Testing | 126 | 125 |
| LIC11637 | 6 | 9 | no change | Testing | 128 | 127 |
| LIC12100 | 6 | 9 | no change | Testing | 130 | 129 |
| LIC12784 | 6 | 14 | no change | Testing | 132 | 131 |
| LIC13002 | 31 | no change | 3 | Testing | 134 | 133 |
| LIC13023 | 6 | 6 | no change | Testing | 136 | 135 |
| LIC13017 | 3 | 5 | no change | Testing | 138 | 137 |
| LIC11711 | 2 | no change | no change | Testing | 46 | 45 |
| LIC10380 | 4 | 21 | 4 | Testing | 140 | 139 |
| LIC10551 | 21 | 4 | no change | Testing | 142 | 141 |
| LIC10740 | 9 | 8 | no change | Testing | 144 | 143 |
| LIC11580 | 7 | 13 | no change | Testing | 146 | 145 |
| LIC11990 | 3 | 8 | 3 | Testing | 148 | 147 |
| LIC12339 | 12 | 12 | no change | Testing | 150 | 149 |
| LIC12691 | 5 | 13 | no change | Testing | 152 | 151 |
| LIC12805 | no change | 7 | no change | Testing | 154 | 153 |
| LIC13195 | 10 | 13 | no change | Testing | 156 | 155 |
| LIC13313 | 10 | 22 | no change | Testing | 158 | 157 |
| LIC13386 | 42 | 46 | 4 | Testing | 160 | 159 |
| LIC13491 | 6 | 29 | 3 | Testing | 162 | 161 |
| LIC20165 | no change | 26 | no change | Testing | 164 | 163 |

TABLE 2

Additional Leptospira spp. antigens determined to have good technical feasibility (LIC10927 and LIC11003 are particularly advantageous)

| ID | Description | Peptide SEQ ID | DNA SEQ ID |
|---|---|---|---|
| LIC10314 | few publications; surface exposed sera recognition | 12 | 11 |
| LIC10326 | localization data only by Yang et al. | 14 | 13 |
| LIC10927 | Evaluated by Murray et al. | 16 | 15 |
| LIC10968 | upregulated caimano paper, upregulated salt | 18 | 17 |
| LIC11003 | LruA/LipL71, involved uveitis | 20 | 19 |
| LIC12576 | localization data only by Yang et al. | 22 | 21 |
| LIC13434 | evaluated by Murray et al. | 24 | 23 |
| LIC13071 | localization data only by Yang et al. | 26 | 25 |
| LIC11224 | localization data only by Yang et al. | 28 | 27 |
| LIC10027 | upregulated Caimano paper | 30 | 29 |
| LIC10474 | not described | 32 | 31 |
| LIC10411 | not described | 34 | 33 |
| LIC20035 | evaluated by Murray et al. in a non-relevant hamster model | 36 | 35 |
| LIC20197 | evaluated by Murray et al.. in a non-relevant hamster model | 38 | 37 |
| LIC11088 | not described, predicted cytC peroxidase | 40 | 39 |
| LIC11089 | evaluated by murray et al.. in a non-relevant hamster model | 42 | 41 |
| LIC11687 | predicted nuclease, downregulated at 37° C. few publications | 44 | 43 |
| LIC11711 | downreg 37 | 46 | 45 |
| LIC10115 | downreg 37 | 48 | 47 |
| LIC12433 | not described, predicted sugar transf | 50 | 49 |
| LIC10868 | entirely not described | 52 | 51 |
| LIC10898 | LipL48 no expression change upon temp or iron reg | 54 | 53 |
| LIC11299 | Murray et al. | 56 | 55 |
| LIC11693 | downreg salt | 58 | 57 |
| LIC12030 | downreg in vivo | 60 | 59 |
| LIC20153 | downreg in vivo | 62 | 61 |

TABLE 2-continued

Additional *Leptospira* spp. antigens determined to have good technical feasibility (LIC10927 and LIC11003 are particularly advantageous)

| ID | Description | Peptide SEQ ID | DNA SEQ ID |
|---|---|---|---|
| LIC10672 | evaluated by Atzingen et al . . . in a non-relevant hamster model | 64 | 63 |
| LIC11966 | 0% protection in Cheng et al . . . 2007. But upregulated in vivo in Caimano et al . . . , 2014 | 66 | 65 |
| LIC10973 | OmpL1 | 68 | 67 |
| Lp1118 | Chang et al., 2007 | 70 | 69 |
| MceII | Chang et al., 2007 | 72 | 71 |
| Lsa21 | Atzingen et al., 2012 | 74 | 72 |

TABLE 3

*Leptospira* spp. proteins common to both screens outlined in Examples 1 and 2

| ID | Description | Peptide SEQ ID | DNA SEQ ID |
|---|---|---|---|
| LIC11089 | Murray et al. | 42 | 41 |
| LIC10973 | OmpL1 | 68, 106 | 67, 105 |
| LIC10318 | Glucanase | 122 | 121 |

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein.

DETAILED DESCRIPTION OF THE INVENTION

In an embodiment, the method for identifying immunoprotective *Leptospira* spp. proteins comprises the steps of:

(a) identifying likely membrane-localizing genes, which are conserved between pathogenic *Leptospira* serovars;

(b) identifying conserved *Leptospira* membrane proteins that are expressed in vivo or in vivo-like conditions; and (c) correlating the results of the genetic (a) and protein (b) studies to identify pan-protective *Leptospira* proteins; thereby identifying the immunoprotective *Leptospira* spp. proteins, which may be used in formulating broadly immunoprotective *Leptospira* vaccines.

In an embodiment of the identification method, analyses may be carried out using any of the following or equivalents or superiors thereof: CLC GENOMICS WORKBENCH and GENOSTAR SUITE 4.0 (software for assembly annotation); WALLGENE GENOSTAR 1.3.1.2 (software for comparative genomics); and SIGNALP, LIPOP, SPLIP, TMHMM and MCMBB (software for prediction of membrane localization).

Figure 1:
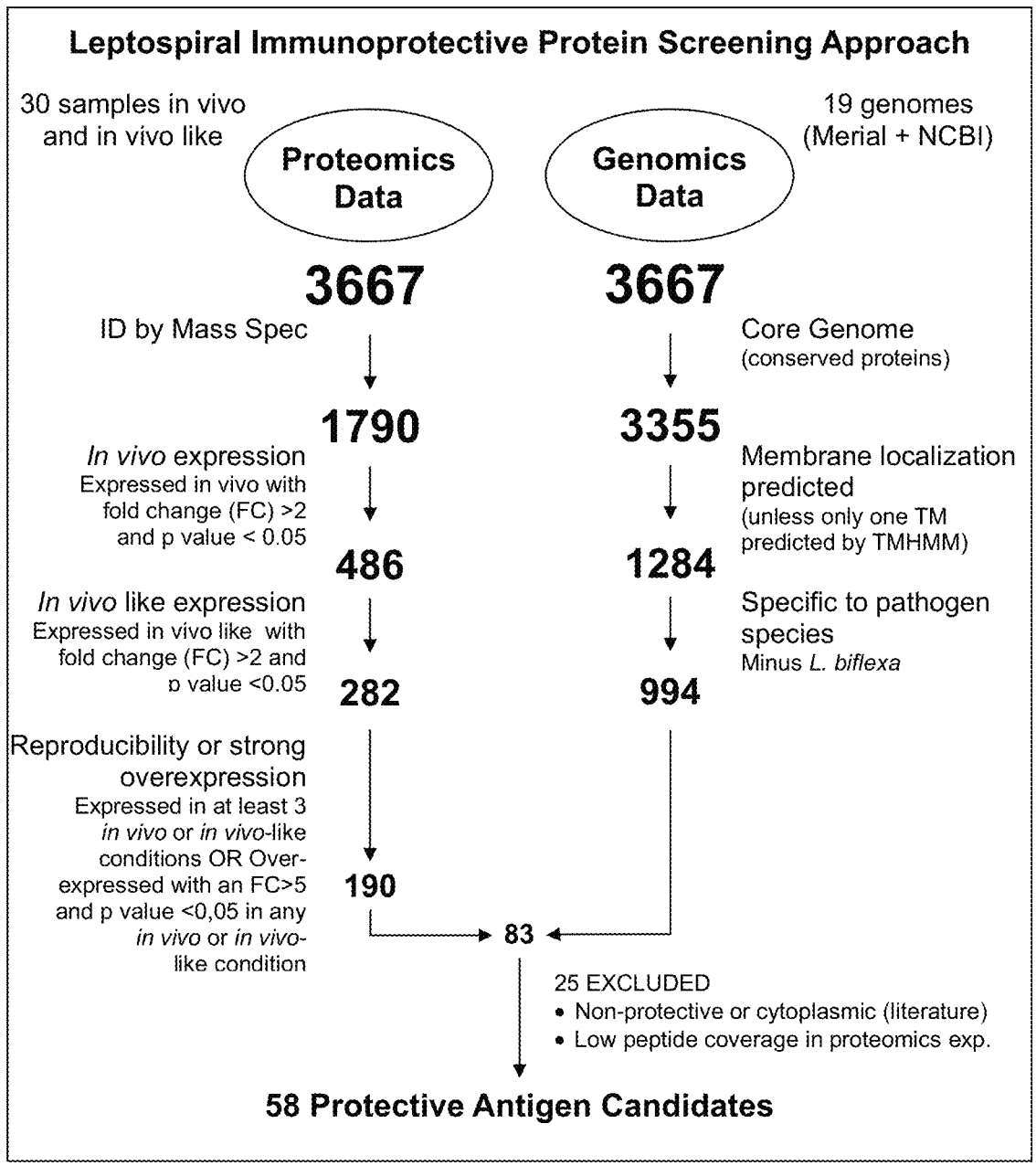
FIG. 1 is a schematic of the *Leptospira* spp. protein screening process.
Figure 2:
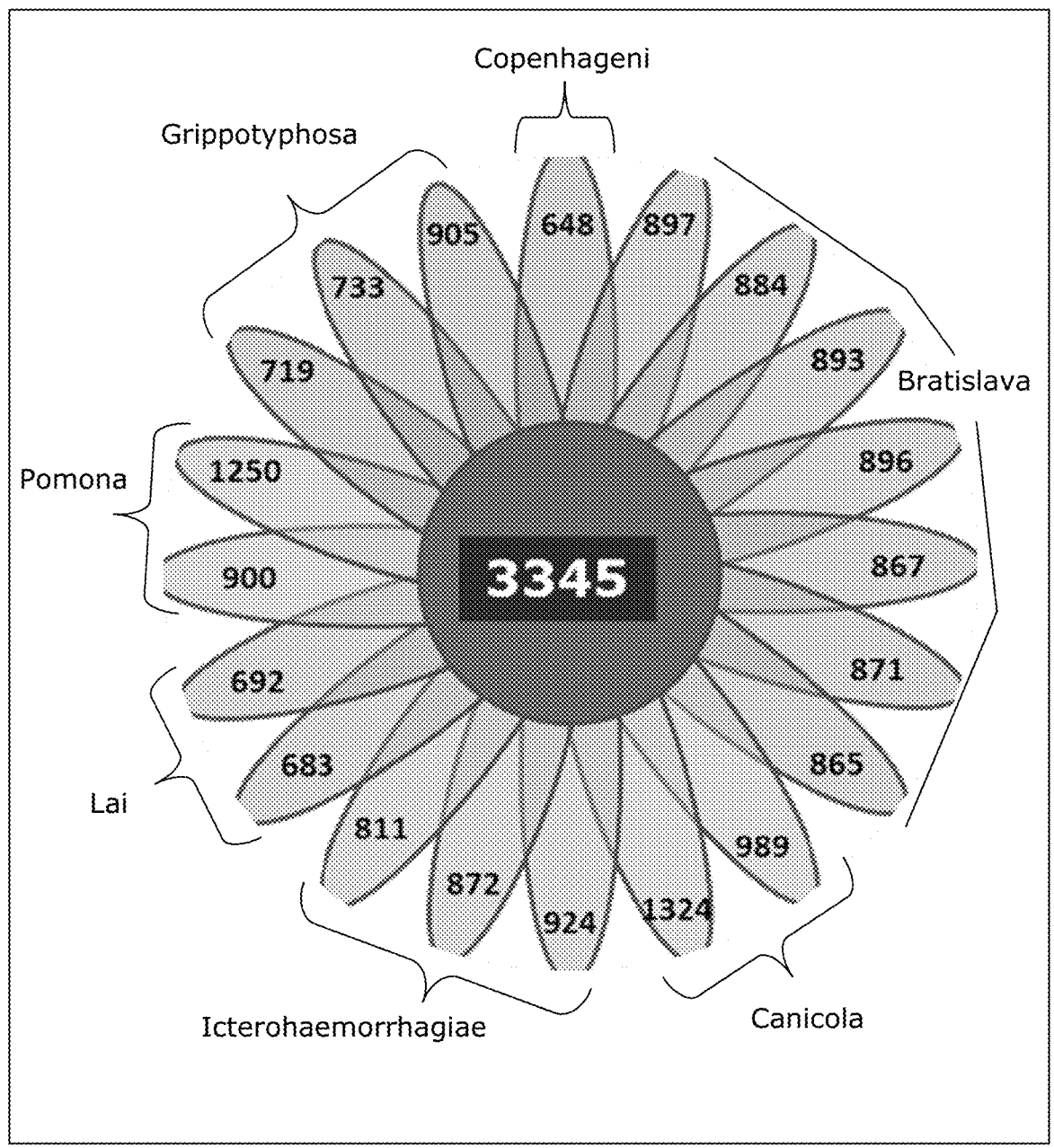
FIG. 2 depicts the determination of the "core genome," which means the set of genes common to all studied genomes across the *Leptospira* genus minus those genes present in the non-pathogenic species (i.e. *L. biflexa*)
Figure 3:
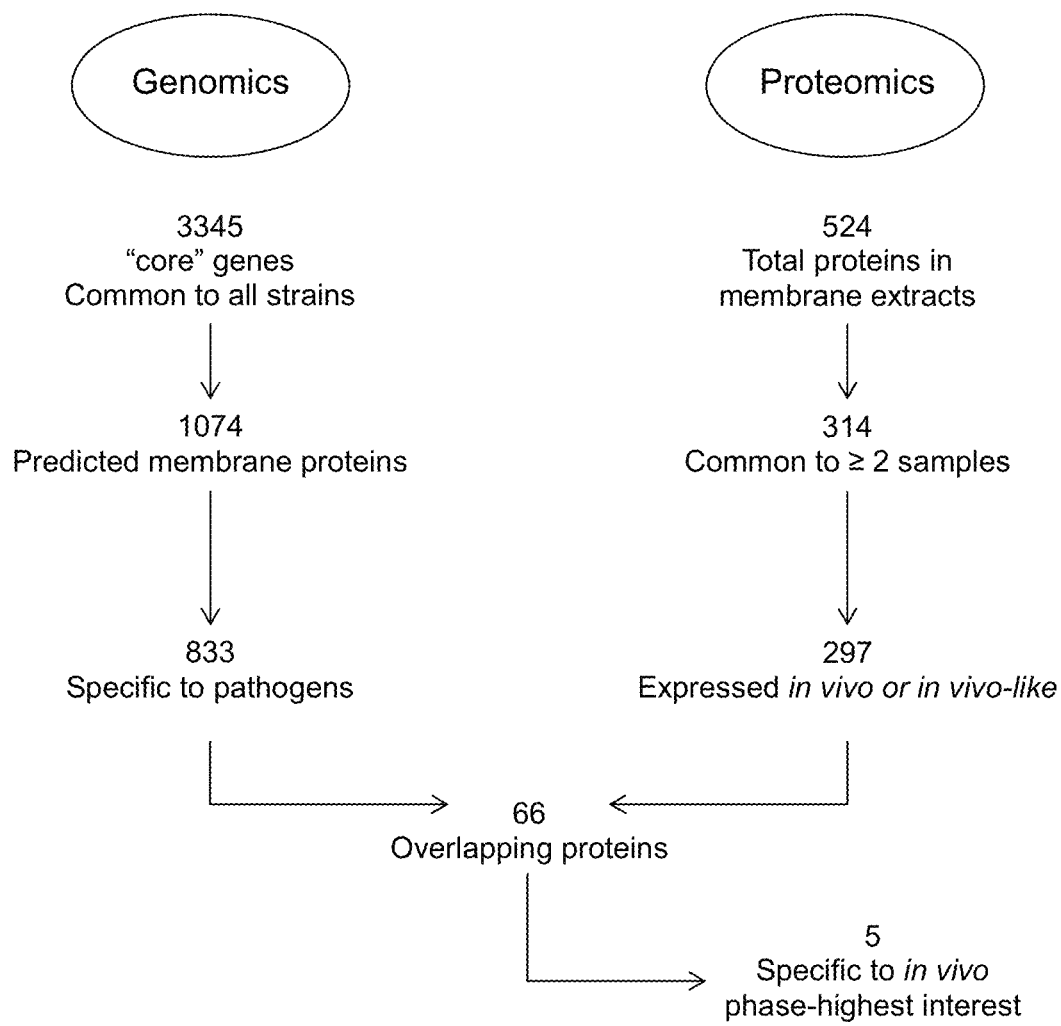
FIG. 3 is a flow diagram showing how the parallel genomic and proteomic screening approach yielded the five high interest vaccine candidate *Leptospira* spp. proteins recited in Table 1 above.

In a particular embodiment, an overview of the method and results are presented in FIGS. 1 and 2.

In an embodiment, the disclosure provides a composition for providing to an animal in need thereof protective immunity against at least one *Leptospira* spp., comprising at least one *Leptospira* polypeptide having at least 80%, 85%, 90%, 91%, 92%, 93%, 94%, 95%, 96%, 97%, 98%, 99% or 99.5% identity to LIC13074p, LIC13050p, LIC13314p, LIC10117p, LIC10879p, LIC10879p, LIC13050p, LIC10411p, LIC13314p, LIC10117p, LIC11088p, LIC11089p, LIC13074p, LIC20229p, LIC11181p, LIC13059p, LIC10959p, LIC11289p, LIC12349p, LIC13250p, LIC20146p, LIC10321p, LIC10662p, LIC11183p, LIC11489p, LIC12258p, LIC12731p, LIC12332p, LIC10793p, LIC11884p, LIC20197p, LIC11224p, LIC11693p, LIC12285p, LIC10672p, LIC10509p, LIC10596p, LIC11028p, LIC11874p, LIC13090p, LIC10318p, LIC10655p, LIC11553p, LIC11637p, LIC12100p, LIC12784p, LIC13002p, LIC13023p, LIC13017p, LIC11711p, LIC10380p, LIC10551p, LIC10740p, LIC11580p, LIC11990p, LIC12339p, LIC12691p, LIC12805p, LIC13195p, LIC13313p, LIC13386p, LIC13491p, LIC20165p, LIC10314p, LIC10326p, LIC10927p, LIC10968p, LIC11003p, LIC12576p, LIC13434p, LIC13071p, LIC11224p, LIC10027p, LIC10474p, LIC10411p, LIC20035p, LIC20197p, LIC11088p, LIC11687p, LIC11711p, LIC10115p, LIC12433p, LIC10868p, LIC10898p, LIC11299p, LIC11693p, LIC12030p, LIC20153p, LIC10672p, LIC11966p, LIC10973p, Lp1118p, MceIIp, Lsa21p or combinations thereof or effective immunological equivalent portions thereof. By "immunological equivalent portions," it is intended that the portion is capable of eliciting a statistically similar or better safe and effective immune response, relative to the larger polypeptide sequence from which the portion was taken. As such, if a composition comprising LIC13074p protects 80% of vaccinated animals with protection from subsequent virulent challenge, and a given truncation of LIC13074p protects 82% of vaccinated animals, then the truncation is an "immunologically equivalent portion" of LIC In another embodiment, the composition for providing protective immunity against *Leptospira*, or diseases caused by *Leptospira*, comprises at least one *Leptospira* polypeptide having at least 80% identity to LIC11089p, LIC10973p, LIC10318p, combinations thereof or immunological equivalent portions thereof. In other embodiments, the *Leptospira* polypeptide has at least 90%, 91%, 92%, 93%, 94%, 95%, 96%, 97%, 98%, 99% or 100% identity to LIC11089p, LIC10973p or LIC10318p.

In yet another embodiment, the composition comprises a polypeptide encoded by a nucleic acid sequence having at least 80%, 85%, 90%, 91%, 92%, 93%, 94%, 95%, 96%, 97%, 98%, 99% or 100% identity to one of the sequences as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161 or 163.

In another embodiment, the nucleic acid sequence has at least 98% identity to one of the sequences as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161 or 163.

In another embodiment, the nucleic acid sequence has 100% identity to one of the sequences as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161 or 163.

In another embodiment, the nucleic acid sequence is as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161 or 163.

In another aspect, the disclosure provides a method for providing to an animal in need thereof protective immunity against one or more pathogenic or virulent *Leptospira* spp., comprising administering to an animal a vaccine comprising an immunoprotective effective amount of a *Leptospira* spp. polypeptide selected from, or having at least 80% identity to, a polypeptide having the sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162 or 164.

In an embodiment, the method of providing protective immunity comprises the steps of administering to an animal a vaccine comprising an immunoprotective effective amount of a polypeptide selected from, or having at least 80% identity to, a polypeptide having the sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162 or 164.

In another aspect, the disclosure provides a vector capable of expressing a recombinant DNA, wherein the recombinant DNA is selected from any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161 and 163.; or wherein the recombinant DNA is at least 75%, 80%, 85%, 90%, 95% or 98% homologous to the sequences as set forth in any one of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161 and 163.

In yet another aspect, the disclosure provided a recombinant DNA vaccine comprising:

(a) a recombinant DNA wherein the recombinant DNA comprises one or more of the sequences as set forth in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161 and 163; and (b) a vector capable of expressing the recombinant DNA when the recombinant DNA is inserted into the vector, wherein the recombinant DNA is inserted into the vector such that a recombinant protein is expressed when the vector is provided in an appropriate host.

The disclosure also provides a method for producing a vaccine against a *Leptospira*-related disorder comprising the steps of:

(a) providing a recombinant DNA, wherein the recombinant DNA comprises any one or more of the sequences as set forth in SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161 and 163;

(b) providing a vector capable of expressing the recombinant DNA when the recombinant DNA is inserted into the vector; and (c) inserting the recombinant DNA into the vector, wherein the recombinant DNA is inserted into the vector such that a recombinant protein is expressed when the vector is provided in an appropriate host, thereby producing the vaccine.

The disclosure further provides a method for producing an immunoprotective peptide for use in a vaccine against a *Leptospira*-related disorder comprising:

(a) providing a recombinant DNA, wherein the recombinant DNA is selected from:

(i) a recombinant DNA that encodes an immunogenic epitope or immunologically active fragment of any one or more of the nucleic acid sequences as set forth in SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161 and 163; or (ii) a recombinant DNA that encodes a protein fragment of at least 40%, 50%, 60% 70%, 80%, 90% or 95% of the length of the amino acid sequence as set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162 or 164;

(b) providing a vector capable of expressing the recombinant DNA when the recombinant DNA is inserted into the vector;

(c) inserting the recombinant DNA into the vector;

(d) providing a bacterial strain;

(e) transforming the vector into the bacterial strain such that a recombinant protein is expressed when the vector is transformed into the bacterial strain; and (f) harvesting the recombinant protein from the bacterial strain, thereby producing the immunoprotective protein.

In an embodiment of the method, the animal is protected against *Leptospira icterohaemorrhagiae, Leptospira canicola, Leptospira grippotyphosa, Leptospira australis, Leptospira bratislava* and *Leptospira pomona*. In an embodiment, the animal may be administered about 1 ml of vaccine. The vaccine may also be administered as two subcutaneous doses, for example, at 21-day intervals. In an example, the animal is a canine, and the vaccine may comprise additional antigens that provide immunity against additional canine pathogens. The additional antigens may be selected from canine parvovirus (CPV), canine parainfluenza virus (CPi2), canine distemper virus (CDV), adenovirus, herpesvirus, rabies, canine coronavirus, and combinations thereof.

In still another aspect, the disclosure provides a T-cell epitope vaccine comprising a recombinant protein, wherein the recombinant protein comprises a T-cell epitope, and wherein the T-cell epitope comprises at least one polypeptide sequence having at least 80% identity to at least one polypeptide having the sequence set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162 or 164.

In an embodiment of the T-cell epitope vaccine, the polypeptide sequence comprises one or more of the sequences as set forth in SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162 or 164. In a particular embodiment, the vaccine comprises a polypeptide having the sequence as set forth in SEQ ID NO: 2, 4, 6, 8, 10, 42 (LIC11089), 68 (LIC10973) or 122 (LIC10318).

In some embodiments, the polypeptide has the sequence set forth in SEQ 42, 68 or 122.

DESCRIPTIONS/DEFINITIONS

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

The invention will now be further described by way of the following non-limiting examples.

EXAMPLES

Example 1—Identification of Broadly Immunoprotective Leptospira Ssp. Proteins Through a Novel High Throughput Method Leptospira spp. were subjected to culture conditions that mimic the in vivo conditions, including relatively higher osmolarity, relatively higher temperature and relatively lower levels of iron (e.g. by chelation). Briefly, L. interrogans australis strain 700 was be grown under three conditions: 1) EMJH at 29° C. (in vitro control culture); 2) add to #1 40 µM bipyridil and 120 mM NaCl (in vivo-like conditions); and 3) two or more passages in hamster liver and spleen (actual in vivo conditions).

When the osmolarity and temperature were raised as disclosed herein, the expression of cross-immunoprotective proteins increased significantly relative to their expression levels in standard culture conditions (see Table 1 above). Development and exploitation of this inventive method has allowed Applicants to produce heretofore unknown vaccine compositions, which are highly safe and effective in eliciting in an animal in need thereof protective immunity against at least two pathogenic Leptospira spp.

Example 2—Examination of the Leptospiral Exoproteome

Leptospira are spirochete bacteria capable of saprophytic and pathogenic lifestyles. These zoonotic bacteria have a worldwide prevalence and pathogenesis manifests in the disease known as leptospirosis. The aim in this study was to gain a global understanding of the composition of the Leptospira exoproteome and to elucidate how these proteins contribute to the saprophytic and pathogenic life cycle of these bacteria. Leptospiral exoproteins were quantified under various in vitro Leptospira culture conditions mimicking infection using normalized spectral index quantitative proteomics. About 208 exoproteins were identified, having equal or higher quantities in culture supernatants when compared to cellular quantities. Culture conditions demonstrated that 52 of these proteins were regulated in response to temperature while 69 were regulated in response to osmotic changes, with the majority displaying lowered abundances. Exoproteins were mainly classified into clusters of orthologous groups encompassing metabolism and energy production, suggesting that exoproteins likely serve essential functions for Leptospira viability. Proteins associated with virulence (factors causing tissue damage and cytotoxicity) were underrepresented.

In accordance, disruption of two exoprotein encoding genes resulted in significant growth defects in vitro, while disruption of six other exoprotein encoding genes neither affected in vitro growth rates nor disease manifestation in the animal infection model. These observations suggest that Leptospira genomes contain exoprotein encoding genes with redundant functions, the majority of which seem to be dedicated to heterotrophic processes with potential secondary functioning in disease pathogenesis.

Leptospira interrogans serovar Manilae strain $L_{495}$ was culture maintained in EMJH medium (44, 45) at 30° C. Leptospira transposon mutagenesis has previously been described (46-48) and L495 transposon mutants used in this study were obtained from an in house maintained library of mutants. The mutant strains were culture maintained as described above for the parent strain. To perform proteomic analysis on culture supernatants EMJH was constituted with the following modifications. Albumin was omitted from the recipe and TWEEN® 80 and glycerol were added to 0.01% (v/v). A separate batch of modified EMJH was made to contain 120 mM NaCl. Prior to shifting to modified EMJH media, *Leptospira* were cultured in EMJH at 30° C. to a density of 10^9 bacteria per ml, and subsequently pelleted via centrifugation at 3,200×g for 15 min, using a swinging bucket rotor. Pelleted bacteria were washed 3 times with modified EMJH using 20 ml of media for each washing step. Bacteria were then resuspended in modified EMJH and enumerated via darkfield microscopy. Bacteria were then diluted in modified EMJH to a concentration of 10^8 bacteria per ml in a total volume of 100 ml for each condition (for incubation at 30° C., 37° C. and in modified EMJH with 120 mM NaCl at 30° C.), in two biological replicates for each condition. After 18 hours of incubation, bacteria were enumerated via darkfield microscopy to validate bacterial viability.

Initial Protein Analyses

*Leptospira* were centrifuged at 3,200×g for 10 minutes and the pelleted bacteria were separated from culture supernatants by siphoning supernatants. The pellets were stored at −20° C. and the culture supernatants were transferred to VIVASPIN® 20 1,000,000 MWCO PES ultrafiltration devices (Sartorius Stedim Biotech, Goettingen, Germany). The latter step ensured removal of any remaining whole *Leptospira* cells from the culture supernatants. Subsequent centrifugation was performed according to manufacturer's instructions and all manipulations were carried out at room temperature. The flow-through was then concentrated using AMICON® Ultra Centrifugal Filters ULTRACEL® 3K (Merck Millipore Ltd., Cork, Ireland) and subsequently with low volume AMICON® Ultra—0.5 ml 3k (Merck Millipore Ltd.). Each 100 ml culture supernatant was concentrated down to a final volume of 20 µl.

To obtain protein from the pelleted whole *Leptospira* cells, bacterial pellets were resuspended in the respective modified EMJH media to a final volume of 200 µl and sonicated to lyse the bacteria. Protein concentration was measured via UV spectrometry at 280 nm. Samples were diluted 3:1 in Laemmli (4×) sample loading buffer and equal concentrations of protein were used in SDS PAGE.

Recombinant AAS70781.1 (LIC12209) protein (henceforth referred to as *Leptospira* Beta Propeller 52 or LbP52) was produced essentially as previously described. Rabbit antisera generated against F1aA-2 (49), GroL (50) and LigA (50) were generously provided by Dr. David Haake. Rabbit antisera against recombinant LbP52 (rLbP52) protein was generated using routine procedures.

To obtain *Leptospira* positive sera, Hartley male guinea pigs (Charles River Laboratories) were obtained at 6 weeks of age and weighed between 450-500 g. Guinea pigs (N=6) were anaesthetized via intramuscular injection with 40 mg ketamine and 4 mg xylazine (per kg body weight) and blood (~1 ml) was collected into 10 ml Venosafe Plastic Tubes (Terumo, Guyancourt, France) via cardiac heart puncture. Animals were then maintained under normal care conditions for 7 days and then injected intraperitoneal with $10^5$ *L. interrogans* strain L495 in 1 ml albumin free EMJH. Blood samples from infected animals were collected by terminal cardiac puncture of anaesthetized animals. Serum was collected by incubation of blood samples in Venosafe Plastic tubes (Terumo) at room temperature for 30 min, followed by centrifugation at 1,500×g for 10 min. The supernatant was collected for use in ELISA and immunoblot experiments. Protocols for animal experiments conformed to the guidelines of the Animal Care and Use Committees of the Institut Pasteur (Paris, France).

SDS-PAGE and protein immunoblots were performed as previously described (32, 51) with the following modifications. The SDS-PAGE and immunoblot experiments were performed using 10 µg of total protein from whole cell lysates and culture supernatants. Antiserum to F1aA-2, GroL, LigA and LbP52 was used at 1:2,000, 1:8,000, 1:750 and 1:1,000, respectively. Guinea pig *Leptospira* positive and pre-immune sera were used at 1:100 and goat polyclonal secondary antibody to guinea pig IgG-Fc (HRP) (Abcam) and IgM-Fc (HRP) (*Acris*) were used at a dilution of 1:20,000.

Mass Spec Protein Analysis

For mass spectrometry experiments, 10 µg of protein was allowed to separate for 10 mm on a 4-12% gradient TGX gel, without the addition of any dyes. Samples were then cored and diced into ~1 mm sections. Protein samples were analysed on an ULTIMATE 3000 RSLCNANO HPLC (Dionex, Camberley, UK) system run in direct injection mode coupled to a QEXACTIVE™ ORBITRAP™ mass spectrometer (Thermo Electron, Hemel Hempstead, UK). Samples were resolved on a 25 cm by 75 µm inner diameter picotip analytical column (New Objective, Woburn, Mass., USA) which was packed in-house with PRONTOSIL 120-3 C18 ACE-EPS phase, 3 µm diameter beads (Bischoff Chromatography, Germany). The system was operated at a flow-rate of 300 nl min$^{-1}$ and a 120 min gradient was used to separate the peptides. The mass spectrometer was operated in a "Top 10" data dependent acquisition mode. Precursor scans were performed in the ORBITRAP™ at a resolving power of 70,000, from which the ten most intense precursor ions were selected by the quadrupole and fragmented by HCD at a normalized collision energy of 28%. The quadrupole isolation window was set at 3 m/z. Charge state +1 ions and undetermined charge state ions were rejected from selection for fragmentation. Dynamic exclusion was enabled for 40 s. Data were converted from .RAW to .MGF using PROTEOWIZARD software (52).

Example 4—Data Analyses

Data Manipulation Downstream of Identification and Quantification

Identified proteins and the corresponding relative spectral indices were exported to Microsoft Excel for further analyses. The following comparisons of relative protein abundances were made: supernatant protein at 30° C. versus whole cell protein at 30° C. (S vs P 30° C.), supernatant protein at 37° C. versus whole cell protein at 37° C. (S vs P 37° C.), supernatant protein at 30° C. exposed to 120 mM NaCl versus whole cell protein at 30° C. exposed to 120 mM NaCl (S vs P NaCl), supernatant protein at 37° C. versus supernatant protein at 30° C. (37° C. vs 30° C. S) and supernatant protein at 30° C. exposed to 120 mM NaCl versus supernatant protein at 30° C. (NaCl vs 30° C. S). To be deemed as an actively exported exoprotein, proteins had to be detected in all 6 supernatant samples and must have displayed equal to or higher quantity in the supernatant than whole cell *Leptospira* (for S vs P 30° C., only). To compare exoprotein quantities in culture supernatants (37° C. vs 30° C. S and NaCl vs 30° C. S), protein spectral abundances were compared and only those exoproteins displaying altered expression of at least 2 fold (average between replicate experiments), were deemed as altered in expression in response to temperature and osmotic shifts (Tables 4 and 5).

TABLE 4

Exoprotein regulation in response to a temperature shift to 37° C.

| Accession # | Locus tag | Annotation | ▼Signal peptide | ▲Non-Classical | RQ at 37° C. |
|---|---|---|---|---|---|
| AAS70942.1 | LIC12373 | Conserved protein of unknown function | Yes | No | 6.8 |
| AAS71238.1 | LIC12679 | Thiamine biosynthesis protein | No | No | 5.7 |
| AAS70572.1 | LIC11996 | Conserved protein of unknown function | Yes | Yes | 2.7 |
| AAS71860.1 | LIC13318 | Fatty acid synthase subunit beta | No | Yes | 2.2 |
| AAS70439.1 | LIC11853 | Homoserine O-acetyltransferase | No | Yes | 2.1 |
| AAS68936.1 | LIC10309 | Glycine cleavage system P-protein | No | No | 2.1 |
| AAS68899.1 | LIC10272 | Translation elongation factor G | No | No | −2.0 |
| AAS69094.1 | LIC10473 | Valyl-tRNA synthetase | No | No | −2.0 |
| AAS69105.1 | LIC10484 | Threonine synthase | No | No | −2.0 |
| AAS70662.1 | LIC12091 | Phosphoglycerate kinase | No | No | −2.0 |
| AAS70781.1 | LIC12209 | Putative lipoprotein | Yes | Yes | −2.0 |
| AAS71887.1 | LIC13345 | Glutamyl-tRNA synthetase | No | No | −2.0 |
| AAS70679.1 | LIC12108 | Aspartyl-tRNA synthetase | No | No | −2.2 |
| AAS70804.1 | LIC12232 | Thymidylate synthase | No | No | −2.2 |
| AAS70906.1 | LIC12337 | Conserved protein of unknown function | Yes | Yes | −2.2 |
| AAS72087.1 | LIC20058 | Methylmalonyl-CoA mutase | No | No | −2.2 |
| AAS71651.1 | LIC13105 | Glucose-6-phosphate isomerase | No | No | −2.2 |
| AAS72234.1 | LIC20208 | Methylmalonyl-COA mutase small subunit | No | No | −2.2 |
| AAS68701.1 | LIC10064 | Conserved protein of unknown function | Yes | Yes | −2.5 |
| AAS69195.1 | LIC10574 | Dihydroorotase | No | No | −2.5 |
| AAS69321.1 | LIC10700 | 3-oxoacyl-[acyl-carrier-protein] reductase oxidoreductase | Yes | No | −2.5 |
| AAS69380.1 | LIC10763 | Alanyl-tRNA synthetase | No | No | −2.5 |
| AAS69625.1 | LIC11016 | Adenylosuccinate lyase | No | No | −2.5 |
| AAS70211.1 | LIC11616 | ADP-L-glycero-D-mannoheptose-6-epimerase | Yes | No | −2.5 |
| AAS70356.1 | LIC11767 | N-acetylornithine aminotransferase | No | No | −2.5 |
| AAS71336.1 | LIC12782 | Hydroxymethylglutaryl-CoA lyase | No | No | −2.5 |
| AAS71060.1 | LIC12495 | 3-hydroxybutyryl-CoA dehydratase | No | No | −2.5 |
| AAS71819.1 | LIC13275 | Conserved protein of unknown function | No | No | −2.5 |
| AAS69048.1 | LIC10425 | Conserved protein of unknown function | No | No | −2.9 |
| AAS70738.1 | LIC12166 | Alcohol dehydrogenase | No | No | −3.3 |
| AAS69213.1 | LIC10592 | Peptidoglycan-associated cytoplasmic membrane protein | No | No | −3.3 |
| AAS70391.1 | LIC11803 | Dihydrolipoamide dehydrogenase | No | No | −3.3 |
| AAS71017.1 | LIC12451 | Chorismate mutase and prephenate dehydratase | No | No | −3.3 |
| AAS71030.1 | LIC12465 | Threonyl-tRNA synthetase | No | No | −3.3 |
| AAS71081.1 | LIC12516 | Acetoacetyl-CoA synthetase | No | No | −3.3 |
| AAS71282.1 | LIC12725 | 3-hydroxybutyryl-CoA dehydratase | No | No | −3.3 |
| YP_002257.2 | pyrF | Orotidine 5'-phosphate decarboxylase | No | No | −3.3 |
| AAS70910.1 | LIC12341 | Conserved protein of unknown function | Yes | No | −4.0 |
| AAS71178.1 | LIC12618 | Diaminopimelate decalboxylase | No | No | −4.0 |
| AAS71250.1 | LIC12692 | Conserved protein of unknown function | No | No | −4.0 |
| AAS68996.1 | LIC10373 | Putative lipoprotein | Yes | No | −5.0 |
| AAS70417.1 | LIC11831 | Guanine monophosphate synthase | No | No | −5.0 |
| AAS70822.1 | LIC12250 | Unnamed protein product | No | No | −5.0 |
| AAS70969.1 | LIC12400 | Isoleucyl-tRNA synthetase | No | No | −5.0 |
| AAS71101.1 | LIC12536 | RibD | No | No | −5.0 |
| AAS69951.1 | LIC11350 | Acyl-CoA dehydrogenase | No | No | −6.7 |
| AAS70496.1 | LIC11913 | Unnamed protein product | No | No | −6.7 |
| AAS71615.1 | LIC13066 | Putative lipoprotein | Yes | Yes | −6.7 |
| AAS72275.1 | LIC20254 | Response regulator | No | No | −9.5 |
| AAS69386.1 | LIC10769 | Processing metalloprotease | No | No | −10.0 |
| AAS70318.1 | LIC11729 | 2,4-dienoyl-CoA reductase | No | No | −10.0 |
| AAS71115.1 | LIC12551 | Acyl-CoA dehydrogenase | No | No | −10.0 |

RQ: Relative quantity, average between experimental replicates
▼Signal peptide as predicted using Phobius (55)
▲Non-classical secretion predicted using SecretomeP 2.0 Server (56)

TABLE 5

Exoprotein regulation in response to an osmotic shift to modified EMJH with 120 mM NaCl

| Accession # | Locus tag | Annotation | ▼Signal peptide | ▲Non-Classical | RQ in 120 mM NaCl |
|---|---|---|---|---|---|
| AAS71238.1 | LIC12679 | Thiamine biosynthesis protein | No | No | 6.9 |
| AAS71937.1 | LIC13397 | Phosphodiesterase | No | Yes | 5.6 |

TABLE 5-continued

Exoprotein regulation in response to an osmotic shift to modified EMJH with 120 mM NaCl

| Accession # | Locus tag | Annotation | ▼Signal peptide | ▲Non-Classical | RQ in 120 mM NaCl |
|---|---|---|---|---|---|
| AAS70781.1 | LIC12209 (LbP52) | Putative lipoprotein | No | No | 5.5 |
| AAS70980.1 | LIC12412 | Chromosome segregation protein | No | Yes | 4.4 |
| AAS70942.1 | LIC12373 | Conserved protein of unknown function | Yes | No | 4.3 |
| AAS71615.1 | LIC13066 | Putative lipoprotein | No | No | 3.5 |
| AAS69086.1 | LIC10465 | Putative immunoglobulin-like protein A | Yes | Yes | 2.9 |
| AAS69409.1 | LIC10793 | Surface antigen | Yes | No | 2.8 |
| AAS71094.1 | LIC12529 | Sulfate ABC transporter periplasmic sulphate-binding protein precursor | No | No | 2.6 |
| AAS71837.1 | LIC13293 | Conserved protein of unknown function | Yes | Yes | 2.5 |
| AAS70328.1 | LIC11739 | Conserved protein of unknown function | Yes | No | 2.3 |
| AAS70662.1 | LIC12091 | Phosphoglycerate kinase | No | No | 2.2 |
| AAS69094.1 | LIC10473 | Valyl-tRNA synthetase | No | No | −2.0 |
| AAS70417.1 | LIC11831 | Guanine monophosphate synthase | No | No | −2.0 |
| AAS70883.1 | LIC12312 | Glucokinase | No | No | −2.0 |
| AAS71795.1 | LIC13251 | Udp-n-acetylglucosamine 1-carboxyvinyltransferase | No | No | −2.0 |
| AAS71866.1 | LIC13324 | Argininosuccinate synthase | No | No | −2.0 |
| AAS72234.1 | LIC20208 | Methylmalonyl-COA mutase small subunit | No | No | −2.0 |
| AAS69951.1 | LIC11350 | Acyl-CoA dehydrogenase | No | No | −2.2 |
| AAS70804.1 | LIC12232 | Thymidylate synthase | No | No | −2.2 |
| AAS71081.1 | LIC12516 | Acetoacetyl-CoA synthetase | No | No | −2.2 |
| AAS71252.1 | LIC12694 | Glutamate synthase (NADPH) alpha chain precursor | Yes | No | −2.2 |
| AAS71556.1 | LIC13006 | LenC | No | No | −2.2 |
| AAS72270.1 | LIC20249 | Aconitate hydratase | No | Yes | −2.2 |
| AAS68821.1 | LIC10193 | Conserved protein of unknown function | No | No | −2.5 |
| AAS69213.1 | LIC10592 | Peptidoglycan-associated cytoplasmic membrane protein | No | No | −2.5 |
| AAS69466.1 | LIC10852 | Uridylate kinase | No | No | −2.5 |
| AAS71110.1 | LIC12545 | Outer membrane lipoprotein carrier protein | No | Yes | −2.5 |
| AAS71250.1 | LIC12692 | Conserved protein of unknown function | No | No | −2.5 |
| AAS69677.1 | LIC11070 | Alcohol dehydrogenase | No | No | −2.9 |
| AAS71178.1 | LIC12618 | Diaminopimelate decarboxylase | Yes | Yes | −2.9 |
| AAS72019.1 | LIC13481 | Conserved protein of unknown function | Yes | No | −2.9 |
| AAS72032.1 | LIC20001 | Conserved protein of unknown function | No | No | −2.9 |
| AAS72235.1 | LIC20209 | Methylmalonyl-COA mutase large subunit | No | No | −3.3 |
| AAS69048.1 | LIC10425 | Conserved protein of unknown function | No | No | −3.3 |
| AAS70245.1 | LIC11652 | Transaldolase | No | No | −3.3 |
| AAS69782.1 | LIC11175 | Translation initiation factor | No | No | −4.0 |
| AAS69935.1 | LIC11334 | Conserved protein of unknown function | Yes | No | −4.0 |
| AAS70603.1 | LIC12028 | Cysteinyl-tRNA synthetase | No | No | −4.0 |
| AAS70820.1 | LIC12248 | Pyridoxal phosphate biosynthetic protein | Yes | No | −4.0 |
| AAS71031.1 | LIC12466 | Carbamoyl-phosphate synthase small chain | No | No | −4.0 |
| AAS71282.1 | LIC12725 | 3-hydroxybutyryl-CoA dehydratase | No | No | −4.0 |
| AAS71698.1 | LIC13153 | UDP-glucose 4-epimerase | No | Yes | −4.0 |
| AAS71819.1 | LIC13275 | Conserved protein of unknown function | No | No | −4.0 |
| AAS68701.1 | LIC10064 | Conserved protein of unknown function | Yes | Yes | −5.0 |
| AAS68751.1 | LIC10118 | Phoshomethylpyrimidine kinase protein | No | No | −5.0 |
| AAS68826.1 | LIC10198 | Inositol monophosphatase | No | No | −5.0 |
| AAS69321.1 | LIC10700 | 3-oxoacyl-[acyl-carrier-protein] reductase oxidoreductase | Yes | No | −5.0 |
| AAS69530.1 | LIC10918 | Conserved protein of unknown function | No | No | −5.0 |
| AAS69956.1 | LIC11355 | Transketolase | No | No | −5.0 |
| AAS70910.1 | LIC12341 | Conserved protein of unknown function | No | No | −5.0 |
| AAS71101.1 | LIC12536 | RibD | No | No | −5.0 |
| YP_002257.2 | pyrF | Orotidine 5′-phosphate decarboxylase | No | No | −5.0 |
| EMG20500 | speE | Spermidine synthase | No | No | −5.0 |
| AAS68791.1 | LIC10162 | Fumarate hydratase | No | No | −6.7 |
| AAS70990.1 | LIC12422 | Aspartate aminotransferase a | Yes | Yes | −6.7 |
| AAS71060.1 | LIC12495 | 3-hydroxybutyryl-CoA dehydratase | No | No | −6.7 |
| AAS69606.1 | LIC10995 | Conserved protein of unknown function | Yes | Yes | −6.7 |
| AAS72275.1 | LIC20254 | Response regulator | No | No | −9.5 |
| AAS69377.1 | LIC10760 | Conserved protein of unknown function | Yes | Yes | −10.0 |
| AAS69380.1 | LIC10763 | Alanyl-tRNA synthetase | No | No | −10.0 |
| AAS70413.1 | LIC11825 | Phosphoheptose isomerase | No | No | −10.0 |
| AAS70965.1 | LIC12396 | Conserved protein of unknown function | No | Yes | −10.0 |
| AAS71115.1 | LIC12551 | Acyl-CoA dehydrogenase | No | No | −10.0 |
| AAS71651.1 | LIC13105 | Glucose-6-phosphate isomerase | No | No | −10.0 |

TABLE 5-continued

Exoprotein regulation in response to an osmotic shift to modified EMJH with 120 mM NaCl

| Accession # | Locus tag | Annotation | ▼Signal peptide | ▲Non-Classical | RQ in 120 mM NaCl |
|---|---|---|---|---|---|
| AAS69186.1 | LIC10565 | Enoyl-CoA hydratase | No | No | −20.0 |
| AAS70318.1 | LIC11729 | 2,4-dienoyl-CoA reductase | No | No | −20.0 |
| AAS70679.1 | LIC12108 | aspartyl-tRNA synthetase | No | No | −20.0 |
| AAS71792.1 | LIC13248 | LenF | No | No | −20.0 |

RQ: Relative quantity, average between experimental replicates
▼Signal peptide as predicted using Phobius (55)
▲Non-classical secretion predicted using SecretomeP 2.0 Server (56)

Assignment of Proteins to Clusters of Orthologous Groups

The protein products of *Leptospira* genomes have been automatically classified into clusters of orthologous groups (COG) by the MICROSCOPE platform (53). This data was used to sort the detected exoproteins into COGs and the resulting frequencies were compared to those predicted genome-wide. Statistics was performed assuming a binomial distribution where assignment of exoproteins into a COG would be considered a "success" and absence a "failure". The percentage of coding sequences classified into a COG (as calculated in MICROSCOPE genome-wide) was used as the probability of observing a "success" and the total number of detected exoproteins (208 which were present in all 6 supernatants and that also displayed equal or higher quantities in the supernatant than cell pellets) was used as the sampling size to generate COG specific binomial probability distributions. A p value of p<0.01 was used as a cut-off for significance. For comparison of temperature and osmotic shift regulated exoproteins, a similar analyses was performed with the following modifications. The COG specific probabilities used were from those calculated for exoproteins (not those that would be observed genome-wide) and the sampling size was adjusted to reflect the number of exoproteins being regulated (51 and 69 for temperature and osmotic shifts, respectively).

Bacterial Strains, Growth Rates and Infection Experiments

Transposon mutagenesis was previously performed in the parental strain (*Manilae* L495) and insertion sites initially identified via semi-random PCR (46-48). The insertion sites for exoprotein mutants were validated via PCR and the primers, insertion sites and transposon mutants are listed in Table 6.

TABLE 6

Primers used for confirmation of transposon insertion sites.

| | Locus tag | Gene | S vs P 30° C. | ◀37° C. vs 30° C. S | ◀NaCl vs 30° C. S |
|---|---|---|---|---|---|
| 218* | LIC10713 | lruB | S only | 0.7 | 0.6 |
| Primer s | AGCAAACAACGACTCA GAACG (SEQ ID NO: 165) | GTTTTTGCGGCATCGG TGAT (SEQ ID NO: 166) | | | |
| 178* | LIC11852 | O-acetylhomoserine (thiol) lyase | 12.3 | 0.9 | 1.1 |
| Primer s | CACTGAACACGCCGCT AAAC (SEQ ID NO: 167) | GAGTCGTAGACGCTGG ATGG (SEQ ID NO: 168) | | | |
| 902* | LIC13006 | Lenc | S only | 0.7 | 0.4 |
| Primer s | ATCTGGTAACGACAGT GCGG (SEQ ID NO: 169) | AGTCTTGCACCACCTG CAAA (SEQ ID NO: 170) | | | |
| 403* | LIC12208 | Putative lipoprotein (beta propeller) | S only | 0.8 | 1.4 |
| Primer s | AACAACCGGTGGGATT ACA (SEQ ID NO: 171) | TCGTTCGTTCCACTGA TTGG (SEQ ID NO: 172) | | | |
| 69* | LIC13060 | LipL36 | 2.9 | 0.8 | 1.5 |
| Primer s | CTGTTGCTCTAACGGC ATGT (SEQ ID NO: 173) | GCAGCCTGATAGGATG CTTTA (SEQ ID NO: 174) | | | |

TABLE 6-continued

Primers used for confirmation of transposon insertion sites.

| | Locus tag | Gene | S vs P 30° C. | ◄37° C. vs 30° C. S | ◄NaCl vs 30° C. S |
|---|---|---|---|---|---|
| 988* | LIC10373 | Putative lipoprotein (beta propeller) | S only | 0.2 | 1.2 |
| Primer s | GCCCACTTCTGGCAAA GAGA (SEQ ID NO: 175) | TCCCAGTCTTCCGATT TGACG (SEQ ID NO: 176) | | | |
| 899* | LIC10898 | LipL48 | 12.1 | 1.6 | 1.9 |
| Primer s | ACGTAACTCCTTCCCT CTATCT (SEQ ID NO: 177) | AGCCCAGTTCAAACCG CTTA (SEQ ID NO: 178) | | | |
| 1456* | LIC11977 | Cyclic nucleotide binding protein | 6.3 | 1.2 | 1.1 |
| Primer s | ACCTTCAGATTGGCTC ACCG (SEQ ID NO: 179) | ACTCAGTATCCGTTTC CGCTC (SEQ ID NO: 180) | | | |

*Insertion (bp into gene)
Grey and white rows indicate experimental replicates 1 and 2, respectively.
P = Whole *Leptospira* proteins
S = Culture supernatant proteins
►Whole cell lysate *Leptospira* protein comparison
◄Culture supernatant protein comparison
▼Signal peptide as predicted using Phobius
▲Non-classical secretion predicted using SecretomeP 2.0 Server Exoprotein mutants LIC13006⁻ (lenC⁻), LIC12208⁻, LIC13060⁻ (lipL36⁻), LIC10373⁻, LIC10898⁻ (lipL48⁻), LIC11977⁻, LIC11852⁻, LIC10713⁻ (lruB⁻) and *Manilae* L495 were compared for in vitro growth rates in EMJH media at 30° C. Bacterial growth was measured on a daily basis by measuring optical densities via spectroscopy at 420 nm. Exoproteins that demonstrated similar growth rates to *Manilae* L495 were used in subsequent virulence measurement experiments in Mongolian gerbils (Janvier). To measure virulence, groups of 4 gerbils were injected intraperitoneal with 10^4 bacteria per animal. Animals were administered *Manilae* L495 or mutants LIC13006⁻ (lenC⁻), LIC12208⁻, LIC13060⁻ (lipL36⁻), LIC10373⁻, LIC10898⁻ (lipL48⁻) and LIC11977⁻. Animals were monitored on a daily basis for 23 days and sacrificed when moribund. Protocols for animal experiments conformed to the guidelines of the Animal Care and Use Committees of the Institut Pasteur (Paris, France).

Results

Overview of Whole Cell and Exoproteomes

Figure 4:
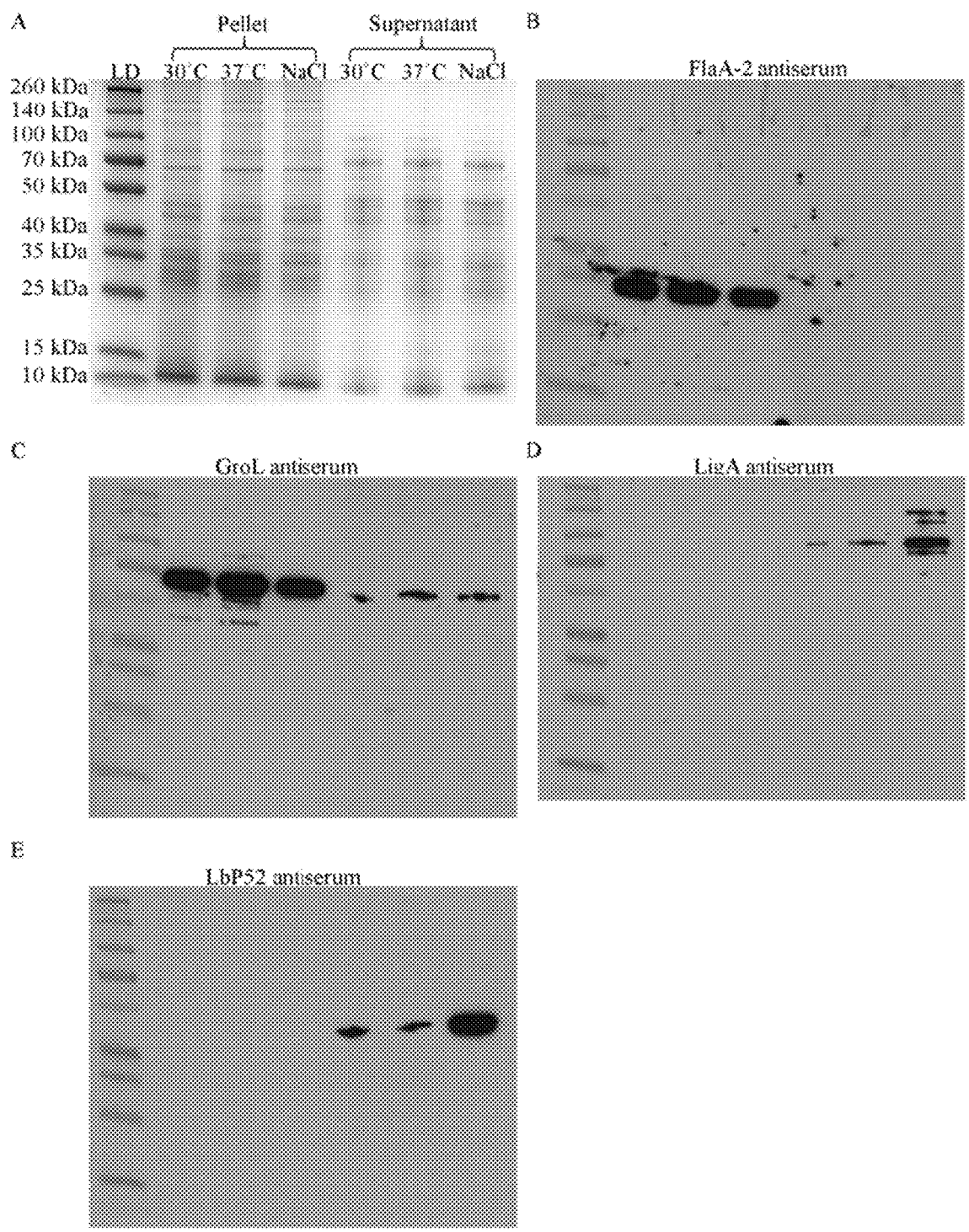
FIG. 4 shows Western blots demonstrating differential protein localization and expression in Leptospiral culture supernatants.

To survey the types of proteins found in culture supernatants, whole cell proteins (WCP) and culture supernatant proteins (CSP) from each culture condition were subjected to SDS-PAGE and immunoblot analyses (FIG. 4). *Leptospira* were cultured at 30° C., 37° C. or in media containing 120 mM NaCl. Proteins from whole cells and culture supernatants were subsequently used in immunoblot experiments with the indicated antisera. FIG. 4A, a representative coomassie stained SDS-PAGE demonstrating disparate protein composition when comparing whole cell lysate proteins to those obtained from culture supernatant; FIG. 4B, protein immunoblot demonstrating localization of flagellar protein F1aA-2 in whole cells but not in the supernatant; FIG. 4C, Protein immunoblot suggesting increased expression of the chaperone protein GroL at 37° C.; FIG. 4D, Protein immunoblot indicating expression of immunoglobulin protein LigA in CSP and increased expression in the CSP from *Leptospira* exposed to 120 mM NaCl. E, Protein immunoblot confirming expression of LbP52 protein in culture supernatants and increased expression in CSP from *Leptospira* exposed to 120 mM NaCl. The coomassie stained SDS-PAGE gel (FIG. 4A) revealed 2 observable differences between WCP and CSP. The first difference was in protein banding patterns and the second was a bias in the size of proteins where the majority of CSP migrated between 25-90 kDa, as opposed to WCP where protein bands as large as 260 kDa were observed. There was no visual difference in protein banding in response to temperature or osmotic shifts in WCP or CSP.

Protein immunoblots using antiserum against the 27.2 kDa periplasmic flagellar protein (F1aA-2) revealed protein bands migrating between 25-35 kDa in WCP but no reactivity with CSP (FIG. 4B). The *Leptospira* 60 kDa chaperonin (GroL) has been demonstrated to be upregulated in response to elevated growth temperatures (54) and the immunoglobulin-like protein A (LigA) has been demonstrated to be upregulated and released into culture supernatants upon exposure of *Leptospira* to 120 mM NaCl (23, 34). To assess whether a similar response was observed at 37° C., antisera against GroL was used in immunoblot experiments (FIG. 4C). The WCP from *Leptospira* exposed to 37° C. displayed a slight increase in GroL reactivity (FIG. 4C). Unexpectedly, there was detectable levels of GroL in all CSP samples, albeit at significantly lower levels compared to WCP. Using similar reasoning, WCP and CSP were subjected to immunoblot analysis using antiserum cross reactive with *Leptospira* immunoglobulin proteins A (LigA with a MW of 128 kDa) and B (LigB with a MW of 201 kDa) (FIG. 4D). Neither LigA nor LigB were observed in WCP samples whereas LigA was detected in CSP samples, with pronounced reactivity being observed in CSP samples from *Leptospira* exposed to 120 mM NaCl (FIG. 4D). The CSP samples from 120 mM NaCl exposed *Leptospira* also displayed 2 unique bands that migrated between 100-140 kDa and one unique band that migrated below 100 kDa (FIG. 4D). As will be evident in subsequent results sections we observed higher abundance of numerous proteins in culture supernatants. One such protein was encoded by the locus LIC12209 and is annotated as a lipoprotein, which we refer to as LbP52 for *Leptospira* beta-propeller (due to the presence of N-terminal beta propeller domains) protein 52 kDa. Immunoblot analysis of WCP and CSP resulted in detection of LbP52 in CSP samples only, with elevated expression being observed in 120 mM NaCl samples (FIG. 4E).

The immunoblot experiments described above, demonstrated that CSP preparations and temperature and osmotic shift experiments were performed in a manor acceptable for subsequent quantitative global proteome analyses via mass spectrometry. Thus, WCP and CSP (in replicates) were subjected to LC-orbitrap mass spectrometry for identification of proteins and for relative protein quantification, using label-free normalized quantification of peptide mass spectra. These analyses lead to the detection of 982-1,139 proteins in WCP and 613-766 proteins in CSP (Table 8 and Annex_Table S1 and Annex_Table S2). Other notable differences between the samples included detection of relatively large proteins (300 kDa) in WCP which were absent in CSP, and detection of F1aA-2 and AAS68995.1/LIC10371 proteins in WCP and CSP, respectively, but not vice versa (Table 7). The latter protein consists of multiple repeating beta-propeller domains which we found to also be present in 4 other exoproteins and displayed high abundance in all culture supernatants. Normalized spectral index ($SI_N$) has been described (41) and this method of protein quantification revealed a dynamic range approaching 5 orders of magnitude in protein quantities (Table 7).

TABLE 7

Overview of proteomic results. The spectral index is displayed for the periplasmic flagellar sheath protein FlaA-2 and for an exoprotein (AAS68995.1/LIC10371) which was detected in high abundance in culture supernatants.

|  | P30° C.[a] | P37° C.[a] | PNaCl[a] | S30° C.[b] | S37° C.[b] | SNaCl[b] |
|---|---|---|---|---|---|---|
| [c]Unique proteins detected | 982 | 1021 | 1139 | 766 | 646 | 613 |
| Smallest protein (Da) | 11224.70 | 11224.70 | 8515.17 | 8515.17 | 9544.17 | 9544.17 |
| Largest protein (Da) | 299999.00 | 299999.00 | 299999.00 | 268904.00 | 224157.00 | 218785.00 |
| Spectral index (highest/lowest) | 1.9E−4/5.3E−9 | 1.3E−4/2.3E−9 | 1.5E−4/4.2E−9 | 2.4E−4/5.5E−9 | 4.8E−4/5.2E−9 | 3.5E−4/6.2E−9 |
| [d]AAS69403.1/FlaA-2[e] | 1.3E−05 | 1.6E−05 | 7.6E−06 | Not detected | Not detected | Not detected |
| [d]AAS68995.1/LIC10371[f] | Not detected | Not detected | Not detected | 6.9E−06 | 5.6E−06 | 1.1E−05 |

[a]Whole cell *Leptospira*,
[b]Culture supernatants,
[c]Combined experimental replicates,
[d]Average between experiments,
[e]Periplasmic localization,
[f]Extracellular localization Identification of Exported Proteins Via Relative Protein Quantities In tandem to protein identification, comparison of individual protein $SI_N$ in CSP to WCP enabled assignment of proteins that were likely actively localized extracellular, as opposed to being detected as a result of cell lysis and/or outer membrane release due to experimental manipulation. Specifically, proteins that displayed at least equal or higher abundances in the supernatant compared to whole cells and were detected in all 6 supernatants were considered to be actively transported exoproteins. This approach identified 208 unique exoproteins (Annex_Table S3). It should be highlighted that this assumption was only valid under specified conditions, since culture conditions likely alter protein export (as will be evident later). Thus, relative protein quantification used to generate the list of 208 proteins was from comparison of protein quantities in CSP to WCP at 30° C., only. The relative abundance of these exoproteins in supernatants ranged from equal abundance to only being detected in supernatants (Annex_Table S3 and Table 8).

TABLE 8

The 20 most abundant proteins in the supernatant of *L. interrogans* cultures at 30° C.

| Accession # | Locus tag | Protein | $SI_N$ P 30° C. | $SI_N$ S 30° C. | S vs P 30° C. | RQ |
|---|---|---|---|---|---|---|
| AAS70653.1 | LIC12082 | Cysteine synthase | 3.0E−05 | 2.2E−04 | 7.2 | 1.0 |
| AAS69512.1 | LIC10898 | LipL48 | 1.6E−05 | 1.8E−04 | 11.3 | 0.8 |
| AAS70370.1 | LIC11781 | Malate dehydrogenase | 8.2E−06 | 6.5E−05 | 7.9 | 0.3 |
| AAS71860.1 | LIC13318 | Fatty acid synthase subunit beta | 5.4E−06 | 5.6E−05 | 10.4 | 0.3 |
| AAS71933.1 | LIC13393 | Ketol-acid reductoisomerase | 1.2E−05 | 5.4E−05 | 4.7 | 0.2 |
| AAS69456.1 | LIC10842 | Dihydrodipicolinate synthase protein | 2.3E−06 | 2.1E−05 | 9.1 | 0.1 |
| AAS69825.1 | LIC11219 | Peroxiredoxin | 1.4E−05 | 4.1E−05 | 2.9 | 0.2 |
| AAS69801.1 | LIC11194 | Putative citrate lyase | 1.8E−05 | 4.8E−05 | 2.6 | 0.2 |
| AAS68899.1 | LIC10272 | Translation elongation factor G | 7.0E−06 | 3.9E−05 | 5.6 | 0.2 |
| AAS68639.1 | LIC10002 | DNA polymerase III beta subunit | 5.5E−06 | 3.6E−05 | 6.5 | 0.2 |
| AAS71788.1 | LIC13244 | Isocitrate dehydrogenase | 5.6E−06 | 3.3E−05 | 5.9 | 0.2 |
| AAS72270.1 | LIC20249 | Aconitate hydratase | 6.4E−06 | 2.8E−05 | 4.3 | 0.1 |
| AAS68844.1 | LIC10216 | Phosphoenolpyruvate carboxykinase | 4.9E−06 | 2.7E−05 | 5.6 | 0.1 |
| YP_000422.1 | speE | Spermidine synthase | 1.2E−05 | 3.0E−05 | 2.4 | 0.1 |
| AAS68881.1 | LIC10253 | Crotonyl-Coa reductase | 4.7E−06 | 2.6E−05 | 5.5 | 0.1 |
| AAS70661.1 | LIC12090 | Glyceraldehyde-3-phosphate dehydrogenase | 1.7E−05 | 2.5E−05 | 1.5 | 0.1 |
| AAS71394.1 | LIC12841 | Aspartate aminotransferase | 1.4E−06 | 3.2E−05 | 23.0 | 0.1 |
| AAS70904.1 | LIC12335 | Serine hydroxymethyltransferase | 4.4E−06 | 2.5E−05 | 5.7 | 0.1 |
| AAS70553.1 | LIC11977 | Cyclic nucleotide binding protein | 3.9E−06 | 2.3E−05 | 5.8 | 0.1 |
| AAS71476.1 | LIC12925 | Citrate synthase | 5.3E−06 | 2.3E−05 | 4.4 | 0.1 |

P = Whole *Leptospira* proteins
S = Culture supernatant proteins
RQ = Relative quantity To further evaluate assignment of exoproteins, corresponding primary sequences were used in bioinformatic analyses to predict N-terminal signal peptides using Phobius (55) and non-classical protein export using SecretomeP 2.0 server (56). Of the 208 proteins deemed to be exported, 46 were calculated to contain an N-terminal signal peptide and 38 were predicted to be exported via a non-classical pathway, defined as a pathway that exports proteins lacking a classical signal peptide (Table S3).

Overrepresentation of Exoproteins in COGs Relating to Energy Production and Metabolism Exoproteins were assigned to clusters of orthologous groups (COGs) based on automatic classification of *Leptospira* genomes in the MICROSCOPE platform (53). Compared to genome-wide expected frequencies, exoproteins in the COGs; cell motility (N), signal transduction mechanisms (T), replication recombination and repair (L), general function (R), function unknown (S) and unclassified (−) were underrepresented (FIG. 5). *L. interrogans* serovar Copenhageni strain Fiocruz L1-130 genes have been automatically classified into clusters of orthologous groups (COG) in the GENOSCOPE website. The COG categories and the predicted percentages of strain L1-130 genes in the respective COG are as follows: D: Cell cycle control, cell division, chromosome partitioning (0.9%); M: Cell wall/membrane/envelope biogenesis (5.3%); N: Cell motility (2.4%); O: Posttranslational modification, protein turnover, chaperones (30.2%); T: Signal transduction mechanisms (5.9%); U: Intracellular trafficking, secretion, and vesicular transport (1.7%); V: Defense mechanisms (1.6%); Z: Cytoskeleton (0.06%); B: Chromatin structure and dynamics (0.04%); J: Translation, ribosomal structure and biogenesis (3.5%); K: Transcription (30.1%); L: Replication, recombination and repair (40.6%); C: Energy production and conversion (30.2%); E: Amino acid transport and metabolism (70.0%); F: Nucleotide transport and metabolism (1.6%); G: Carbohydrate transport and metabolism (30.6%); H: Coenzyme transport and metabolism (2.8%); I: Lipid transport and metabolism (2.9%); P: Inorganic ion transport and metabolism (4.5%); Q: Secondary metabolites biosynthesis, transport and catabolism (1.8%); R: General function prediction only (11.0%); S: Function unknown (50.0%);-: Unclassified (390.0%). This information was used to classify the exoproteins detected in this study. Statistical analysis was performed by assuming a binomial distribution using a p value cut off of p<0.01. The * symbol represents a significant difference between the observed number of exoproteins and the genome-wide expected probabilities for the given COG, in a sample size of 208 proteins.

Figure 5:
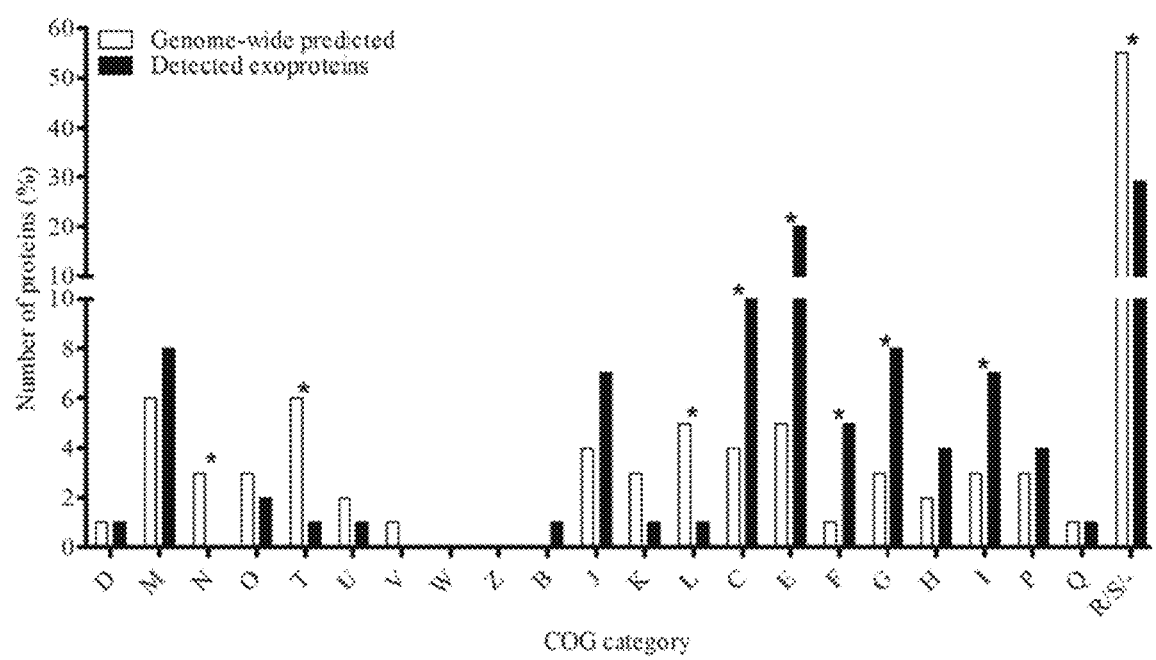
FIG. 5 shows the classification of *L. interrogans* exoproteins, which indicates that most proteins to be involved in metabolic processes.

In contrast, there was a 2 to 4 fold overrepresentation of exoproteins classified in the COGs; energy production and conversion (C), amino acid transport and metabolism (E), nucleotide transport and metabolism (F), carbohydrate transport and metabolism (G) and lipid transport and metabolism (FIG. 5).

Regulation of Exoprotein Expression in Response to Temperature and Osmotic Shifts Comparison of protein abundance in CSP from *Leptospira* shifted to 37° C. or to modified EMJH containing 120 mM NaCl to CSP from *Leptospira* at 30° C. (37° C. vs 30° C. S and NaCl vs 30° C. S, respectively) revealed altered expression of 52 proteins in 37° C. vs 30° C. S and 69 proteins in NaCl vs 30° C. S. Both temperature and osmotic shifts resulted in reduced expression of the majority of exoproteins, 45 of the 52 exoproteins displayed reduced abundance of −2 to −10 fold at 37° C. and 57 of 69 exoproteins displayed reduced quantities of −2 to −20 fold in 120 mM NaCl samples. Six proteins were detected between 2.1 to 6.8 fold higher at 37° C. while 12 proteins displayed 2.2 to 6.9 fold higher abundance at 120 mM NaCl. In the latter case, LigA and LbP52 proteins were observed at 2.9 and 5.5 fold higher abundance, respectively, at 120 mM NaCl consistent with what was observed in immunoblot experiments (FIGS. 4D and E).

Figure 6:
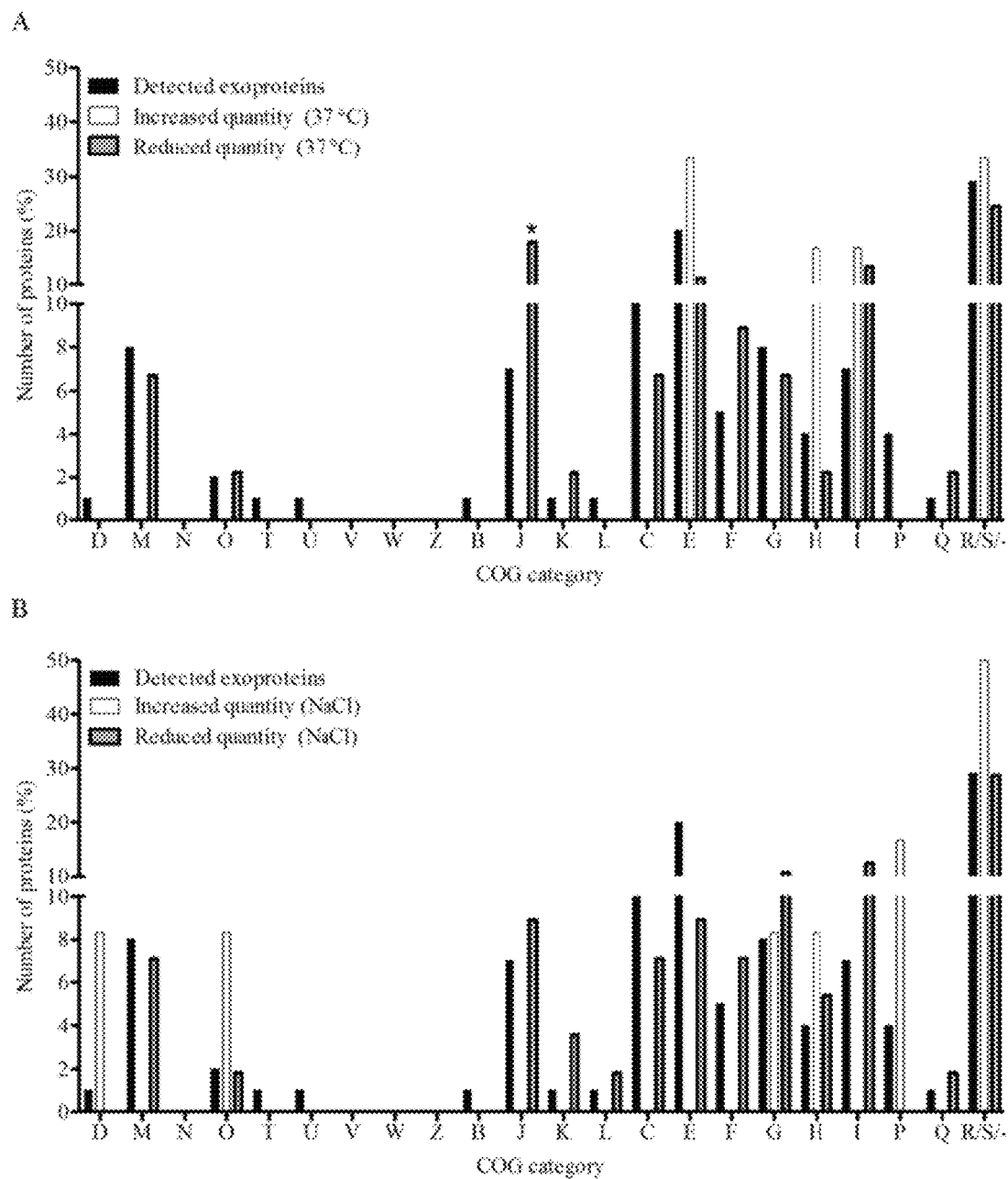
FIG. 6 shows exoprotein regulation in response to salt is functional category independent whereas temperature affects exoproteins in the translation, ribosomal structure and biogenesis.

Exoproteins displaying altered expression in response to temperature and osmotic shift were subsequently classified into COGs using the MICROSCOPE (53) platform to determine whether a temperature and/or osmotic shift had an effect(s) on the expression/export of COG specific exoproteins (FIGS. 6A and B). Exoproteins which displayed altered expression in culture supernatants of *Leptospira* shifted to 37° C. or modified EMJH containing 120 mM NaCl, were classified into COGs as described for FIG. 5. The frequencies of these exoproteins were then compared to those observed for the 208 detected exoproteins. The percentage of exoproteins for each COG was calculated by dividing the number of exoproteins regulated in a given COG by the total number of exoproteins regulated in that condition (51 and 69 total exoproteins displayed altered expression after a shift to 37° C. and 120 mM NaCl, respectively). A, The percentage of exoproteins that displayed increased or reduced expression versus the percentage observed for all identified exoproteins (208 in total), for each COG, at 37° C. B, Similar analyses as described for panel A but using the 120 mM NaCl data. The COG categories and the predicted percentages of strain L1-130 genes in the respective COG are listed above. Statistical analyses was performed with the following modification: the sample size was set at 51 and 69 for calculating frequency probabilities for 37° C. and 120 mM NaCl data sets, respectively.

These comparisons did not reveal significant differences in frequency distributions with the exception of the COG; translation, ribosomal structure and biogenesis (J) (FIG. 6A). For COG J, there was a significant overrepresentation of exoproteins that were classified into this group that displayed reduced expression at 37° C. (FIG. 6A).

Exoproteins with Potential Moonlighting Functions

Moonlighting proteins are a class of proteins where a single polypeptide chain performs more than 1 biochemical function (57). Classification of exoproteins into COGs revealed overrepresentation of proteins involved in nutrient uptake and metabolism with the latter comprising of numerous proteins involved in the glycolytic pathway (FIG. 5 and Annex 3 Table S3). Enzymes in the glycolytic pathway have been implicated for moonlighting properties in other bacteria (58-61) and in *Leptospira* (37). To search proteins in culture supernatants for potential moonlighting functions, moonlighting protein that have been experimentally characterized in other organisms were collected from MoonProt (57). The primary sequence of these proteins were then used in basic local alignment searches (BLAST) using the *L. interrogans* serovar *Copenhageni* strain Fiocruz L1-130 genome. The search results were then compared to the proteomic data in Table S3, Table 51 and Table S2 to identify orthologous proteins in the proteomic data. This approach identified 19 proteins detected in the supernatant that could be classified as moonlighting proteins (Table 5). Interestingly, 41 orthologous proteins to moonlighting proteins were identified in *Leptospira,* 19 of these were exoproteins and 18 others were detected in supernatants.

TABLE 9

Potential and confirmed moonlighting proteins in *Leptospira*.

| Accession # | Locus tag | Gene/annotation | [a]Moonlighting function in other organisms |
|---|---|---|---|
| AAS71252.1 | LIC12694 | Glutamate synthase (NADPH) alpha chain precursor | Binds plasminogen, fibronectin, laminin and collagen I |
| AAS69825.1 | LIC11219 | Peroxiredoxin | Molecular chaperones |
| AAS71651.1 | LIC13105 | Glucose-6-phosphate isomerase | Binds laminin and collagen I |
| AAS72117.1 | LIC20088 | Pyrophosphate-fructose-6-phosphate 1-phosphotransferase | Binds, invertase and plasminogen |
| AAS69569.1 | LIC10958 | Alcohol dehydrogenase | Binds plasminogen, fibronectin, laminin and collagen II |
| AAS70661.1 | LIC12090 | Glyceraldehyde-3-phosphate drogenase | NAD ribosylating activity, binds mucin, Caco-2 cells, invertase, fibronectin, laminin, type I collagen, plasminogen, uPAR/CD87 receptor, transferrin-binding protein |
| AAS69802.1 | LIC11195 | Ornithine carbamoyltransferase | Binds fibronectin |
| AAS70607.1 | LIC12032 | Catalase | Binds plasminogen |
| AAS70662.1 | LIC12091 | Phosphoglycerate kinase | Binds plasminogen |
| AAS72270.1 | LIC20249 | Aconitate hydratase | Iron-responsive protein, binds iron-responsive elements |
| AAS68899.1 | LIC10272 | Translation elongation factor G | Binds mucin |
| AAS69466.1 | LIC10852 | Uridylate kinase | Transcriptional regulator |
| AAS70653.1 | LIC12082 | Cysteine synthase | Transcriptional regulator |
| AAS71909.1 | LIC13367 | Sulfite reductase | |
| [b]AAS69936.1 | LIC11335 | GroL | Binds glycosphinngolipids, mucins, epithelial cells, DNA. Toxin. |
| [b]AAS69145.1 | LIC10524 | Heat shock protein 70 (DnaK) | Binds plasminogen and invertase |
| [b]AAS71428.1 | LIC12875 | Elongation factor Tu (Tuf) | Binds human cells, mucins, fibronectin, factor H, plasminogen |
| [b]AAS70536.1 | LIC11954 | Enolase | Binds plasminogen, laminin, fibronectin and mucin |
| [b]AAS70976.1 | LIC12407 | Glutamine synthetase protein (GlnA) | Binds plasminogen, fibronectin, laminin, collagen I, transcription factor TnrA |

[a]Moonlighting functions were obtained from MoonProt (57)
[b]Proteins were detected in all supernatants but displayed a relative abundance <1, compared to respective abundance in whole *Leptospira* (WCP)

Figure 7:
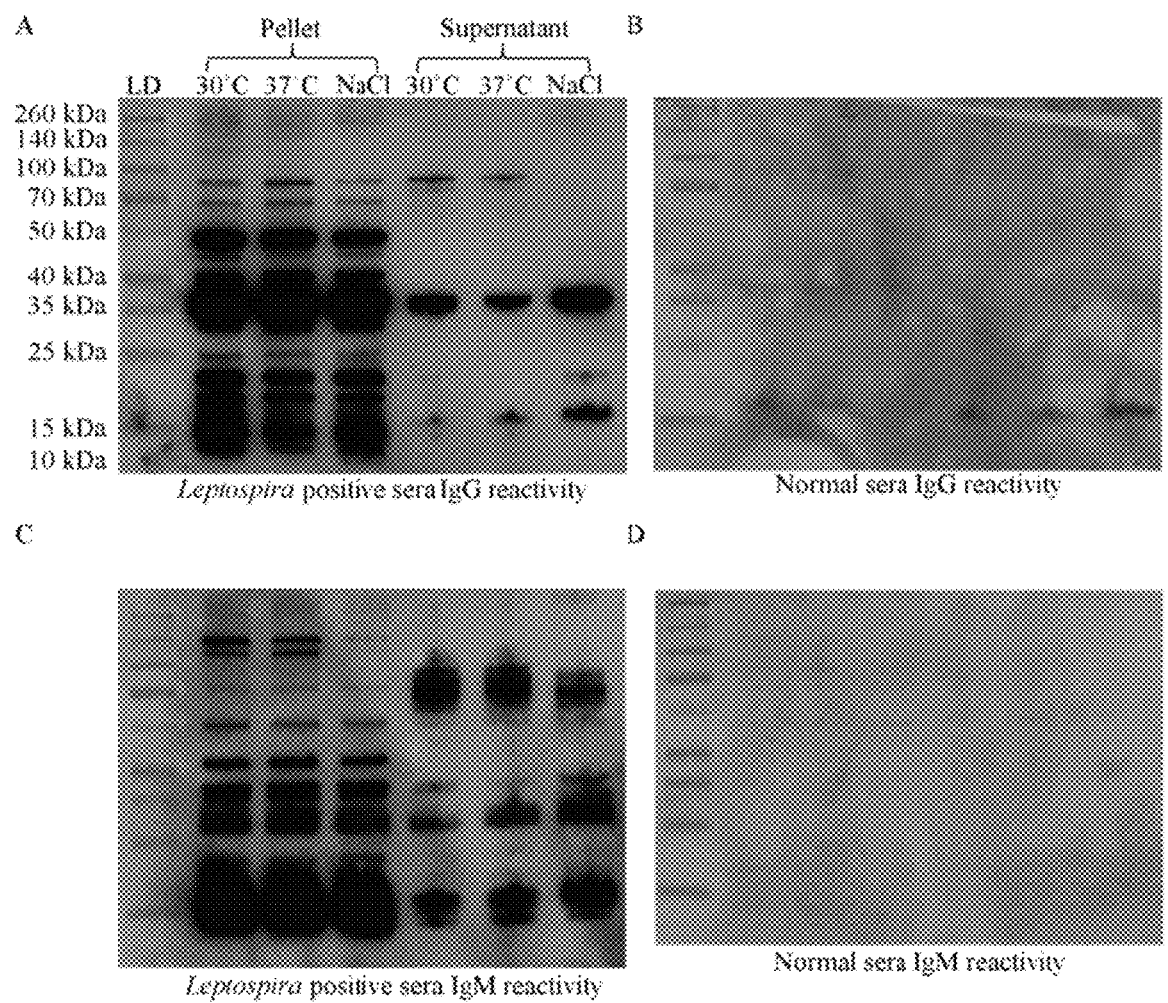
FIG. 7 shows *Leptospira* positive sera predominantly display IgM reactivity to Leptospiral exoproteins.

Exoproteins are Immunogenic but Display Limited Involvement in Disease Manifestation in Gerbils To begin to characterize exoproteins in the context of pathogenesis, WCP and CSP were used in immunoblot experiments with *Leptospira* positive guinea pig sera (S+) to observe the antibody response to exoproteins, which would also be suggestive of exoprotein expression during the infection process (FIG. 7). Guinea pig sera obtained prior to and post *Leptospira* infection were used in protein immunoblot experiments to test immunoglobulin reactivity with whole *Leptospira* lysates or culture supernatants. A, Protein immunoblot comparing IgG reactivity with whole cell proteins and exoproteins when using *Leptospira* positive sera. B, Protein immunoblot demonstrating a lack of IgG reactivity to whole cell and extracellular proteins when using pre-infection sera. C, Protein immunoblot comparing IgM reactivity to whole cell proteins and exoproteins when using *Leptospira* positive sera. D, Protein immunoblot demonstrating a lack of IgM reactivity to whole cell and extracellular proteins when using pre-infection sera.

These analyses revealed IgG and IgM reactivity against *Leptospira* exoproteins in S+ sera (FIGS. 7A and C) and no reactivity in the control pre-infection sera (FIGS. 7B and D). Exoprotein reactivity with IgG was significantly less prominent when compared to WCP and a similar trend was observed with IgM reactivity (FIGS. 7A and C). Comparison of IgG and IgM reactivity with exoproteins was distinguishable in that the proteins displaying reactivity with IgG did not display reactivity with IgM and vice versa (FIGS. 7A and C). Furthermore, CSP from 120 mM NaCl exposure also lead to altered IgG and IgM reactivity of exoproteins when compared to CSP from 30° C. and 37° C. (FIGS. 7A and C). Specifically, reduced IgG and IgM reactivity was observed for protein bands migrating between 70-100 kDa (FIGS. 7A and C) and increased IgG reactivity was observed for two proteins at 35 kDa and 15 kDa (FIG. 7A).

To further assess the necessity of exoproteins in *Leptospira* viability in vitro and within the host, select *Leptospira* mutants which had been inactivated in an exoprotein encoding gene were tested for in vitro growth rates and for disease manifestation in gerbils. *Leptospira* mutants in exoproteins were tested for in vitro viability and their capacity to establish infection in the gerbil infection model measured as time to death of animals. A, Bacteria were inoculated at $10^4$ per ml in EMJH media, cultured at 30° C. and monitored for growth via measuring optical density at 420 nm. Mutants lruB$^-$ and lic11852$^-$ displayed delayed in vitro growth rates when compared to wt parental strain, whereas all other tested exoprotein mutants displayed comparable growth rates to wt (not shown). B, Mutants displaying in vitro growth rates comparable to wt were used to challenge gerbils at $10^4$ bacteria per animal for the purpose of testing virulence. The protein product of the gene labelled with the * symbol did not fulfill all criteria used to generate the list of exoproteins presented in Annex_3 Table S3, but was detected in culture supernatants. In vitro growth rates of mutants identified two genes that when inactivated result in significantly reduced in vitro growth; lruB (LIC10713) and O-acetylhomoserine (thiol) lyase (LIC11852) (FIG. 8A).

Figure 8:
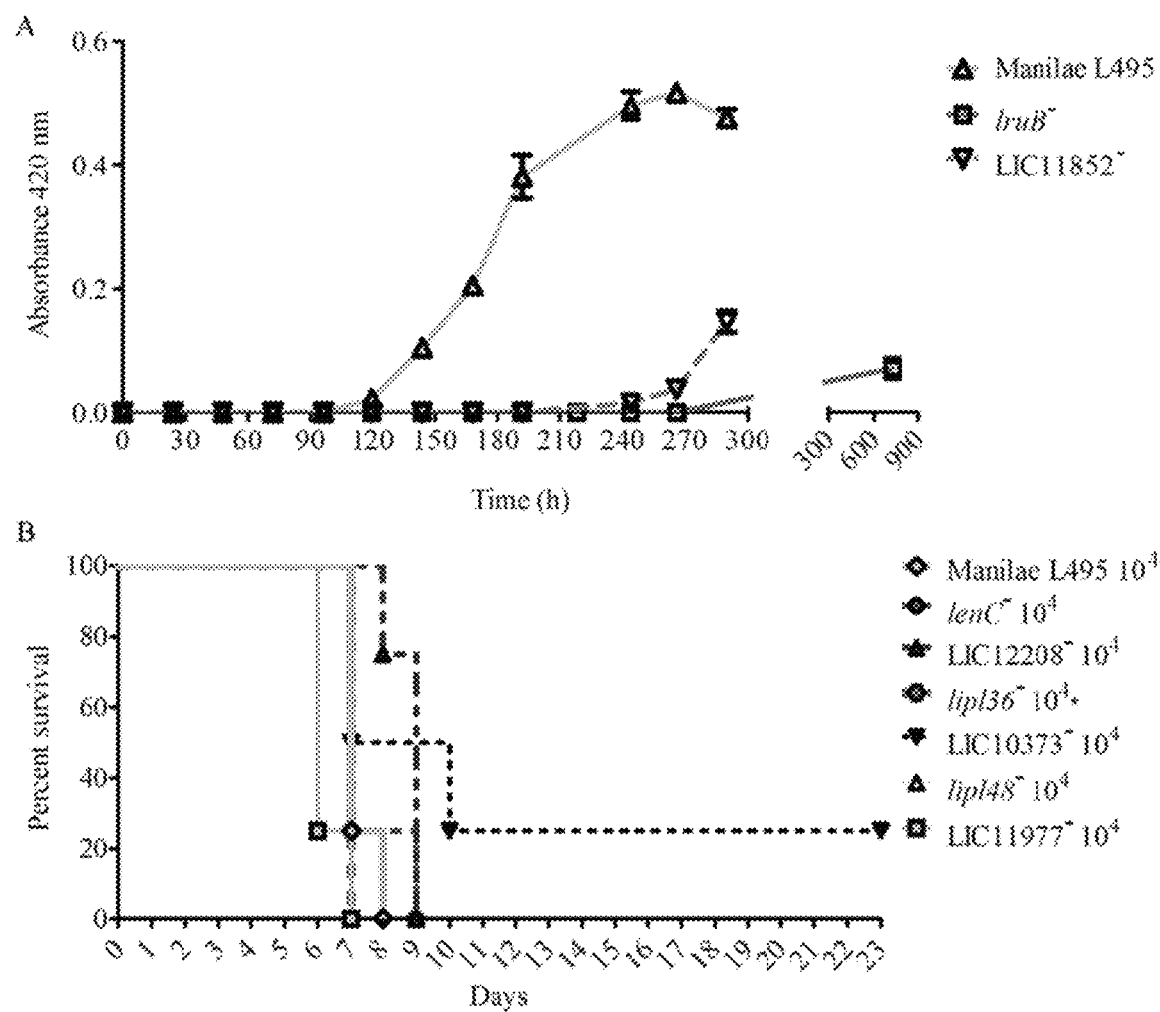
FIG. 8 shows select exoprotein encoding genes are required for in vitro growth and for full virulence.
Figure 9:
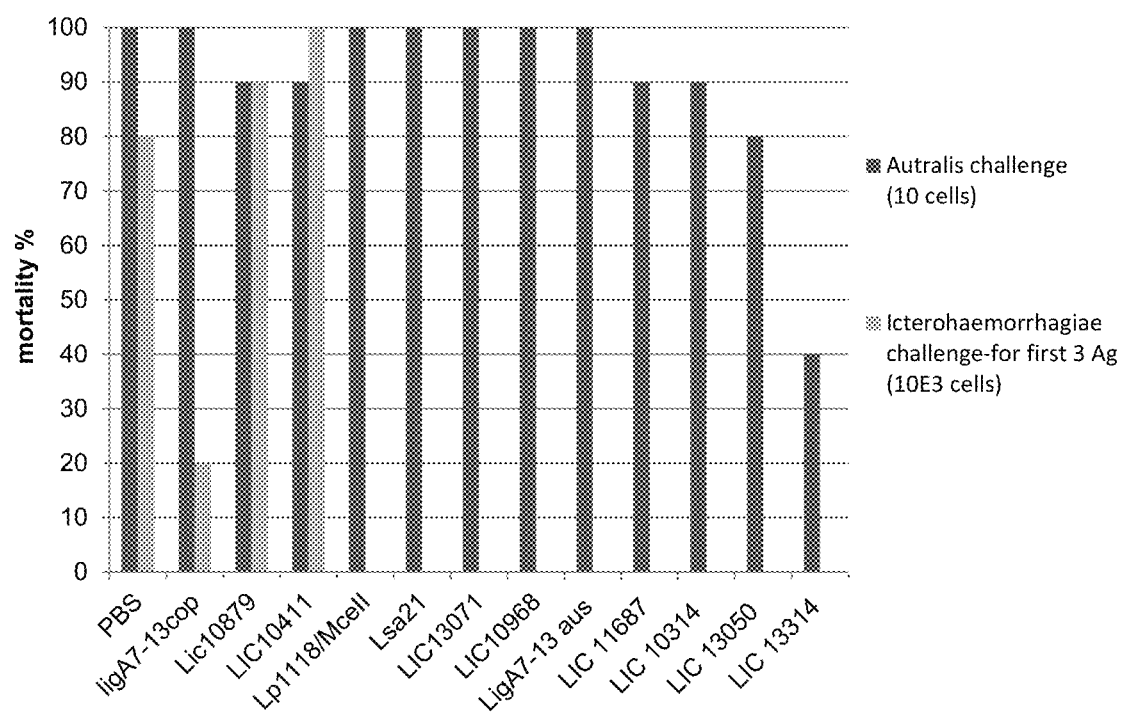
FIG. 9 is a graph presenting the hamster challenge study results (Example 3).

The other tested *Leptospira* mutants (in exoprotein encoding genes) did not display an in vitro growth defect (data not shown) and were subsequently used to infect groups of four gerbils via intraperitoneal injection with $10^4$ bacteria per animal (FIG. 8B). The tested mutants had very little effect on disease manifestation in gerbils in that animals challenged with mutant strains displayed similar mortality rates compared to wt L495 (FIG. 8B). Mutants in genes LIC13086 and LIC10373 displayed delayed and reduced mortality rates, respectively (FIG. 8B), but these differences were not statistically significant when compared to mortality rates attributed to wt L495 challenge.

DISCUSSION

Global characterization of *Leptospira* exoproteins has revealed that the majority of exoproteins contain metabolic and energy generation functions, which are likely essential for survival in the diverse environments encountered by these bacteria. *Leptospira interrogans* evolved from *L. biflexa* and has likely retained the majority of these exoprotein encoding genes from the saprophyte (62). Classification of exoproteins into COGs indicated that most exoproteins are involved in nutrient acquisition and metabolism, including amino acid, carbohydrate and lipid uptake. Lipid uptake is essential for *Leptospira* as beta-oxidation is the primary method of energy generation in these bacteria. Evidence for the latter claim is provided in the culturing medium in which the only source of energy is polysorbate 80; a derivative of polyethoxylated sorbitan and oleic acid. The ability of *Leptospira* to utilize polysorbate 80 as an energy source is in itself evidence of the plasticity of exoprotein function since polysorbate 80 is a synthetic compound which the bacteria have likely not been exposed to in their evolutionary history. It remains to be elucidated whether *Leptospira* also utilize beta-oxidation during the infection process and if so, whether there would be implications for tissue tropism.

In addition to their metabolic activities, 19 exoproteins also displayed orthology to moonlighting proteins in other microorganisms. The moonlighting properties of two of these proteins have already been demonstrated in *Leptospira* (37, 63). One of these proteins, phosphopyruvate hydratase (Eno/LIC11954) has been characterized as an enolase, is detected in culture supernatants and displays plasminogen binding activity (37). The other protein, elongation factor Tu (Tuf/LIC12875) is detected on the surface of *Leptospira* and displays plasminogen and factor H binding (63). Another potential moonlighting protein, a catalase (KatE/LIC12032), has previously been characterized to be required for *Leptospira* oxidative stress resistance and virulence (51), but the plasminogen binding capacity of this protein (as demonstrated for *Candida albicans* catalase (64)) remains to be elucidated in *Leptospira*. In line with a potential role in host-pathogen interactions, 5 putative *Leptospira* moonlighting proteins have been shown to be immunoreactive (65); suggestive of their expression during the infection process. An exoprotein (not detected in culture supernatants in the present study) directly associated with pathogenesis has been characterized as a collagenase required for tissue invasiveness and virulence in animals (38) while another protein (Lsa32/LIC11089), detected in culture supernatants in the present study, has been characterized and demonstrates laminin and plasminogen binding capacity (66). Additionally a known *Leptospira* virulence factor high-temperature protein G (HtpG) (67), was detected at high abundance in all culture supernatants. Inactivation of this gene results in attenuation of pathogenesis whereas the complemented strain, which displays increased htpG transcription, shows increased virulence, manifesting in increased hemorrhage and lesions in organs (67). Moreover, the htpG mutant does not display in vitro growth defects, suggesting the extracellular presence of this protein as the cause for disease pathogenesis in animals, either through unidentified moonlighting properties or host inflammatory response to this protein. Taken together, these observations make a compelling case for exoprotein mediated host-pathogen interactions and disease pathogenesis.

While disease pathogenesis can be associated with exoprotein function, the *Leptospira* mutants disrupted in exoprotein encoding genes tested in this study displayed similar disease manifestation in animals to that observed for the parent strain. It should be highlighted that one of the inactivated genes encoded LipL48 (LIC10898) which was the second most abundant protein in culture supernatants and was detected at levels 11.3 fold higher than that found within the bacteria. Similarly, another inactivated gene (LIC11977) encoding a cyclic nucleotide binding protein was also detected at high abundance in supernatants and displayed a 5.8 fold higher abundance in culture supernatants relative to that found inside the bacteria. Other notable proteins included the endostatin-like protein LenC which has been shown to bind fibronectin (24) and was unique to the supernatants and a *Leptospira* antigen LipL36. The other 2 mutants were inactivated in genes annotated as lipoproteins. Our curiosity in these genes (LIC12208 and LIC10373) stemmed from the observation that these exoproteins, amongst 3 others, contained multiple repeating beta-propeller domains, were unique to culture supernatants and displayed increased abundance of 5.5 (LpP52) and 3.5 (AAS71615.1/LIC13066) fold, in culture conditions mimicking physiological NaCl concentration. In contrast to the lack of impact on disease pathogenesis, inactivation of two exoprotein encoding genes, annotated as a lipoprotein (containing an imelysin peptidase domain) (lruB/LIC10713) and an O-acetylhomoserine (thiol) lyase (AAS70438.1/LIC11852), rendered the bacteria with in vitro growth defects. The LruB protein has been associated with uveitis (68-70), indicative of expression during pathogenesis. However, LruB also appears to be essential for Leptospiral viability outside the host, is in the COG class P: Inorganic ion transport and metabolism and structural analysis of imelysine-like proteins implicates a role in iron uptake (71). The other vital exoprotein O-acetylhomoserine (thiol) lyase, is in the COG class E: Amino acid transport and metabolism and likely involved in methionine and cysteine regulation (72). It follows that 43 out of the 208 exoproteins were classified in COG class E implicative of exoprotein function in heterotrophic processes.

Example 3—Vaccination and Challenge Experiments

Immunization and challenge experiments. Preliminary screening of recombinant putative immunoprotective proteins were performed in a group of 4 week-old Golden Syrian hamsters, 5 to 10 hamsters per group. Hamsters may be immunized twice by subcutaneous injection with recombinant proteins (50 μg) at an interval of three weeks (Day 0 and Day 21). Hamsters receiving only Freund's adjuvant represent the control group. Prior to immunization, the recombinant proteins were mixed with an equal volume of Freund's adjuvant.

Immunized hamsters were challenged intraperitoneally with 10 to 10e3 leptospires/dose, depending on the serovar. For each serovar the smallest dose inducing at least 80 death after day 10 pots challenge have been determined. The animals were monitored twice daily, sacrificed on day 71. The tissues from infected animals were collected aseptically for histopathological analysis and culture.

Recombinant protective antigens (LIC10879, LIC13050, LIC10411, LIC13314, LIC10117, LIC11088, LIC11089, LIC13074, LIC20229, LIC11181, LIC13059, LIC10959, LIC11289, LIC12349, LIC13250, LIC20146, LIC10321, LIC10662, LIC11183, LIC11489, LIC12258, LIC12731, LIC12332, LIC10793, LIC11884, LIC20197, LIC11224, LIC11693, LIC12285, LIC10672, LIC10509, LIC10596, LIC11028, LIC11874, LIC13090, LIC10318, LIC10655, LIC11553, LIC11637, LIC12100, LIC12784, LIC13002, LIC13023, LIC13017, LIC11711, LIC10380, LIC10551, LIC10740, LIC11580, LIC11990, LIC12339, LIC12691, LIC12805, LIC13195, LIC13313, LIC13386, LIC13491, LIC20165, LIC10314, LIC10326, LIC10927, LIC10968, LIC11003, LIC12576, LIC13434, LIC13071, LIC11224, LIC10027, LIC10474, LIC10411, LIC20035, LIC20197, LIC11088, LIC11687, LIC11711, LIC10115, LIC12433, LIC10868, LIC10898, LIC11299, LIC11693, LIC12030, LIC20153, LIC10672, LIC11966, LIC10973, Lp1118, MceII and Lsa21) were analyzed again as discussed above in a group of hamsters (5 to 10 animals per group). Animals immunized with Freund's were deemed negative controls. The protective efficacy of the recombinant antigens in combination (50 μg of each antigen) were assessed in a group of hamsters (5 to 10 hamsters per group).

Hamster Protection.

Groups of 10 animals were immunized twice 14 d apart via the SQ route with 100 μG (or 50 μG*) of *E. coli* purified recombinant proteins or PBS combined 1:1 with Freund's complete (V1) or incomplete (V2) adjuvant. Hamsters were challenged intraperitoneally 14 d after V2 as indicated and observed daily during 21 d for clinical signs and mortality. As indicated in FIG. 9, LIC13314 was shown to confer 60% protection against lethal *Australis* challenge.

Hamster Model Method

Abbreviations

BSA—Bovine Serum Albumin; CM—Controlled Method; CMD—Challenge Model Development; DMSO—Dimethyl Sulfoxide; EMJH—Ellinghausen, McCullough, Johnson, and Harris; IO—Industrial Operations; LGM—*Leptospira* Growth Medium; MR—Manufacturing Record; PoC—Proof of Concept; QC—Quality Control; R&D—Research and Development; SAM—Supplemental Assay Method; USDA—United States Department of Agriculture.

Hamsters.

Golden Syrian hamsters, approximately 3 weeks old upon arrival, were used for the studies. The hamsters were no more than 4 weeks old, after an acclimation period, which was typically 3-5 days. Hamsters were vaccinated at approximately 4 weeks of age, and then boosted with a second vaccination (as needed) at the age of 6 weeks. The hamsters were then challenged at approximately 6 or 8 weeks old, depending on whether a second vaccination was required. During Challenge Model Development (CDM) studies 6-8 weeks was used.

Media.

Three types of media were used: EMJH (Difco); *Leptospira* Growth Medium (PROBUMIN®—Celliance/Millipore); and M26C (Merial recipe)—used by IO. The protocol for the preparation of each media can be found in the corresponding product literature. *Leptospira* Growth Media and LGM-SemiSolid (LGM) is a diluted form of PROBUMIN®, which is a Bovine Serum Albumin (BSA) product provided by Celliance/Millipore. It should also be noted that the concentrations of TWEEN® and BSA within the 10×BSA Supplement M26A vary depending on the serovar being grown. The following are the concentrations of Tween and BSA with in the 10×BSA Supplement used for each of the 4 serovars: i) *L. canicola*: TWEEN®—375 g/L, BSA—60 g/L; 2) *L. grippo*: TWEEN®—125 g/L, BSA—100 g/L; 3) *L. ictero*: TWEEN®—375 g/L, BSA—60 g/L; and 4) *L. pomona*: TWEEN®—150 g/L, BSA—100 g/L.

There are also two types of preparations for each of these media—a broth and a semisolid. The semisolid version of these media can be made by adding agar at a final concentration of 1.5 g/L to the basal portions of each of these media before autoclaving and the subsequent addition of the BSA supplement. The storage temperature of each media is 4° C. If media is stored at higher temperatures for extended periods of time a reduced Leptospiral growth rate has been observed. The media used for the propagation of *Leptospira* should be relatively fresh and an expiration date of 3 months from the time it is made should be adhered to. As each of these media age, it is thought that some of the essential proteins within the media could possibly begin to break down and, thus, lead to a reduced growth rate as well as a diminishment in culture activity or vitality.

*Leptospira*.

Serovars for these studies include the following: *L. ictero*—CF1 strain (NVSL ID 11403, Lot 14 February 2); *L. canicola*—Moulton strain (Prot 02096/11 Jun. 2); *L. pomona*—MLS, NVSL No. 11000 (22 May 9); *L. grippo*—Oregon Shrew Isolate NVSL No. 11808 (1 Apr. 2010); *L. copenhageni*—Fiocruz L130 strain (6 Nov. 2007); *L. australis* strain 11 500 16700. *Leptospira* were grown in non-vented 15 and 50 mL Falcon tubes (VWR catalog #21008-929 and 21008-938 respectively), at 30° C., under static (not shaking) conditions, and exposed to as little light as possible. *Leptospira* in a log state of growth are preferred for most applications rather than *Leptospira* that are in the lag or stationary phases of growth. Once the quantity of *Leptospira* reaches $10^8$ organisms per mL determined by Petroff-Hausser enumeration, a media passage is typically performed. During media passage, the growing culture is diluted using fresh media by 1:10 and/or 1:100 depending on the logistics of the study and when the culture will be needed. However, it is important to minimize media passages as this will eventually result in attenuation of virulence. After 9 passages in vitro (media) it is important to perform a series of in vivo passages (hamster passages) in order to restore virulence.

Hamster Passage.

Using a *Leptospira* culture in the log phase of growth, the quantity/concentration was determined via Petroff-Hausser enumeration. Based on the quantity the culture was diluted using fresh growth media to a concentration of 3,000 organisms per mL which served as the challenge material for the donor/passage hamsters. Five (5) hamsters were administered the following volumes of the challenge material via IP inoculation: Hamster #1-1 mL; Hamster #2-0.75 mL; Hamster #3-0.5 mL; Hamster #4-0.5 mL; Hamster #5-0.25 mL.

When performing this method, if the *Leptospira* concentration at 3,000 organisms per mL proves to be ineffective at causing timely death, the concentration should be increased to 6,000 org./mL and then 9,000 org./mL if the 6,000 dose is ineffective. The onset of illness/death should occur between 7 and 10 days post-challenge for Lc, Li, Lp, and Lg. The onset of illness/death for *L. copenhageni* is between 10-14 days post challenge. If the onset of illness/death occurs after 10 days post-challenge, or 14 days for *copenhageni*, additional hamster passages, and a possible increase in challenge dose, should be performed until the onset of illness/death occurs in this range.

Re-Isolation from Hamster.

Once illness/death occurs the liver and kidney of the infected hamster should be removed, homogenized, and either: diluted in media (or other acceptable diluents that will support *Leptospira* viability), quantified via Petroff-Hausser enumeration, further diluted (if necessary) to 3000 org./mL, and used to challenge 5 more hamsters as described above; diluted in media and filtered (provided that a sufficient number of *Leptospira* are observable in the homogenate), as specified below in order to remove as many contaminants from the liver homogenate before further propagation and subsequent storage; or diluted 1:10, 1:100, and 1:1,000 in semi-solid media supplemented with 0.1 g/L 5-Fluorouracil (provided that no *Leptospira* are observable in the homogenate) and allowed to grow for 7-14 days until *Leptospira* growth is observed. This method is required for the *L. copenhageni* serovar as there is typically no observable *Leptospira* immediately after homogenization of the liver and kidney.

Filtration of Liver and Kidney Homogenate.

After independently homogenizing approximately 1 g of infected liver and/or kidney in 9 mL of growth media, the infected homogenate was further diluted by 1:100 in 30 mL of growth media (0.3 mL of homogenate into 29.7 mL media) and then slowly passed through a series of filters as follows using a 60 ml syringe: $1^{st}$—Cheese cloth (syringe not needed); $2^{nd}$—5 µm syringe filter (PALL Acrodisc, Versapor Membrane, Non-Pyrogenic, Part #4199); $3^{rd}$—1.2 µm syringe filter (PALL Acrodisc, Versapor Membrane, Non-Pyrogenic, Part #4190); $4^{th}$—0.45 µm syringe filter (PALL Acrodisc, HT Tuffryn Membrane, Non-Pyrogenic, Part #4184); $5^{th}$—0.2 µm syringe filter (PALL Acrodisc, GHP membrane, Part # AP-4564T). After filtration, the filtrate was observed in order to confirm the presence of *Leptospira* (typically about 1-5 organisms per viewing field at 400× magnification). After *Leptospira* was confirmed, the filtrate was used to inoculate semisolid media at a 1:10 dilution for temporary storage and the remaining filtrate was incubated until the culture was at the peak of the log phase of growth ($10^6$—$10^7$ org./mL) at which point the culture was frozen. It is important that at least a 1:100 dilution from the original homogenate be performed as high concentrations of the liver homogenate appear to be toxic or inhibitory to *Leptospira* growth. To freeze *Leptospira*, an equal volume (1:1) of fresh growth media containing 5% DMSO was added to a culture at the peak of the log phase of growth, aliquot 1 mL into acceptable vials for liquid nitrogen storage, and immediately store in liquid nitrogen. Applicants experimented with gradual freezing, as well as other cryopreservatives, and this method has proven superior for all 5 serovars currently under investigation.

Inoculation/Seeding from Frozen.

A 1 mL aliquot was removed, thawed at room temperature, and added 0.5 mL to 9.5 mL of fresh semisolid media. The remaining 0.5 mL was added to 9.5 mL of fresh broth media and incubated. Growth was generally observed in the semisolid culture within 14 days.

Challenge Material Preparation.

Challenge material may be prepared two different ways in, depending on the type of test or study:

Challenge with Culture.

For studies involving the testing of experimental candidates, the challenge material is a broth culture, with minimal media passages, that originates from a bank of frozen seeds in which the virulence and target dose have been previously determined after repeated CMD studies with this material. It is advised once a new bank of seeds is made that at least two CMD studies are completed in order to pinpoint the minimal challenge dose to result in 80-100% mortality for that particular bank of seeds. In the CMD studies, several groups of hamsters should be challenged with varying concentrations of a culture.

Challenge with Liver or Kidney Homogenate.

For studies involving the testing of a manufactured serial's potency, it is specified in the Supplemental Assay Methods, provided by the USDA, that the challenge material be the homogenate of a hamster liver/kidney previously infected with the *Leptospira* serovar of choice. To do this, *Leptospira* should be passed through a set of hamsters (as described above) and the liver of the infected hamster homogenized. This homogenate, or a dilution of it, then serves as the challenge material.

Challenge Model Development.

When challenging hamsters for a study evaluating the efficacy of an experimental vaccine candidate or a study testing the potency of a manufactured serial, it is important not to over-challenge the hamster as this might act to overwhelm any potentially protective effects the vaccines might induce. To minimize the possibility of a potential over-challenge it is important to establish a model for each serovar being used in which the minimal concentration that results in 80-100% mortality is determined.

, *L. australis* and *L. canicola*. In order to determine the lowest concentration to result in 80-100% mortality, one must challenge several groups, containing 8-10 hamsters, with varying concentrations of *Leptospira*. Since *L. ictero, L. australis* and *L. canicola* tend to be more virulent, the best concentrations to test in an initial CMD study would be as follows: 10 organisms; 100 organisms; 500 organisms and 1,000 organisms. Depending on the results of the initial CMD study, the concentrations could be expanded or tightened in subsequent CMD studies to get a more accurate idea of the best challenge concentration.

*L. pomona* & *L. grippo*. Because *L. pomona* and *L. grippo* tend to be less virulent, the best concentrations to test in an initial CMD study are as follows: 1. 100 organisms; 2. 1,000 organisms; 3. 5,000 organisms; 4. 10,000 organisms. Again, depending on the results of the initial CMD study, the concentrations could be expanded or tightened to get a more accurate idea of the best challenge concentration.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A vaccine for providing an animal with immunity against *Leptospira australis*, comprising:
at least 50 μg of an immunoprotective peptide, wherein the immunoprotective peptide is a recombinant, conserved, immunoprotective *Leptospira* polypeptide comprising the sequence set forth in SEQ ID NO: 6, and wherein the immunoprotective peptide elicits in the animal cross-protective immunity against subsequent challenge by a *Leptospira australis* serovar; and
an immuno-effective amount of an oil-in-water adjuvant.

2. The vaccine of claim 1, wherein the immunoprotective polypeptide was expressed from a nucleic acid sequence comprising the sequence set forth in SEQ ID NO: 5.

3. The vaccine of claim 1, wherein the immunoprotective polypeptide was expressed from the nucleic acid sequence set forth in SEQ ID NO: 5.

4. A method of providing an animal with protective immunity against *Leptospira australis*, comprising:
administering to the animal an immunoprotective effective amount of the vaccine according to claim 1.

5. The method of claim 4, wherein the immunoprotective polypeptide was expressed from a nucleic acid sequence comprising the sequence set forth in SEQ ID NO: 5.

6. The method of claim 4, wherein the animal is administered about 1 ml of the vaccine.

7. The method of claim 4, wherein the animal is administered 2 subcutaneous doses of the vaccine.

8. The method of claim 7, wherein the 2 doses are administered at a 21-day interval.

9. The vaccine of claim 1, wherein the vaccine comprises an additional antigen that provides immunity against an additional canine pathogen.

10. The vaccine of claim 9, wherein the additional canine pathogen is selected from canine parvovirus, canine parainfluenza virus, canine distemper virus, adenovirus, herpesvirus, rabies, canine coronavirus, or any combination thereof.

11. The vaccine of claim 1, wherein the immunoprotective peptide is a recombinant, conserved, immunoprotective *Leptospira* polypeptide consisting of the sequence set forth in SEQ ID NO: 6.

* * * * *